(12) United States Patent
Shi et al.

(10) Patent No.: US 9,975,893 B2
(45) Date of Patent: May 22, 2018

(54) PYRAZOLO[3,4-C]PYRIDINE DERIVATIVES

(71) Applicant: CSPC ZHONGQI PHARMACEUTICAL TECHNOLOGY (SHIJIAZHUANG) CO., LTD., Shijiazhuang (CN)

(72) Inventors: Ying Shi, Shijiazhuang (CN); Qingzhi Gao, Shijiazhuang (CN); Yi Mi, Shijiazhuang (CN); Xuliang Wang, Shijiazhuang (CN)

(73) Assignee: CSPC ZHONGQI PHARMACEUTICAL TECHNOLOGY (SHIJIAZHUANG) CO., LTD., Shijiazhuang (CN)

( * ) Notice: Subject to any disclaimer, the term of this patent is extended or adjusted under 35 U.S.C. 154(b) by 0 days. days.

(21) Appl. No.: 15/507,956

(22) PCT Filed: Sep. 2, 2015

(86) PCT No.: PCT/CN2015/088898
§ 371 (c)(1),
(2) Date: Mar. 1, 2017

(87) PCT Pub. No.: WO2016/034137
PCT Pub. Date: Mar. 10, 2016

(65) Prior Publication Data
US 2017/0291896 A1    Oct. 12, 2017

(30) Foreign Application Priority Data

Sep. 2, 2014 (CN) .......................... 2014 1 0442948
Jun. 1, 2015 (CN) .......................... 2015 1 0291890

(51) Int. Cl.
*C07D 401/14* (2006.01)
*A61K 31/437* (2006.01)
*C07D 471/04* (2006.01)

(52) U.S. Cl.
CPC ................. *C07D 471/04* (2013.01)

(58) Field of Classification Search
CPC ....................... C07D 401/14; A61K 31/437
USPC .......................................... 546/119; 514/303
See application file for complete search history.

(56) References Cited

U.S. PATENT DOCUMENTS

| | | | | |
|---|---|---|---|---|
| 6,750,225 B2 * | 6/2004 | Pinto | .................... | C07D 471/04 514/303 |
| 7,115,627 B2 * | 10/2006 | Pinto | .................... | A61K 31/423 514/303 |
| 7,304,157 B2 * | 12/2007 | Mudryk | ................ | C07D 471/04 546/120 |
| 7,388,096 B2 * | 6/2008 | Gleeson | ............... | C07D 471/04 546/120 |
| 2010/0048611 A1 * | 2/2010 | Rohrig | ................. | C07D 471/04 514/303 |

FOREIGN PATENT DOCUMENTS

| CN | 104311556 | * | 9/2014 |
|---|---|---|---|
| EP | 3072892 A1 | | 9/2016 |
| WO | 0039131 | | 6/2000 |
| WO | 02065356 A1 | | 10/2002 |
| WO | 03048081 | | 6/2003 |
| WO | 2003048158 | * | 6/2003 |
| WO | 2006036926 | | 4/2006 |
| WO | 2007137801 | | 12/2007 |
| WO | 2013119328 A1 | | 8/2013 |
| WO | 2016034137 | | 3/2016 |

OTHER PUBLICATIONS

Pinto et al., Journal of Medicinal Chemistry (2007), 50(22), 5339-5356.*
International Application No. PCT/CN2015/088898, International Preliminary Report on Patentability dated Dec. 20, 2016, 31 pages (23 pages for the original document and 8 pages for the English translation).
International Application No. PCT/CN2015/088898, International Search Report and Written Opinion dated Nov. 6, 2015, 12 pages (9 pages for the original document and 3 pages for the English translation).
European Application No. 1583851.7 Extended European Search Report dated Jan. 8, 2018, 8 pages.

(Continued)

*Primary Examiner* — Niloofar Rahmani
(74) *Attorney, Agent, or Firm* — Kilpatrick Townsend & Stockton LLP; John K. McDonald

(57) ABSTRACT

Disclosed are a compound of formula (I), a tautomer, an optical isomer or a pharmaceutically acceptable salt thereof, and a pharmaceutical composition containing the above-mentioned compounds. The above-mentioned compounds have the activity of inhibiting Xa factor positive effect, and can be used for the preparation of a medicament for preventing and/or treating diseases inhibiting Xa factor positive effect in case of low bleeding risk.

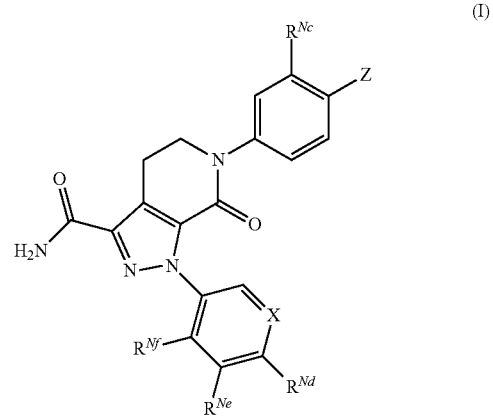

14 Claims, No Drawings

(56) References Cited

OTHER PUBLICATIONS

Pinto et al., Case History: Eliquis™ (Apixaban), a Potent and Selective Inhibitor of Coagulation Factor Xa for the Prevention and Treatment of Thrombotic Diseases, Annual Reports in Medicial Chemistry, vol. 47, Jan. 2012, pp. 123-141.

Pinto et al., Discovery of 1-(4-Methoxyphenyl)-7-oxo-6-(4-(2-oxopiperidin-1-yl)phenyl)-4, 5,6,7,-tetrahydro-1H-pyrazolo[3,4-c]pyridine-3-carboxamide (Apixaban, BMS-562247), a Highly Potent, Selective, Efficacious, and Orally Bioavailable Inhibitor of Blood Coagulation Factor Xa, J. Med. Chem, vol. 50, No. 22, May 2007, pp. 5339-5355.

Wang et al., In Vitro Assessment of Metabolic Drug-Drug Interaction Potential of Apixaban through Cytochrome P450 Phenotyping, Inhibition, and Induction Studies, Drug Metabolism and Disposition, vol. 38, No. 3, Mar. 2010, pp. 448-458.

\* cited by examiner

PYRAZOLO[3,4-C]PYRIDINE DERIVATIVES

CROSS REFERENCE TO RELATED APPLICATION

This application is a national stage application under 35 U.S.C. § 371 of PCT/CN2015/088898 filed Sep. 2, 2015, which claims priority to Chinese Application Nos. 201410442948.2 filed Sep. 2, 2014 and 201510291890.0 filed Jun. 1, 2015 the disclosures of each which are hereby incorporated by reference herein in their entireties.

TECHNICAL FIELD

The present invention belongs to the field of medicine, and relates to a novel class of pyrazolo[3,4-c]pyridine derivatives, pharmaceutical compositions containing them, their preparation processes and their use as medicine.

BACKGROUNDS

Thrombus disease is caused by thrombosis and embolism. Under certain pathological conditions, blood clots may be formed from blood components in blood vessel. Blood clots come off from the sites where they form, and will partially or completely block veins or blood-supplying arteries in their flowing process along with the blood flow, causing a series of pathological processes, such as vascular or systematic ischemia, anoxia and necrosis. Common thrombus disease thrombosis, including myocardial infarction, cerebral thrombosis, deep vein thrombosis, pulmonary embolism, and peripheral arterial thromboembolism, seriously damage people's life and the quality of life. Coronary heart disease is an important kind of thrombus diseases, and includes myocardial infarction and angina pectoris. Each year about 0.8-1.5 million new patients suffer from coronary heart disease in China. Coronary heart disease ranks as the fourth leading cause of death, while cerebrovascular disease ranks second. In addition, although there is no specific statistics about the incidence of deep vein thrombosis, but according to a preliminary estimation, the number of deep vein thrombosis patients in China may reach one million. Moreover, with the improvement of people's living quality, the significant improvement of the national average life expectancy, and the increasing proportion of elderly population, the incidence of deep vein thrombosis will increase gradually, and become a common disease.

Thrombosis is caused by the activation of two systems, i.e., coagulation factors and platelets. Coagulation factors are a series of protein components participating in blood clotting. During the angiorhagia or under some pathological condition, these proteins are activated, and adhered together with platelets to form blood clots. There exist two coagulation systems in the body, i.e. endogenous and exogenous. The former refers to that the blood is contacted with abnormal surface to activate Coagulation factor XII. The latter refers to that due to tissue injury, Coagulation factor III is released, and therefore Coagulation factor VII is activated. Both can trigger a series of chain reactions, and converge at Coagulation factor X, which finally lead to the activation of prothrombin and the formation of fibrin.

In recent years, antithrombotic therapies with heparin, aspirin and warfarin have been widely used in clinic. Among them, warfarin inhibits the post-translational maturation of coagulation factors VII, IX, X and prothrombin, and has proven effective in both venous and arterial thrombosis. However, its usage is limited due to its narrow therapeutic index, slow onset of therapeutic effect, numerous dietary and drug interactions, and a need for monitoring and dose adjustment. Heparin is also the main drug in the antithrombotic therapy. But common heparin can't be orally absorbed, and the injection is not convenient. Therefore, more effective oral antithrombotic drugs will have great market demand in China.

Coagulation factor X is a good target for the antithrombotic treatment. First, coagulation factor X is upstream of thrombin in the coagulation cascade amplification. One coagulation factor X molecule can activate hundreds of thrombin molecules. Therefore, theoretically speaking, it would be more effective to inhibit coagulation factor X than to inhibit thrombin. Second, inhibition of coagulation factor X does not affect the thrombin that has been activated. Reversible inhibitors of coagulation factor X may not completely inhibit the generation of thrombin, while a small amount of thrombin can activate platelet to support the hemostatic process. Thus the inhibition of coagulation factor X might have relatively mild adverse effects of bleeding than thrombin. This was confirmed in animal models. Third, the indirect coagulation factor X inhibitor fondaparinux has been clinically successful, demonstrating that the inhibition of coagulation factors is indeed an effective means of anti-thrombosis.

In the conversion process of prothrombin into thrombin, Factor Xa is the most important drug target in the coagulation cascade. Factor Xa inhibitors can closely attach to the active site of Factor Xa, resulting in the inactivation of Factor Xa that is free or combined with fibrin so as to have the anti-coagulant effect. Compared with heparin with low molecular weight, factor Xa inhibitors can significantly reduce the occurrence of venous thrombosis, and does not increase the incidence of bleeding. Compared with warfarin, factor Xa inhibitors are convenient without the requirement for dosage adjustment and routine surveillance, and have little interaction with food and drugs so as to can be co-administrated with others.

At present, a series of patent applications with respect to factor Xa inhibitors have been disclosed, including WO2001047919, WO2008006479, WO2007137801, WO2006047528 and the like. In addition, there have been several coagulation factor X inhibitors in the abroad market, including the Rivaroxaban of Bayer, Apixaban of Bristol-Myers Squibb (BMS) and the like. Apixaban is jointly developed by BMS and Pfizer. It is another direct oral factor Xa inhibitor following Rivaroxaban, and is useful in preventing venous thrombosis in adult elective total hip or total knee arthroplasty, and was listed in the European Union in July 2011

Although the bleeding tendency of factor Xa inhibitors is lower than those of traditional anti-coagulants, the main clinical adverse reaction is still bleeding. Therefore it is a research focus in the field to reduce the risk of bleeding, and improve the therapeutic window.

Although a series of Factor Xa inhibitors with anti-thrombosis effect have been disclosed, it is still urgently demanded to develop new drugs with better efficacy and lower bleeding risk.

SUMMARY OF THE INVENTION

The present invention provides new compounds with good antithrombotic effect and lower bleeding risk.

Specifically, these compounds are the following compounds of technical solutions 1-13.

Technical Solution 1.

A compound of formula (I), a tautomer thereof, or an optical isomer thereof, or a pharmaceutically acceptable salt thereof:

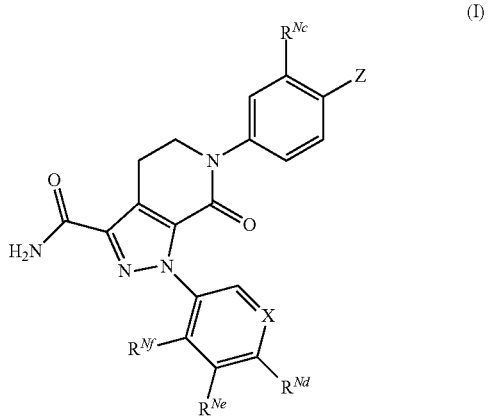

(I)

wherein
X is selected from CH and N;
Z is selected from

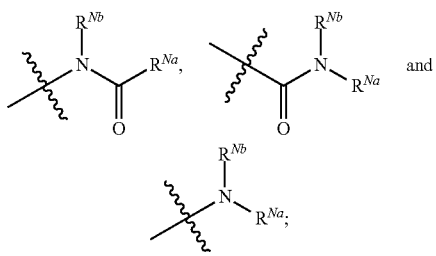

and $R^{Na}$ and $R^{Nb}$ are each independently selected from hydrogen, $C_{1-6}$alkyl, $C_{2-6}$alkenyl, $C_{2-6}$ alkynyl, $C_{1-6}$alkoxy-$C_{0-6}$alkyl, $(C_{0-6}$alkyl$)(C_{0-6}$alkyl$)$N—$C_{1-6}$alkyl, $(C_{2-6}$alkylene$)$N—$C_{1-6}$alkyl or carbamoyl-$C_{1-6}$alkyl; or
$R^{Na}$ and $R^{Nb}$, together with the atoms attached thereto, form a 5, 6 or 7-membered cyclic moiety,
wherein
the 5, 6 or 7-membered cyclic moiety is substituted by one $R^{Ng}$, wherein the $R^{Ng}$ is selected from hydrogen, $C_{1-4}$alkyl, hydroxyl, $C_{1-4}$alkoxy, halogen, oxo and amino,
the 5, 6 or 7-membered cyclic moiety, besides the N atom attaching to $R^{Nb}$, comprises 0, 1, 2, 3 or 4 heteroatoms selected from N, O and S,
the 5, 6 or 7-membered cyclic moiety comprises 0, 1, 2 or 3 double bonds;
$R^{Nc}$ is selected from hydrogen, $C_{1-6}$alkyl and $C_{1-6}$alkoxy;
$R^{Nd}$ is selected from hydrogen, $C_{1-6}$alkoxy, halogen-substituted $C_{1-6}$alkoxy, carbamoyl-$C_{1-6}$alkyl and $C_{1-6}$alkoxy-$C_{1-6}$alkyl;
$R^{Ne}$ is selected from hydrogen, halogen, $C_{1-6}$alkoxy, halogen-substituted $C_{1-6}$alkoxy, carbamoyl-$C_{1-6}$alkyl and $C_{1-6}$alkoxy-$C_{1-6}$alkyl;
$R^{Nf}$ is selected from hydrogen, halogen, $C_{1-6}$alkoxy, halogen-substituted $C_{1-6}$alkoxy, carbamoyl-$C_{1-6}$alkyl and $C_{1-6}$alkoxy-$C_{1-6}$alkyl;
with the proviso that the compound of formula (I) does not comprise the compounds which are excluded from claim 1.

Technical Solution 2.

The compound of formula (I) according to any of previous solutions, a tautomer thereof, or an optical isomer thereof, or a pharmaceutically acceptable salt thereof, wherein
X is CH.

Technical Solution 3.

The compound of formula (I) according to any of previous solutions, a tautomer thereof, or an optical isomer thereof, or a pharmaceutically acceptable salt thereof, wherein
Z is selected from

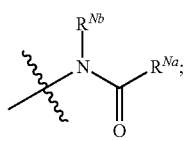

$R^{Na}$ and $R^{Nb}$, together with the atoms attached thereto, form a 5, 6 or 7-membered cyclic moiety,
wherein
the 5, 6 or 7-membered cyclic moiety is substituted by one $R^{Ng}$, wherein the $R^{Ng}$ is selected from hydrogen, $C_{1-4}$alkyl, hydroxyl, $C_{1-4}$alkoxy, halogen, oxo and amino,
the 5, 6 or 7-membered cyclic moiety, besides the N atom attaching to $R^{Nb}$ comprises 0, 1, 2, 3 or 4 heteroatoms selected from N, O and S,
the 5, 6 or 7-membered cyclic moiety comprises 0, 1, 2 or 3 double bonds.

Technical Solution 4.

The compound of formula (I) according to any of previous solutions, a tautomer thereof, or an optical isomer thereof, or a pharmaceutically acceptable salt thereof, wherein
Z is selected from:

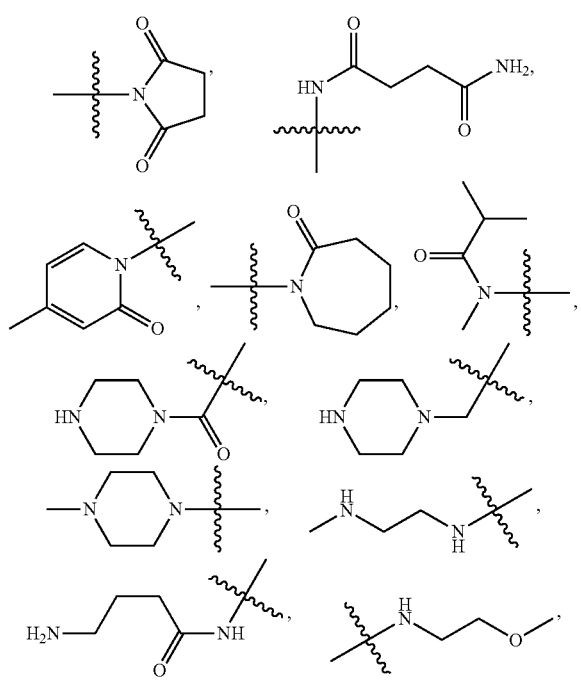

-continued

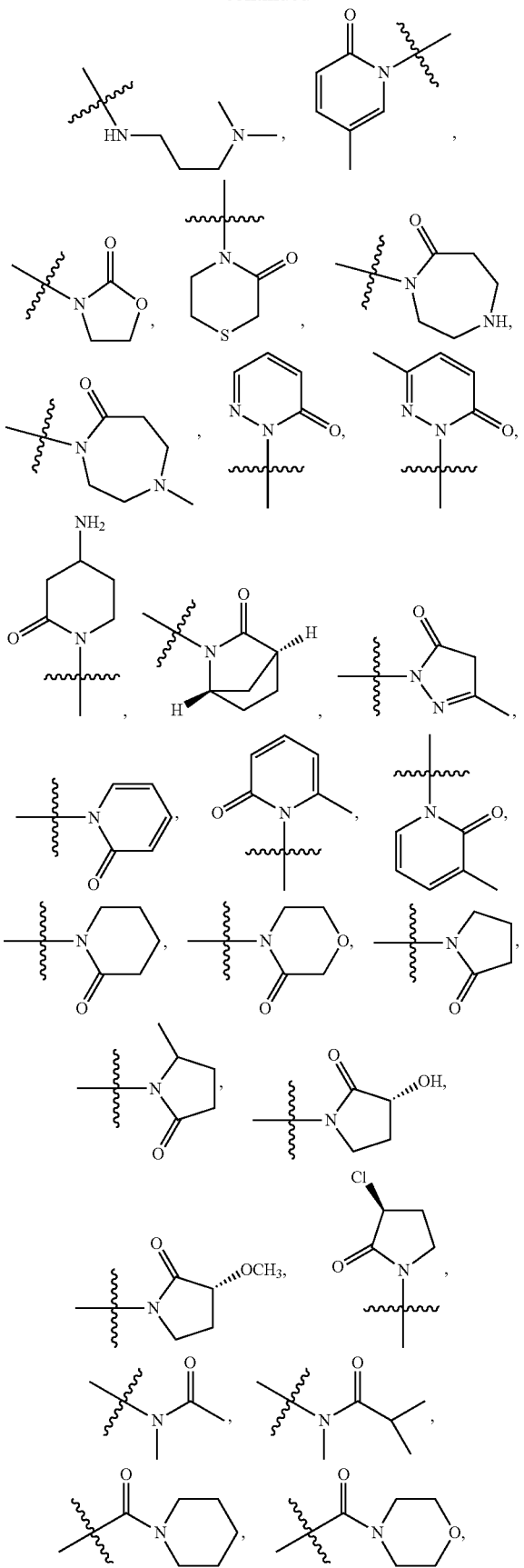

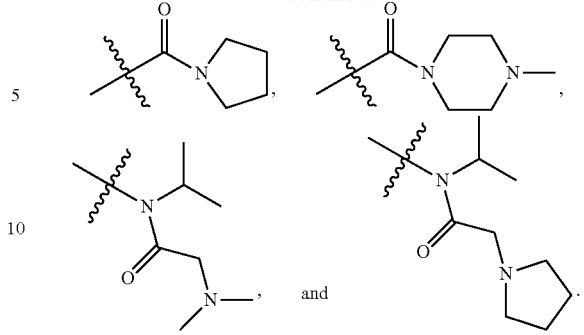

Technical Solution 5.
The compound of formula (I) according to any of previous solutions, a tautomer thereof, or an optical isomer thereof, or a pharmaceutically acceptable salt thereof, wherein
$R^{Nc}$ is selected from hydrogen and methyl.

Technical Solution 6.
The compound of formula (I) according to any of previous solutions, a tautomer thereof, or an optical isomer thereof, or a pharmaceutically acceptable salt thereof, wherein
$R^{Nd}$ is selected from $C_{1-3}$alkoxy.

Technical Solution 7.
The compound of formula (I) according to any of previous solutions, a tautomer thereof, or an optical isomer thereof, or a pharmaceutically acceptable salt thereof, wherein
$R^{Ne}$ is selected from hydrogen, chlorine and fluorine.

Technical Solution 8.
The compound of formula (I) according to any of previous solutions, a tautomer thereof, or an optical isomer thereof, or a pharmaceutically acceptable salt thereof, wherein
$R^{Nf}$ is selected from hydrogen, chlorine and fluorine.

Technical Solution 9.
The compound of formula (I) according to any of previous solutions, or a tautomer thereof, or an optical isomer thereof, or a pharmaceutically acceptable salt thereof, wherein
Z is selected from

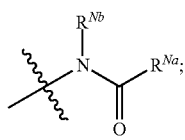

$R^{Na}$ and $R^{Nb}$, together with the atoms attached thereto, form a 5, 6 or 7-membered cyclic moiety,
wherein
the 5, 6 or 7-membered cyclic moiety is substituted by one $R^{Ng}$, wherein the $R^{Ng}$ is selected from hydrogen, $C_{1-4}$alkyl, hydroxyl, $C_{1-4}$alkoxy, halogen, oxo and amino,
the 5, 6 or 7-membered cyclic moiety, besides the N atom attaching to $R^{Nb}$ comprises 0, 1, 2, 3 or 4 heteroatoms selected from N, O and S,
the 5, 6 or 7-membered cyclic moiety comprises 0, 1, 2 or 3 double bonds,
$R^{Nd}$ is selected from $C_{1-6}$alkoxy,
at least one of $R^{Nc}$, $R^{Ng}$, $R^{Ne}$ and $R^{Nf}$ is not hydrogen.

Technical Solution 10.

The compound of formula (I) according to any of previous solutions, a tautomer thereof, or an optical isomer thereof, or a pharmaceutically acceptable salt thereof, wherein X is CH;

Z is selected from

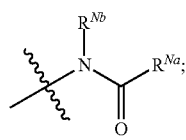

$R^{Na}$ and $R^{Nb}$, together with the atoms attached thereto, form a 5, 6 or 7-membered cyclic moiety, wherein the 5, 6 or 7-membered cyclic moiety is substituted by one $R^{Ng}$, wherein the $R^{Ng}$ is selected from hydrogen and methyl, the 5, 6 or 7-membered cyclic moiety, besides the N atom attaching to $R^{Nb}$, comprise 0, 1, 2, 3 or 4 heteroatoms selected from N, O and S, the 5, 6 or 7-membered cyclic moiety comprises 0, 1, 2 or 3 double bonds, $R^{Nd}$ is selected from ethoxy;

at least one of $R^{Nc}$, $R^{Ng}$, $R^{Ne}$ and $R^{Nf}$ is not hydrogen.

Technical Solution 11.

The compound of formula (I) according to any of previous solutions, a tautomer thereof, or an optical isomer thereof, or a pharmaceutically acceptable salt thereof, wherein X is CH;

Z is selected from

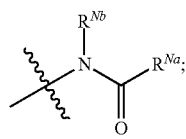

$R^{Na}$ and $R^{Nb}$, together with the atoms attached thereto, form a 5, 6 or 7-membered cyclic moiety, wherein the 5, 6 or 7-membered cyclic moiety is substituted by one $R^{Ng}$, wherein the $R^{Ng}$ is selected from hydrogen and methyl, the 5, 6 or 7-membered cyclic moiety, besides the N atom attaching to $R^{Nb}$ comprises 0, 1, 2, 3 or 4 heteroatoms selected from N, O and S, the 5, 6 or 7-membered cyclic moiety comprises 0, 1, 2 or 3 double bonds, $R^{Nd}$ is selected from ethoxy;

$R^{Nc}$ is methyl.

Technical Solution 12.

The compound according to technical solution 10 or 11, a tautomer thereof, or an optical isomer thereof, or a pharmaceutically acceptable salt thereof, wherein Z is selected from:

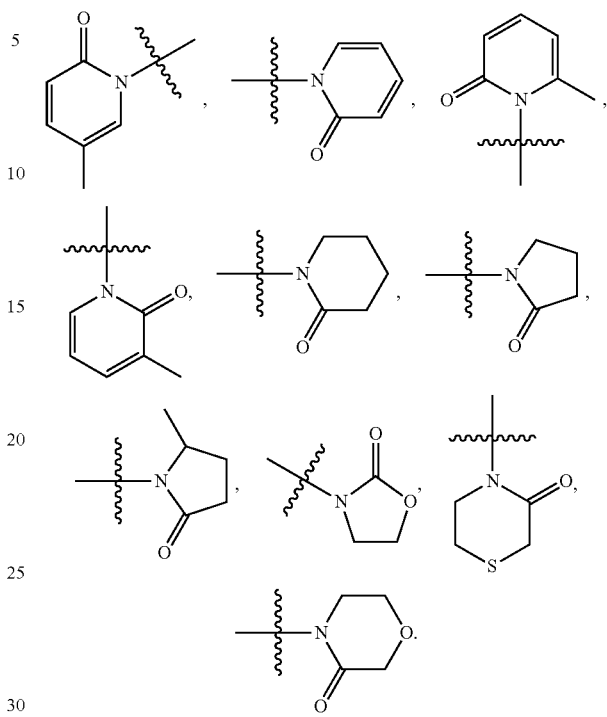

Technical Solution 13.

The following compounds, tautomers thereof, or optical isomers thereof, or pharmaceutically acceptable salts thereof:

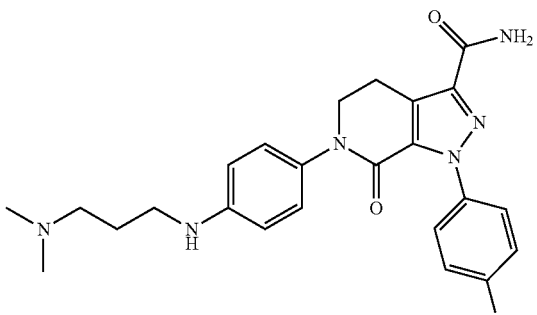

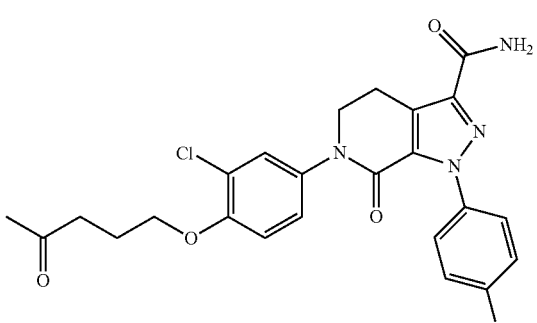

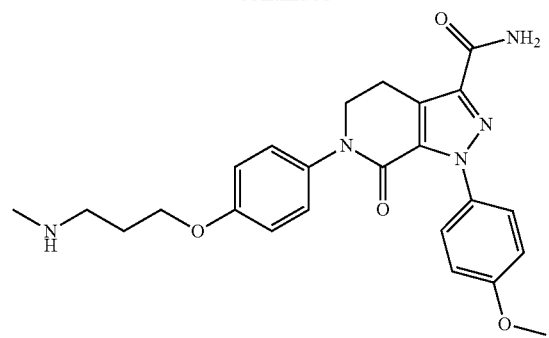
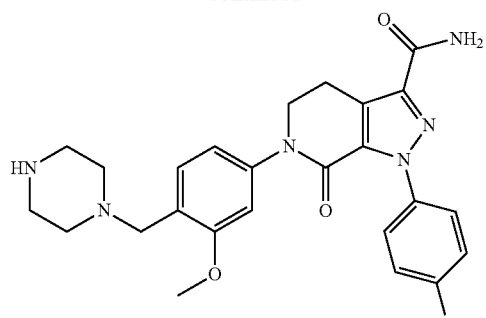
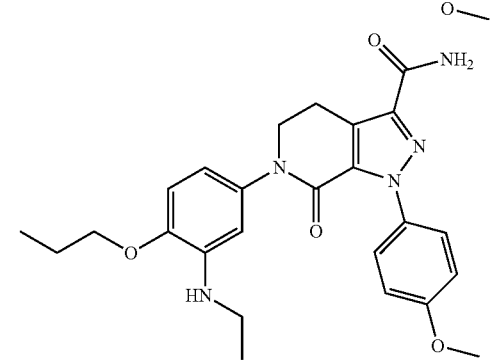
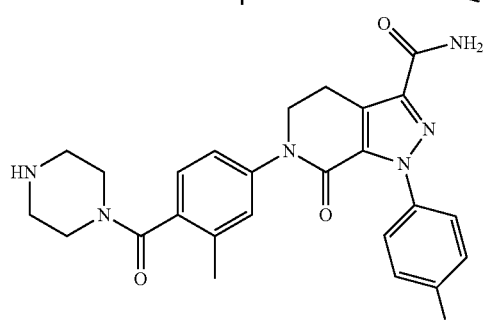
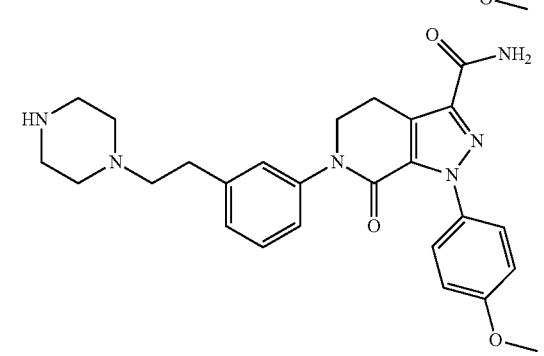
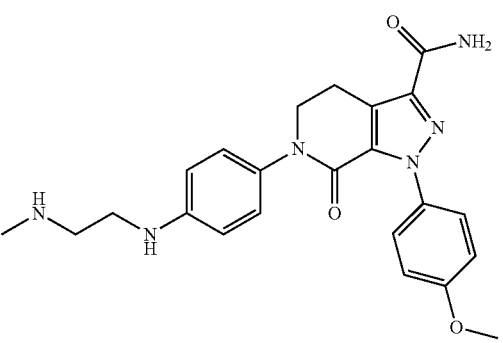
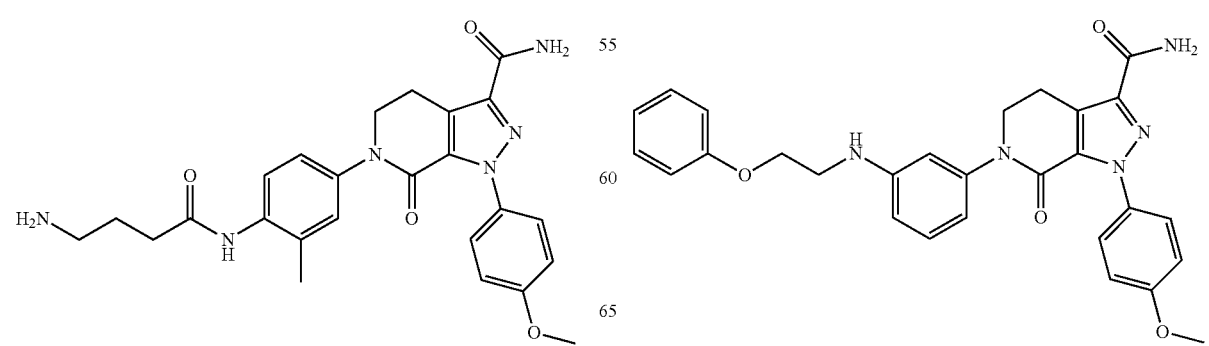

11
-continued
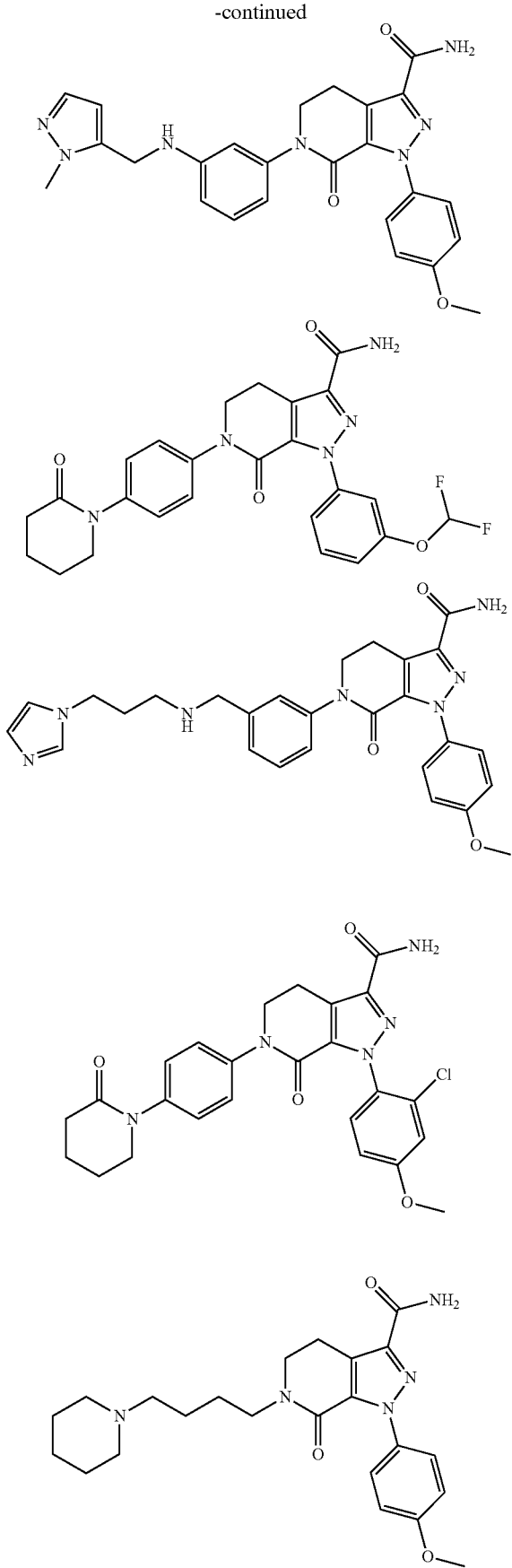
12
-continued
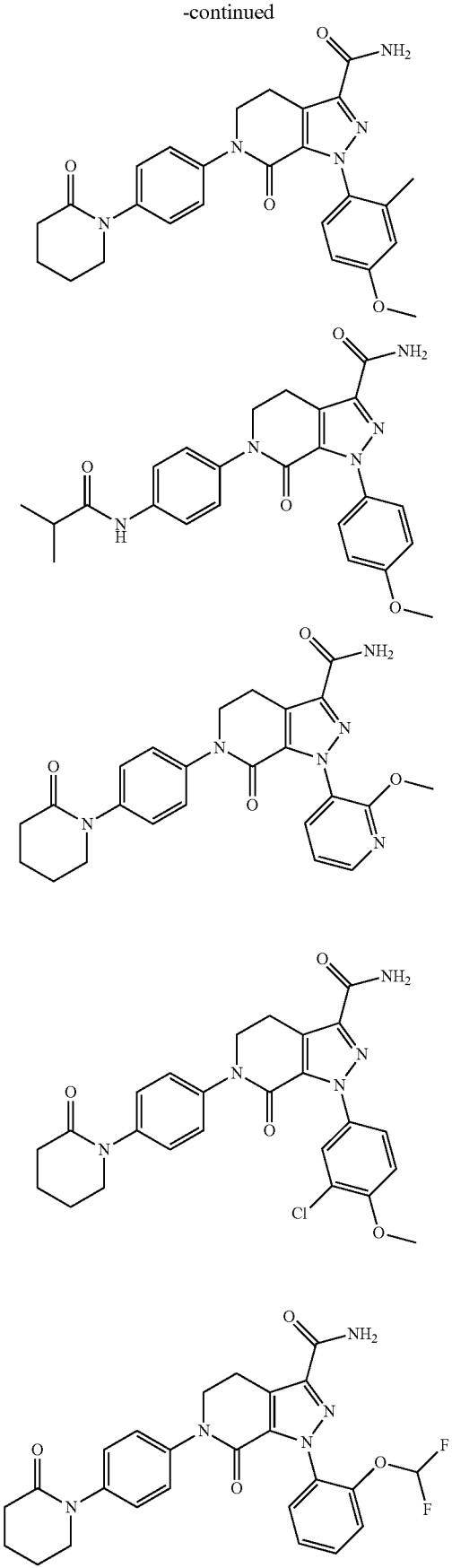

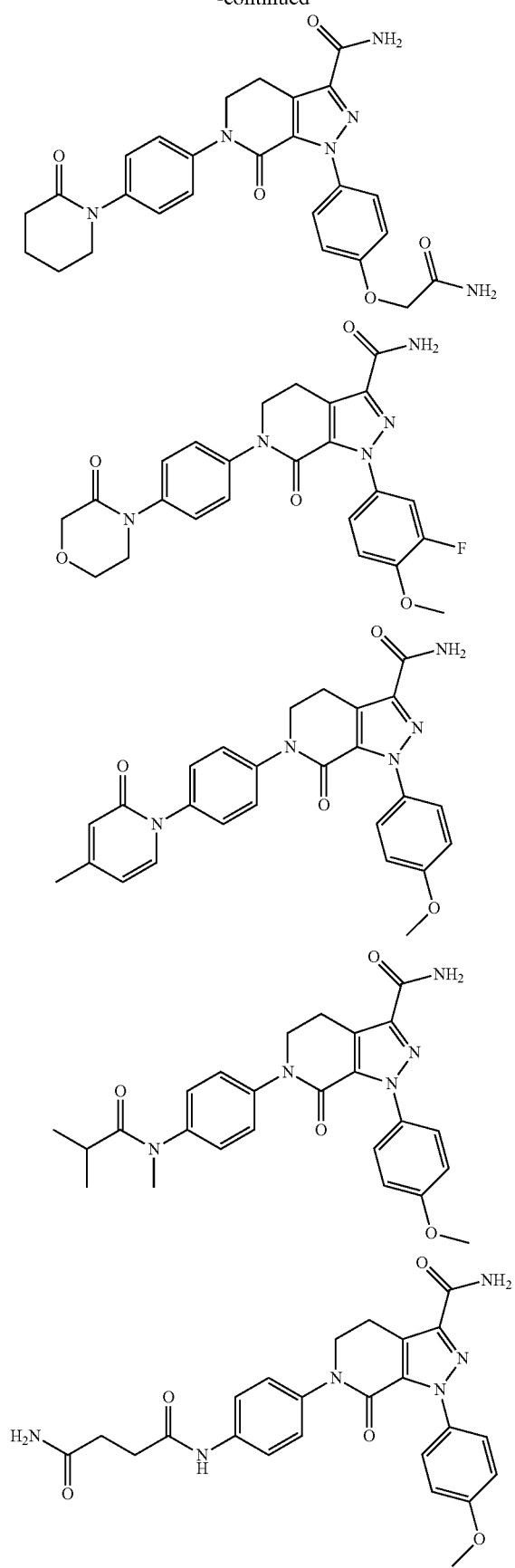
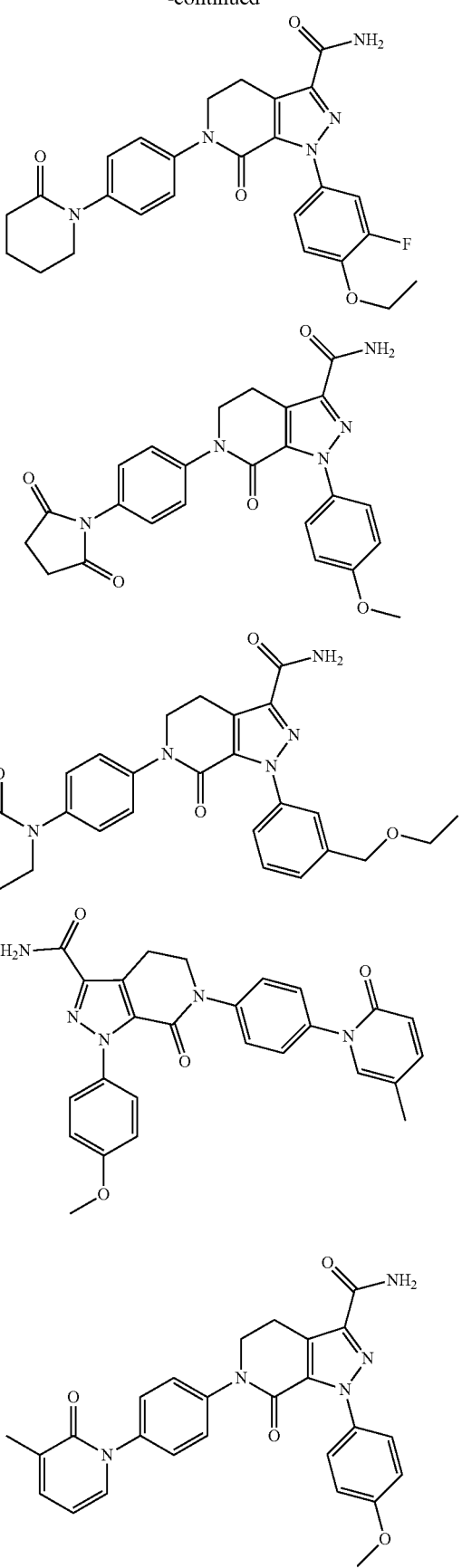

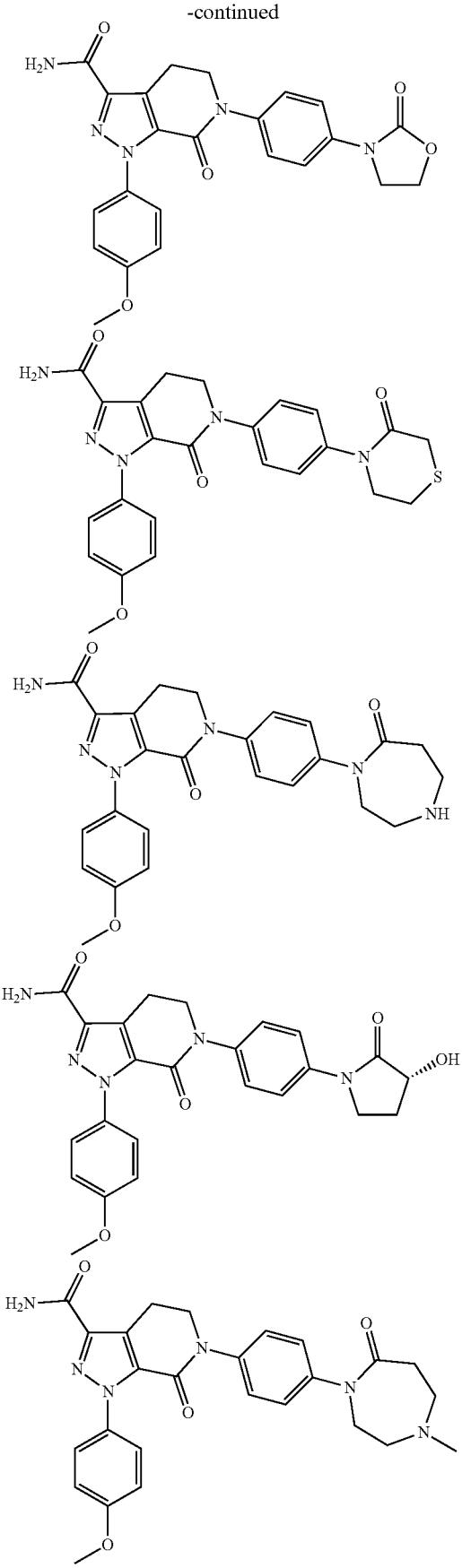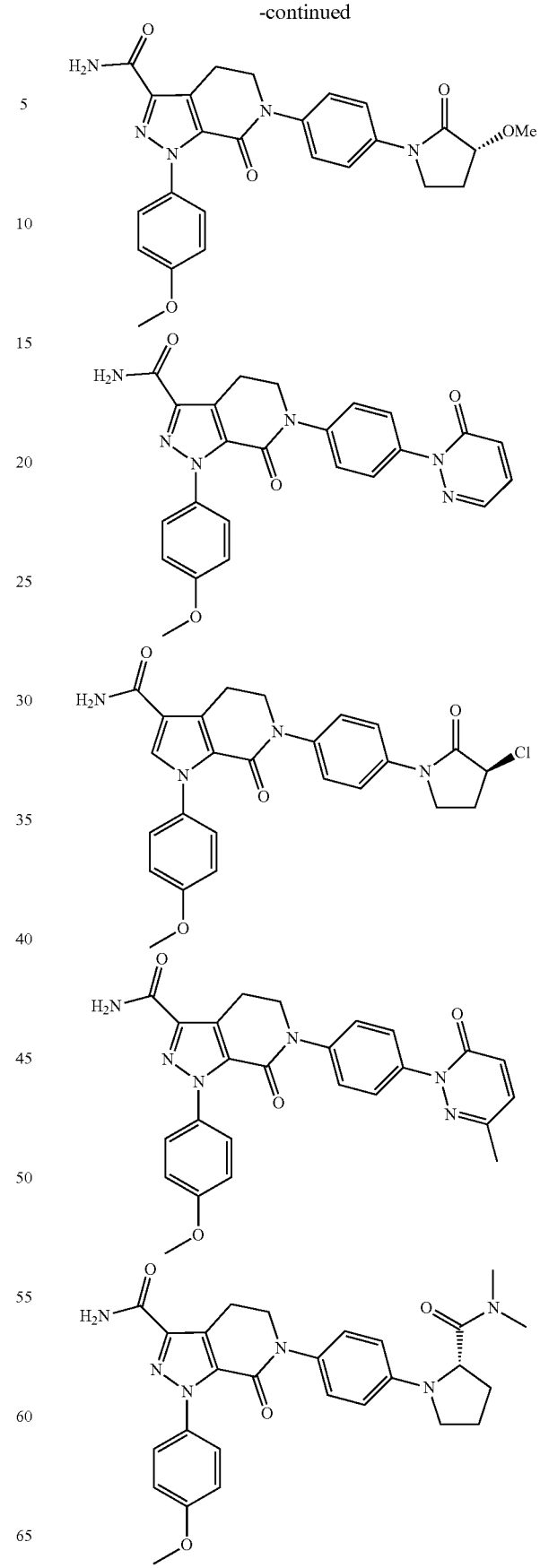

17
-continued
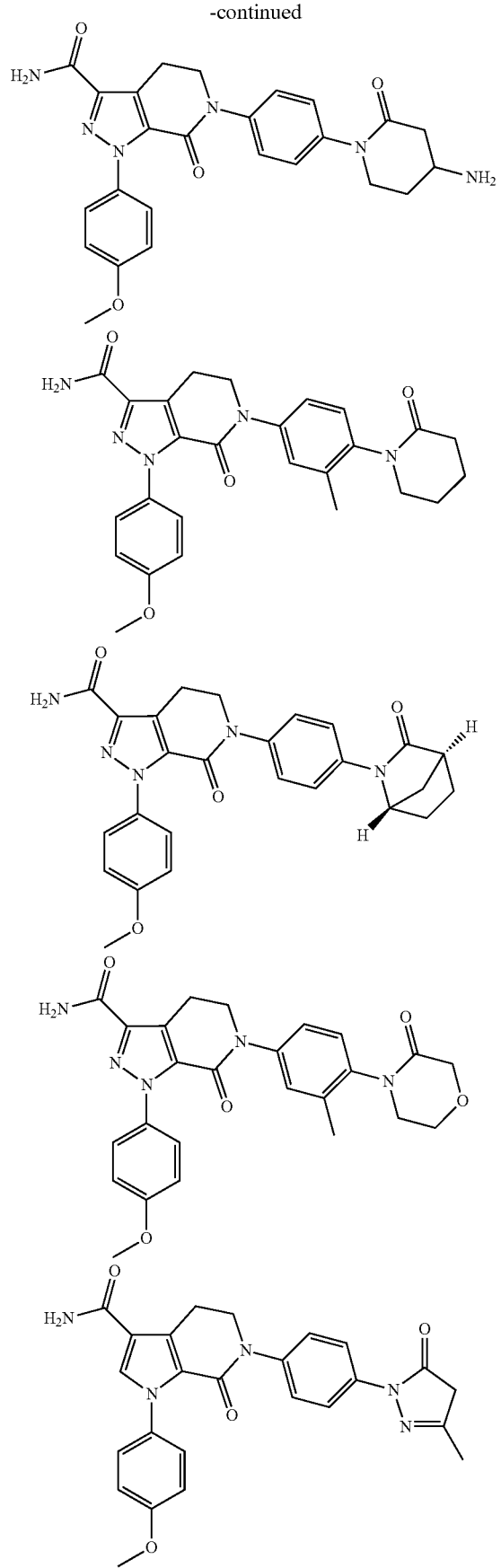
18
-continued
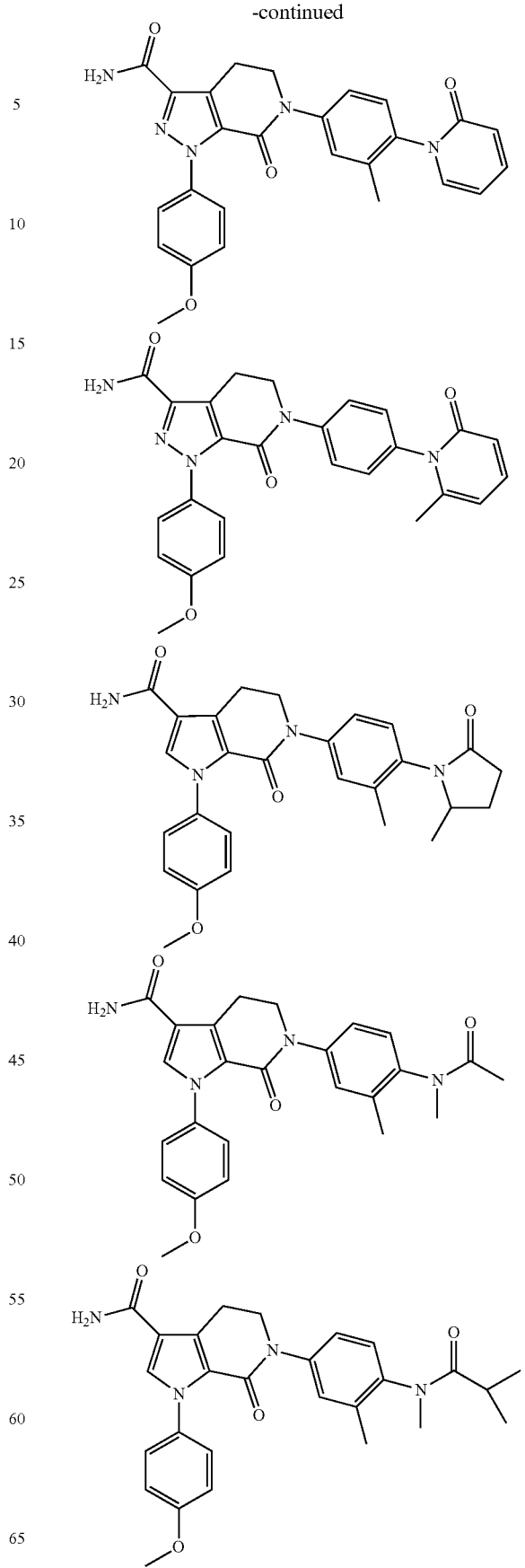

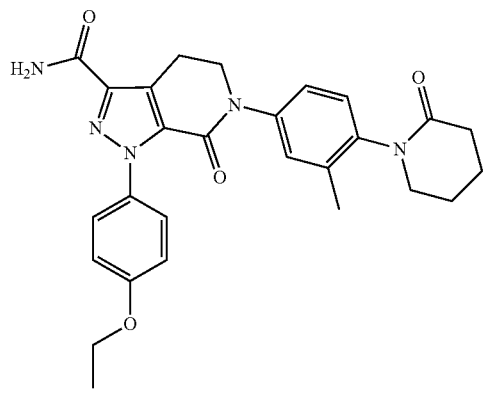
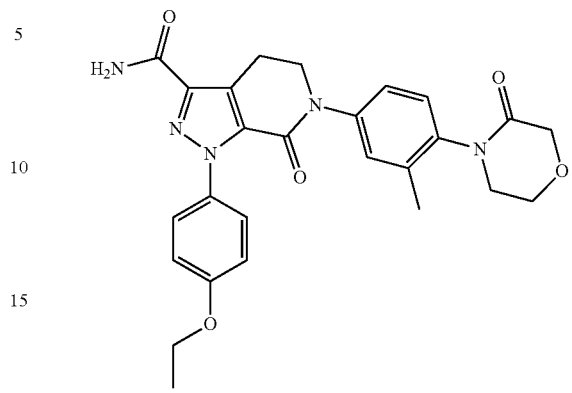
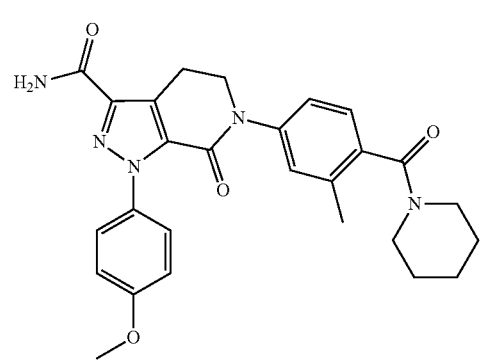
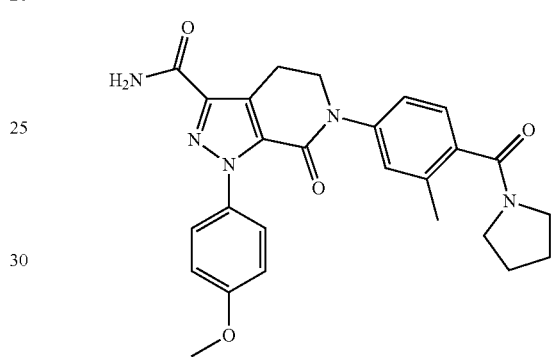
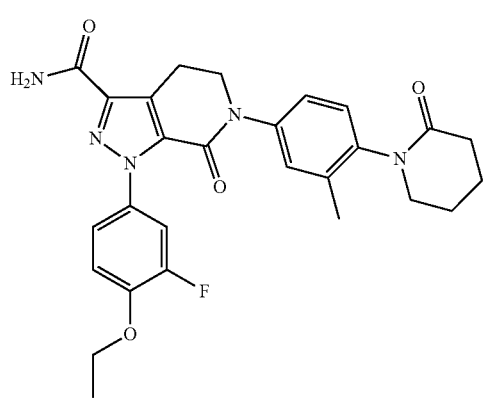
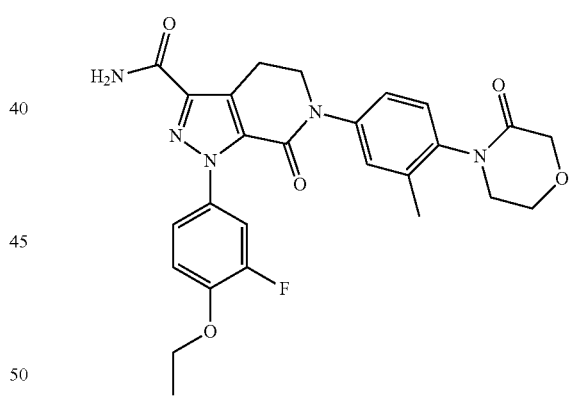
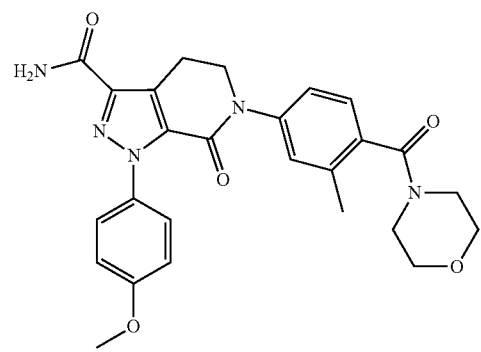
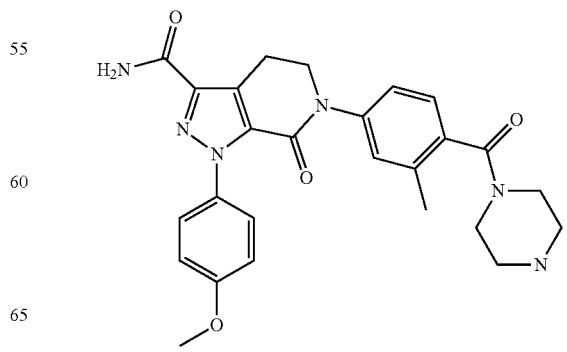

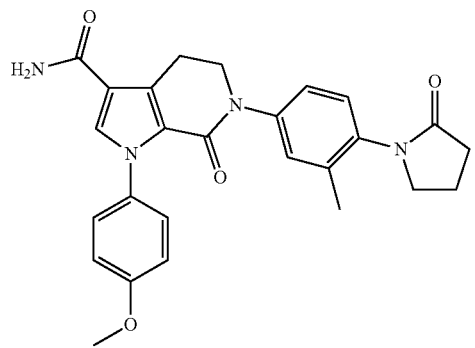
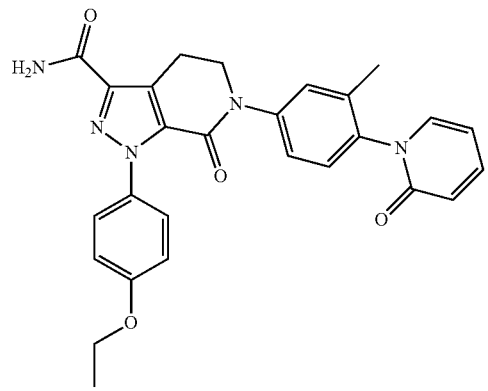
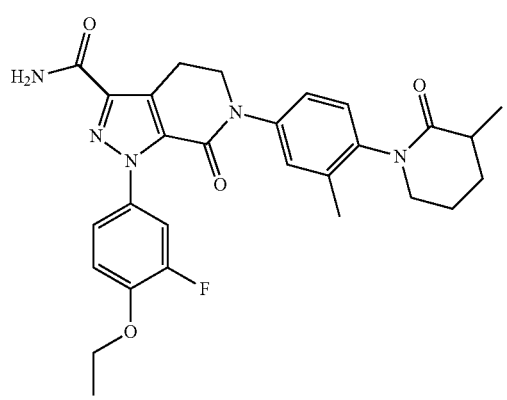
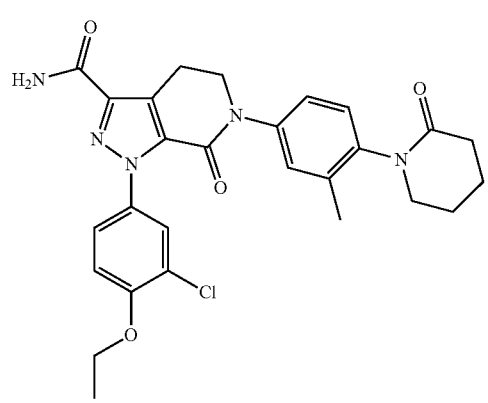
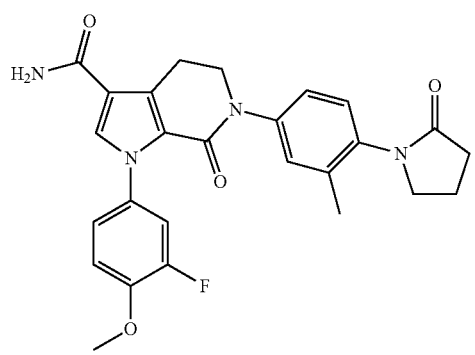
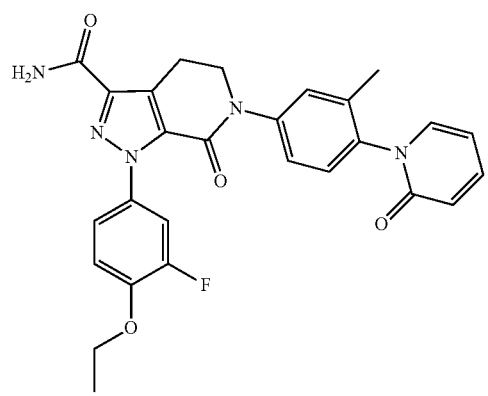
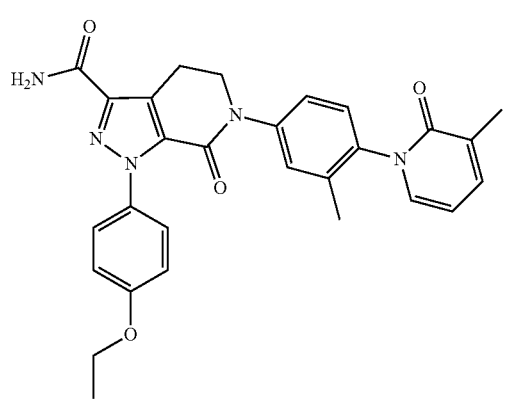
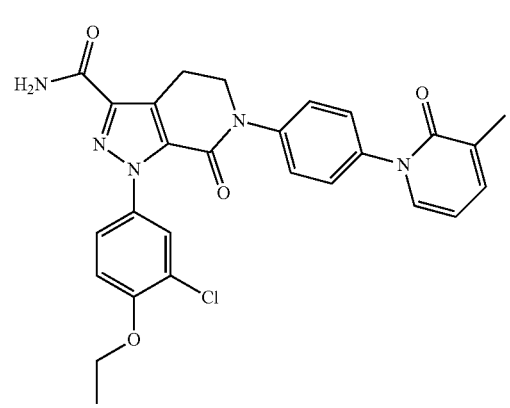

-continued
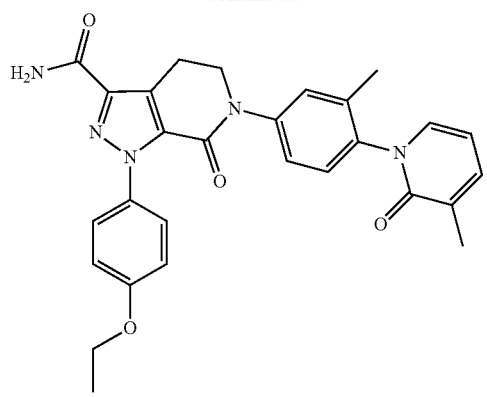
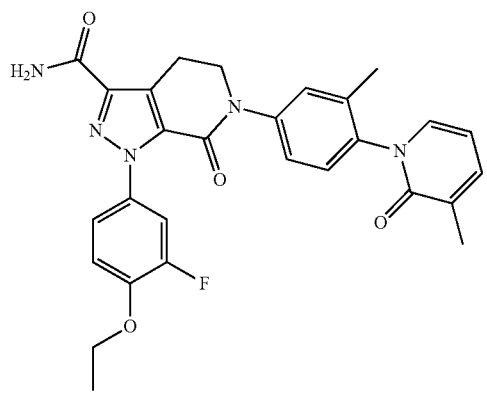
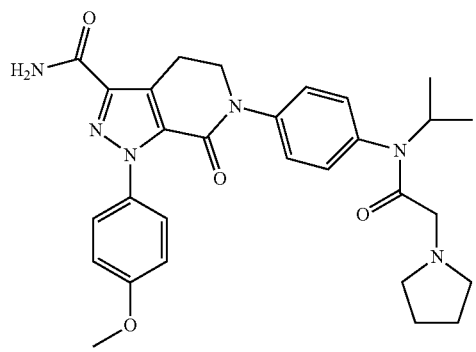
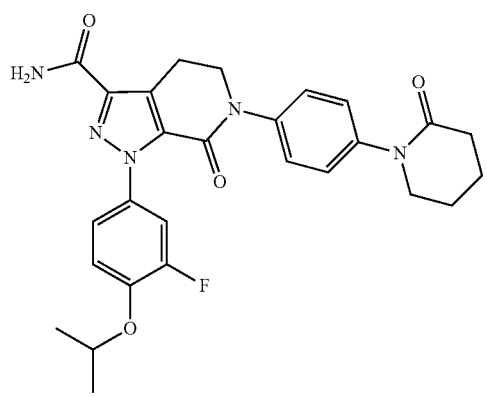
-continued
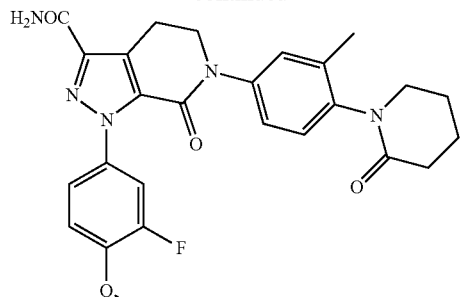
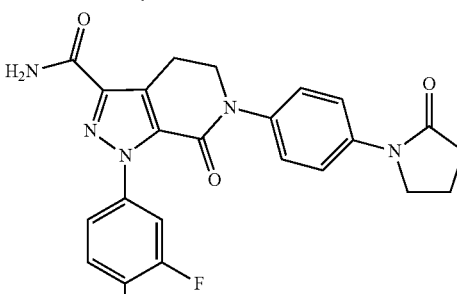
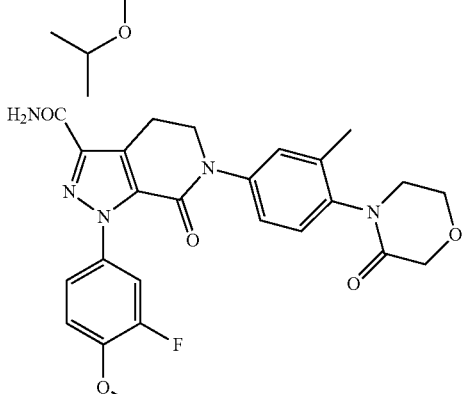
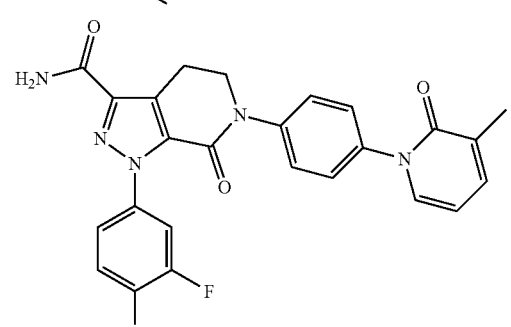
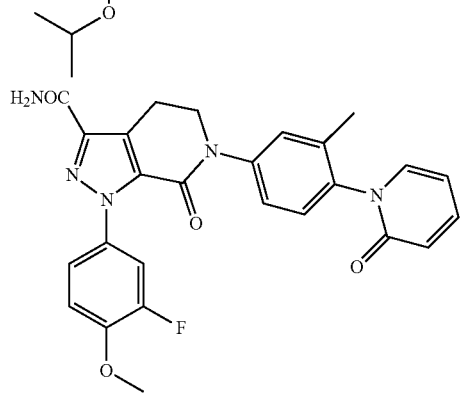

-continued

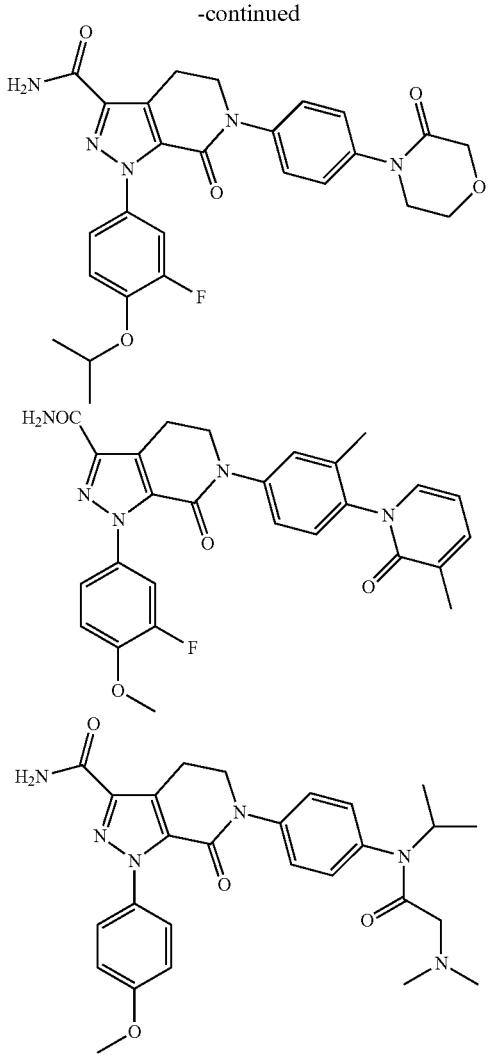

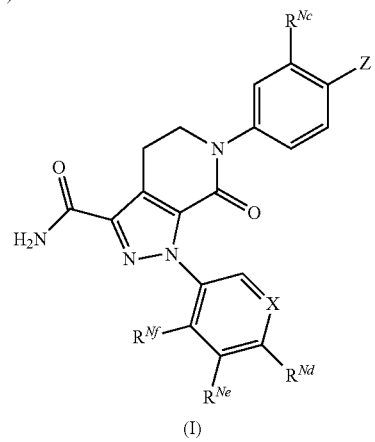

(II)

The present invention also provides a new pharmaceutical composition with good antithrombotic effect and lower bleeding risk, containing the compound of formula (I) according to any of technical solutions 1-13, a tautomer thereof, or an optical isomer thereof, or a pharmaceutically acceptable salt thereof.

The present invention also provides use of the compound of formula (I) according to any of technical solutions 1-13, a tautomer thereof, or an optical isomer thereof, or a pharmaceutically acceptable salt thereof, or the pharmaceutical composition according to above technical solution, in manufacture of a medicament for preventing and/or treating a disease that inhibits Factor Xa positive effect; wherein, the described disease, for instance, is selected from thromboembolism and disseminated intravascular coagulation; for instance, the described disease is selected from myocardial infarction, stenocardia, reocclusion and restenosis after angioplasty or aortocoronary bypass, stroke, transient partial seizures, peripheral arterial occlusive disease, pulmonary embolism or deep venous thrombosis.

The present invention also provides a method for preparing the compound of formula (I) according to technical solution 1, a tautomer thereof, or an optical isomer thereof, or a pharmaceutically acceptable salt thereof, said method comprises ammonifying the compound of formula (II) to obtain the compound of formula (I):

The present invention also provides use of a compound of formula (I) according to any of technical solutions 1-13, a tautomer thereof, or an optical isomer thereof, or a pharmaceutically acceptable salt thereof, or the pharmaceutical composition according to the previous technical solution, in manufacture of a medicament preventing and/or treating a disease that inhibits Factor Xa positive effect in case of low bleeding risk (for instance, a bleeding risk lower than Apixaban); wherein the described disease, for instance, is selected from thromboembolism and disseminated intravascular coagulation; for instance, the described disease is selected from myocardial infarction, stenocardia, reocclusion and restenosis after angioplasty or aortocoronary bypass, stroke, transient partial seizures, peripheral arterial occlusive disease, pulmonary embolism or deep venous thrombosis.

DETAILED DESCRIPTION

Geometric isomers may exist in the present compounds. Compounds of this invention may contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers. Substituents around a cycloalkyl or heterocycloalkyl are designated as being of cis or trans configuration.

Compounds of this invention may contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, preferably an excess of about 85%-90%, more preferably an excess of about 95% 99%, and still more preferably an excess greater than about 99%. Accordingly, this invention includes racemic mixtures, relative and absolute stereoisomers, and mixtures of relative and absolute stereoisomers.

Compounds of this invention containing NH, C(O)OH, OH or SH moieties may have attached there to prodrug forming moieties. The prodrug-forming moieties are removed by metabolic processes and release the compounds having the freed hydroxyl, amino or carboxylic acid in vivo. Prodrugs are useful for adjusting such pharmacokinetic properties of the compounds as solubility and/or hydrophobicity, absorption in the gastrointestinal tract, bioavailability, tissue penetration, and rate of clearance.

Prodrugs are derivatives of an active drug designed to ameliorate some identified, undesirable physical or biological property. The physical properties are usually solubility (too much or not enough lipid or aqueous solubility) or stability related, while problematic biological properties include too rapid metabolism or poor bioavailability which itself may be related to a physicochemical property.

Prodrugs are usually prepared by: a) formation of ester, hemi esters, carbonate esters, nitrate esters, amides, hydroxamic acids, carbamates, imines, Mannich bases, phosphates, phosphate esters, and enamines of the active drug, b) functionalizing the drug with azo, glycoside, peptide, and ether functional groups, c) use of aminals, hemiaminals, polymers, salts, complexes, phosphoramides, acetals, hemiacetals, and ketal forms of the drug. For example, see Andrejus Korolkovas's, "Essentials of Medicinal Chemistry", John Wiley-lnterscience Publications, John Wiley and Sons, New York (1988), pp. 97-118, which is incorporated in its entirety by reference herein. Esters can be prepared from substrates containing either a hydroxyl group or a carboxyl group by general methods known to persons skilled in the art. The typical reactions of these compounds are substitutions replacing one of the heteroatoms by another atom. Amides can be prepared from substrates containing either an amino group or a carboxyl group in similar fashion. Esters can also react with amines or ammonia to form amides. Another way to make amides is to heat carboxylic acids and amines together.

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^2$H, $^3$H, $^{13}$C, $^{14}$C, $^{15}$N, $^{18}$O, $^{32}$P, $^{35}$S, $^{18}$F, $^{36}$Cl, and $^{125}$I. Compounds that contain other isotopes of these and/or other atoms are within the scope of this invention.

In this paper, the term "tautomer" denotes a chemically equilibrium state between one form and another form, rapidly interconverted to each other through the movement of a proton and the shifting of bonding electrons. One kind of form is priority, such as keto-enol tautomerism.

In this paper, the term "optical isomer" denotes substance with identical molecular structure, similar physical and chemical character, differently optical activity.

In this paper, the term "salt" is selected from hydrochloride, hydrobromide, sulfate, sulfite, phosphate, mesylate, p-toluenesulfonate, maleate, tartrate, malate, fumarate, citrate, and the like.

In this paper, the term "$C_{1-6}$alkyl" denotes straight or branded chain saturated hydrocarbon radical containing 1-6 carbon atoms, for example, methyl, ethyl, n-propyl, isopropyl, n-butyl, sec-butyl, isobutyl, tertiary butyl, and the like.

In this paper, the term "$C_{2-6}$alkenyl" denotes straight or branched chain unsaturated hydrocarbon radical containing 2 to 6 carbon atoms and containing at least one double bond, including but not limited to ethylenyl, 1-propenyl, 2-propenyl (allyl), isopropenyl, 2-methyl-1-propenyl, 1-butenyl, 2-butenyl, and the like.

In this paper, the term "$C_{2-6}$alkynyl" denotes straight or branched chain unsaturated hydrocarbon radical containing 2 to 6 carbon atoms and containing at least one triple bond, including but not limited to ethynyl, propynyl, butynyl, and the like.

In this paper, the term "halogen" generally denotes fluorine, chlorine, bromine or iodine.

In this paper, the term "$C_{1-6}$alkoxy" denotes "$C_{1-6}$alkyl-O—", wherein $C_{1-6}$alkyl is defined as above.

In this paper, the term "carbamoyl" denotes "$NH_2$—CO—".

In this paper, the term "$C_{2-6}$alkylene" denotes a bivalent radical, derived from $C_{2-6}$ alkane by removal of two hydrogen atoms. $C_{2-6}$alkylene includes, but is not limited to 1,2-ethylene, 1,3-propylene, 1,4-butylene, and the like.

In this paper, the term "$C_{0-6}$alkyl" denotes a collection of a chemical bond and $C_{1-6}$ alkyl.

In this paper, the term "$C_{1-6}$alkoxy-$C_{0-6}$alkyl" denotes $C_{0-6}$alkyl substituted by $C_{1-6}$ alkoxy. $C_{1-6}$alkoxy-$C_{0-6}$alkyl denotes $C_{1-6}$alkoxy.

In this paper, the term "($C_{0-6}$alkyl)($C_{0-6}$alkyl)N—$C_{1-6}$alkyl" denotes $C_{1-6}$alkyl substituted by an amino group, wherein said amino group is further substituted by two $C_{0-6}$alkyl groups, being independent each other, wherein the $C_{0-6}$alkyl substitution denotes no substitution.

In this paper, the term "($C_{2-6}$alkylene)N—$C_{1-6}$alkyl" denotes $C_{1-6}$alkyl substituted by an amino group, wherein the N atom of said amino is combined with said $C_{2-6}$alkylene to form a saturated ring.

In this paper, the term "carbamoyl-$C_{1-6}$alkyl" denotes $C_{1-6}$alkyl substituted by carbamoyl.

In this paper, the term "5, 6 or 7-membered cyclic moiety" denotes a ring containing 5 to 7 ring member atoms, wherein said ring at least contains one nitrogen atom as ring member, and besides said nitrogen atom, said 5, 6 or 7-membered cyclic moiety can further contain 0, 1, 2, 3 or 4 heteroatoms selected from N, O and S; said 5, 6 or 7-membered cyclic moiety contains 0, 1, 2 or 3 double bonds; said 5, 6 or 7-membered cyclic moiety can be substituted by oxo; said 5, 6 or 7-membered cyclic moiety can be in form of monocyclic ring or bridged ring. Said 5, 6 or 7-membered cyclic moiety includes but is not limited to pyrrole, dihydropyrrole, pyrrolidine, pyridine, dihydropyridine, tetrahydropyridine, piperidine, morpholine, piperazine, azacycloheptane, 2-azabicyclic[2,2,1]heptane and the like.

In another aspect of the present invention, the present invention provides a pharmaceutical composition containing the compound of formula (I) according to the present invention, a tautomer thereof, or an optical isomer thereof, or a pharmaceutically acceptable salt thereof.

The pharmaceutical composition can be administered by oral route, e.g. in the form of granules, tablets or capsules, or by parenteral injection, e.g. intravenous injection, subcutaneous injection, intramuscular injection or intrathecal injection, or by transfusion e.g. in the form of sterile solutions, suspensions or emulsion, or by local application, e.g. in the form of ointment or cream, or by rectally administration, e.g. in form of suppository. Generally, the above-mentioned compositions can be prepared by conventional methods with conventional excipients.

In another aspect of the present invention, the present invention provides use of the compound of formula (I) according to the present invention, a tautomer thereof, or an optical isomer thereof, or a pharmaceutically acceptable salt thereof, or the pharmaceutical composition according to the present invention, in manufacture of a medicament for preventing and/or treating a disease that inhibits Factor Xa positive effect. For instance, said disease is selected from thromboembolism and disseminated intravascular coagulation. For instance, said disease is selected from myocardial infarction, stenocardia, reocclusion and restenosis after angioplasty or aortocoronary bypass, stroke, transient partial seizures, peripheral arterial occlusive disease, pulmonary embolism or deep venous thrombosis.

In another aspect of the present invention, the present invention also provided a method for preparing the compound of formula (I) according to the present invention, a tautomer thereof, or an optical isomer thereof, or a pharmaceutically acceptable salt thereof, comprising ammonifying the compound of formula (II) to achieve the compound of formula (I).

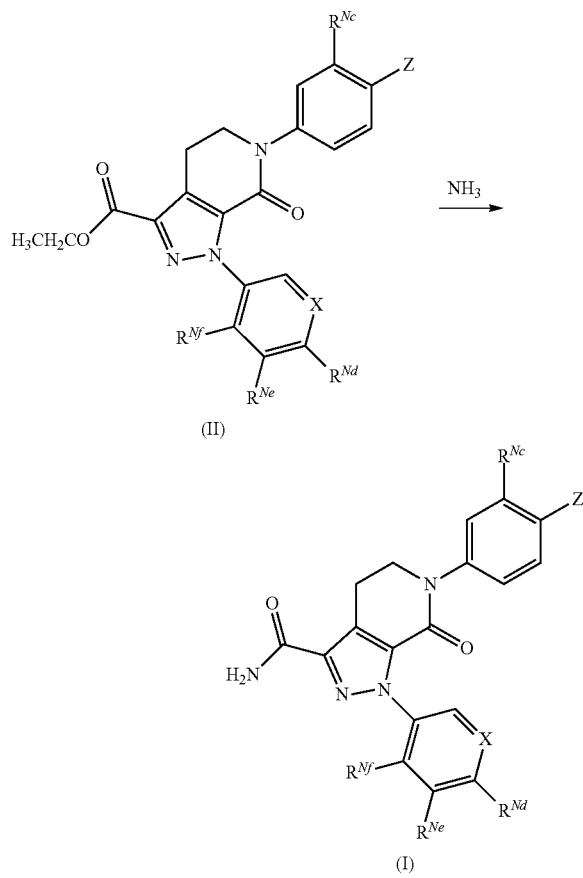

The compounds of the present invention have good antithrombotic effects and lower risk of bleeding. These effects may be determined and confirmed by the following biological activity assay.

I. Anti-Factor Xa Activity Assay

Materials:

Enzyme: Factor Xa (MERK)

Substrate: CS-1122 (Hyphen)

Buffer: 50 mM TrisHCl, 150 mM NaCl, PH8.3

Methods:

100 μL of buffer, 50 μL of different concentrations of compounds (diluted with buffer) and 50 μl of 0.1 U/ml Factor Xa enzyme (diluted with buffer) were added to a 96-well plate. After 15 min of exposure, 50 μL of chromogenic substrate 2.5 mg/ml CS-11 (22) was added. The substrate hydrolysis was monitored by measuring absorbance at 405 nm at 37° C. for up to 30 min (interval: 30 seconds) using a microplate spectrophotometer. IC50 was calculated by bliss. The values of compounds were determined as described below.

TABLE

Inhibitory effects of compounds on Factor Xa

| Part | Compound | IC50(Compound)/IC50(apixaban) |
|---|---|---|
| B | 21 | <1 |
| B | 26 | <1 |
| B | 29 | <1 |
| B | 32 | <1 |
| B | 33 | <1 |
| A | 3 | <1 |
| A | 16 | <1 |
| A | 17 | <1 |
| A | 19 | <1 |
| A | 27 | <2 |
| A | 28 | <1 |
| A | 29 | <2 |
| A | 30 | <2 |
| A | 31 | <1 |
| A | 32 | <1 |
| A | 33 | <1 |
| A | 34 | <1 |
| A | 35 | <2 |
| A | 36 | <1 |
| A | 37 | <1 |
| A | 38 | <1 |
| A | 39 | <1 |
| A | 40 | <1 |
| A | 47 | <1 |
| A | 48 | <1 |
| A | 50 | <1 |
| A | 51 | <1 |

II Rat Tail Bleeding Model

Male SD rats were allocated randomly and administrated. After the administration, the rats were anesthetized by intraperitoneal injection of 10% chloral hydrate. At the time point of 0.5 to 4 hours (Tmax in PK) after the administration, the tails of anesthetized rats were transected 3 mm from the tip and vertically immersed in saline at 37° C. The time point when the continuous blood flow ceased for >30 s was measured. The prolongation of bleeding time was expressed as a ratio of treated vs. the mean vehicle value. Effects of compounds were determined as described below.

TABLE

Effect of compounds on rat tail bleeding time

| Part | compound | The Prolongation of bleeding time (compound)/ The Prolongation of bleeding time(apixaban) |
|---|---|---|
| B | 29 | <1 |
| A | 27 | <1 |
| A | 28 | <1 |
| A | 29 | <1 |
| A | 30 | <1 |
| A | 31 | <1 |
| A | 32 | <1 |
| A | 33 | <1 |
| A | 34 | <1 |
| A | 35 | <1 |
| A | 36 | <1 |
| A | 37 | <1 |
| A | 38 | <1 |
| A | 39 | <1 |
| A | 40 | <1 |

III. Arteriovenous Shunt Model in Rats

Two 10 cm-long polyethylene tubings (1.50 and 2.88 mm of inner and outer diameter, respectively) linked to a central part (8 cm-long, 2.11 and 3.77 mm of inner and outer diameter, respectively) containing a 6 cm silk thread and filled with heparin (3.125 U/ml) were placed between the right carotid artery and the left jugular vein in rats.

Male SD rats were anesthetized by intraperitoneal injection of 10% chloral hydrate after oral dose, inverted fixation, then the right catotid artery and left vena jugularis externa were isolated, the proximal and distal sutures of catotid artery were tied. The syringe needle were cannulated into the catotid artery and fasted, the other of the tube was cannulated into the right vena jugularis externa. Rats were given orally 2-4 hours before the shunt was opened. Blood flowed from the right carotid artery into the polyethylene tubing and then return to left vena jugularis externa. The shunt was then disconnected 15 minutes later and the silk thread covered with thrombus was immediately withdrawn and weighed. The wet weight of the thrombus was determined. Then the silk thread was dried at 60° C. for 4 h to get the dry weight of the thrombus. The anti-thrombotic effects of these agents were expressed as percentage inhibition of thrombus formation based on the treated vs. the corresponding mean vehicle. The results showed that compounds displayed a potent antithrombotic activity (inhibition %>60%, even >70%).

TABLE

Effect of compounds on arteriovenous shunt model in rats

| Part | compound | Inhibition of thrombus formation (%) |
|---|---|---|
| B | 29 | 67.5 |
| A | 27 | 68.7 |
| A | 28 | 73.1 |
| A | 29 | 67.4 |
| A | 31 | 71.5 |
| A | 32 | 61.4 |
| A | 33 | 60.8 |
| A | 34 | 62.5 |
| A | 36 | 71.6 |
| A | 37 | 63.7 |
| A | 38 | 70.5 |
| A | 39 | 64.5 |
| A | 40 | 63.4 |

EXAMPLES

In the following part of examples, the method of preparation for the present invention is illustrated by the way of examples. The compounds of raw material are synthesized by the method as described in the present invention, or they are commercially available from the following manufacturers: J&K Chemicals, Beijing InnoChem Science & Technology Co., Ltd., Aladdin, Alfa Aesar, Accela ChemBio Co., Ltd.

The abbreviations of the compounds in the examples have the following meanings:
Boc t-butyloxycarboryl
DCM methylene chloride
DEAD diethyl azodicarboxylate
DIPEA N,N-diisopropylethylamine
DMF dimethylformamide
DMSO dimethyl sulfoxide
EA ethyl acetate
EDCI 1-(3-dimethylaminopropyl)-3-ethylcarbodiimide hydrochloride
HOBt hydroxybenzotrizole
MeOH Methanol
PE petroleum ether
THF tetrahydrofuran
NIS N-iodosuccinimide
Prep-HPLC preparative high performance liquid chromatography
(Boc)2O Di-tert-butyl dicarbonate
NBS N-Bromosuccinimide
HATU O-(7-azabenzotriazol-1-yl)-N,N,N',N'-tetramethyluronium hexafluorophosphate
MTBE methyl t-butyl ether
NIS N-Iodosuccinimide
KTB Potassium tert-butoxide
TEA Triethylamine
MsCl Methanesulfonyl chloride
EG Ethanediol
DMAP 4-dimethylaminopyridine
Part A
(1) Method for the Preparation of Compounds C1-C6.

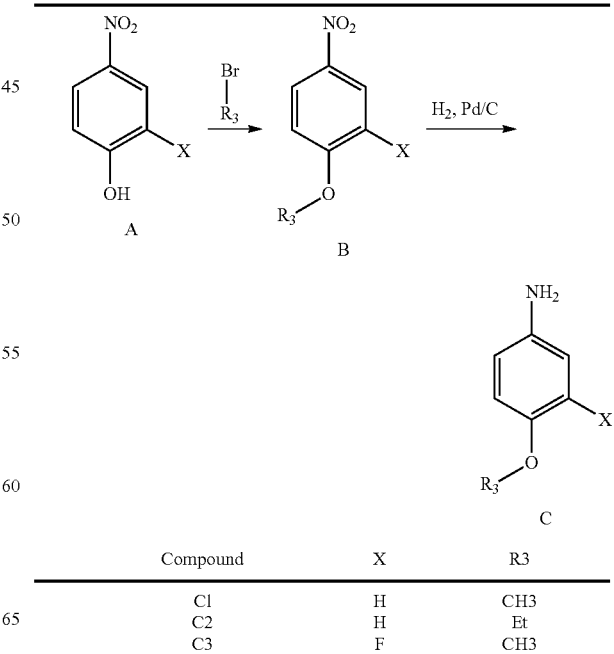

| Compound | X | R3 |
|---|---|---|
| C1 | H | CH3 |
| C2 | H | Et |
| C3 | F | CH3 |

| | | |
|---|---|---|
| C4 | F | Et |
| C5 | F | i-Pr |
| C6 | Cl | Et |

Compound A was a raw material, which was commercially available.

The preparation of compound B: To a reaction flask were added compound A (e.g. 61.8 mmol), bromoalkane (e.g. 154.6 mmol), triethylamine (e.g. 154.6 mmol) and acetonitrile (e.g. 80 mL). The resulting mixture was warmed to 50° C., and stirred for 6 hours to react. After completion of the reaction, the resulting mixture was concentrated, and purified water and ethyl acetate were added. The mixture was stirred and extracted, the organic phase was separated and concentrated to obtain an oil in a yield of >95%.

The compounds C1 and C2 were commercially available.

The preparation of compounds C3 to C6: To a reaction flask were added the starting material B (e.g. 59.5 mmol), Pd/C (e.g. 3.0 g) and methanol (e.g. 200 mL). The mixture was hydrogenated for 2 hours under normal pressure and room temperature. After the completion, the mixture was filtered and concentrated under vacuum to obtain an oil in a yield of about 95%.

(2) The Preparation of Compound F: The Compound F, Namely the Compounds F1-F51, was/were Prepared According to the Following Methods 1 to 4.

Compound F

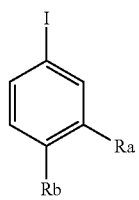

| Compound F | Ra | Rb | G | Method |
|---|---|---|---|---|
| F1 | H | (pyridinone-N-methyl) | (5-methyl-pyridin-2(1H)-one) | Method 1 |
| F2 | H | (oxazolidinone-N) | (oxazolidin-2-one) | Method 1 |
| F3 | H | (thiomorpholin-3-one-N) | (thiomorpholin-3-one) | Method 1 |
| F4 | H | (1,4-diazepan-5-one-N) | (1,4-diazepan-5-one, N-Boc) | Method 2<br>Boc is protection group |
| F5 | H | (4-methyl-1,4-diazepan-5-one-N) | (4-methyl-1,4-diazepan-5-one) | Method 1 |

-continued
Compound F
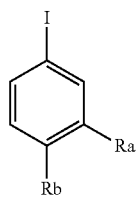
| Compound F | Ra | Rb | G | Method |
|---|---|---|---|---|
| F6 | H | | | Method 1 |
| F7 | H | | | Method 1 |
| F8 | H | | | Method 1 |
| F9 | H | | | Method 1 |
| F10 | H | | | Method 1 |
| F11 | H | | | Method 1 |
| F12 | H | | | Method 1 |

-continued

Compound F

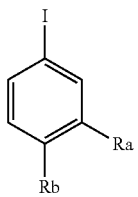

| Compound F | Ra | Rb | G | Method |
|---|---|---|---|---|
| F13 | H | (N-pyrrolidinone with OCH3) | (pyrrolidinone with OCH3, NH) | Method 1 |
| F14 | H | (3-Cl-pyrrolidinone) | (3-Cl-pyrrolidinone, NH) | Method 1 |
| F15 | H | (N,N-dimethyl prolinamide, N-linked) | (N,N-dimethyl prolinamide, NH) | Method 1 |
| F16 | CH3 | (N-piperidinone) | (piperidinone, NH) | Method 1 |
| F17 | CH3 | (morpholinone N-linked) | (morpholinone NH) | Method 1 |
| F18 | CH3 | (N-pyrrolidinone) | (pyrrolidinone NH) | Method 1 |
| F19 | CH3 | (N-pyridinone) | (pyridinone NH) | Method 1 |
| F20 | CH3 | (5-methyl pyrrolidinone N-linked) | (5-methyl pyrrolidinone NH) | Method 1 |

-continued
Compound F
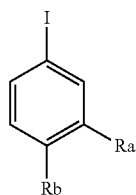
| Compound F | Ra | Rb | G | Method |
|---|---|---|---|---|
| F21 | CH3 | 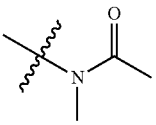 [SMILES: *N(C)C(C)=O] | 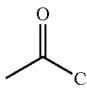 | Method 3<br>Rc = CH3<br>Re = CH3 |
| F22 | CH3 | 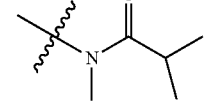 | 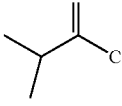 | Method 3<br>Rc = i-Pr<br>Re = CH3 |
| F23 | CH3 | 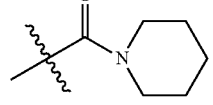 | 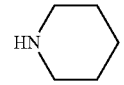 | Method 4<br>Rd = 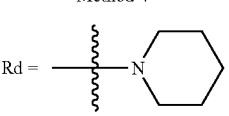 |
| F24 | CH3 | 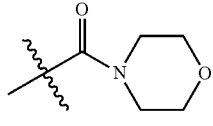 [SMILES: *C(=O)N1CCOCC1] | 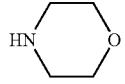 | Method 4<br>Rd = 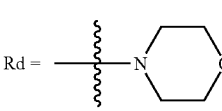 |
| F25 | CH3 | 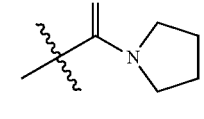 | 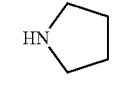 | Method 4<br>Rd = 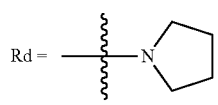 |
| F26 | CH3 | 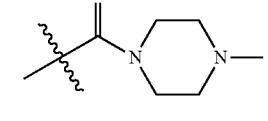 | 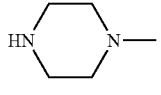 | Method 4<br>Rd = 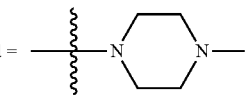 |
| F27 | H | 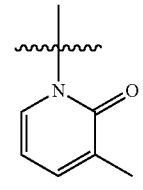 [SMILES: *n1cccc(C)c1=O] | 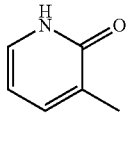 | Method 1 |
| F28 | H | 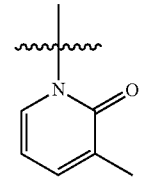 [SMILES: *n1cccc(C)c1=O] | 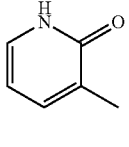 | Method 1 |

Compound F

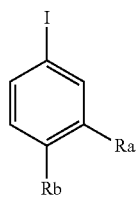

| Compound F | Ra | Rb | G | Method |
|---|---|---|---|---|
| F29 | H | N-piperidin-2-one (N-linked) | piperidin-2-one (NH) | Method 1 |
| F30 | H | 3-methyl-2-oxopyridin-1-yl | 3-methylpyridin-2(1H)-one | Method 1 |
| F31 | CH3 | N-piperidin-2-one | piperidin-2-one (NH) | Method 1 |
| F32 | CH3 | N-piperidin-2-one | piperidin-2-one (NH) | Method 1 |
| F33 | CH3 | 3-oxomorpholin-4-yl | morpholin-3-one (HN) | Method 1 |
| F34 | CH3 | 3-oxomorpholin-4-yl | morpholin-3-one (HN) | Method 1 |
| F35 | CH3 | 2-oxopyrrolidin-1-yl | pyrrolidin-2-one (HN) | Method 1 |
| F36 | CH3 | 2-oxopyrrolidin-1-yl | pyrrolidin-2-one (HN) | Method 1 |

-continued

Compound F

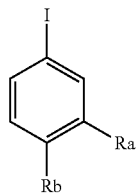

| Compound F | Ra | Rb | G | Method |
|---|---|---|---|---|
| F37 | CH3 | (N-pyridin-2(1H)-one, N-linked) | 2(1H)-pyridinone | Method 1 |
| F38 | CH3 | (N-pyridin-2(1H)-one, N-linked) | 2(1H)-pyridinone | Method 1 |
| F39 | CH3 | (3-methyl-2-oxo-pyridin-1(2H)-yl) | 3-methyl-2(1H)-pyridinone | Method 1 |
| F40 | CH3 | (3-methyl-2-oxo-pyridin-1(2H)-yl) | 3-methyl-2(1H)-pyridinone | Method 1 |
| F41 | H | (2-oxo-piperidin-1-yl) | piperidin-2-one | Method 1 |
| F42 | H | (2-oxo-pyrrolidin-1-yl) | pyrrolidin-2-one | Method 1 |
| F43 | H | (3-methyl-2-oxo-pyridin-1(2H)-yl) | 3-methyl-2(1H)-pyridinone | Method 1 |

-continued

Compound F

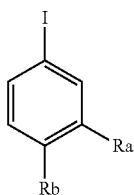

| Compound F | Ra | Rb | G | Method |
|---|---|---|---|---|
| F44 | H | (N-morpholin-3-one attached via N) | morpholin-3-one (HN) | Method 1 |
| F45 | H | N(i-Pr)C(O)CH₂N(CH₃)₂ | ClC(O)CH₂N(CH₃)₂ | Method 3; Rc = CH₂N(CH₃)₂; Re = i-Pr |
| F46 | H | N(i-Pr)C(O)CH₂-pyrrolidinyl | ClC(O)CH₂-pyrrolidinyl | Method 3; Rc = CH₂-pyrrolidinyl; Re = i-Pr |
| F47 | CH3 | 2-oxopiperidin-1-yl | 2-oxopiperidine (HN) | Method 1 |
| F48 | CH3 | morpholin-3-on-4-yl | morpholin-3-one (HN) | Method 1 |
| F49 | CH3 | 2-oxopyrrolidin-1-yl | 2-oxopyrrolidine (HN) | Method 1 |
| F50 | CH3 | 2-oxopyridin-1(2H)-yl | 2-oxo-1,2-dihydropyridine (HN) | Method 1 |

-continued

Compound F

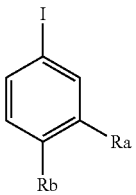

| Compound F | Ra | Rb | G | Method |
|---|---|---|---|---|
| F51 | CH3 | ![Rb group] | ![G structure] | Method 1 |

Method 1

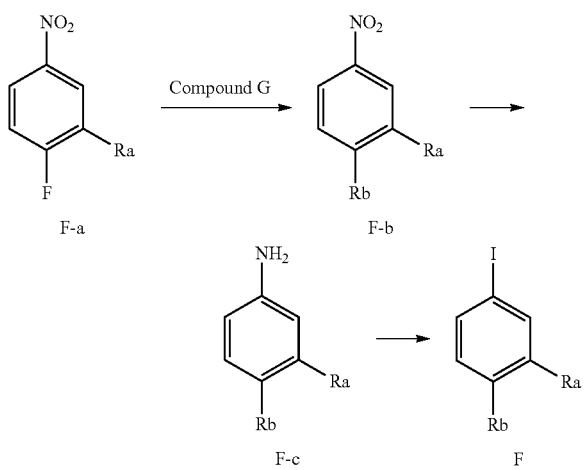

Step 1: The Preparation of Compound F-b

To a 50 mL flask were added compound G (e.g. 40.0 mmol) and potassium tert-butoxide (e.g. 40.0 mmol), then DMF was added (e.g. 30 mL). The mixture was stirred for 1 hour at 0° C., the compound F-a (e.g. 20.0 mmol) was added. The mixture was heated to 90° C. and react for 6 hours. After the completion of reaction, the reaction mixture was cooled to room temperature; purified water and ethyl acetate were added. The organic phase was separated and concentrated to obtain the product in a yield of about 70%.

Step 2: The Preparation of Compound F-c

To a 50 mL flask were added compound F-b (e.g. 10.0 mmol), Pd/C (e.g. 0.5 g) and methanol (e.g. 20 mL). The mixture was hydrogenated at room temperature and normal pressure for 4 h. After the completion of the reaction, the reaction mixture was filtered and the filtrate was concentrated under vacuum to obtain an oil in a yield of >98%.

Step 3: The Preparation of Compound F

To a 50 mL flask were added compound F-c (e.g. 8.0 mmol), purified water (e.g. 10 mL) and concentrated hydrochloric acid (e.g. 1.7 mL, 20.0 mmol). The mixture was cooled to 0-5° C. with stirring. An aqueous sodium nitrite solution (e.g. 10 mL) was added dropwise to the mixture while the temperature of 0-5° C. was maintained. After the completion of the dropwise addition, the mixture was stirred for 20 min while the temperature was maintained. Then sodium iodide (2.99 g, 20.0 mmol) was added to the reaction mixture and the resulting mixture was stirred at room temperature for 2 h. After the completion of the reaction, ethyl acetate was added to the reaction mixture. The aqueous phase and the organic phase were separated. The aqueous phase was extracted with ethyl acetate. The organic phases were combined and concentrated to give the product in a yield of 80%.

Method 2

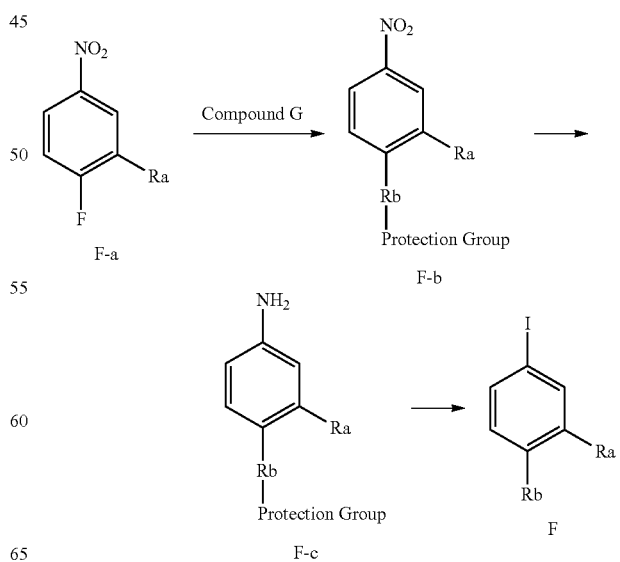

Step 1: The Preparation of Compound F-b, in the Same Way to Method 1

Step 2: The Preparation of Compound F-c, in the Same Way to Method 1

Step 3: The Preparation of Compound F

To a 50 mL flask were added compound F-c (e.g. 8.0 mmol), purified water (e.g. 10 mL) and concentrated hydrochloric acid (e.g. 1.7 mL, 20.0 mmol). The mixture was cooled to 0-5° C. with stirring. An aqueous sodium nitrite solution (e.g. 10 mL) was added dropwise to the mixture while the temperature of 0-5° C. was maintained. After the completion of the dropwise addition, the mixture was stirred for 20 min while the temperature was maintained. Then sodium iodide (2.99 g, 20.0 mmol) was added to the reaction mixture and the resulting mixture was stirred at room temperature for 2 h. After the completion of the reaction, ethyl acetate was added to the reaction mixture. The aqueous phase and the organic phase were separated. The aqueous phase was extracted with ethyl acetate. The organic phases were combined and filtered. Trifluoroacetic acid (e.g. 10.0 mmol) was added to the filtrate. The resulting mixture was stirred for 4 hours at room temperature. Water was added to the mixture, and extracted. The organic phase was concentrated under vacuum to give the product in a yield of about 80%.

Method 3

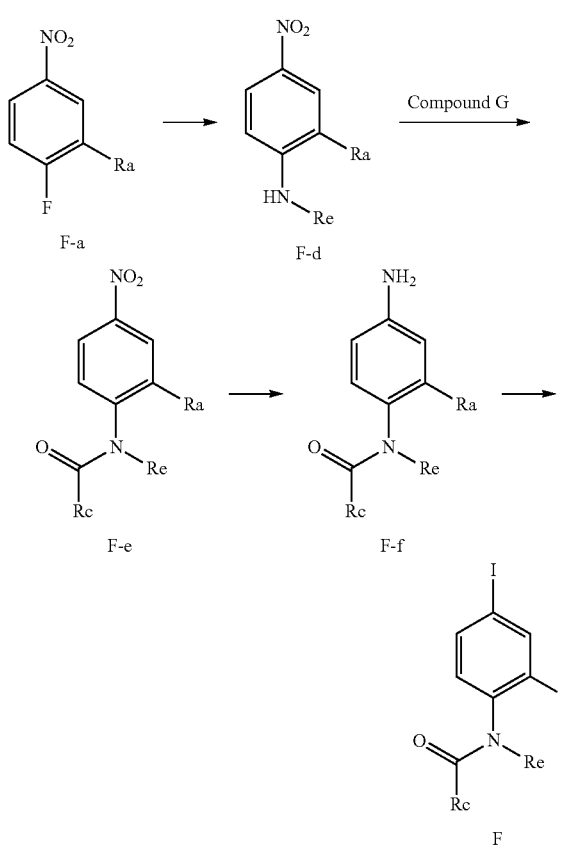

Step 1: The Preparation of Compound F-d

To a 50 mL flask were added compound F-a (e.g. 20.0 mmol), an aqueous alkylamine (such as methyl amine and isopropyl amine) solution (e.g. 60.0 mmol) and potassium carbonate (e.g. 5.5 g, 39.8 mmol), then added DMF (e.g. 30 mL). The mixture was heated to 50° C. and reacted for 4 h. After the completion of the reaction, the reaction mixture was cooled to room temperature and poured into purified water. The resulting mixture was filtered to give the product in a yield of about 80%.

Step 2: The Preparation of Compound F-e

To a 50 mL flask were added compound F-d (e.g. 5.0 mmol), triethylamine (e.g. 1.0 mmol) and dichloromethane (e.g. 20 mL). The mixture was cooled until to 0° C., and the compound G (e.g. 6.0 mmol) was added dropwise. After the completion of the dropwise addition, the mixture was stirred for 1 hour at room temperature. To the resulting mixture was added an aqueous 5% sodium carbonate solution (e.g. 40 mL). The organic phase was separated and concentrated to give the product in a yield of about 90%.

Step 3: The Preparation of Compound F-f

To a 50 mL flask were added compound F-e (e.g. 3.8 mmol), Pd/C (e.g. 0.2 g) and methanol (e.g. 20 mL). The mixture was hydrogenated at room temperature and normal pressure for 4 h. After the completion of the reaction, the reaction mixture was filtered and the filtrate was concentrated to give the product in a yield of >95%.

Step 4: The Preparation of Compound F

To a 50 mL flask were added compound F-f (e.g. 3.9 mmol), purified water (e.g. 10 mL) and concentrated hydrochloric acid (e.g. 0.8 mL, 9.6 mmol). The mixture was cooled to 0-5° C. with stirring. An aqueous sodium nitrite solution (e.g. 10 mL) was added dropwise to the mixture while the temperature of 0-5° C. was maintained. After the completion of the dropwise addition, the mixture was stirred for 20 min while the temperature was maintained. Then sodium iodide (e.g. 1.17 g, 7.8 mmol) was added to the reaction mixture and the resulting mixture was stirred at room temperature for 2 h. After the completion of the reaction, ethyl acetate was added to the reaction mixture. The aqueous phase and the organic phase were separated. The aqueous phase was extracted with ethyl acetate. The organic phases were combined and concentrated to give the product in a yield of about 80%.

Method 4

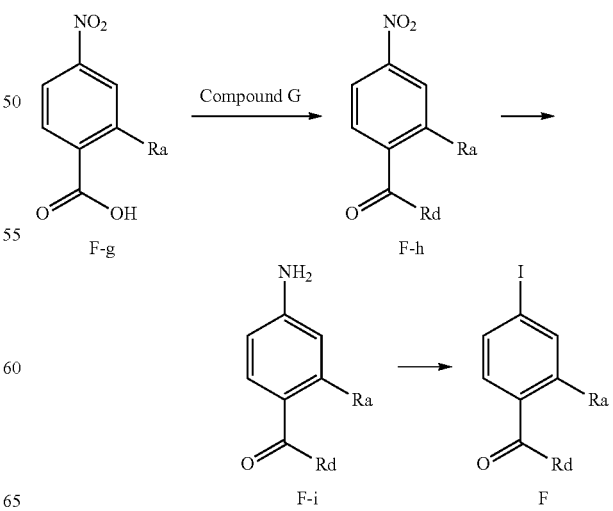

Step 1: The Preparation of Compound F-h

To a 50 mL flask were added compound F-g (e.g. 5.52 mmol), and thionyl chloride (e.g. 16.8 g, 141.2 mmol). The mixture was heated to 50° C. and stirred for 2 hours to react. After the completion of the reaction, the reaction mixture was concentrated under vacuum. After the completion of the concentration, DCM (e.g. 30 mL) was added to the mixture, and compound G (e.g. 6.07 mmol) was added at 0° C. After the completion of the addition, the mixture was stirred for 1 hour at room temperature, and purified water (e.g. 30 mL) was added. The organic phase was separated from the resulting mixture and concentrated to give the product in a yield of about 95%.

Step 2: The Preparation of Compound F-i

To a 100 mL flask were added compound F-h (e.g. 5.24 mmol), Pd/C (e.g. 0.5 g) and methanol (e.g. 50 mL). The mixture was hydrogenated at room temperature and normal pressure for 4 h. After the completion of the reaction, the reaction mixture was filtered and the filtrate was concentrated under vacuum to give the product in a yield of >95%.

Step 3: The Preparation of Compound F

To a 50 mL flask were added compound F-i (e.g. 3.91 mmol), purified water (e.g. 10 mL) and concentrated hydrochloric acid (e.g. 0.8 mL, 9.6 mmol).

The mixture was cooled to 0-5° C. with stirring. An aqueous sodium nitrite solution (e.g. 10 mL) was added dropwise to the mixture while the temperature of 0-5° C. was maintained. After the completion of the dropwise addition, the mixture was stirred for 20 min while the temperature was maintained. Then sodium iodide (e.g. 1.17 g, 7.8 mmol) was added to the reaction mixture and the resulting mixture was stirred at room temperature for 2 h. After the completion of the reaction, ethyl acetate was added to the reaction mixture. The aqueous phase and the organic phase were separated. The aqueous phase was extracted with ethyl acetate. The organic phases were combined and concentrated to give the product in a yield of about 50%.

(3) The Preparation of the Compound of Formula I of the Present Invention, Wherein R3, X, Ra and Rb have the Meanings in the Following Table.

Synthetic Route:

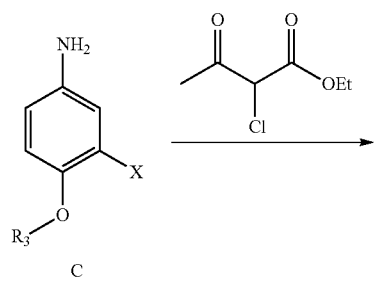

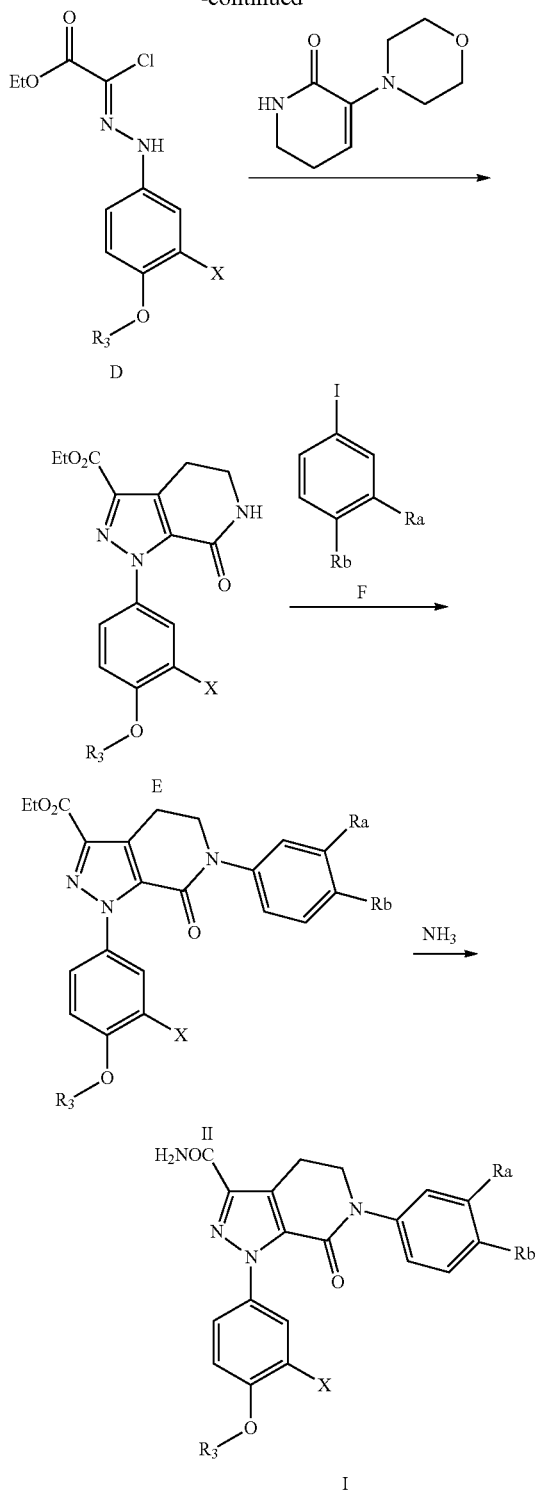

Step 1: The Preparation of Compound D

To a flask was added compound C (e.g. 63.2 mmol), and then added purified water (e.g. 60 mL). The mixture was cooled to −5 to 0° C. with stirring, and concentrated hydrochloric acid (e.g. 26 mL) was added. An aqueous sodium nitrite solution (e.g. 30 mL) was added dropwise to the mixture while the temperature of −5 to 0° C. was maintained. After the completion of the addition, the mixture was stirred for 20 min while the temperature was maintained. To the resulting mixture were added a solution of ethyl 2-chloro-3-oxobutanoate (e.g. 10.7 g, 65.1 mmol) in ethanol (e.g. 100 mL) and a solution of sodium acetate (e.g. 15.5 g, 189.0 mmol) in water (60 mL). After the completion of the addition, the mixture was stirred for 0.5 h. Then the mixture was warmed to room temperature and stirred for 6 h to react. During the reaction, a solid separated out. After the completion of the reaction, the reaction mixture was filtered and the filter cake was dried to produce a yellow solid in a yield of about 70%.

Step 2: The Preparation of Compound E

At room temperature, to a flask (e.g. 100 mL) were added Compound D (e.g. 4.7 mmol), 3-morpholino-5,6-dihydropyridin-2(1H)-one (e.g. 0.94 g, 5.2 mmol), and then added toluene (e.g. 20 mL) and triethylamine. After the completion of the addition, the mixture was heated to 100° C. and reacted under reflux for 12 h. The mixture was cooled to room temperature and concentrated. To the residue was added dichloromethane (e.g. 20 mL), and dropwise added trifluoroacetic acid (e.g. 5.0 mL) at room temperature. The resulting mixture was stirred for 2 h to react. After the completion of the reaction, the reaction mixture was concentrated under vacuum. After the completion of the concentration, ethyl acetate and purified water (q.s.) were added to the mixture. The mixture was stirred and a solid separated out. The resulting mixture was filtered. The filter cake was dried under vacuum to give the product in a yield of about 30%.

Step 3: The Preparation of Compound II

To a flask (50 mL) were added Compound E (e.g. 1.3 mmol), compound F (e.g. 1.4 mmol) and potassium carbonate (376 mg, 2.7 mmol), and then added DMSO (e.g. 10 mL). Cupric iodide (e.g. 114 mg, 0.6 mmol) and 1,10-phenanthroline (e.g. 110 mg, 0.6 mmol) were added under a nitrogen atmosphere. The mixture was heated to 120° C. and stirred for 12 h to react under a nitrogen atmosphere. After the completion of the reaction, the reaction mixture was cooled to room temperature, and purified water was added. The resulting mixture was extracted with ethyl acetate. The organic phase was concentrated to give a product in a yield of about 75%.

Step 4: The Preparation of Compound I

To a seal tube was added compound II (e.g. 0.45 mmol), and then added ethylene glycol (e.g. 10 mL). The mixture was stirred. Then ammonia gas was introduced to the seal tube for 0.5 h. The seal tube was sealed. The mixture was heated to 120° C. and reacted for 3 h. The reaction mixture was cooled to room temperature and then poured into cold water. A solid separated out. The mixture was filtered. The filter cake was dried to give the target product.

| Example | Compound | Structure | X | R3 | Ra | Rb |
|---|---|---|---|---|---|---|
| 1 | 1-(4-methoxyphenyl)-6-(4-(5-methyl-2-oxopyridin-1(2H)-yl)phenyl)-7-oxo-4,5,6,7-tetrahydro-1H-pyrazolo[3,4-c]pyridine-3-carboxamide | 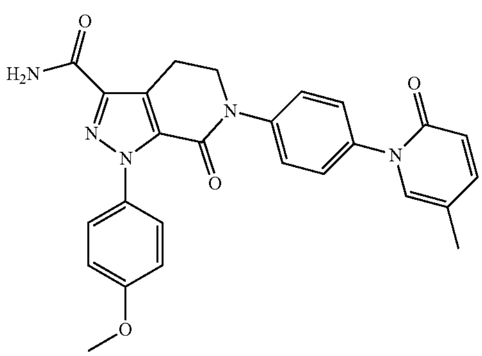 | H | methyl | H | |
| 2 | 1-(4-methoxyphenyl)-7-oxo-6-(4-(2-oxooxazolidin-3-yl)phenyl)-4,5,6,7-tetrahydro-1H-pyrazolo[3,4-c]pyridine-3-carboxamide | 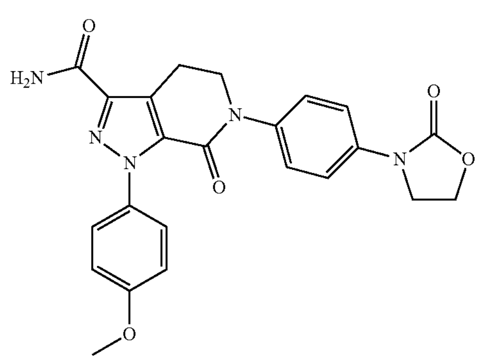 | H | methyl | H | |

-continued

| Example | Compound | Structure | X | R3 | Ra | Rb |
|---|---|---|---|---|---|---|
| 3 | 1-(4-methoxyphenyl)-6-(4-(3-oxothiomorpholino)phenyl)-7-oxo-4,5,6,7-tetrahydro-1H-pyrazolo[3,4-c]pyridine-3-carboxamide | 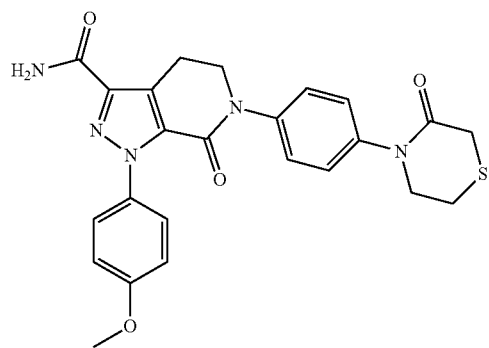 | H | methyl | H | 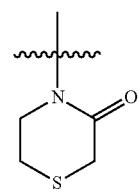 [SMILES: *N1CCSCC1=O] |
| 4 | 1-(4-methoxyphenyl)-6-(4-(7-oxo-1,4-diazepan-1-yl)phenyl)-7-oxo-4,5,6,7-tetrahydro-1H-pyrazolo[3,4-c]pyridine-3-carboxamide | 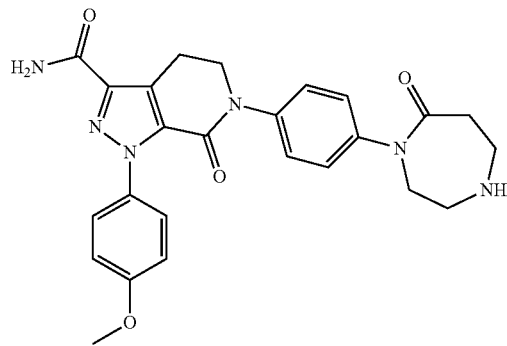 | H | methyl | H | 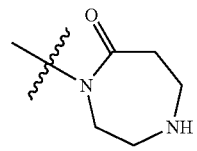 [SMILES: *N1CCNCCC1=O] |
| 5 | 1-(4-methoxyphenyl)-6-(4-(4-methyl-7-oxo-1,4-diazepan-1-yl)phenyl)-7-oxo-4,5,6,7-tetrahydro-1H-pyrazolo[3,4-c]pyridine-3-carboxamide | 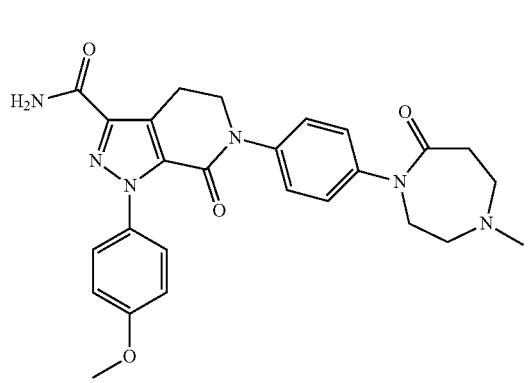 | H | methyl | H | 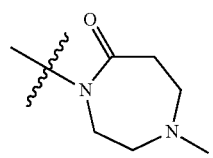 [SMILES: *N1CCN(C)CCC1=O] |
| 6 | 1-(4-methoxyphenyl)-6-(4-(6-oxopyridazin-1(6H)-yl)phenyl)-7-oxo-4,5,6,7-tetrahydro-1H-pyrazolo[3,4-c]pyridine-3-carboxamide | 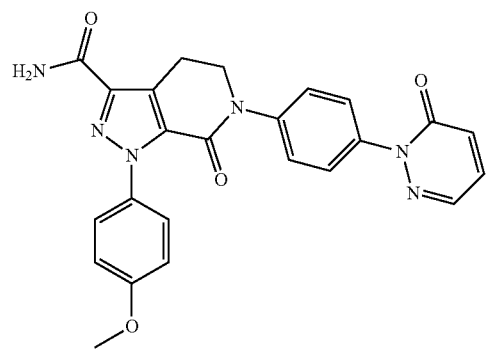 | H | methyl | H | 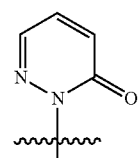 |

-continued

| Example | Compound | Structure | X | R3 | Ra | Rb |
|---|---|---|---|---|---|---|
| 7 | 1-(4-methoxyphenyl)-6-(4-(3-methyl-6-oxopyridazin-1(6H)-yl)phenyl)-7-oxo-4,5,6,7-tetrahydro-1H-pyrazolo[3,4-c]pyridine-3-carboxamide | 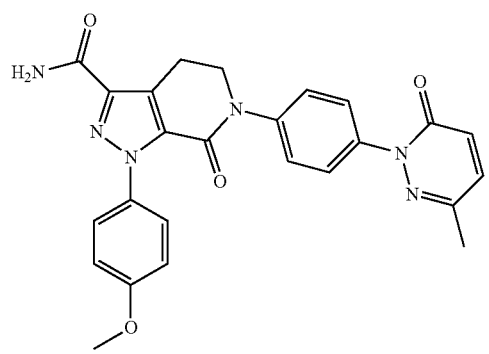 | H | methyl | H | 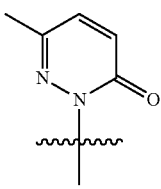 [SMILES: *n1nc(C)ccc1=O] |
| 8 | 1-(4-methoxyphenyl)-6-(4-(4-amino-2-oxopiperidin-1-yl)phenyl)-7-oxo-4,5,6,7-tetrahydro-1H-pyrazolo[3,4-c]pyridine-3-carboxamide | 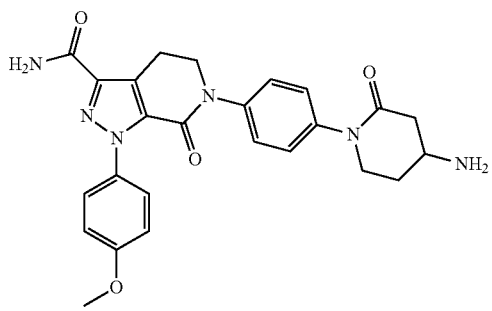 | H | methyl | H | 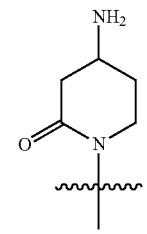 |
| 9 | 1-(4-methoxyphenyl)-6-(4-((1S,4S)-3-oxo-2-azabicyclo[2.2.1]heptan-2-yl)phenyl)-7-oxo-4,5,6,7-tetrahydro-1H-pyrazolo[3,4-c]pyridine-3-carboxamide | 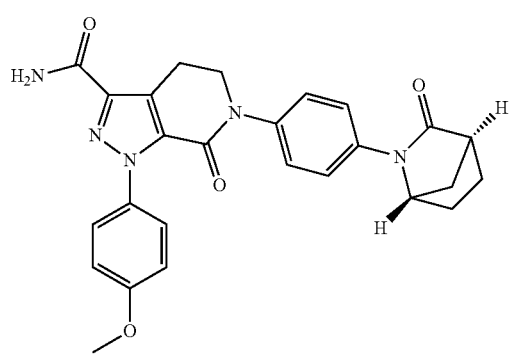 | H | methyl | H | 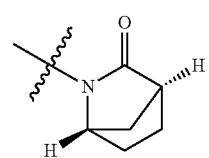 [SMILES: *N1C(=O)[C@H]2CC[C@H]1C2] |
| 10 | 1-(4-methoxyphenyl)-6-(4-(3-methyl-5-oxo-4,5-dihydro-1H-pyrazol-1-yl)phenyl)-7-oxo-4,5,6,7-tetrahydro-1H-pyrazolo[3,4-c]pyridine-3-carboxamide | 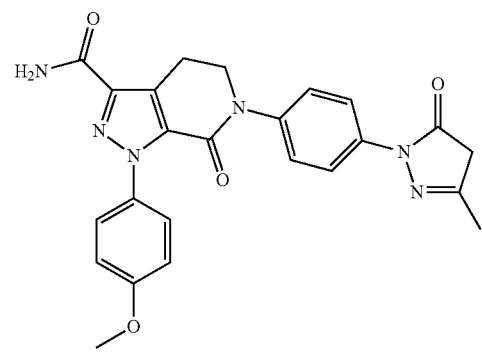 | H | methyl | H | 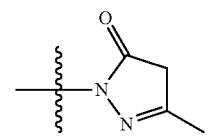 [SMILES: *N1N=C(C)CC1=O] |

| Example | Compound | Structure | X | R3 | Ra | Rb |
|---|---|---|---|---|---|---|
| 11 | 1-(4-methoxyphenyl)-6-(4-(6-methyl-2-oxopyridin-1(2H)-yl)phenyl)-7-oxo-4,5,6,7-tetrahydro-1H-pyrazolo[3,4-c]pyridine-3-carboxamide | 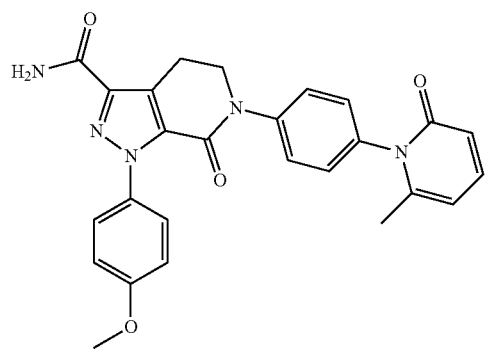 | H | methyl | H | 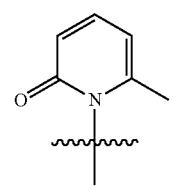 [SMILES: *n1c(C)cccc1=O] |
| 12 | 1-(4-methoxyphenyl)-(R)-6-(4-(3-hydroxy-2-oxopyrrolidin-1-yl)phenyl)-7-oxo-4,5,6,7-tetrahydro-1H-pyrazolo[3,4-c]pyridine-3-carboxamide | 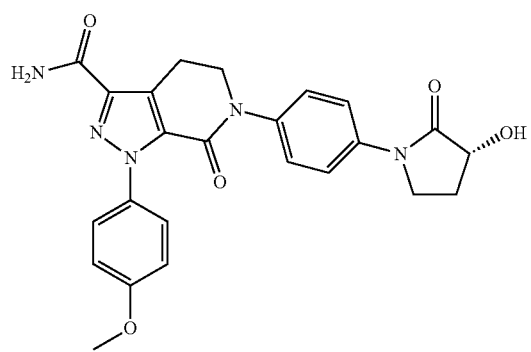 | H | methyl | H | 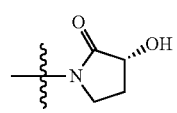 [SMILES: *N1CC[C@@H](O)C1=O] |
| 13 | 1-(4-methoxyphenyl)-(R)-6-(4-(3-methoxy-2-oxopyrrolidin-1-yl)phenyl)-7-oxo-4,5,6,7-tetrahydro-1H-pyrazolo[3,4-c]pyridine-3-carboxamide | 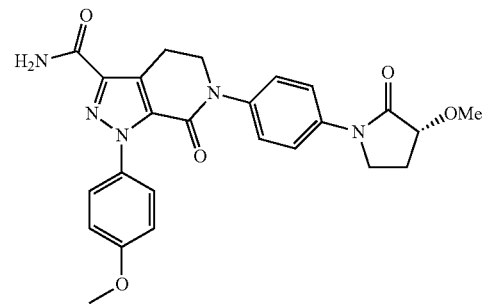 | H | methyl | H | 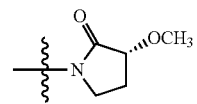 [SMILES: *N1CC[C@@H](OC)C1=O] |
| 14 | 1-(4-methoxyphenyl)-(S)-6-(4-(3-chloro-2-oxopyrrolidin-1-yl)phenyl)-7-oxo-4,5,6,7-tetrahydro-1H-pyrazolo[3,4-c]pyridine-3-carboxamide | 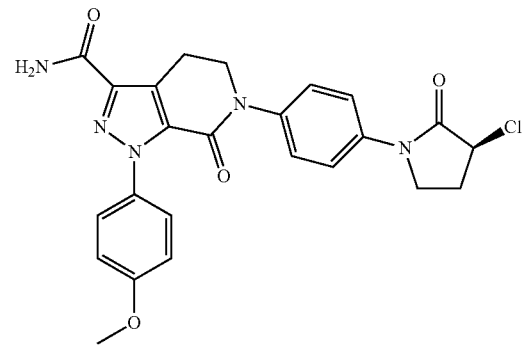 | H | methyl | H | 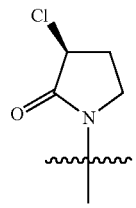 [SMILES: *N1CC[C@H](Cl)C1=O] |

| Example | Compound | Structure | X | R3 | Ra | Rb |
|---|---|---|---|---|---|---|
| 15 | 1-(4-methoxyphenyl)-(S)-6-(4-(2-(dimethylcarbamoyl)pyrrolidin-1-yl)phenyl)-7-oxo-4,5,6,7-tetrahydro-1H-pyrazolo[3,4-c]pyridine-3-carboxamide | 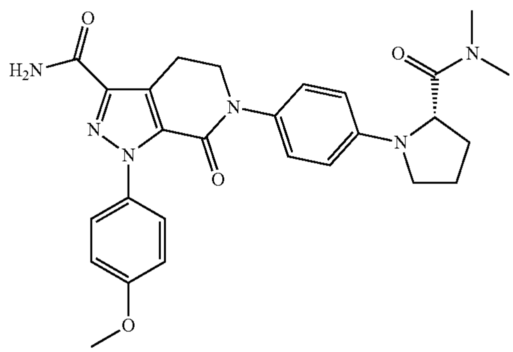 | H | methyl | H | |
| 16 | 1-(4-methoxyphenyl)-6-(3-methyl-4-(2-oxopiperidin-1-yl)phenyl)-7-oxo-4,5,6,7-tetrahydro-1H-pyrazolo[3,4-c]pyridine-3-carboxamide | 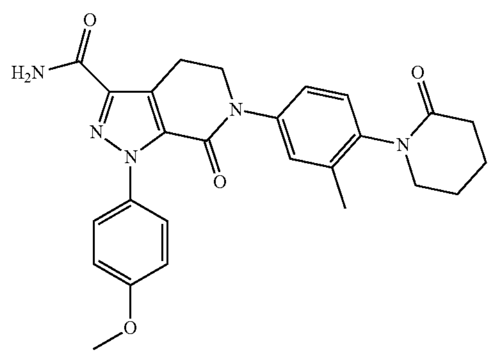 [SMILES: COc1ccc(-n2nc(C(N)=O)c3c2C(=O)N(c2ccc(N4CCCCC4=O)c(C)c2)CC3)cc1] | H | methyl | methyl | |
| 17 | 1-(4-methoxyphenyl)-6-(3-methyl-4-(3-oxomorpholino)phenyl)-7-oxo-4,5,6,7-tetrahydro-1H-pyrazolo[3,4-c]pyridine-3-carboxamide | 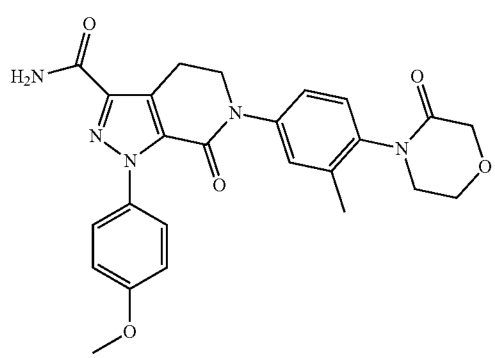 [SMILES: COc1ccc(-n2nc(C(N)=O)c3c2C(=O)N(c2ccc(N4CCOCC4=O)c(C)c2)CC3)cc1] | H | methyl | methyl | |
| 18 | 1-(4-methoxyphenyl)-6-(3-methyl-4-(2-oxopyrrolidin-1-yl)phenyl)-7-oxo-4,5,6,7-tetrahydro-1H-pyrazolo[3,4-c]pyridine-3-carboxamide | 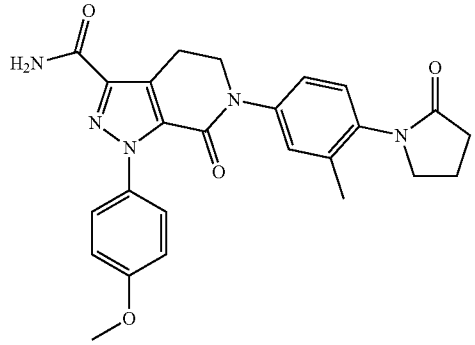 [SMILES: COc1ccc(-n2nc(C(N)=O)c3c2C(=O)N(c2ccc(N4CCCC4=O)c(C)c2)CC3)cc1] | H | methyl | methyl | |

-continued

| Example | Compound | Structure | X | R3 | Ra | Rb |
|---|---|---|---|---|---|---|
| 19 | 1-(4-methoxyphenyl)-6-(3-methyl-4-(2-oxopyridin-1(2H)-yl)phenyl)-7-oxo-4,5,6,7-tetrahydro-1H-pyrazolo[3,4-c]pyridine-3-carboxamide | 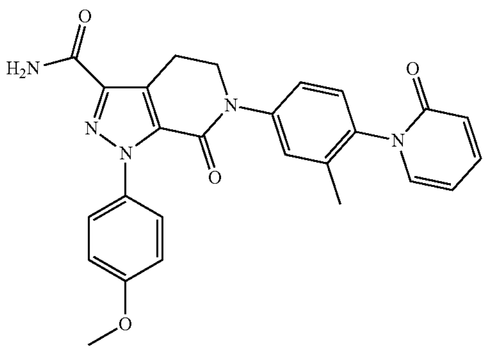 [SMILES: COc1ccc(-n2nc(C(N)=O)c3c2C(=O)N(c2ccc(-n4ccccc4=O)c(C)c2)CC3)cc1] | H | methyl | methyl | (2-oxopyridin-1(2H)-yl) |
| 20 | 1-(4-methoxyphenyl)-6-(3-methyl-4-(2-methyl-5-oxopyrrolidin-1-yl)phenyl)-7-oxo-4,5,6,7-tetrahydro-1H-pyrazolo[3,4-c]pyridine-3-carboxamide | 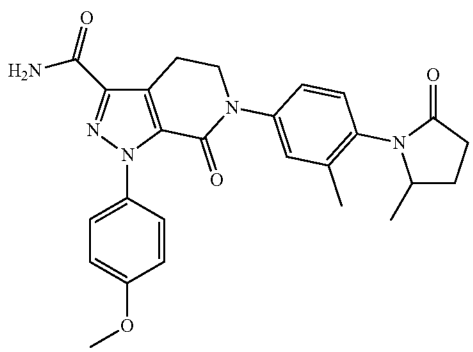 [SMILES: COc1ccc(-n2nc(C(N)=O)c3c2C(=O)N(c2ccc(N4C(=O)CCC4C)c(C)c2)CC3)cc1] | H | methyl | methyl | (2-methyl-5-oxopyrrolidin-1-yl) |
| 21 | 1-(4-methoxyphenyl)-6-(3-methyl-4-(N-methylacetamido)phenyl)-7-oxo-4,5,6,7-tetrahydro-1H-pyrazolo[3,4-c]pyridine-3-carboxamide | 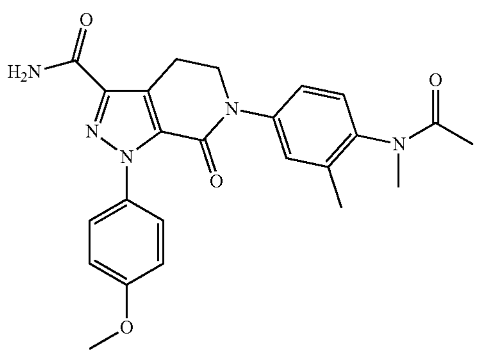 [SMILES: COc1ccc(-n2nc(C(N)=O)c3c2C(=O)N(c2ccc(N(C)C(C)=O)c(C)c2)CC3)cc1] | H | methyl | methyl | N-methylacetamido |
| 22 | 1-(4-methoxyphenyl)-6-(3-methyl-4-(N-methylisobutyramido)phenyl)-7-oxo-4,5,6,7-tetrahydro-1H-pyrazolo[3,4-c]pyridine-3-carboxamide | 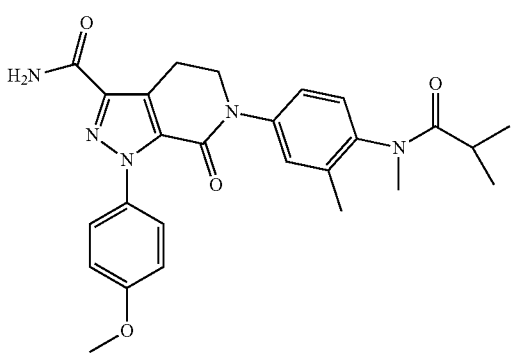 [SMILES: COc1ccc(-n2nc(C(N)=O)c3c2C(=O)N(c2ccc(N(C)C(=O)C(C)C)c(C)c2)CC3)cc1] | H | methyl | methyl | N-methylisobutyramido |

| Example | Compound | Structure | X | R3 | Ra | Rb |
|---|---|---|---|---|---|---|
| 23 | 1-(4-methoxyphenyl)-6-(3-methyl-4-(piperidine-1-carbonyl)phenyl)-7-oxo-4,5,6,7-tetrahydro-1H-pyrazolo[3,4-c]pyridine-3-carboxamide | 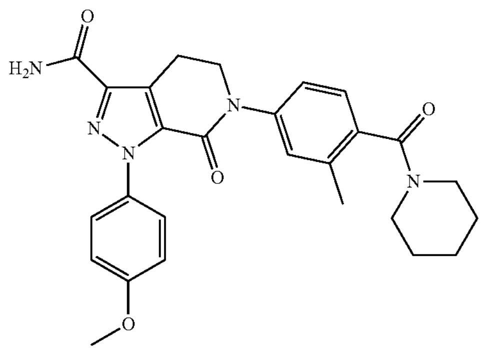 [SMILES: COc1ccc(-n2nc(C(N)=O)c3c2C(=O)N(c2ccc(C(=O)N4CCCCC4)c(C)c2)CC3)cc1] | H | methyl | methyl | (piperidine amide group) |
| 24 | 1-(4-methoxyphenyl)-6-(3-methyl-4-(morpholine-4-carbonyl)phenyl)-7-oxo-4,5,6,7-tetrahydro-1H-pyrazolo[3,4-c]pyridine-3-carboxamide | 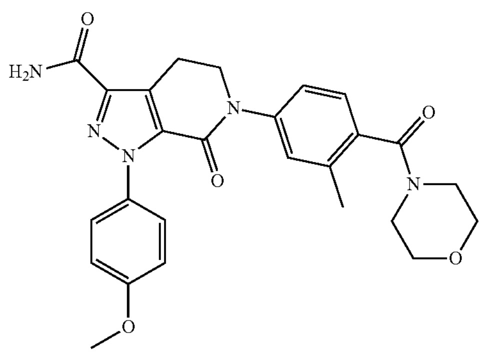 | H | methyl | methyl | (morpholine amide group) |
| 25 | 1-(4-methoxyphenyl)-6-(3-methyl-4-(pyrrolidine-1-carbonyl)phenyl)-7-oxo-4,5,6,7-tetrahydro-1H-pyrazolo[3,4-c]pyridine-3-carboxamide | 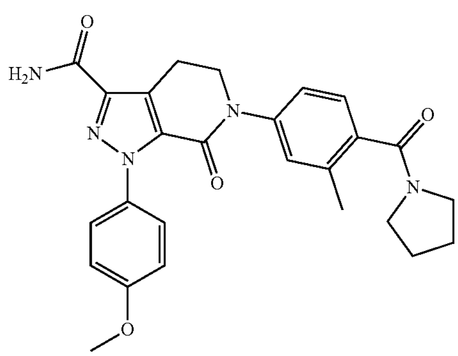 [SMILES: COc1ccc(-n2nc(C(N)=O)c3c2C(=O)N(c2ccc(C(=O)N4CCCC4)c(C)c2)CC3)cc1] | H | methyl | methyl | (pyrrolidine amide group) |
| 26 | 1-(4-methoxyphenyl)-6-(3-methyl-4-(4-methylpiperazine-1-carbonyl)phenyl)-7-oxo-4,5,6,7-tetrahydro-1H-pyrazolo[3,4-c]pyridine-3-carboxamide | 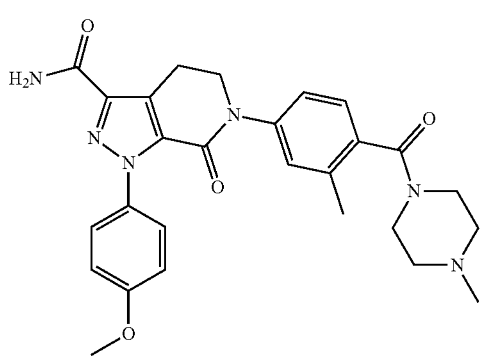 [SMILES: COc1ccc(-n2nc(C(N)=O)c3c2C(=O)N(c2ccc(C(=O)N4CCN(C)CC4)c(C)c2)CC3)cc1] | H | methyl | methyl | (4-methylpiperazine amide group) |

-continued

| Example | Compound | Structure | X | R3 | Ra | Rb |
|---|---|---|---|---|---|---|
| 27 | 1-(3-fluoro-4-ethoxyphenyl)-6-(4-(3-methyl-2-oxopyridin-1(2H)-yl)phenyl)-7-oxo-4,5,6,7-tetrahydro-1H-pyrazolo[3,4-c]pyridine-3-carboxamide | 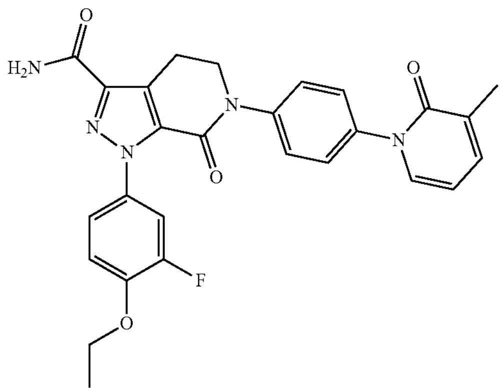 | F | ethyl | H | 3-methyl-2-oxopyridin-1-yl |
| 28 | 1-(4-ethoxyphenyl)-6-(4-(3-methyl-2-oxopyridin-1(2H)-yl)phenyl)-7-oxo-4,5,6,7-tetrahydro-1H-pyrazolo[3,4-c]pyridine-3-carboxamide | 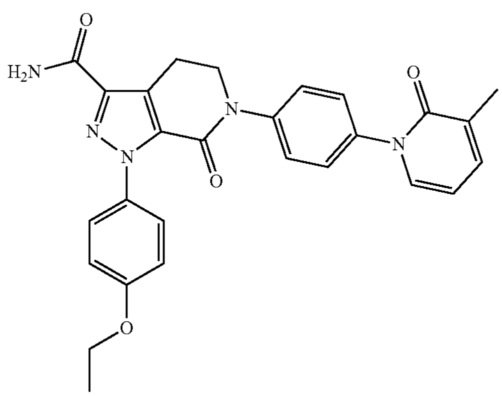 | H | ethyl | H | 3-methyl-2-oxopyridin-1-yl |
| 29 | 1-(3-chloro-4-ethoxyphenyl)-6-(4-(2-oxopiperidin-1-yl)phenyl)-7-oxo-4,5,6,7-tetrahydro-1H-pyrazolo[3,4-c]pyridine-3-carboxamide | 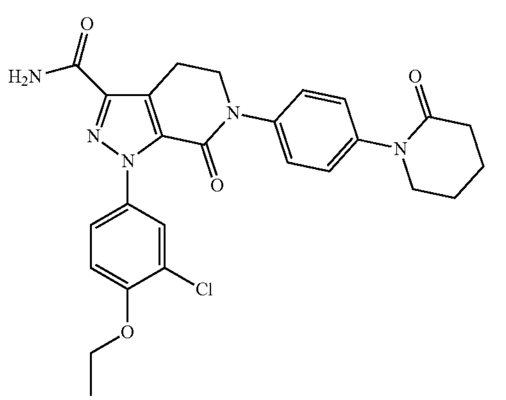 | Cl | ethyl | H | 2-oxopiperidin-1-yl |
| 30 | 1-(3-chloro-4-ethoxyphenyl)-6-(4-(3-methyl-2-oxopyridin-1(2H)-yl)phenyl)-7-oxo-4,5,6,7-tetrahydro-1H-pyrazolo[3,4-c]pyridine-3-carboxamide | 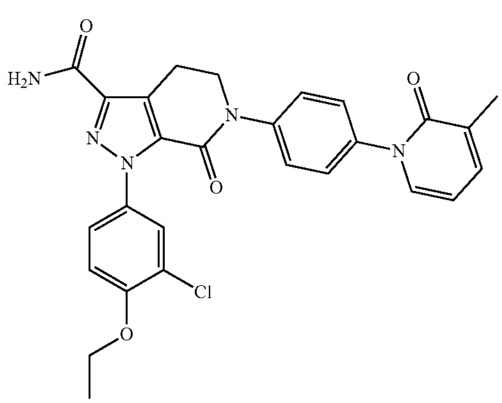 | Cl | ethyl | H | 3-methyl-2-oxopyridin-1-yl |

| Example | Compound | Structure | X | R3 | Ra | Rb |
|---|---|---|---|---|---|---|
| 31 | 1-(4-ethoxyphenyl)-6-(3-methyl-4-(2-oxopiperidin-1-yl)phenyl)-7-oxo-4,5,6,7-tetrahydro-1H-pyrazolo[3,4-c]pyridine-3-carboxamide | 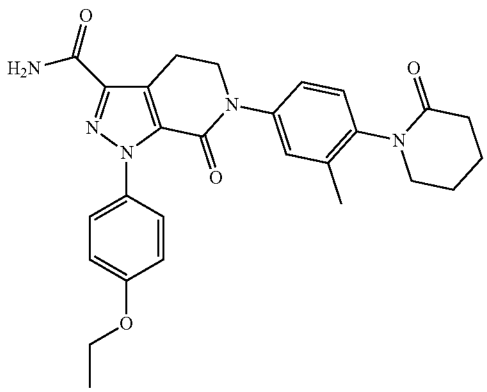 [SMILES: CCOc1ccc(-n2nc(C(N)=O)c3c2C(=O)N(c2ccc(N4CCCCC4=O)c(C)c2)CC3)cc1] | H | ethyl | methyl | (2-oxopiperidin-1-yl) |
| 32 | 1-(3-fluoro-4-ethoxyphenyl)-6-(3-methyl-4-(2-oxopiperidin-1-yl)phenyl)-7-oxo-4,5,6,7-tetrahydro-1H-pyrazolo[3,4-c]pyridine-3-carboxamide | 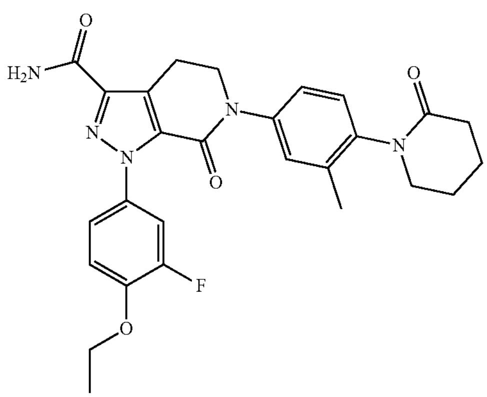 [SMILES: CCOc1ccc(-n2nc(C(N)=O)c3c2C(=O)N(c2ccc(N4CCCCC4=O)c(C)c2)CC3)cc1F] | F | ethyl | Methyl | (2-oxopiperidin-1-yl) |
| 33 | 1-(4-ethoxyphenyl)-6-(3-methyl-4-(3-oxomorpholino)phenyl)-7-oxo-4,5,6,7-tetrahydro-1H-pyrazolo[3,4-c]pyridine-3-carboxamide | 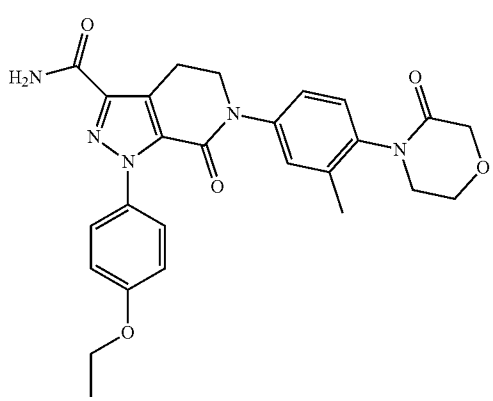 [SMILES: CCOc1ccc(-n2nc(C(N)=O)c3c2C(=O)N(c2ccc(N4CCOCC4=O)c(C)c2)CC3)cc1] | H | ethyl | methyl | (3-oxomorpholino) |

-continued

| Example | Compound | Structure | X | R3 | Ra | Rb |
|---|---|---|---|---|---|---|
| 34 | 1-(3-fluoro-4-ethoxyphenyl)-6-(3-methyl-4-(3-oxomorpholino)phenyl)-7-oxo-4,5,6,7-tetrahydro-1H-pyrazolo[3,4-c]pyridine-3-carboxamide | 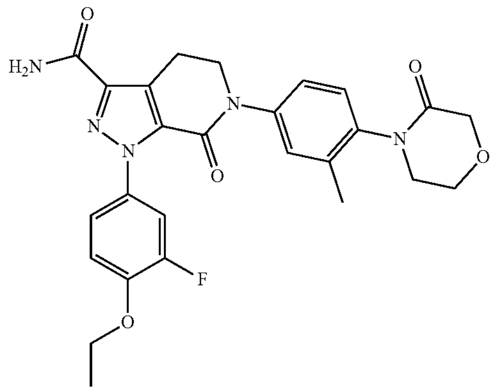 [SMILES: CCOc1ccc(-n2nc(C(N)=O)c3c2C(=O)N(c2ccc(N4CCOCC4=O)c(C)c2)CC3)cc1F] | F | ethyl | methyl | 3-oxomorpholin-4-yl |
| 35 | 1-(4-ethoxyphenyl)-6-(3-methyl-4-(2-oxopyrrolidin-1-yl)phenyl)-7-oxo-4,5,6,7-tetrahydro-1H-pyrazolo[3,4-c]pyridine-3-carboxamide | 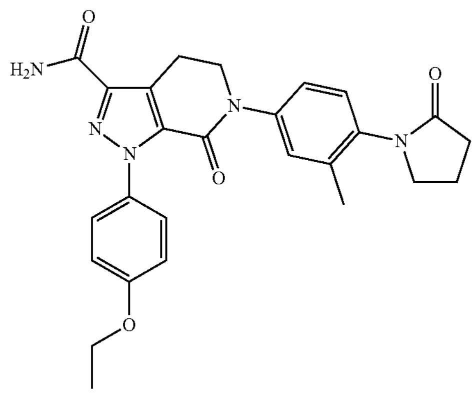 [SMILES: CCOc1ccc(-n2nc(C(N)=O)c3c2C(=O)N(c2ccc(N4CCCC4=O)c(C)c2)CC3)cc1] | H | ethyl | methyl | 2-oxopyrrolidin-1-yl |
| 36 | 1-(3-fluoro-4-ethoxyphenyl)-6-(3-methyl-4-(2-oxopyrrolidin-1-yl)phenyl)-7-oxo-4,5,6,7-tetrahydro-1H-pyrazolo[3,4-c]pyridine-3-carboxamide | 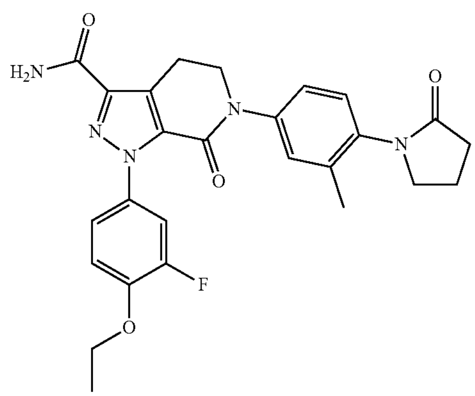 [SMILES: CCOc1ccc(-n2nc(C(N)=O)c3c2C(=O)N(c2ccc(N4CCCC4=O)c(C)c2)CC3)cc1F] | F | ethyl | methyl | 2-oxopyrrolidin-1-yl |
| 37 | 1-(4-ethoxyphenyl)-6-(3-methyl-4-(2-oxopyridin-1(2H)-yl)phenyl)-7-oxo-4,5,6,7-tetrahydro-1H-pyrazolo[3,4-c]pyridine-3-carboxamide | 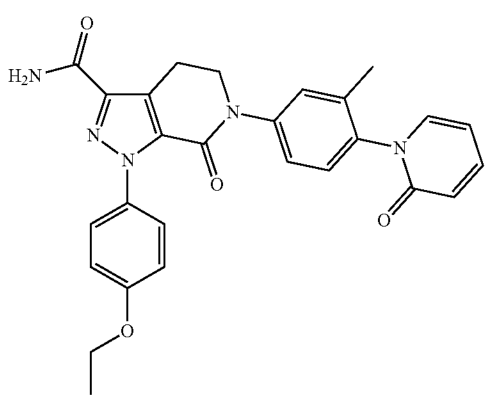 [SMILES: CCOc1ccc(-n2nc(C(N)=O)c3c2C(=O)N(c2ccc(-n4ccccc4=O)c(C)c2)CC3)cc1] | H | ethyl | methyl | 2-oxopyridin-1(2H)-yl |

-continued

| Example | Compound | Structure | X | R3 | Ra | Rb |
|---|---|---|---|---|---|---|
| 38 | 1-(3-fluoro-4-ethoxyphenyl)-6-(3-methyl-4-(2-oxopyridin-1(2H)-yl)phenyl)-7-oxo-4,5,6,7-tetrahydro-1H-pyrazolo[3,4-c]pyridine-3-carboxamide | 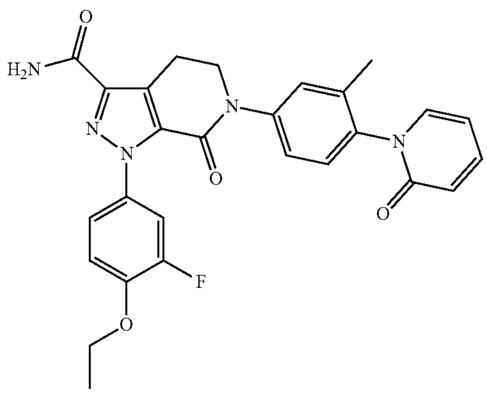 [SMILES: CCOc1ccc(-n2nc(C(N)=O)c3c2C(=O)N(c2ccc(-n4ccccc4=O)c(C)c2)CC3)cc1F] | F | ethyl | methyl | |
| 39 | 1-(4-ethoxyphenyl)-6-(3-methyl-4-(3-methyl-2-oxopyridin-1(2H)-yl)phenyl)-7-oxo-4,5,6,7-tetrahydro-1H-pyrazolo[3,4-c]pyridine-3-carboxamide | 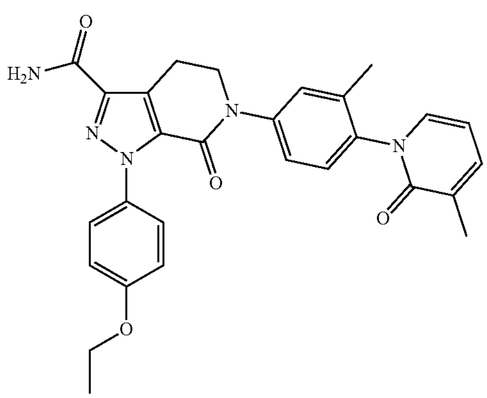 [SMILES: CCOc1ccc(-n2nc(C(N)=O)c3c2C(=O)N(c2ccc(-n4cccc(C)c4=O)c(C)c2)CC3)cc1] | H | ethyl | methyl | |
| 40 | 1-(3-fluoro-4-ethoxyphenyl)-6-(3-methyl-4-(3-methyl-2-oxopyridin-1(2H)-yl)phenyl)-7-oxo-4,5,6,7-tetrahydro-1H-pyrazolo[3,4-c]pyridine-3-carboxamide | 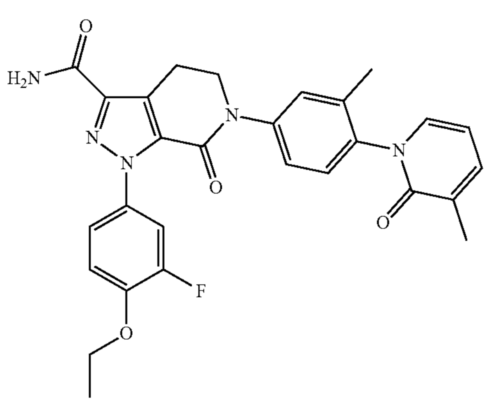 [SMILES: CCOc1ccc(-n2nc(C(N)=O)c3c2C(=O)N(c2ccc(-n4cccc(C)c4=O)c(C)c2)CC3)cc1F] | F | ethyl | methyl | |

-continued

| Example | Compound | Structure | X | R3 | Ra | Rb |
|---|---|---|---|---|---|---|
| 41 | 1-(3-fluoro-4-isopropoxyphenyl)-6-(4-(2-oxopiperidin-1-yl)phenyl)-7-oxo-4,5,6,7-tetrahydro-1H-pyrazolo[3,4-c]pyridine-3-carboxamide | 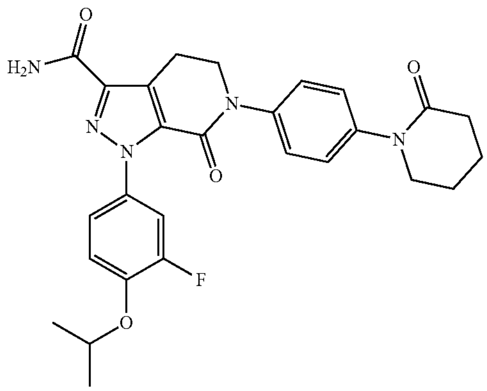 | F | i-propyl | H | piperidin-2-one attached via N |
| 42 | 1-(3-fluoro-4-isopropoxyphenyl)-6-(4-(2-oxopyrrolidin-1-yl)phenyl)-7-oxo-4,5,6,7-tetrahydro-1H-pyrazolo[3,4-c]pyridine-3-carboxamide | 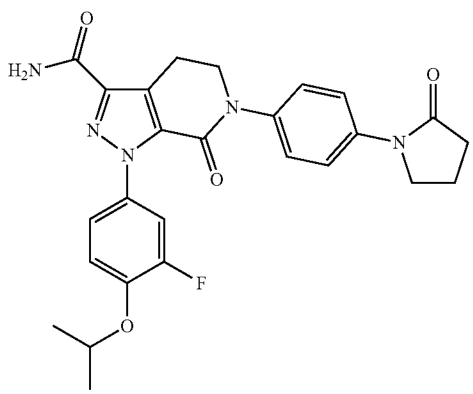 | F | i-propyl | H | pyrrolidin-2-one attached via N |
| 43 | 1-(3-fluoro-4-isopropoxyphenyl)-6-(4-(3-methyl-2-oxopyridin-1(2H)-yl)phenyl)-7-oxo-4,5,6,7-tetrahydro-1H-pyrazolo[3,4-c]pyridine-3-carboxamide | 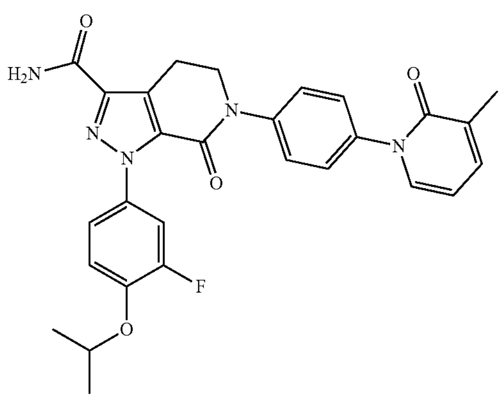 | F | i-propyl | H | 3-methyl-2-oxopyridin-1(2H)-yl |
| 44 | 1-(3-fluoro-4-isopropoxyphenyl)-6-(4-(3-oxomorpholino)phenyl)-7-oxo-4,5,6,7-tetrahydro-1H-pyrazolo[3,4-c]pyridine-3-carboxamide | 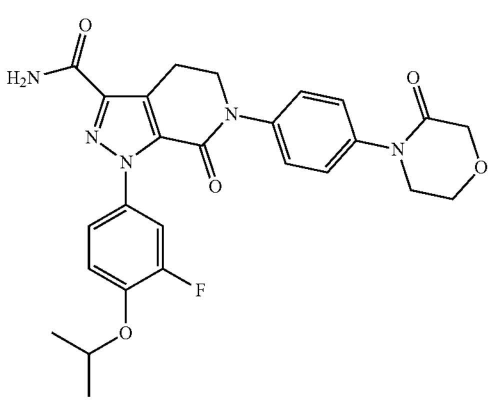 | F | i-propyl | H | 3-oxomorpholino |

| Example | Compound | Structure | X | R3 | Ra | Rb |
|---|---|---|---|---|---|---|
| 45 | 1-(4-methoxyphenyl)-6-(4-(2-(dimethylamino)-N-isopropylacetamido)phenyl)-7-oxo-4,5,6,7-tetrahydro-1H-pyrazolo[3,4-c]pyridine-3-carboxamide | 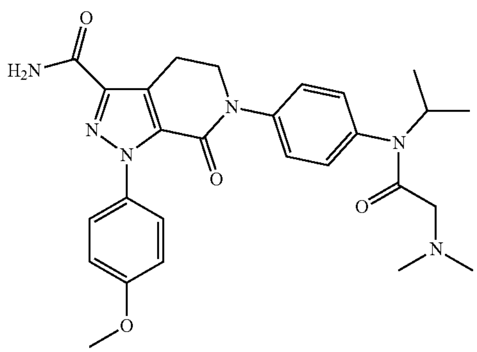 | H | methyl | H | *N-isopropyl-N-(2-(dimethylamino)acetyl) group* |
| 46 | 1-(4-methoxyphenyl)-6-(4-(N-isopropyl-2-(pyrrolidin-1-yl)acetamido)phenyl)-7-oxo-4,5,6,7-tetrahydro-1H-pyrazolo[3,4-c]pyridine-3-carboxamide | 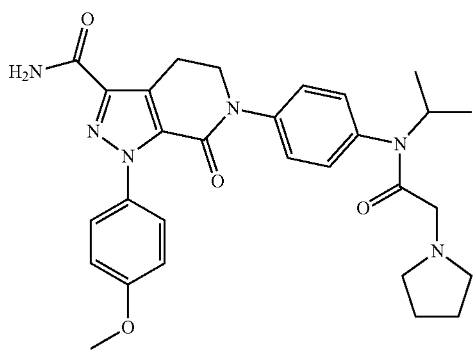 | H | methyl | H | *N-isopropyl-2-(pyrrolidin-1-yl)acetyl group* |
| 47 | 1-(3-fluoro-4-methoxyphenyl)-6-(3-methyl-4-(2-oxopiperidin-1-yl)phenyl)-7-oxo-4,5,6,7-tetrahydro-1H-pyrazolo[3,4-c]pyridine-3-carboxamide | 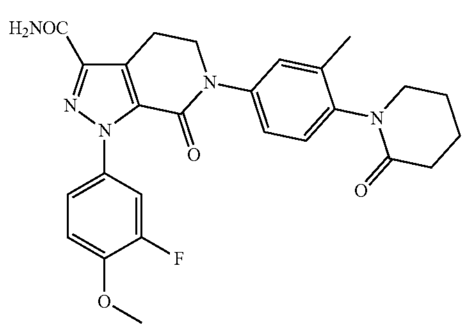 [SMILES: COc1ccc(-n2nc(C(N)=O)c3c2C(=O)N(c2ccc(N4CCCCC4=O)c(C)c2)CC3)cc1F] | F | methyl | methyl | *2-oxopiperidin-1-yl* |
| 48 | 1-(3-fluoro-4-methoxyphenyl)-6-(3-methyl-4-(3-oxomorpholino)phenyl)-7-oxo-4,5,6,7-tetrahydro-1H-pyrazolo[3,4-c]pyridine-3-carboxamide | 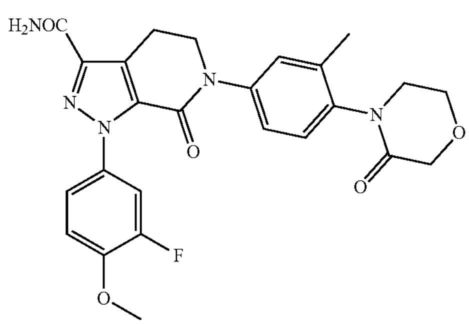 [SMILES: COc1ccc(-n2nc(C(N)=O)c3c2C(=O)N(c2ccc(N4CCOCC4=O)c(C)c2)CC3)cc1F] | F | methyl | methyl | *3-oxomorpholino* |

| Example | Compound | Structure | X | R3 | Ra | Rb |
|---|---|---|---|---|---|---|
| 49 | 1-(3-fluoro-4-methoxyphenyl)-6-(3-methyl-4-(2-oxopyrrolidin-1-yl)phenyl)-7-oxo-4,5,6,7-tetrahydro-1H-pyrazolo[3,4-c]pyridine-3-carboxamide | 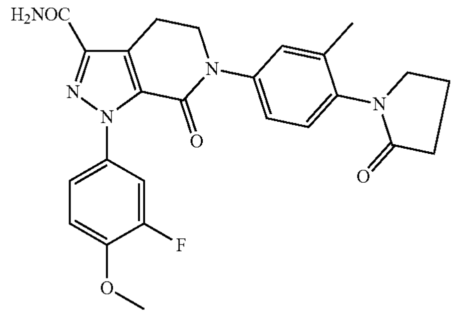 [SMILES: COc1ccc(-n2nc(C(N)=O)c3c2C(=O)N(c2ccc(N4CCCC4=O)c(C)c2)CC3)cc1F] | F | methyl | methyl | (2-oxopyrrolidin-1-yl) |
| 50 | 1-(3-fluoro-4-methoxyphenyl)-6-(3-methyl-4-(2-oxopyridin-1(2H)-yl)phenyl)-7-oxo-4,5,6,7-tetrahydro-1H-pyrazolo[3,4-c]pyridine-3-carboxamide | 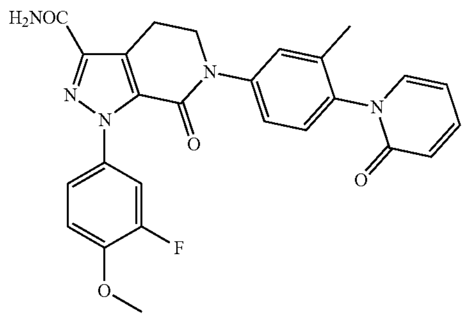 [SMILES: COc1ccc(-n2nc(C(N)=O)c3c2C(=O)N(c2ccc(-n4ccccc4=O)c(C)c2)CC3)cc1F] | F | methyl | methyl | (2-oxopyridin-1(2H)-yl) |
| 51 | 1-(3-fluoro-4-methoxyphenyl)-6-(3-methyl-4-(3-methyl-2-oxopyridin-1(2H)-yl)phenyl)-7-oxo-4,5,6,7-tetrahydro-1H-pyrazolo[3,4-c]pyridine-3-carboxamide | 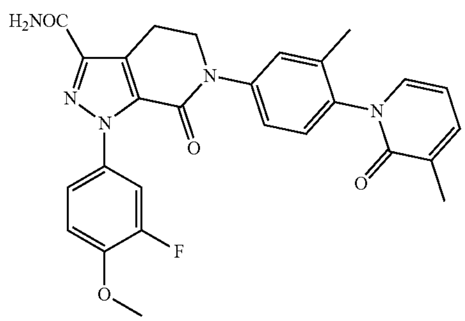 [SMILES: COc1ccc(-n2nc(C(N)=O)c3c2C(=O)N(c2ccc(-n4cccc(C)c4=O)c(C)c2)CC3)cc1F] | F | methyl | methyl | (3-methyl-2-oxopyridin-1(2H)-yl) |

The results of specific physical characterization:

| Example | Compound | Result | $^1$H NMR (600 MHz, DMSO) δ | MS [M + H]$^+$ |
|---|---|---|---|---|
| 1 | 1 | off-white solid, purity 96.18%, yield 47.4% | 2.053 (s, 3H), 3.230-3.234 (m, 2H), 3.805 (s, 3H), 4.093-4.097 (m, 2H), 6.418-6.433 (d, 1H), 6.999-7.014 (d, 2H), 7.380-7.417 (m, 3H), 7.438-7.4480 (d, 2H), 7.475-7.489 (d, 2H), 7.515-7.530 (d, 2H), 7.730 (s, 1H) | 470.1 |
| 2 | 2 | off-white solid, purity 96.72%, yield 39.3% | 3.191-3.212 (t, 2H), 3.800 (s, 3H), 4.018-4.074 (m, 2 × 2H), 4.425-4.452 (t, 2H), 6.992-7.005 (d, 2H), 7.363-7.376 (d, 2H), 7.438 (s, 1H), 7.494-7.507 (d, 2H), 7.558-7.571 (d, 2H), 7.715 (s, 1H) | 448.0 |
| 3 | 3 | light yellow solid, purity 97.59%, yield 52.4% | 2.974-3.041 (m, 2H), 3.140-3.206 (m, 2H), 3.248-3.315 (m, 2H), 3.801 (s, 3H), 3.894-4.051 (m, 2 × 2H), 6.937-7.004 (m, 2H), 7.245-7.510 (m, 7H), 7.711 (s, 1H) | 478.2 |
| 4 | 4 | off-white solid, purity 95.67%, yield 35.5% | 2.658-2.674 (m, 2H), 2.876-2.913 (m, 4H), 3.188-3.210 (t, 2H), 3.179-3.733 (m, 2H), 3.800 (s, 3H), 4.027-4.049 (t, 2H), 6.897-7.002 (d, | 475.3 |

-continued

| Example | Compound | Result | ¹H NMR (600 MHz, DMSO) δ | MS [M + H]⁺ |
|---|---|---|---|---|
| 5 | 5 | off-white solid, purity 95.99%, yield 79.4% | 2H), 7.196-7.210 (d, 2H), 7.321-7.335 (d, 2H), 7.430 (s, 1H), 7.491-7.506 (d, 2H), 7.708 (s, 1H) 1.986 (s, 3H), 2.572-2.707 (m, 3 × 2H), 3.189-3.210 (t, 2H), 3.800-3.815 (m, 3H + 2H), 4.029-4.051 (t, 2H), 6.989-7.004 (d, 2H), 7.202-7.217 (d, 2H), 7.329-7.343 (d, 2H), 7.443 (s, 1H), 7.492-7.507 (d, 2H), 7.724 (s, 1H) | 489.2 |
| 6 | 6 | off-white solid, purity 96.73%, yield 40.3% | 3.230 (m, 2H), 3.828 (s, 3H), 4.107-4.118 (m, 2H), 6.998-7.013 (m, 2H), 7.065-7.080 (m, 1H), 7.441-7.485 (m, 4H), 7.508-7.523 (d, 2H), 7.563-7.577 (d, 2H), 7.722 (s, 1H), 8.067 (s, 1H) | 457.0 |
| 7 | 7 | off-white solid, purity 95.63%, yield 48.6% | 2.312 (s, 3H), 3.218-3.239 (t, 2H), 3.805 (s, 3H), 4.087-4.108 (t, 2H), 6.992-7.012 (m, 3H), 7.416-7.467 (m, 4H), 7.509-7.557 (m, 4H), 7.725 (s, 1H) | 471.0 |
| 8 | 8 | off-white solid, purity 95.83%, yield 18.7% | 1.700 (m, 1H), 2.008 (m, 1H), 2.187 (m, 1H), 2.483-2.592 (m, 2H), 3.335 (s, 3H), 3.570-3.629 (m, 2H), 3.781-3.820 (m, 2H), 4.032-4.068 (m, 2H), 6.984-7.023 (m, 2H), 7.256-7.295 (m, 2H), 7.332-7.416 (m, 2H), 7.456-7.526 (m, 3H), 7.696-7.734 (m, 1H) | 474.9 |
| 9 | 9 | off-white solid, purity 97.11%, yield 29.6% | 1.516-1.532 (m, 2H), 1.662-1.694 (m, 1H), 1.912-1.952 (m, 3H), 2.806 (s, 1H), 3.181-3.203 (m, 2H), 3.801 (s, 3H), 3.997-4.019 (m, 2H), 4.605 (s, 1H), 6.988-7.003 (d, 2H), 7.306-7.321 (s, 2H), 7.427 (m, 1H), 7.488-7.503 (d, 2H), 7.540-7.554 (d, 2H), 7.704 (s, 1H) | 472.2 |
| 10 | 10 | off-white solid, purity 96.07%, yield 70.7% | 2.199 (s, 3H), 3.190-3.195 (m, 2H), 3. 801 (s, 3H), 3.997-4.019 (m, 2H), 5.617 (s, 1H), 6.989-7.004 (d, 2H), 7.032-7.047 (d, 2H), 7.291-7.7.305 (d, 2H), 7.433 (s, 1H), 7.487-7.502 (d, 2H), 7.711 (s, 1H), 12.046 (s, 1H) | 459.2 |
| 11 | 11 | light yellow solid, purity 95.94%, yield 95.7% | 2.317 (s, 3H), 3.205-3.227 (m, 2H), 3.804 (s, 3H), 4.047-4.069 (m, 2H), 6.779-6.792 (d, 1H), 6.988-7.011 (m, 3H), 7.112-7.126 (d, 2H), 7.367-7.382 (d, 2H), 7.450 (s, 1H), 7.502-7.517 (m, 2H), 7.713-7.739 (m, 2H) | 470.2 |
| 12 | 12 | light yellow solid, purity 95.53%, yield 64.6% | 1.815-1.881 (m, 1H), 2.382-2.424 (m, 1H), 3.191-3.212 (m, 2H), 3.670-3.763 (m, 2H), 3.801 (s, 3H), 4.021-4.043 (m, 2H), 4.284-4.322 (m, 1H), 5.740-5.750 (d, 1H), 6.991-7.005 (d, 2H), 7.356-7.371 (d, 2H), 7.433 (s, 1H), 7.492-7.507 (d, 2H), 7.683-7.698 (d, 2H), 7.710 (s, 1H) | 462.1 |
| 13 | 13 | off-white solid, purity 97.47%, yield 50.2% | 1.927 (m, 1H), 2.501 (m, 1H), 3.200 (m, 2H), 3.4643 (s, 3H), 3.730-3.801 (m, 5H), 4.033-4.134 (m, 3H), 6.995 (d, 2H), 7.372 (d, 2H), 7.431 (s, 1H), 7.496 (d, 2H), 7.675 (d, 2H), 7.708 (s, 1H) | 476.3 |
| 14 | 14 | off-white solid, purity 96.21%, yield 28.8% | 2.255 (m, 1H), 2.744 (m, 1H), 3.195-3.216 (m, 2H), 3.801 (s, 3H), 3.844-3.881 (m, 1H), 3.909-3.955 (m, 1H), 4.011-4.052 (m, 3H), 4.875 (m, 1H), 6.992-7.007 (d, 2H), 7.389-7.404 (d, 2H), 7.441 (s, 1H), 7.495-7.510 (d, 2H), 7.678-7.692 (d, 2H), 7.718 (s, 1H) | 480.1 |
| 15 | 15 | yellow solid, purity 95.89%, yield 51.5% | 1.874-1.988 (m, 3H), 2.236-2.300 (m, 1H), 2.817(s, 3H), 3.120 (s, 3H), 3.154-3.176 (m, 2H), 3.318-3.450 (m, 2H), 3.805 (s, 3H), 3.954-3.967 | 503.3 |

| Example | Compound | Result | ¹H NMR (600 MHz, DMSO) δ | MS [M + H]⁺ |
|---|---|---|---|---|
| | | | (m, 2H), 4.647-4.665 (m, 1H), 6.330-6.345 (d, 2H), 6.988-7.003 (d, 2H), 7.068-7.073 (d, 2H), 7.462-7.477 (d, 2H) | |
| 16 | 16 | white solid, purity 99.15%, yield 39.5% | 1.845 (m, 4H), 2.082 (s, 3H), 2.367-2.388 (m, 2H), 3.182-3.204 (m, 2H), 3.314 (m, 1H), 3.531-3.549 (m, 1H), 3.800 (s, 3H), 4.029-4.050 (m, 2H), 6.988-7.003 (d, 2H), 7.152-7.166 (m, 1H), 7.188-7.204(m, 1H), 7.250 (s, 1H), 7.431 (s, 1H), 7.485-7.500 (d, 2H), 7.708 (s, 1H) | 474.1 |
| 17 | 17 | off-white solid, purity 95.80%, yield 69.1% | 2.108-2.127 (m, 5H), 2.395-2.422 (m, 2H), 3.184-3.205 (m, 2H), 3.651-3.674 (m, 2H), 3.801 (s, 3H), 4.027-4.049 (m, 2H), 6.989-7.004 (d, 2H), 7.195-7.225 (m, 2H), 7.266 (s, 1H), 7.441 (s, 1H), 7.487-7.501 (d, 2H), 7.721 (s, 1H) | 476.1 |
| 18 | 18 | off-white solid, purity 99.14%, yield 42.6% | 2.130 (s, 3H), 3.187-3.209 (m, 2H), 3.462 (m, 1H)3.678(m, 1H), 3.801 (s, 3H), 3.979(m, 2H), 4.040-4.061 (m, 2H), 4.157-4.242(m, 2H), 6.990-7.004 (d, 2H), 7.231-7.269 (m, 2H), 7.292 (s, 1H), 7.437 (s, 1H), 7.489-7.503 (d, 2H), 7.721 (s, 1H) | 460.2 |
| 19 | 19 | off-white solid, purity 95.99%, yield 59.1% | 2.024 (s, 3H), 3.211-3.233 (m, 2H), 3.801 (s, 3H), 4.080-4.103 (m, 2H), 6.307-6.331(m, 1H), 6.481-6.497(m, 1H), 6.999-7.014 (d, 2H), 7.235-7.249 (m, 1H), 7.311-7.329 (m, 1H), 7.389-7.392(m, 1H), 7.445 (s, 1H), 7.497-7.553 (m, 4H), 7.726 (s, 1H) | 470.2 |
| 20 | 20 | Khaki solid, purity 97.05%, yield 37.6% | 1.014 (d, 3H), 1.684-1.730 (m, 1H), 2.115 (s, 3H), 2.320-2.375(m, 1H), 2.403-2.503(m, 2H), 3.186-3.208 (m, 2H), 3.803 (s, 3H), 4.042-4.064 (m, 3H), 6.990-7.010 (m, 2H), 7.131-7.148 (m, 1H), 7.204-7.222(m, 1H), 7.277-7.280 (m, 1H), 7.437 (s, 1H), 7.486-7.501 (d, 2H), 7.715 (s, 1H) | 474.1 |
| 21 | 21 | off-white solid, purity 95.89%, yield 45.5% | 1.652 (s, 3H), 2.167 (s, 3H), 3.036 (s, 3H), 3.189-3.215 (m, 2H), 3.803 (s, 3H), 4.035-4.064 (m, 2H), 6.993-7.008 (m, 2H), 7.260-7.262 (m, 2H), 7.354 (m, 1H), 7.411 (s, 1H), 7.487-7.503 (m, 2H), 7.721 (s, 1H) | 448.2 |
| 22 | 22 | off-white solid, purity 96.43%, yield 49.1% | 0.897-0.912 (d, 6H), 2.156 (s, 3H), 2.176-2.221 (m, 1H), 3.037 (s, 3H), 3.191-3.213 (m, 2H), 3.805 (s, 3H), 4.061-4.083 (m, 2H), 6.995-7.010 (m, 2H), 7.268 (m, 2H), 7.363 (m, 1H), 7.444 (s, 1H), 7.487-7.503 (m, 2H), 7.724 (s, 1H) | 476.2 |
| 23 | 23 | off-white solid, purity 99.47%, yield 54.7% | 1.386 (m, 2H), 1.542-1.597 (m, 4H), 2.192 (s, 3H), 3.102 (m, 2H), 3.186-3.208 (m, 2H), 3.549-3.658 (m, 2H), 3.803 (s, 3H), 4.043-4.064 (m, 2H), 6.992-7.007 (d, 2H), 7.207 (m, 2H), 7.252 (s, 1H), 7.438 (s, 1H), 7.486-7.501 (d, 2H), 7.718 (s, 1H) | 488.0 |
| 24 | 24 | off-white solid, purity 98.37%, yield 34.7% | 2.214 (s, 3H), 3.135-3.204 (m, 4H), 3.188-3.210 (m, 2H), 3.494 (m, 2H), 3.643(m, 4H), 3.803 (s, 3H), 4.047-4.059 (m, 2H), 7.000 (m, 2H), 7.197-7.274 (m, 3H), 7.431-7.711 (m, 3H), 7.720 (s, 1H) | 490.2 |
| 25 | 25 | off-white solid, purity 96.18%, yield 93.7% | 1.798 (m, 2H), 1.850 (m, 2H), 2.204 (s, 3H), 3.055-3.077 (m, 2H), 3.188-3.210 (m, 2H), 3.450-3.473 (m, 2H), 3.803 (s, 3H), 4.040-4.062 (m, 2H), 6.993-7.008 (d, 2H), 7.207 (m, 2H), 7.252 (s, 1H), 7.438 (s, 1H), 7.486-7.501 (d, 2H), 7.717 (s, 1H) | 474.1 |

-continued

| Example | Compound | Result | ¹H NMR (600 MHz, DMSO) δ | MS [M + H]⁺ |
|---|---|---|---|---|
| 26 | 26 | off-white solid, purity 96.55%, yield 79.5% | 2.183-2.198 (m, 8H), 2.352 (m, 2H), 3.124 (m, 2H), 3.186-3.208 (m, 2H), 3.637 (m, 2H), 3.803 (s, 3H), 4.043-4.065 (m, 2H), 6.992-7.007 (d, 2H), 7.150-7.164 (d, 1H), 7.207-7.221 (d, 1H), 7.260 (s, 1H), 7.439 (s, 1H), 7.483-7.498 (d, 2H), 7.719 (s, 1H) | 503.3 |
| 27 | 27 | off-white solid, purity 97.85%, yield 72.0% | 1.357-1.380 (m, 3H), 2.043 (s, 3H), 3.215-3.237 (m, 2H), 4.086-4.107 (m, 2H), 4.147-4.182 (m, 2H), 6.231-6.253 (t, 1H), 7.221-7.251 (t, 1H), 7.391-7.427 (m, 4H), 7.478-7.500 (m, 4H), 7.582-7.606 (dd, 1H), 7.767 (s, 1H) | 502.3 |
| 28 | 28 | off-white solid, purity 98.65%, yield 87.4% | 1.345-1.352 (H, 3H), 2.042 (s, 3H), 3.230-3.236 (m, 2H), 3.393-3.401 (m, 2H), 4.075-4.106 (m, 2H), 6.240-6.246 (m, 1H), 6.980-6.995 (m, 2H), 7.404-7.445 (m, 4H), 7.481-7.510 (m, 5H), 7.731 (s, 1H) | 484.3 |
| 29 | 29 | off-white solid, purity 96.48%, yield 77.6% | 1.365-1.389 (H, 3H), 1.828-1.868 (m, 4H), 2.376-2.397 (t, 2H), 3.185-3.206 (t, 2H), 3.586-3.604 (t, 2H), 4.038-4.060 (t, 2H), 4.156-4.191 (m, 2H), 7.201-7.216 (d, 1H), 7.276-7.291 (d, 2H), 7.345-7.359 (d, 2H), 7.460 (s, 1H), 7.536-7.554 (dd, 1H), 7.736-7.740 (d, 1H), 7.767 (s, 1H) | 508.1 |
| 30 | 30 | off-white solid, purity 96.65%, yield 66.0% | 1.369-1.392 (t, 3H), 2.043 (s, 3H), 3.215-3.236 (t, 2H), 4.092-4.113 (t, 2H), 4.162-4.185 (m, 2H), 6.231-6.253 (t, 1H), 7.212-7.227 (d, 1H), 7.392-7.428 (m, 3H), 7.483-7.497 (m, 4H), 7.561-7.575 (d, 1H), 7.758-7.782 (m, 2H) | 518.0 |
| 31 | 31 | off-white solid, purity 99.02%, yield 36.4% | 1.343 (t, 3H), 1.845-1.871 (m, 4H), 2.082 (s, 3H), 2.358-2.378 (m, 2H), 3.180-3.202 (m, 2H), 3.313 (m, 1H), 3.523-3.550 (m, 1H), 4.020-4.086 (m, 4H), 6.969-6.983 (d, 2H), 7.152-7.203 (m, 2H), 7.248 (s, 1H), 7.426 (s, 1H), 7.468-7.483 (d, 2H), 7.709 (s, 1H) | 488.2 |
| 32 | 32 | off-white solid, purity 97.92%, yield 37.3% | 1.366 (t, 3H), 1.847 (m, 4H), 2.088 (s, 3H), 2.361-2.381 (m, 2H), 3.176-3.198 (m, 2H), 3.315 (m, 1H), 3.536-3.554 (m, 1H), 4.035 (m, 2H), 4.166 (m, 2H), 7.161-7.256 (m, 4H), 7.380-7.394 (m, 1H), 7.458 (s, 1H), 7.553-7.575 (m, 1H), 7.748 (s, 1H) | 506.2 |
| 33 | 33 | light yellow solid purity 96.65%, yield 72.6% | 1.343 (t, 3H), 2.130 (s, 3H), 3.186-3.207 (m, 2H), 3.462 (m, 1H), 3.678 (m, 1H), 3.979 (m, 2H), 4.037-4.086 (m, 4H), 4.157-4.241 (m, 2H), 6.970-6.985 (d, 2H), 7.228-7.291 (m, 3H), 7.430 (s, 1H), 7.471-7.486 (d, 2H), 7.713 (s, 1H) | 490.3 |
| 34 | 34 | off-white solid, purity 95.60%, yield 31.1% | 1.366 (t, 3H), 2.136 (s, 3H), 3.128-3.203 (m, 2H), 3.466 (m, 1H), 3.701 (m, 1H), 4.076-4.323 (m, 8H), 7.212-7.299 (m, 4H), 7.383-7.397 (m, 1H), 7.461 (s, 1H), 7.559-7.575 (m, 1H), 7.752 (s, 1H) | 508.2 |
| 35 | 35 | off-white solid, purity 97.88%, yield 28.7% | 1.343 (t, 3H), 2.108-2.145 (m, 5H), 2.408 (m, 2H), 3.183-3.204 (m, 2H), 3.650-3.673 (m, 2H), 4.024-4.087 (m, 4H), 6.790-6.984 (d, 2H), 7.209 (m, 2H), 7.265 (m, 1H), 7.428 (s, 1H), 7.469-7.484 (d, 2H), 7.710 (s, 1H) | 474.2 |
| 36 | 36 | off-white solid, purity 97.88%, yield 28.7% | 1.366 (t, 3H), 2.110-2.133 (m, 5H), 2.411 (m, 2H), 3.179-3.220 (m, 2H), 3.654-3.676 (m, 2H), 4.023-4.044 (m, 2H), 4.144-4.178 (m, 2H), 7.218-7.240 (m, 3H), 7.272 (m, 1H), | 492.2 |

-continued

| Example | Compound | Result | ¹H NMR (600 MHz, DMSO) δ | MS [M + H]⁺ |
|---|---|---|---|---|
| 37 | 37 | off-white solid, purity 95.40%, yield 14.8% | 7.381-7.395 (s, 1H), 7.460 (s, 1H), 7.555-7.575 (m, 1H), 7.750 (s, 1H) 1.335-1.358 (t, 3H), 2.024 (s, 3H), 3.210-3.231 (m, 2H), 4.057-4.099 (m, 4H), 6.308-6.329 (m, 1H), 6.481-6.496 (m, 1H), 6.980-6.994 (d, 2H), 7.235-7.249 (m, 1H), 7.310-7.326 (m, 1H), 7.388 (s, 1H), 7.439 (s, 1H), 7.523-7.550 (m, 4H), 7.724 (s, 1H) | 484.0 |
| 38 | 38 | off-white solid, purity 95.55%, yield 42.6% | 1.358-1.382 (t, 3H), 2.029 (s, 3H), 3.205-3.228 (m, 2H), 4.075-4.097 (m, 2H), 4.149-4.183 (q, 2H), 6.309-6.333 (m, 1H), 6.484-6.499 (m, 1H), 7.221-7.258 (m, 2H), 7.321-7.338 (m, 1H), 7.398-7.415 (m, 2H), 7.472 (s, 1H), 7.498-7.597 (m, 3H), 7.764 (s, 1H) | 502.0 |
| 39 | 39 | off-white solid, purity 96.75%, yield 39.1% | 1.336-1.359 (t, 3H), 2.007 (s, 3H), 2.046 (s, 3H), 3.210-3.232 (m, 2H), 4.058-4.100 (m, 4H), 6.227-6.250 (m, 1H), 6.981-6.995 (m, 2H), 7.220-7.234 (m, 1H), 7.303-7.347 (m, 2H), 7.383 (s, 1H), 7.413-7.441 (m, 2H), 7.487-7.502 (m, 2H), 7.727 (s, 1H) | 498.0 |
| 40 | 40 | off-white solid, purity 97.45%, yield 49.1% | 1.359-1.382 (t, 3H), 2.012 (s, 3H), 2.048 (s, 3H), 3.206-3.228 (m, 2H), 4.076-4.098 (m, 2H), 4.149-4.184 (q, 2H), 6.230-6.252 (m, 1H), 7.221-7.251 (m, 2H), 7.331-7.351 (m, 2H), 7.389-7.425 (m, 3H), 7.473 (s, 1H), 7.573-7.597 (m, 1H), 7.765 (s, 1H) | 516.0 |
| 41 | 41 | off-white solid, purity 98.51%, yield 71.0% | 1.301-1.311 (d, 6H), 1.828-1.868 (m, 4H), 2.376-2.396 (t, 2H), 3.184-3.206 (t, 2H), 3.585-3.603 (t, 2H), 4.033-4.054 (t, 2H), 4.678-4.718 (m, 1H), 7.7.237-7.291 (m, 3H), 7.347-7.388 (m, 3H), 7.465 (s, 1H), 7.555-7.575 (d, 1H), 7.752 (s, 1H) | 506.2 |
| 42 | 42 | off-white solid, purity 95.78%, yield 40.1% | 1.305 (s, 6H), 2.058-2.070 (m, 2H), 3.187-3.196 (m, 2H), 3.317-3.330 (m, 2H), 3.827-3.838 (m, 2H), 4.018-4.028 (m, 2H), 4.698 (s, 1H), 7.246-7.260 (m, 1H), 7.353-7.366 (m, 3H), 7.458 (s, 1H), 7.550-7.580 (m, 1H), 7.648 (s, 2H), 7.742-7.751 (m, 1H) | 492.1 |
| 43 | 43 | off-white solid, purity 95.54%, yield 71.4% | 1.307-1.315 (d, 6H), 2.044 (s, 3H), 3.226-3.237 (t, 2H), 4.086-4.108 (t, 2H), 4.685-4.725 (m, 1H), 6.232-6.255 (t, 1H), 7.248-7.2771 (t, 1H), 7.393-7.429 (m, 4H), 7.480-7.500 (m, 4H), 7.576-7.600 (dd, 1H), 7.767 (s, 1H) | 516.2 |
| 44 | 44 | off-white solid, purity 98.12%, yield 35.6% | 1.301-1.310 (d, 6H), 3.191-3.210 (t, 2H), 3.735 (s, 2H), 3.977 (s, 2H), 4.043-4.062 (t, 2H), 4.203 (s, 2H), 4.680-4.718 (m, 1H), 7.239-7.268 (m, 1H), 7.378-7.423 (m, 5H), 7.466 (s, 1H), 7.559-7.579 (d, 1H), 7.753 (s, 1H) | 508.1 |
| 45 | 45 | off-white solid, purity 99.20%, yield 78.4% | 0.960 (s, 3H), 0.971 (s, 3H), 2.093 (s, 6H), 2.652 (s, 2H), 3.218 (m, 2H), 3.805 (s, 3H), 4.098 (m, 2H), 4.809 (m, 1H), 6.999-7.014 (m, 2H), 7.205-7.218 (m, 2H), 7.422-7.449 (m, 3H), 7.498-7.531 (m, 2H), 7.731 (m, 1H) | 505.3. |
| 46 | 46 | off-white solid, purity 97.84%, yield 78.7% | 0.964 (s, 3H), 0.975 (s, 3H), 1.614 (m, 2H), 2.440 (m, 2H), 3.219 (m, 2H), 3.337(m, 2H), 3.805 (s, 3H), 4.098 (m, 2H), 4.449 (s, 2H), 4.803 (m, 1H), 6.998-7.013 (m, 2H), | 531.27 |

-continued

| Example | Compound | Result | $^1$H NMR (600 MHz, DMSO) δ | MS [M + H]$^+$ |
|---|---|---|---|---|
| 47 | 47 | off-white solid, purity 96.49%, yield 19.5% | 7.218-7.231 (m, 2H), 7.426-7.450 (m, 3H), 7.498-7.513 (m, 2H), 7.731 (m, 1H) 1.847 (m, 4H), 2.087 (s, 3H), 2.332-2.410 (m, 2H), 3.178-3.200 (m, 2H), 3.320 (m, 1H), 3.535-3.554 (m, 1H), 3.891 (s, 3H), 4.037 (m, 2H), 7.160-7.260 (m, 4H), 7.404-7.420 (m, 1H), 7.461 (s, 1H), 7.560-7.584 (m, 1H), 7.745 (s, 1H) | 492.3 |
| 48 | 48 | off-white solid, purity 98.32%, yield 52.1% | 2.136 (s, 3H), 3.183-3.205 (m, 2H), 3.465 (m, 1H), 3.680 (m, 1H), 3.891 (s, 3H), 3.981 (m, 2H), 4.047 (m, 2H), 4.186-4.220 (m, 2H), 7.226-7.300 (m, 4H), 7.404-7.420 (m, 1H), 7.461 (s, 1H), 7.560-7.584 (m, 1H), 7.745 (s, 1H) | 494.2 |
| 49 | 49 | off-white solid, purity 96.99%, yield 29.1% | 2.098-2.148 (m, 5H), 2.397-2.411 (m, 2H), 3.180-3.202 (m, 2H), 3.654-3.677 (m, 2H), 3.891 (s, 3H), 4.035 (m, 2H), 7.219-7.274 (m, 4H), 7.409-7.423 (m, 1H). 7.465 (s, 1H), 7.563-7.587 (m, 1H), 7.750 (s, 1H) | 478.2 |
| 50 | 50 | off-white solid, purity 95.10%, yield 23.2% | 2.029 (s, 3H), 3.207-3.228 (m, 2H), 3.896 (s, 3H), 4.088 (m, 2H), 6.320 (m, 1H), 6.490 (m, 1H), 7.236-7.258 (m, 2H), 7.266-7.339 (m, 1H), 7.396-7.555 (m, 5H), 7.580-7.604 (m, 1H), 7.742 (s, 1H) | 488.2 |
| 51 | 51 | off-white solid, purity 95.51%, yield 33.1% | 2.012 (s, 3H), 2.047 (s, 3H), 3.207-3.229 (m, 2H), 3.897 (s, 3H), 4.089 (m, 2H), 6.241 (m, 1H), 7.228-7.267 (m, 2H), 7.313-7.471 (m, 6H), 7.579-7.603 (m, 1H), 7.759 (s, 1H) | 502.3. |

Part B

The invention also provides the following compounds 1-35, respectively, corresponding to the compounds of examples 1-35.

Intermediate 1: tert-butyl (3-(dimethylamino)propyl)(4-iodophenyl)carbamate

Step 1: the preparation of tert-butyl (4-iodophenyl)carbamate

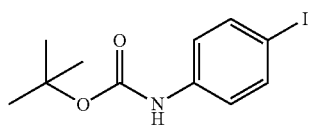

4-iodoaniline (5.0 g, 22.83 mmol) was dissolved in DMF (50 mL). DIPEA (2.5 mL) was added to the reaction. Then to the reaction was dropwise added (Boc)2O (11.0 g, 50.04 mmol) in an ice-water bath. After stirring at room temperature for 14 h, the reaction mixture was poured into ice-water (250 mL). The resulting mixture was extracted with DCM. The organic phases were concentrated under vacuum to give a crude product. The crude product was mixed with hexane under heating to form a slurry, and then the slurry was cooled and filtered to give 3.5 g of the product as a white solid in a yield of 48.0%.

Step 2: tert-butyl (3-(dimethylamino)propyl)(4-iodophenyl)carbamate

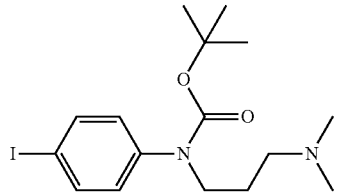 [SMILES: CN(C)CCCN(C(=O)OC(C)(C)C)c1ccc(I)cc1]

At room temperature, tert-butyl (4-iodophenyl)carbamate (2.0 g, 6.27 mmol), 3-chloro-1-(N,N-dimethyl)propylamine (0.9 g, 7.40 mmol), cesium carbonate (3.0 g, 9.21 mmol) and potassium iodide (0.1 g, 0.63 mmol) were dispersed in DMF (20 mL). The mixture was warmed up to 80° C. and reacted for 48 h. The reaction mixture was poured into ice-water (100 mL). The resulting mixture was extracted with EA. The organic phases were concentrated under vacuum to give a crude product. The crude product was purified via silica gel column chromatography (PE:EA=20:1) to give 1.0 g of the title compound as a yellow solid in a yield of 40%.

Intermediate 2:
3-chloro-5,6-dihydropyridin-2(1H)-one

Step 1: 3,3-dichloropiperidin-2-one

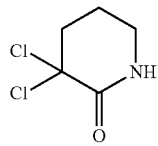

To a flask were added piperidin-2-one (20 g, 20.2 mmol) and chloroform (500 mL). Then to the mixture was added phosphorus pentachloride (168 g, 80.7 mmol) in batches at 0-5° C. After the completion of the addition, the reaction mixture was heated to 66° C. and reacted under reflux for 12 h. After the completion of the reaction, the mixture was cooled down to room temperature and slowly poured to an ice-water mixture (1.5 L). The resulting mixture was extracted with DCM and the organic phases were concentrated under vacuum to produce 31.0 g of a white solid, i.e., a crude product of 3,3-dichloropiperidin-2-one, which was used in the next step without purification in a yield of 91.3%.

Step 2: 3-chloro-5,6-dihydropyridin-2(1H)-one

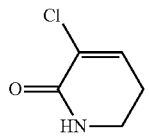

3,3-dichloropiperidin-2-one (31.0 g, 0.18 mmol) was dissolved in DMF (200 mL) at room temperature. To the resulting mixture was added lithium carbonate (33.3 g, 0.45 mmol). The mixture was heated to 120° C. and stirred for 12 h to react. After the completion of the reaction, the solvent was removed by evaporation. The residue was diluted with DCM (300 mL), and filtered by suction. The filtrate was concentrated under vacuum to produce 45.0 g of the crude title compound as a brown oil.

Intermediate 3: tert-butyl
(3-(4-iodophenoxy)propyl)(methyl)carbamate

Step 1: 3-(methylamino)propan-1-ol

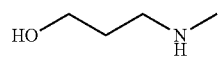

3-Bromopropan-1-ol (10.0 g, 71.94 mmol) was slowly dropwise added into an aqueous methylamine solution (50 mL) in an ice-water bath. After the completion of the dropwise addition, the reaction mixture was reacted for 14 h at room temperature. The resulting reaction mixture was directly concentrated under vacuum to produce 6.0 g of the title compound as a yellow oil, which was directly used in the next step.

Step 2: tert-butyl
(3-hydroxypropyl)(methyl)carbamate

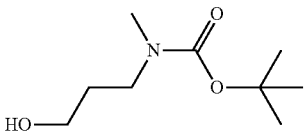

3-(Methylamino)propan-1-ol (6.0 g, 67.3 mmol) was dissolved in DCM (100 mL) at room temperature. To the resulting mixture was added triethylamine (29.0 g, 0.287 mol). Then to the resulting mixture was slowly dropwise added Boc2O (22.0 g, 0.101 mol) in an ice-water bath. After the completion of the dropwise addition, the reaction mixture was reacted for 14 h at room temperature. The reaction mixture was concentrated under vacuum to give a crude product. The crude product was purified via silica gel column chromatography (PE:EA=50:1) to give 6.7 g of the title compound as an anhydrous oil.

Step 3: tert-butyl
(3-(4-iodophenoxy)propyl)(methyl)carbamate

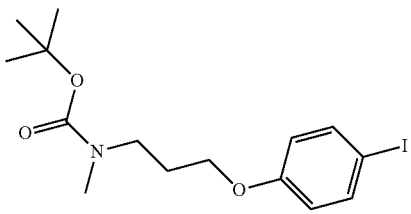 [SMILES: CN(CCCOc1ccc(I)cc1)C(=O)OC(C)(C)C]

At room temperature, 4-iodophenol (2.0 g, 9.09 mmol), tert-butyl (3-hydroxypropyl)(methyl)carbamate (2.06 g, 10.89 mmol), and triphenylphosphine (3.6 g, 13.64 mmol) were successively added to anhydrous THF (20 mL). To the resulting mixture was slowly dropwise added DEAD (2.3 g, 13.21 mmol) in an ice-water bath. After the completion of the dropwise addition, the resulting mixture was acted for 14 h. Then the resulting mixture was directly concentrated under vacuum to give a crude product. The crude product was purified via silica gel column chromatography (DCM: MeOH=10:1) to give 2.2 g of the title compound as a colorless oil in a yield of 61.9%.

Intermediate 4: tert-butyl
(4-bromo-2-fluorophenyl)(2-methoxyethyl)carbamate Step 1: 4-bromo-2-fluoroaniline

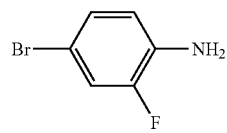

2-Fluoroaniline (3.0 g, 27.0 mmol) was dissolved in DMF (15 mL) at room temperature. To the resulting mixture was slowly dropwise added a solution of NBS (5.3 g, 29.7 mmol)

in DMF (15 mL) in an ice-water bath under the N2 protection. After the completion of the dropwise addition, the resulting mixture was reacted for 1 h while the temperature was maintained. The mixture was poured into ice-water (100 mL). The resulting mixture was extracted with EA. The organic phases were concentrated under vacuum to produce 5.0 g of the title compound as a brown oil that was used in the next step without further purification.

Step 2: tert-butyl (4-bromo-2-fluorophenyl)carbamate

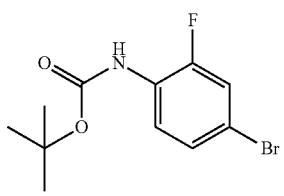 [SMILES: CC(C)(C)OC(=O)Nc1ccc(Br)cc1F]

4-Bromo-2-fluoroaniline (2 g, 10.47 mmol) was dissolved in DMF (20 mL) at room temperature. To the mixture was added DIEPA (1 mL). Boc2O (4.6 g, 20.93 mol) was slowly dropwise added in an ice-water bath. After the completion of the dropwise addition, the resulting mixture was reacted for 14 h at room temperature. The reaction mixture was poured into ice-water (100 mL). The resulting mixture was extracted with EA. The organic phases were concentrated under vacuum to give a crude product. The crude product was purified via silica gel column chromatography (PE:EA=50:1) to give 0.8 g of the title compound as a yellow solid in a yield of 26.3%.

Step 3: tert-butyl (4-bromo-2-fluorophenyl)(2-methoxyethyl)carbamate

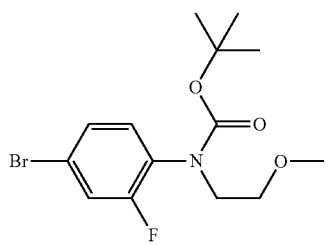 [SMILES: COCCN(C(=O)OC(C)(C)C)c1ccc(Br)cc1F]

Tert-butyl (4-bromo-2-fluorophenyl)carbamate (1.6 g, 5.51 mmol), 1-bromo-2-methoxyethane (1.1 g, 7.91 mmol), cesium carbonate (3.6 g, 139.4 mmol) and potassium iodide (300 mg, 1.81 mmol) were successively dissolved in DMSO (20 mL) at room temperature. The mixture was warmed up to 120° C. and acted for 14 h. The reaction mixture was cooled down to room temperature, poured into ice-water (100 mL). The resulting mixture was extracted with EA. The organic phases were concentrated under vacuum to give a crude product. The crude product was purified by silica gel column chromatography (PE:EA=20:1) to give 1.6 g of the title compound as a colorless oil in a yield of 83.5%.

Intermediate 5: tert-butyl (4-((4-iodo-2-methylphenyl)amino)-4-oxobutyl)carbamate

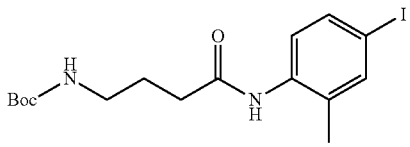 [SMILES: Cc1cc(I)ccc1NC(=O)CCCNC(=O)OC(C)(C)C]

4-Iodo-2-methylaniline (4.46 g, 19.1 mmol), potassium carbonate (5.3 g, 38.4 mmol), 4-((tert-butoxycarbonyl)amino)butanoic acid (7 g, 34.4 mmol) and HATU (8.7 g, 22.9 mmol) were successively added to acetonitrile (50 mL) at room temperature. The mixture was stirred and reacted at room temperature for 3 h. The resulting mixture was concentrated under vacuum, and then water was added. The resulting mixture was extracted with EA. The organic phases were concentrated under vacuum to give a crude product. The crude product was purified by silica gel column chromatography (DCM:MeOH=50:1) to give 6.72 g of the title compound as a white solid in a yield of 84.2%.

Intermediate 6: N-ethyl-5-iodo-2-propoxyaniline

Step 1: 4-iodo-2-nitrophenol

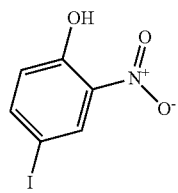 [SMILES: O=[N+]([O-])c1cc(I)ccc1O]

4-Iodophenol (7.0 g, 31.8 mmol) was dissolved in acetic acid (50 mL) at room temperature. The mixture was cooled down to 0° C. To the cooled mixture was added dropwise nitric acid (2.4 mL). The resulting mixture was warmed up to room temperature and stirred and acted for 3 h. The reaction mixture was poured into ice-water (200 mL), stirred and filtered by suction. The filter cake was dried under vacuum to give 8.0 g of the title compound as a yellow solid that was used in the next step without purification.

Step 2: 4-iodo-2-nitro-1-propoxybenzene

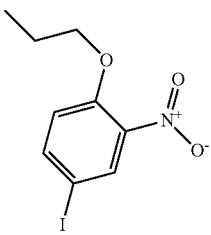

4-Iodo-2-nitrophenol (8.0 g, 30.2 mmol), potassium carbonate (8.3 g, 60.1 mmol) and 1-iodopropane (10.3 g, 60.4 mmol) were successively added to acetonitrile (100 mL) at room temperature. The mixture was heated to 80° C., and stirred and acted for 14 h. The reaction mixture was poured into ice-water (100 mL). The resulting mixture was extracted with EA. The organic phases were concentrated under vacuum to give a crude product. The crude product was purified by silica gel column chromatography (PE:EA=50:1) to give 5.1 g of the title compound as a yellow oil in a yield of 50.0%.

Step 3: 5-iodo-2-propoxyaniline

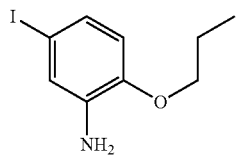

4-Iodo-2-nitro-1-propoxybenzene (5.1 g, 16.6 mmol), Fe(2.79 g, 49.8 mmol) and ammonium chloride (4.44 g, 83.0 mmol) were successively added to a solution of ethanol (50 mL) in water (50 mL) at room temperature. The resulting mixture was heated to 60° C. and stirred and reacted for 3 h. The mixture was filtered by suction. The filtrate was extracted with ethyl acetate. The organic phases were concentrated under vacuum to give a crude product. The crude product was purified by silica gel column chromatography (PE:EA=50:1) to give 2.7 g of the title compound as a brown oil in a yield of 58.7%.

Step 4: N-ethyl-5-iodo-2-propoxyaniline

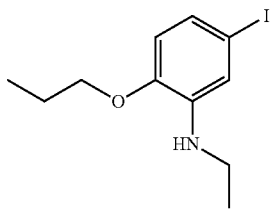

5-Iodo-2-propoxyaniline (2.0 g, 7.2 mmol), acetaldehyde (0.95 g, 21.6 mmol) and magnesium sulphate (3.0 g, 25.0 mmol) was added in MeOH (50 mL). The mixture was stirred and reacted at room temperature for 2 h. The reaction mixture was cooled to 0° C. To the cooled mixture was added sodium cyanoborohydride (3.8 g, 60.4 mmol) in batches. Then the resulting mixture was stirred and reacted at room temperature for 14 h. The reaction mixture was concentrated under vacuum to give a crude product. The crude product was purified by silica gel column chromatography (PE:EA=3:1) to give 0.94 g of the title compound as a brown oil in a yield of 42.8%.

Intermediate 7: tert-butyl (2-((4-iodophenyl)amino)ethyl)(methyl)carbamate

Step 1: 2-((tert-butoxycarbonyl)(methyl)amino)acetic acid

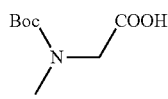

2-(Methylamino)acetic acid (10.0 g, 112.2 mmol), Boc2O (29.4 g, 134.8 mmol) and sodium hydroxide (20.0 g, 0.5 mol) were added to a mixture of water (100 mL) and 1,4-dioxane (200 mL) at room temperature. The resulting mixture was stirred and reacted at room temperature for 14 h. The mixture was evaporated to remove the 1,4-dioxane. The remaining aqueous phase was adjusted with dilute hydrochloric acid until the pH was 2. The mixture was extracted with EA. The organic phases were concentrated under vacuum to give 12.0 g of the title compound as a brown oil in a yield of 56.6%.

Step 2: tert-butyl (2-((4-iodophenyl)amino)-2-oxo-ethyl)(methyl)carbamate

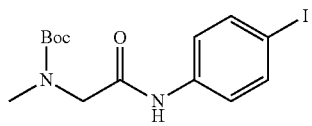 [SMILES: CN(CC(=O)Nc1ccc(I)cc1)C(=O)OC(C)(C)C]

2-((tert-butoxycarbonyl)(methyl)amino)acetic acid (12.0 g, 63.8 mmol), 4-iodoaniline (11.6 g, 53.2 mmol), EDCl (20.3 g, 105 mmol), HOBt (1.43 g, 10.6 mmol) and triethylamine (16 g, 159 mmol) were successively added to THF (150 mL) at room temperature. The resulting mixture was stirred and reacted at room temperature for 14 h. The resulting reaction mixture was concentrated. The residue was diluted with water (100 mL). The resulting mixture was extracted with EA. The organic phases were concentrated under vacuum to give a crude product. The crude product was mixed with MTBE (200 mL) to form a slurry. The slurry was filtered by suction. The filter cake was dried under vacuum to produce 8.0 g of the tile compound as a white solid in a yield of 32.2%.

Step 3: tert-butyl (2-((4-iodophenyl)amino)ethyl)(methyl)carbamate

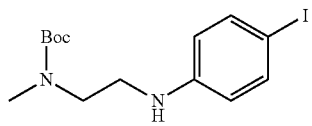 [SMILES: CN(CCNc1ccc(I)cc1)C(=O)OC(C)(C)C]

tert-Butyl (2-((4-iodophenyl)amino)-2-oxoethyl)(methyl) carbamate (2.0 g, 5.12 mmol) was dissolved in THF (20 mL). The mixture was cooled down to 0° C., and to the cooled mixture was added dropwise borane-tetrahydrofuran solution (16 mL). After the completion of the dropwise addition, the resulting mixture was heated to 50° C. and stirred and reacted for 14 h. Then the resulting mixture was cooled down to 0° C., to the cooled mixture was added MeOH (0.82 g, 25.6 mmol). The resulting mixture was heated to 80° C. and stirred for 2 h. The mixture was evaporated under vacuum to remove the solvent and the residue was dissolved in a solution of methylbenzene (10 mL) in n-BuOH (10 mL). The mixture was stirred and reacted for 14 h at 100° C. The reaction mixture was cooled down to room temperature and concentrated to give a crude product. The crude product was purified by silica gel column chromatography (PE:EA=10:1) to give 1.6 g of the title compound as a yellow oil in a yield of 83.1%.

Intermediate 8:
5-(4-bromo-2-chlorophenoxy)pentan-2-one

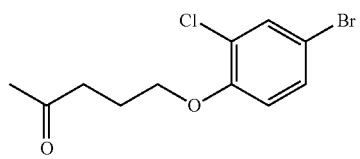

4-Bromo-2-chlorophenol (5.0 g, 24.1 mmol), potassium carbonate (9.97 g, 72.3 mmol) and 5-chloropentan-2-one (4.36 g, 36.1 mmol) were successively added to DMF (50 mL) at room temperature. The resulting mixture was heated to 80° C. and stirred and reacted for 14 h. The mixture was cooled down to room temperature and then poured into water (300 mL). The resulting mixture was extracted with EA. The organic phases were concentrated under vacuum to give a crude product. The crude product was purified by silica gel column chromatography (PE:EA=20:1) to give 2.0 g of the title compound as a light yellow oil in a yield of 28.6%.

Intermediate 9:
1-(4-iodophenyl)-4-methylpiperazine

Step 1: 1-(4-iodophenyl)piperazine

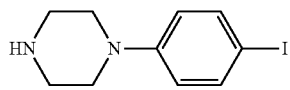

4-Iodoaniline (5.0 g, 22.8 mmol) and potassium carbonate (10 g, 72.4 mmol) were added to n-BuOH (50 mL) at room temperature. The mixture was cooled down to 0° C. To the cooled mixture was added bis(2-chloroethyl)amine hydrochloride (5.0 g, 28.0 mmol) in batches. After the completion of the addition, the reaction mixture was headed to 100° C. and stirred and reacted for 14 h. The mixture was cooled down to room temperature and filtered by suction. The filter cake was dried under vacuum to give 2.5 g of the title compound as a dark yellow solid in a yield of 38.0%.

Step 2: 1-(4-iodophenyl)-4-methylpiperazine

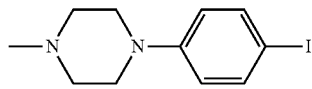

1-(4-Iodophenyl)piperazine (1.0 g, 3.5 mmol) and sodium hydride (0.13 g, 5.4 mmol) were added to THF (10 mL) at room temperature. The mixture was stirred and reacted for 0.5 h under the nitrogen protection. The mixture was cooled down to 0° C. To the cooled mixture was added dropwise CH3I (0.54 g, 3.8 mmol). After the completion of the dropwise addition, the mixture was stirred and reacted at room temperature for 2 h. The reaction mixture was quenched by the addition of water. The resulting mixture was extracted with EA. The organic phases were concentrated to give a crude product. The crude product was purified by silica gel column chromatography (DCM:MeOH=20:1) to give 150 g of the title compound as a yellow solid in a yield of 14.2%.

Intermediate 10: tert-butyl
4-(3-bromophenethyl)piperazine-1-carboxylate Step 1: 2-(3-bromophenyl)acetic acid

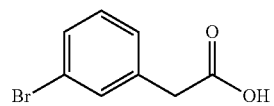 [SMILES: O=C(O)Cc1cccc(Br)c1]

Ethyl 2-(3-bromophenyl)acetate (5.0 g, 20.6 mmol) and lithium hydroxide (1.0 g, 41.8 mmol) were added to a mixture of THF (30 mL) and water (20 mL) at room temperature. The mixture was stirred and reacted at room temperature for 1 h. The mixture was adjusted with a 2N aqueous HCl solution until the pH was 2. The resulting mixture was extracted with EA. The organic phases were concentrated to produce 4.1 g of the title compound as a white solid.

Step 2: 2-(3-bromophenyl)acetyl chloride

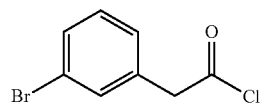 [SMILES: O=C(Cl)Cc1cccc(Br)c1]

2-(3-Bromophenyl)acetic acid (4.1 g, 19.1 mmol) and DMF (1 mL) were added to DCM (40 mL). The mixture was cooled down to 0° C. To the cooled mixture was added dropwise oxalyl chloride (5.6 g, 43.7 mmol). After the completion of the dropwise addition, the mixture was stirred and reacted at room temperature for 2 h. The resulting reaction mixture was directly concentrated to produce 4.3 g of the title compound as a yellow liquid that was directly used in the next step.

Step 3: tert-butyl 4-(2-(3-bromophenyl)acetyl)piperazine-1-carboxylate

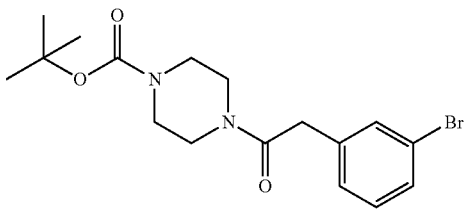 [SMILES: CC(C)(C)OC(=O)N1CCN(C(=O)Cc2cccc(Br)c2)CC1]

2-(3-Bromophenyl)acetyl chloride (4.3 g, 18.4 mmol) and triethylamine (4.8 g, 47.1 mmol) were added to THF (50 mL). The resulting mixture was cooled down to 0° C. To the cooled mixture was added dropwise 1-boc-piperazine (5.7 g, 30.6 mmol). After the completion of the dropwise addition, the mixture was stirred and reacted at room temperature for 14 h, and then poured into water (50 mL). The resulting mixture was extracted with EA. The organic phases were concentrated to produce 7.0 g of the title compound as a yellow liquid that was directly used in the next step.

Step 4: tert-butyl 4-(3-bromophenethyl)piperazine-1-carboxylate

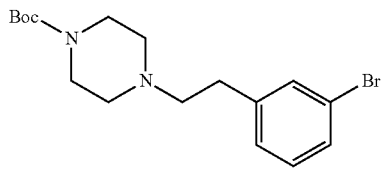 [SMILES: CC(C)(C)OC(=O)N1CCN(CCc2cccc(Br)c2)CC1]

Tert-butyl 4-(2-(3-bromophenyl)acetyl)piperazine-1-carboxylate (7.0 g, 18.3 mmol) was dissolved in THF (70 mL) at room temperature. To the reaction mixture was added dropwise borane-tetrahydrofuran solution (37 mL, 33.6 mmol) under the nitrogen protection. Then the resulting mixture was heated to 50° C. and stirred and reacted for 14 h. The resulting mixture was cooled down to room temperature. To the cooled mixture was added dropwise MeOH (20 mL). Then the resulting mixture was heated to 80° C. and stirred for 2 h. The reaction mixture was concentrated. To the residue was added n-BuOH (10 mL) and methylbenzene (40 mL). The mixture was stirred for 14 h at 80° C. The mixture was concentrated to give a crude product. The crude product was purified by silica gel column chromatography (DCM:MeOH=50:1) to give 3.9 g of the title compound as a yellow oil in a yield of 57.7%.

Intermediate 11: tert-butyl 4-(4-bromo-2-methoxybenzyl)piperazine-1-carboxylate

Step 1: tert-butyl 4-(4-bromo-2-hydroxybenzoyl)piperazine-1-carboxylate

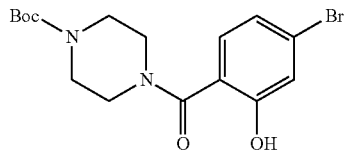 [SMILES: CC(C)(C)OC(=O)N1CCN(C(=O)c2ccc(Br)cc2O)CC1]

4-Bromo-2-hydroxybenzoic acid (5.0 g, 23 mmol), EDCl (8.8 g, 46 mmol), HOBt (257 mg, 1.9 mmol) and N-Boc-piperazine (4.7 g, 25 mmol) were dissolved in DMF (50 mL) at room temperature. The mixture was stirred and reacted at room temperature for 3 h. Then the reaction mixture was poured into ice-water (70 mL). A white solid separated out. The mixture was filtered by suction. The filter cake was dried to give 5.3 g of the title compound as a white solid in a yield of 60.0%.

Step 2: tert-butyl 4-(4-bromo-2-methoxybenzoyl)piperazine-1-carboxylate

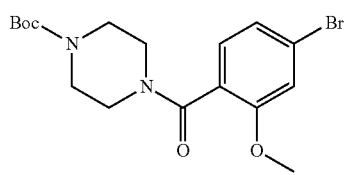 [SMILES: COc1cc(Br)ccc1C(=O)N1CCN(C(=O)OC(C)(C)C)CC1]

NaH (1.0 g, 41.7 mmol) was dissolved in DMF (30 mL) at room temperature. After the nitrogen purge, the mixture was cooled to 0° C. To the cooled mixture was added tert-butyl 4-(4-bromo-2-hydroxybenzoyl)piperazine-1-carboxylate (5 g, 13 mmol). Then the resulting mixture was naturally warmed to room temperature, and stirred and reacted for 2 h. Then to the resulting mixture was slowly added dropwise CH3I (2.3 g, 16 mmol). After the completion of the dropwise addition, the resulting mixture was reacted at room temperature for 2 h, and then cooled to 0° C. The reaction was quenched with the addition of ice-water (100 mL). A solid separated out, and the mixture was filtered by suction. The filter cake was dried to give 4.5 g of the title compound as a yellow solid in a yield of 87%.

Step 3: tert-butyl 4-(4-bromo-2-methoxybenzyl)piperazine-1-carboxylate

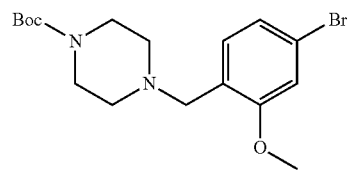 [SMILES: COc1cc(Br)ccc1CN1CCN(C(=O)OC(C)(C)C)CC1]

Tert-butyl 4-(4-bromo-2-methoxybenzoyl)piperazine-1-carboxylate (4.5 g, 11 mmol) was dissolved in THF (30 mL). After the nitrogen purge, the mixture was cooled to 0° C. To the cooled mixture was added dropwise borane-tetrahydrofuran solution (33 mL). After the completion of the dropwise addition, the mixture was warmed up to 60° C., and reacted under reflux for 14 h. The resulting mixture was concentrated. To the concentrated mixture was added a mixture of toluene (30 mL) and isopropanol (30 mL). The resulting mixture was heated to 80° C. and stirred and reacted for 8 h. After the completion of the reaction, the reaction mixture was concentrated to give a crude product. The crude product was purified by silica gel column chromatography (PE:EA=5:1) to give 2.3 g of the title compound as a white solid in a yield of 54.3%.

Intermediate 12: tert-butyl 4-(4-bromo-2-methylbenzoyl)piperazine-1-carboxylate

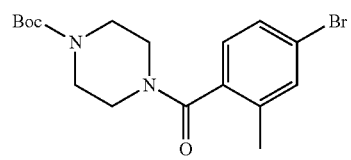 [SMILES: Cc1cc(Br)ccc1C(=O)N1CCN(C(=O)OC(C)(C)C)CC1]

4-Bromo-2-methylbenzoic acid (2.15 g, 10 mmol), EDCl (3.80 g, 20 mmol), HOBt (112 mg, 1 mmol), and N-Boc-piperazine (2.05 g, 11 mmol) were added to DMF (30 mL) at room temperature. The mixture was stirred and reacted at room temperature for 3 h. To the mixture was poured ice-water (30 mL). A white solid separated out, and the mixture was filtered by suction. The resulting filter cake was dried to give 2.0 g of the title compound as a white solid in a yield of 52.4%.

Intermediate 13: 3-bromo-N-(2-phenoxyethyl)aniline

Step 1: 2-phenoxyacetaldehyde

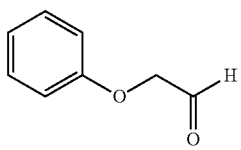

3-Phenoxypropane-1,2-diol (5.04 g, 30 mmol) was dissolved in DCM (90 mL). To the resulting mixture was slowly added sodium periodate (8.40 g, 39.3 mmol) in batches under the nitrogen protection and in an ice-water bath. Then the mixture was stirred and reacted at room temperature for 2 h. To the reaction mixture was added water (120 mL). The resulting mixture was extracted with DCM. The organic phases were concentrated under vacuum to produce 3.63 g of the title compound as a light yellow oil in a yield of 89.0%.

Step 2: 3-bromo-N-(2-phenoxyethyl)aniline

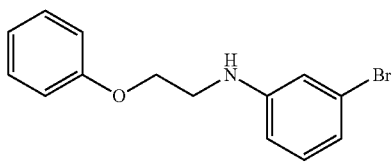 [SMILES: Brc1cccc(NCCOc2ccccc2)c1]

2-Phenoxyacetaldehyde (3.2 g, 23.5 mmol), 3-bromoaniline (4.25 g, 24.7 mmol), and acetic acid (5 mL) were dissolved in THF (50 mL). The resulting mixture was stirred at room temperature for 3 h. To the reaction mixture was added sodium triacetoxyborohydride (12.45 g, 58.75 mmol). The resulting mixture was stirred overnight. After the completion of the reaction, water was added. The mixture was extracted with DCM. The organic phases were concentrated under vacuum to produce 3.0 g of a yellow oil, which was directly used in the next step.

Intermediate 14: 3-bromo-N-((1-methyl-1H-pyrazol-5-yl)methyl)aniline

Step 1: 1-methyl-1H-pyrazole-5-carboxylic acid

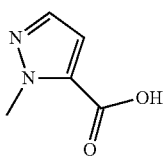

1-Methyl-1H-pyrazole (2.0 g, 24.4 mmol) was dissolved in THF (30 mL) at room temperature. The mixture was cooled to −78° C. under the nitrogen protection. To the resulting mixture was slowly added n-BuLi (10.72 mL, 26.8 mmol). The resulting mixture was stirred for 2 h at −78° C. and then warmed to room temperature. The mixture was stirred for another one hour. Then while the temperature was maintained, a dry CO2 gas was introduced to the reaction mixture for 5 min. To the resulting mixture was added water (30 mL) to quench the reaction and dilute the mixture. The resulting mixture was extracted with DCM. The pH of the aqueous phase was adjusted, and a large amount of the solid separated out. The mixture was filtered by suction. The filter cake was dried to produce 1.5 g of the title compound as a white solid in a yield of 48.8%.

Step 2: N-(3-bromophenyl)-1-methyl-1H-pyrazole-5-carboxamide

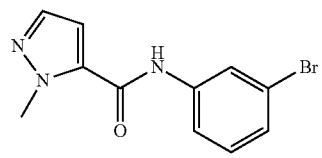 [SMILES: Cn1nccc1C(=O)Nc1cccc(Br)c1]

1-Methyl-1H-pyrazole-5-carboxylic acid (4 g, 31.7 mmol) and DMF (0.2 mL) were dissolved in EA (70 mL) at room temperature. The resulting mixture was warmed up to 35° C. To the warmed mixture were added dropwise SOCl2 (4 mL) and a solution of 3-bromoaniline (5.5 g, 31.7 mmol) in EA (20 mL) respectively. After the completion of the dropwise addition, the mixture was stirred and reacted for 14 h at 35° C. Then the resulting mixture was cooled to room temperature. To the cooled mixture was added water (60 mL). The resulting mixture was extracted with EA. The organic phases were concentrated under vacuum to give 6.0 g of the title compound as a yellow solid that was directly used in the next step.

Step 3: 3-bromo-N-((1-methyl-1H-pyrazol-5-yl)methyl)aniline

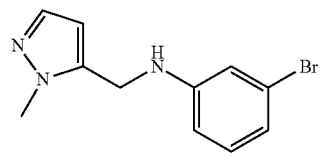

N-(3-bromophenyl)-1-methyl-1H-pyrazole-5-carboxamide (1.0 g, 3.6 mmol) was dissolved in THF (20 mL) at room temperature. To the mixture was added LiAlH4 (0.35 g, 9 mmol) in batches in an ice-water bath. After the completion of the addition, the mixture was stirred and reacted at 40° C. for 14 h. After the completion of reaction, water was added to quench the reaction, and the reaction mixture was extracted with EA. The organic phases were concentrated under vacuum to produce 0.8 g of the title compound as a yellow solid in a yield of 83.5%.

Intermediate 15: N-(3-bromobenzyl)-3-(1H-imidazol-1-yl)propan-1-amine

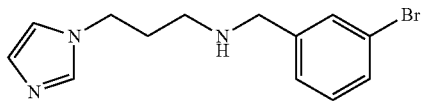 [SMILES: Brc1cccc(CNCCCn2ccnc2)c1]

3-Bromobenzaldehyde (2.0 g, 10.8 mmol) and 3-(1H-imidazol-1-yl)propan-1-amine (1.48 g, 11.8 mmol) were dissolved in MeOH (20 mL) at room temperature. The mixture was cooled to 0° C. in an ice bath. To the cooled mixture was slowly added sodium cyanoborohydride (1.0 g, 16.2 mmol) in batches. After the completion of the addition, the mixture was reacted at room temperature for 3 h. The resulting mixture was concentrated, and then water (100 mL) was added. The resulting mixture was extracted with DCM. The resulting organic phases were concentrated to give a crude product. The crude product was purified by silica gel column chromatography (DCM/MeOH=10/1) to afford 1.57 g of the title compound as a yellow oil in a yield of 49.4%.

Intermediate 16: N-(4-iodophenyl)isobutyramide

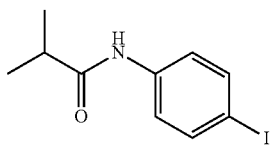

4-Iodoaniline (5.0 g, 22.8 mmol) was dissolved in acetonitrile (25 mL). The resulting mixture was cooled to below 0° C. To the cooled mixture was added pyridine (1.85 mL). Then to the resulting mixture was added dropwise isobutyryl chloride (2.3 mL, 22.8 mmol). After the completion of the dropwise addition, the mixture was reacted for 3 h. After the completion of the reaction, the reaction mixture was poured into ice-water (70 mL). A solid separated out. The mixture was filtered by suction. The filter cake was dried to afford 6.4 g of the title compound as a white solid in a yield of 97.1%.

Intermediate 17: 1-(4-iodophenyl)pyrrolidin-2-one

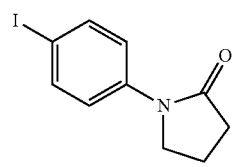 [SMILES: O=C1CCCN1c1ccc(I)cc1]

To a flask were successively added N-phenylpyrrolidin-2-one (5.0 g, 31 mmol), NIS (10.4 g, 46 mmol), cesium carbonate (340 mg), and acetic acid (100 mL) at room temperature. The resulting mixture was warmed up to 100° C., and reacted for 4 h. The reaction mixture was poured into water (650 mL). The resulting mixture was extracted with EA. The organic phases were washed with a saturated aqueous sodium bicarbonate solution and water, dried over anhydrous sodium sulfate and filtered by suction. The filtrate was concentrated to give 6.15 g of the title compound as a brown yellow solid in a yield of 69.1%.

Intermediate 18: ethyl 2-(4-aminophenoxy)acetate

Step 1: ethyl 2-(4-nitrophenoxy)acetate

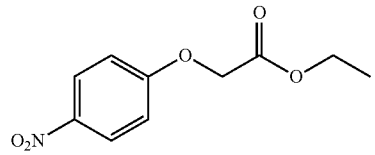 [SMILES: CCOC(=O)COc1ccc([N+](=O)[O-])cc1]

4-Nitrophenol (5.0 g, 36.0 mL), ethyl chloroacetate (8.8 g, 72.0 mmol) and triethylamine (9.1 g, 90.0 mmol) were successively added into acetonitrile (30 mL) at room temperature. After the completion of the addition, the resulting mixture was warmed up to 80° C. with stirring and reacted for 6 h. After the completion of the reaction, the mixture was concentrated under vacuum. Water was added to the residue. The resulting mixture was extracted with EA. The organic phases were concentrated under vacuum to dryness to afford 6.0 g of the title compound as a light yellow solid in a yield of 74.1%.

Step 2: ethyl 2-(4-aminophenoxy)acetate

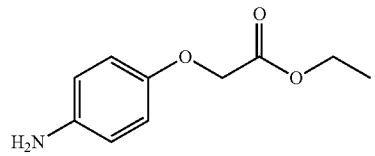

Ethyl 2-(4-nitrophenoxy)acetate (6.0 g, 26.6 mmol) and Pd/C (1.0 g) were added to methanol (30 mL) at room temperature. The mixture was hydrogenated at room temperature for 2 h. After the completion of the reaction, the resulting mixture was filtered. The filtrate was concentrated under vacuum to afford 5.0 g of the title compound in a yield of 95.9%.

Intermediate 19: N-(4-iodophenyl)-N-methylisobutyramide

Step 1: N-(4-iodophenyl)isobutyramide

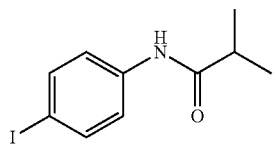

4-Iodoaniline (5.0 g, 22.8 mmol) and triethylamine (2.42 g, 24.0 mmol) were successively added into acetonitrile (45 mL) at room temperature. The mixture was cooled to 0 to 5° C. with stirring. To the cooled mixture was added dropwise isobutyryl chloride (2.55 g, 24.0 mmol). After the completion of the dropwise addition, the resulting mixture was stirred for 0.5 h while the temperature was maintained. After the completion of the reaction, water was added to the mixture. A solid separated out. The mixture was filtered and dried to produce 6.2 g of the title compound in a yield of 94.1%.

Step 2: N-(4-iodophenyl)-N-methylisobutyramide

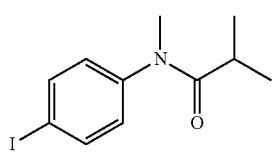

At room temperature, N-(4-iodophenyl)isobutyramide (5.78 g, 20 mmol) and potassium tert-butoxide (6.73 g, 60 mmol) were added to THF (50 mL). Then to the mixture was added dropwise iodomethane (5.67 g, 40 mmol) with stirring. Then the mixture was stirred at room temperature for 2 h. After the completion of the reaction, the reaction mixture was poured into an aqueous 5% hydrochloric acid solution (100 ml). The resulting mixture was extracted with EA. The organic phases were concentrated to afford 5.3 g of the title compound in a yield of 87.4%.

Intermediate 20: 4-ethoxy-3-fluoroaniline

Step 1: 1-ethoxy-2-fluoro-4-nitrobenzene

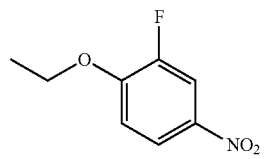

At room temperature, 2-fluoro-4-nitrophenol (5.0 g, 31.8 mmol), bromoethane (8.67 g, 79.6 mmol) and triethylamine (8.05 g, 79.6 mmol) were successively added into acetonitrile (40 mL). After the completion of the addition, the mixture was warmed up to 50° C., and stirred and reacted for 6 h. After the completion of the reaction, the reaction mixture was concentrated under vacuum. Water was added to the residue. The resulting mixture was extracted with EA. The organic phases were concentrated under vacuum to produce 5.3 g of the title compound as a light yellow solid in a yield of 89.9%.

Step 2: 4-ethoxy-3-fluoroaniline

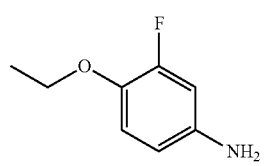

1-Ethoxy-2-fluoro-4-nitrobenzene (5.3 g, 28.6 mmol) and Pd/C (0.75 g) were successively added to methanol (100 mL) at room temperature. The mixture was hydrogenated at room temperature for 2 h. After the completion of the reaction, the reaction mixture was filtered. The filtrate was concentrated under vacuum to afford 3.9 g of the title compound as an oil in a yield of 88.6%.

Intermediate 21: 3-(ethoxymethyl)aniline

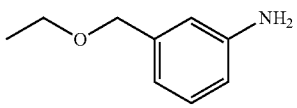

(3-Nitrophenyl)methanol (3.3 g, 21.5 mmol), bormoethane (3.5 g, 32.3 mmol), and potassium hydroxide (2.4 g, 43.0 mmol) were successively added to DMSO (20 mL) at room temperature. After the completion of the addition, the mixture was stirred and reacted at room temperature for 6 h. After the completion of the reaction, water and EA were added to the reaction mixture. The resulting mixture was stirred and left to stand to form an aqueous phase and an organic phase. The aqueous phase was extracted with EA. The combined organic phases were concentrated under vacuum. To the residue were successively added water (30 mL), THF (30 mL), Fe powder (3.6 g, 64.5 mmol) and ammonia chloride (0.5 g). After the completion of the addition, the mixture was warmed up to 75° C. and reacted for 1 h. After the completion of the reaction, the reaction mixture was cooled to room temperature. The resulting mixture was extracted with EA. The organic phases were concentrated under vacuum to afford 3.3 g of the title compound as an oil.

Intermediate 22: ethyl 6-(4-iodophenyl)-1-(4-methoxyphenyl)-7-oxo-4,5,6,7-tetrahydro-1H-pyrazolo[3,4-c]pyridine-3-carboxylate

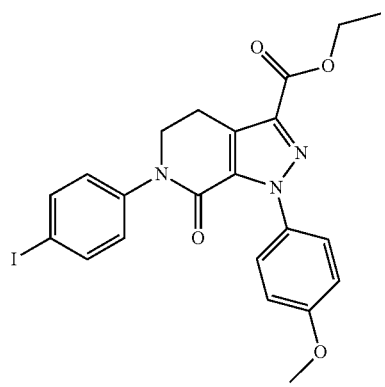 [SMILES: CCOC(=O)c1nn(-c2ccc(OC)cc2)c2c1CCN(c1ccc(I)cc1)C2=O]

Ethyl 6-(4-aminophenyl)-1-(4-methoxyphenyl)-7-oxo-4,5,6,7-tetrahydro-1H-pyrazolo[3,4-c]pyridine-3-carboxylate (8.0 g, 19.7 mmol) and concentrated hydrochloric acid (3.3 mL, 39.4 mmol) were added to water (100 mL) at room temperature. The mixture was stirred and cooled to 0 to 5° C. To the cooled mixture was added sodium nitrite (1.63 g, 23.6 mmol) in batches. After the completion of the addition, the mixture was stirred at 5-10° C. for 1 h. Then to the mixture was added sodium iodide (4.43 g, 29.6 mmol), and the resulting mixture was stirred at room temperature for 4 h. After the completion of the reaction, the reaction mixture was extracted with ethyl acetate. The organic phases were concentrated under vacuum to give a crude product. The crude product was purified by silica gel column chromatography (PE:EA=1:1) to give 5.2 g of the title compound in a yield of 51.0%.

Example 1

6-(4-((3-(dimethylamino)propyl)amino)phenyl)-1-(4-methoxyphenyl)-7-oxo-4,5,6,7-tetrahydro-1H-pyrazolo[3,4-c]pyridine-3-carboxamide Step 1: ethyl 2-chloro-2-(2-(4-methoxyphenyl)hydrazono)acetate

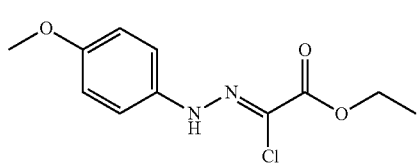 [SMILES: CCOC(=O)/C(Cl)=N/Nc1ccc(OC)cc1]

To a flask were successively added 4-methoxyaniline (30.0 g, 244 mmol) and water (100 mL) at room temperature. The mixture was stirred and cooled to −5 to 0° C. To the resulting mixture were successively added concentrated hydrochloric acid (35 mL) and an aqueous sodium nitrite solution (50 mL). After the completion of the addition, the mixture was stirred for 0.5 h, while the temperature was maintained. To the mixture were added dropwise a solution of ethyl 2-chloro-3-oxobutanoate (40.2 g, 244 mmol) in ethanol (200 mL) and a solution of sodium acetate (60.0 g, 732 mmol) in water (500 mL). After the completion of the dropwise addition, the mixture was stirred for 0.5 h at −5 to 0° C. Then the mixture was warmed to room temperature, and stirred and reacted for 6 h. After the completion of the reaction, the reaction mixture was filtered. The filter cake was dried under vacuum and purified by silica gel column chromatography (PE:EA=10:1) to give 31.6 g of the title compound in a yield of 50.4%.

Step 2: ethyl 1-(4-methoxyphenyl)-7-oxo-4,5,6,7-tetrahydro-1H-pyrazolo[3,4-c]pyridine-3-carboxylate

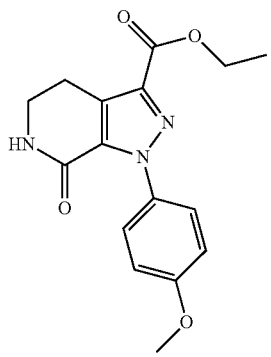 [SMILES: CCOC(=O)c1nn(-c2ccc(OC)cc2)c2c1CCNC2=O]

To a flask were successively added toluene (500 mL), 3-chloro-5,6-dihydropyridin-2(1H)-one (35 g, crude product), ethyl 2-chloro-2-(2-(4-methoxyphenyl)hydrazono)acetate (30.8 g, 0.120 mmol) and triethylamine (24.2 g, 0.240 mmol) at room temperature. The resulting mixture was heated to reflux with stirring, and reacted under reflux for 12 h. The reaction mixture was cooled to room temperature and poured into a solution of EA (500 mL) in water (500 mL). The mixture was filtered by suction. The filter cake was dried under vacuum to produce 25.0 g of the title compound as a yellow solid in a yield of 66.1%.

Step 3: ethyl 6-(4-((tert-butoxycarbonyl)(3-(dimethylamino)propyl)amino)phenyl)-1-(4-methoxyphenyl)-7-oxo-4,5,6,7-tetrahydro-1H-pyrazolo[3,4-c]pyridine-3-carboxylate

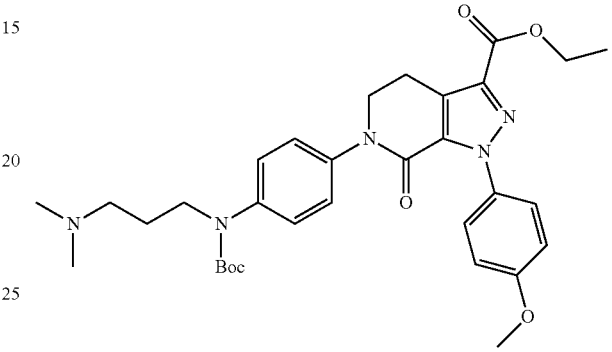

tert-Butyl (3-(dimethylamino)propyl)(4-iodophenyl)carbamate (930 mg, 2.30 mmol), ethyl 1-(4-methoxyphenyl)-7-oxo-4,5,6,7-tetrahydro-1H-pyrazolo[3,4-c]pyridine-3-carboxylate (604 mg, 1.92 mmol), potassium carbonate (530 mg, 3.83 mmol), 1,10-phenanthroline (138 mg, 0.77 mmol) and cupric iodide (73 mg, 0.38 mmol) were successively dispersed in DMSO (10 mL) at room temperature. The mixture was heated to 120° C., and stirred and reacted for 14 h under the nitrogen protection. After the completion of the reaction, the reaction mixture was cooled and poured into ice-water (50 mL). The resulting mixture was extracted with DCM. The organic phases were concentrated under vacuum to give a crude product. The crude product was purified by silica gel column chromatography (DCM:MeOH=20:1) to give 1.0 g of the title compound as a brown oil in a yield of 88.0%.

Step 4: tert-butyl (4-(3-carbamoyl-1-(4-methoxyphenyl)-7-oxo-4,5-dihydro-1H-pyrazolo[3,4-c]pyridin-6(7H)-yl)phenyl)(3-(dimethylamino)propyl)carbamate

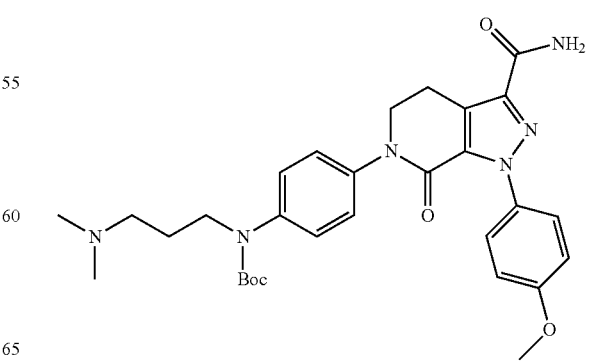

Ethyl 6-(4-((tert-butoxycarbonyl)(3-(dimethylamino)propyl)amino)phenyl)-1-(4-methoxyphenyl)-7-oxo-4,5,6,7-tetrahydro-1H-pyrazolo[3,4-c]pyridine-3-carboxylate (600 mg, 1.01 mmol) was dissolved in an ammonia gas/ethylene glycol solution (15 mL) at room temperature. The mixture was placed in a seal tube and kept in a sealing condition, and reacted at 100° C. for 14 h. After the completion of the reaction, the reaction mixture was poured into ice-water (100 mL). The resulting mixture was extracted with DCM. The organic phases were concentrated under vacuum to give a crude product. The crude product was purified by silica gel column chromatography (DCM:MeOH=50:1) to give 250 mg of the title compound as a yellow oil in a yield of 44.0%.

Step 5: 6-(4-((3-(dimethylamino)propyl)amino)phenyl)-1-(4-methoxyphenyl)-7-oxo-4,5,6,7-tetrahydro-1H-pyrazolo[3,4-c]pyridine-3-carboxamide

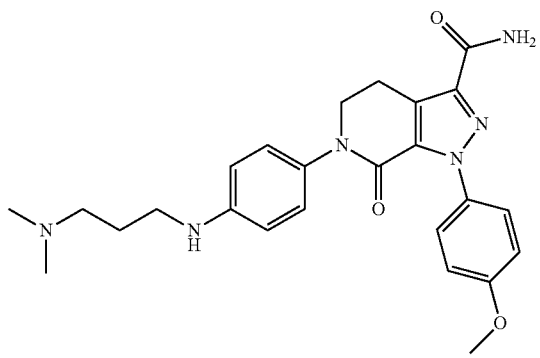 [SMILES: COc1ccc(-n2nc(C(N)=O)c3c2C(=O)N(c2ccc(NCCCN(C)C)cc2)CC3)cc1]

Tert-Butyl (4-(3-carbamoyl-1-(4-methoxyphenyl)-7-oxo-4,5-dihydro-1H-pyrazolo[3,4-c]pyridin-6(7H)-yl)phenyl)(3-(dimethylamino)propyl)carbamate (250 mg, 0.44 mmol) was dissolved in an HCl/EA solution (10 mL). The mixture was reacted at room temperature for 14 h, and then adjusted to a neutral pH with an aqueous sodium hydroxide solution. The resulting mixture was concentrated under vacuum to produce a grey solid. The resulting solid was purified by silica gel column chromatography (DCM:MeOH=20:1) to give 180 mg of the title compound as a white solid in a yield of 88.5%.

$^1$H-NMR (400 MHz, DMSO_d6&D$_2$O) δ: 7.52-7.46 (m, 2H), 7.23-7.17 (m, 2H), 7.03-6.97 (m, 2H), 6.91-6.84 (m, 2H), 3.97 (t, 2H), 3.80 (s, 3H), 3.23-3.11 (m, 6H), 2.77 (s, 6H), 2.02-1.90 (m, 2H);

MS 463 [M+H]$^+$.

Example 2: 1-(4-methoxyphenyl)-6-(4-(3-(methylamino)propoxy)phenyl)-7-oxo-4,5,6,7-tetrahydro-1H-pyrazolo[3,4-c]pyridine-3-carboxamide Step 1: ethyl 6-(4-(3-((tert-butoxycarbonyl)(methyl)amino)propoxy)phenyl)-1-(4-methoxyphenyl)-7-oxo-4,5,6,7-tetrahydro-1H-pyrazolo[3,4-c]pyridine-3-carboxylate

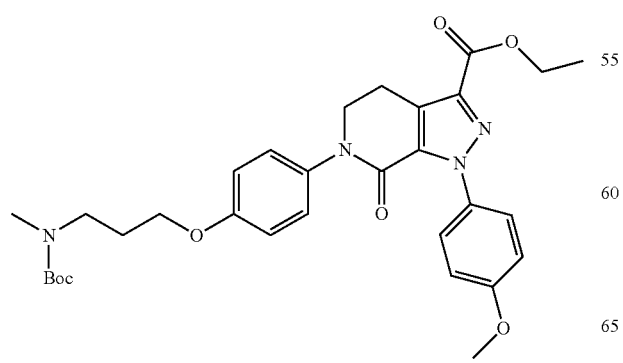

Tert-Butyl (3-(4-iodophenoxy)propyl)(methyl)carbamate (932 mg, 2.38 mmol), ethyl 1-(4-methoxyphenyl)-7-oxo-4,5,6,7-tetrahydro-1H-pyrazolo[3,4-c]pyridine-3-carboxylate (500 mg, 1.59 mmol), potassium carbonate (438 mg, 3.18 mmol), 1,10-phenanthroline (114 mg, 0.64 mmol) and cupric iodide (60 mg, 0.32 mmol) were successively dispersed in DMSO (10 mL) at room temperature. The mixture was heated to 120° C. and stirred and reacted for 14 h under the nitrogen protection. The reaction mixture was cooled, and poured into ice-water (50 mL). The resulting mixture was extracted with DCM. The organic phases were concentrated under vacuum to give a crude product. The crude product was purified by silica gel column chromatography (DCM:MeOH=50:1) to give 600 mg of the title compound as a yellow oil in a yield of 65.2%.

Step 2: tert-butyl (3-(4-(3-carbamoyl-1-(4-methoxyphenyl)-7-oxo-4,5-dihydro-1H-pyrazolo[3,4-c]pyridin-6(7H)-yl)phenoxy)propyl)(methyl)carbamate

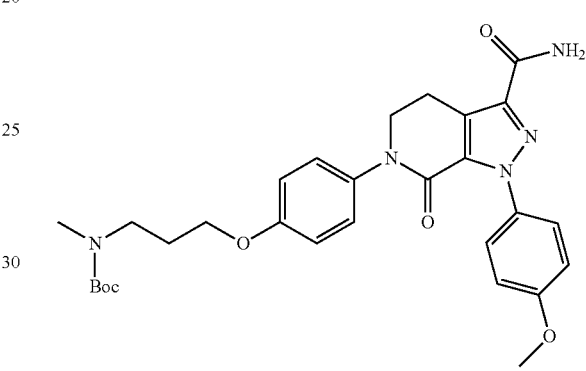

Ethyl 6-(4-(3-((tert-butoxycarbonyl)(methyl)amino)propoxy)phenyl)-1-(4-methoxyphenyl)-7-oxo-4,5,6,7-tetrahydro-1H-pyrazolo[3,4-c]pyridine-3-carboxylate (400 mg, 0.69 mmol) was dissolved in an ammonia gas/EG solution (15 mL) at room temperature. The mixture was placed in a seal tube and kept in a sealing condition, and reacted at 100° C. for 14 h. After the completion of the reaction, the reaction mixture was poured into ice-water (100 mL). The resulting mixture was extracted with DCM. The organic phases were concentrated under vacuum to produce 330 mg of the title compound as a yellow solid, which was used in the next step without purification.

Step 3: 1-(4-methoxyphenyl)-6-(4-(3-(methylamino)propoxy)phenyl)-7-oxo-4,5,6,7-tetrahydro-1H-pyrazolo[3,4-c]pyridine-3-carboxamide

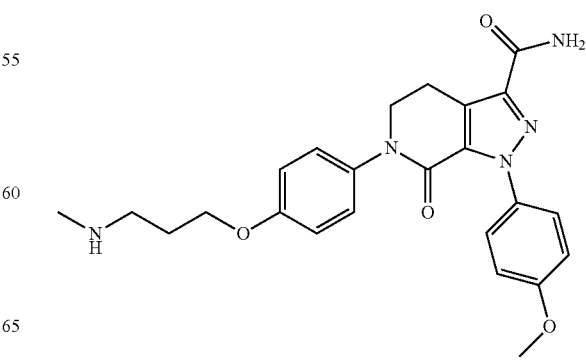

Tert-Butyl (3-(4-(3-carbamoyl-1-(4-methoxyphenyl)-7-oxo-4,5-dihydro-1H-pyrazolo[3,4-c]pyridin-6(7H)-yl)phenoxy)propyl)(methyl)carbamate (300 mg, 0.55 mmol) was dissolved in an HCl/EA solution (10 mL). The mixture was reacted at room temperature for 14 h, and then adjusted to a neutral pH with an aqueous sodium hydroxide solution. The resulting mixture was concentrated under vacuum. The residue was purified by silica gel column chromatography (DCM:MeOH=20:1) to give 220 mg of the title compound as a white solid in a yield of 89.1%.

¹H-NMR (400 MHz, DMSO_d6) δ: 8.61 (brs, 2H), 7.71 (s, 1H), 7.52-7.41 (m, 2H), 7.43 (s, 1H), 7.30-7.24 (m, 2H), 7.03-6.92 (m, 4H), 4.06 (t, 2H), 3.98 (t, 2H), 3.80 (s, 3H), 3.19 (t, 2H), 3.09-3.00 (m, 2H), 2.58 (t, 3H), 2.10-2.01 (m, 2H);

MS 450 [M+H]⁺.

Example 3: 6-(3-fluoro-4-((2-methoxyethyl)amino)phenyl)-1-(4-methoxyphenyl)-7-oxo-4,5,6,7-tetrahydro-1H-pyrazolo[3,4-c]pyridine-3-carboxamide Step 1: ethyl 6-(4-((tert-butoxycarbonyl)(2-methoxyethyl)amino)-3-fluorophenyl)-1-(4-methoxyphenyl)-7-oxo-4,5,6,7-tetrahydro-1H-pyrazolo[3,4-c]pyridine-3-carboxylate

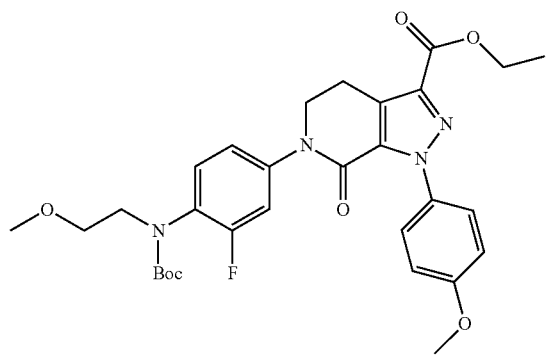 [SMILES: CCOC(=O)c1nn(-c2ccc(OC)cc2)c2c1CCN(c1ccc(N(CCOC)C(=O)OC(C)(C)C)c(F)c1)C2=O]

Tert-Butyl (4-bromo-2-fluorophenyl)(2-methoxyethyl)carbamate (862 mg, 2.48 mmol), ethyl 1-(4-methoxyphenyl)-7-oxo-4,5,6,7-tetrahydro-1H-pyrazolo[3,4-c]pyridine-3-carboxylate (600 mg, 1.91 mmol), potassium carbonate (1050 mg, 7.62 mmol), potassium iodide (700 mg, 4.22 mmol), cupric iodide (145 mg, 0.76 mmol) and N,N'-dimethyl-1,2-ethanediamine (84 mg, 0.95 mmol) were successively dissolved in DMSO (10 mL) at room temperature. The mixture was heated to 120° C. and stirred overnight under the nitrogen protection. Then the reaction mixture was cooled to room temperature, and poured into ice-water (50 mL). The resulting mixture was extracted with DCM. The organic phases were concentrated under vacuum to give a crude product. The crude product was purified by silica gel column chromatography (DCM:MeOH=80:1) to give 1.0 g of the title compound as a yellow solid in a yield of 89.9%.

Step 2: tert-butyl (4-(3-carbamoyl-1-(4-methoxyphenyl)-7-oxo-4,5-dihydro-1H-pyrazolo[3,4-c]pyridin-6(7H)-yl)-2-fluorophenyl)(2-methoxyethyl)carbamate

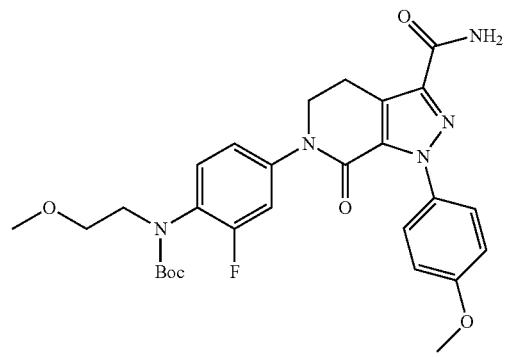 [SMILES: COCCN(C(=O)OC(C)(C)C)c1ccc(N2CCc3c(C(N)=O)nn(-c4ccc(OC)cc4)c3C2=O)cc1F]

Ethyl 6-(4-((tert-butoxycarbonyl)(2-methoxyethyl)amino)-3-fluorophenyl)-1-(4-methoxyphenyl)-7-oxo-4,5,6,7-tetrahydro-1H-pyrazolo[3,4-c]pyridine-3-carboxylate (1.0 g, 1.72 mmol) was dissolved in an ammonia gas/EG solution (15 mL) at room temperature. The mixture was placed in a seal tube and kept in a sealing condition, and reacted at 100° C. for 14 h. After the completion of the reaction, the reaction mixture was poured into ice-water (100 mL). The resulting mixture was extracted with DCM. The organic phases were concentrated under vacuum to produce 800 mg of the title compound as a yellow solid, which was used in the next step without purification.

Step 3: 6-(3-fluoro-4-((2-methoxyethyl)amino)phenyl)-1-(4-methoxyphenyl)-7-oxo-4,5,6,7-tetrahydro-1H-pyrazolo[3,4-c]pyridine-3-carboxamide

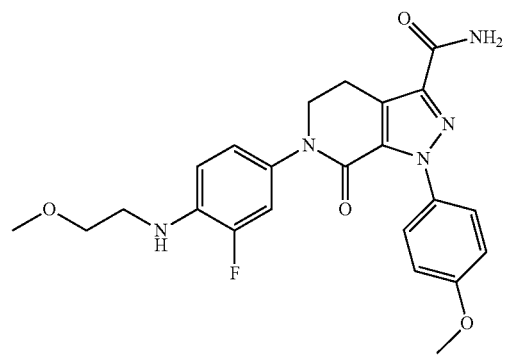 [SMILES: COCCNc1ccc(N2CCc3c(C(N)=O)nn(-c4ccc(OC)cc4)c3C2=O)cc1F]

Tert-Butyl (4-(3-carbamoyl-1-(4-methoxyphenyl)-7-oxo-4,5-dihydro-1H-pyrazolo[3,4-c]pyridin-6(7H)-yl)-2-fluorophenyl)(2-methoxyethyl)carbamate (300 mg, 0.54 mmol) was dissolved in an HCl/EA solution (10 mL). The mixture was reacted at room temperature for 14 h, and then adjusted to a neutral pH with an aqueous sodium hydroxide solution. The resulting mixture was concentrated under vacuum. The residue was purified by silica gel column chromatography (DCM:MeOH=25:1) to give 220 mg of the title compound as a white solid in a yield of 90.0%.

¹H-NMR (400 MHz, DMSO_d6) δ: 7.69 (s, 1H), 7.53-7.46 (m, 2H), 7.42 (s, 1H), 7.09 (dd, 1H), 7.03-6.95 (m, 3H), 6.77 (t, 1H), 5.80 (br s, 4H), 3.95 (t, 2H), 3.80 (s, 3H), 3.49 (t, 2H), 3.27 (t, 5H), 3.17 (t, 2H);
MS 454 [M+H]⁺.

Example 4: 6-(4-(4-aminobutanamido)-3-methylphenyl)-1-(4-methoxyphenyl)-7-oxo-4,5,6,7-tetrahydro-1H-pyrazolo[3,4-c]pyridine-3-carboxamide Step 1: ethyl 6-(4-(4-((tert-butoxycarbonyl)amino)butanamido)-3-methylphenyl)-1-(4-methoxyphenyl)-7-oxo-4,5,6,7-tetrahydro-1H-pyrazolo[3,4-c]pyridine-3-carboxylate

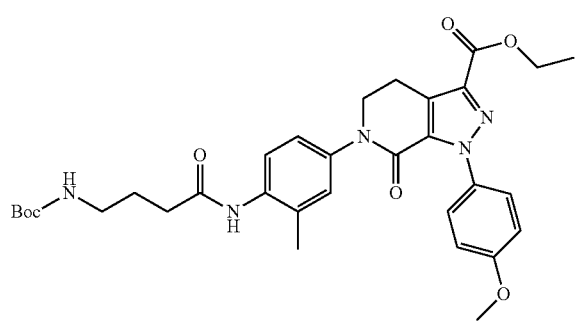 [SMILES: CCOC(=O)c1nn(-c2ccc(OC)cc2)c2c1CCN(c1ccc(NC(=O)CCCNC(=O)OC(C)(C)C)c(C)c1)C2=O]

Tert-Butyl (4-((4-iodo-2-methylphenyl)amino)-4-oxobutyl)carbamate (1.27 g, 3.0 mmol), potassium carbonate (0.7 g, 5.0 mmol), ethyl 1-(4-methoxyphenyl)-7-oxo-4,5,6,7-tetrahydro-1H-pyrazolo[3,4-c]pyridine-3-carboxylate (0.8 g, 2.5 mmol), cupric iodide (0.12 g, 0.63 mmol) and 1,10-phenanthroline (0.18 g, 10 mmol) were successively dissolved in DMSO (10 mL) at room temperature. The mixture was heated to 120° C., and stirred and reacted for 14 h under the nitrogen protection. The reaction mixture was cooled to room temperature, and poured into ice-water (40 mL). The resulting mixture was extracted with EA. The organic phases were concentrated under vacuum to give a crude product. The crude product was purified by silica gel column chromatography (DCM:MeOH=50:1) to give 0.72 g of the title compound as a yellow solid in a yield of 47.5%.

Step 2: tert-butyl (4-((4-(3-carbamoyl-1-(4-methoxyphenyl)-7-oxo-4,5-dihydro-1H-pyrazolo[3,4-c]pyridin-6(7H)-yl)-2-methylphenyl)amino)-4-oxobutyl)carbamate

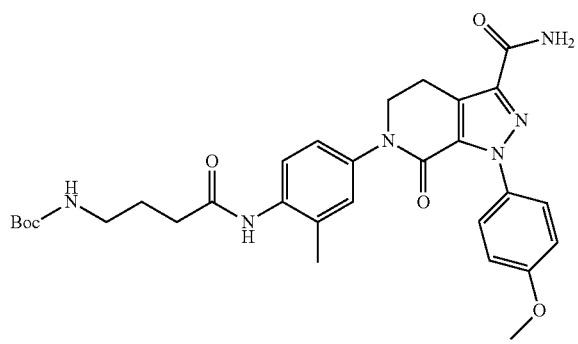 [SMILES: COc1ccc(-n2nc(C(N)=O)c3c2C(=O)N(c2ccc(NC(=O)CCCNC(=O)OC(C)(C)C)c(C)c2)CC3)cc1]

Ethyl 6-(4-(4-((tert-butoxycarbonyl)amino)butanamido)-3-methylphenyl)-1-(4-methoxyphenyl)-7-oxo-4,5,6,7-tetrahydro-1H-pyrazolo[3,4-c]pyridine-3-carboxylate (0.72 g, 1.18 mmol) was dissolved in an ammonia gas/EG solution (15 mL) at room temperature. The mixture was placed in a seal tube and kept in a sealing condition, and reacted at 100° C. for 14 h. The reaction mixture was cooled to room temperature, and poured into water (30 mL). The resulting mixture was extracted with EA. The organic phases were concentrated under vacuum to give a crude product. The crude product was purified by prep-HPLC to yield 400 mg of the title compound as a yellow solid in a yield of 58.8%.

Step 3: 6-(4-(4-aminobutanamido)-3-methylphenyl)-1-(4-methoxyphenyl)-7-oxo-4,5,6,7-tetrahydro-1H-pyrazolo[3,4-c]pyridine-3-carboxamide

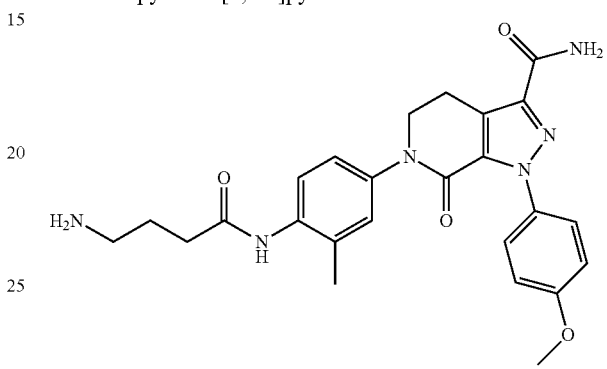

Tert-Butyl (4-((4-(3-carbamoyl-1-(4-methoxyphenyl)-7-oxo-4,5-dihydro-1H-pyrazolo[3,4-c]pyridin-6(7H)-yl)-2-methylphenyl)amino)-4-oxobutyl)carbamate (400 mg, 0.69 mmol) was dissolved in an HCl/EA solution (10 mL). The mixture was stirred at room temperature for 2 h, and then concentrated. The residue was dissolved in water. The resulting mixture was purified by prep-HPLC to yield 200 mg of the title compound as a flesh-color solid in a yield of 60.6%.

¹H-NMR (400 MHz, DMSO-d6) δ: 9.37 (br s, 1H), 7.72 (s, 1H), 7.49 (d, 2H), 7.44 (s, 1H), 7.37 (d, 1H), 7.19 (s, 1H), 7.13 (d, 1H), 7.00 (d, 2H), 4.04-4.00 (m, 2H), 3.81 (s, 3H), 3.21-3.18 (m, 2H), 2.65-2.62 (m, 2H), 2.39-2.36 (m, 2H), 2.18 (s, 3H), 1.75-1.69 (m, 2H).
MS 477 [M+H]⁺.

Example 5: 6-(3-(ethylamino)-4-propoxyphenyl)-1-(4-methoxyphenyl)-7-oxo-4,5,6,7-tetrahydro-1H-pyrazolo[3,4-c]pyridine-3-carboxamide Step 1: ethyl 6-(3-(ethylamino)-4-propoxyphenyl)-1-(4-methoxyphenyl)-7-oxo-4,5,6,7-tetrahydro-1H-pyrazolo[3,4-c]pyridine-3-carboxylate

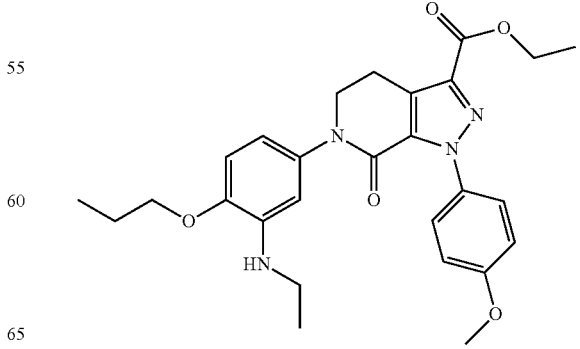

N-ethyl-5-iodo-2-propoxyaniline (0.94 g, 3.1 mmol), ethyl 1-(4-methoxyphenyl)-7-oxo-4,5,6,7-tetrahydro-1H-pyrazolo[3,4-c]pyridine-3-carboxylate (0.69 g, 2.2 mmol), 1,10-phenanthroline (0.16 g, 0.88 mmol) and potassium carbonate (0.61 g, 4.4 mmol) were successively added to DMSO (5 mL) at room temperature. The mixture was heated to 120° C. and stirred and reacted for 14 h under the nitrogen protection. The reaction mixture was cooled to room temperature, and then poured into ice-water (50 mL). The resulting mixture was extracted with EA. The organic phases were concentrated under vacuum to give a crude product. The crude product was purified by prep-HPLC to yield 400 mg of the title compound as a yellow solid in a yield of 36.9%.

Step 2: 6-(3-(ethylamino)-4-propoxyphenyl)-1-(4-methoxyphenyl)-7-oxo-4,5,6,7-tetrahydro-1H-pyrazolo[3,4-c]pyridine-3-carboxamide

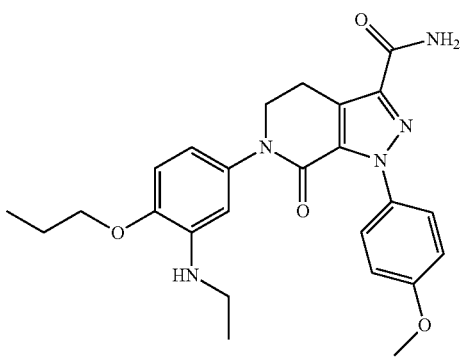 [SMILES: CCCOc1ccc(N2CCc3c(C(N)=O)nn(-c4ccc(OC)cc4)c3C2=O)cc1NCC]

Ethyl 6-(3-(ethylamino)-4-propoxyphenyl)-1-(4-methoxyphenyl)-7-oxo-4,5,6,7-tetrahydro-1H-pyrazolo[3,4-c]pyridine-3-carboxylate (250 mg, 0.51 mmol) was dissolved in an ammonia gas/EG solution at room temperature. The mixture was placed in a seal tube and kept in a sealing condition, and stirred and reacted at 100° C. for 14 h. The reaction mixture was cooled to room temperature, and then poured into water. The resulting mixture was extracted with EA. The organic phases were concentrated under vacuum to produce 150 mg of the title compound as a yellow solid in a yield of 63.5%.

$^1$H-NMR (400 MHz, DMSO-d6) δ: 7.69 (s, 1H), 7.48 (d, 2H), 7.42 (s, 1H), 6.99 (d, 2H), 6.67 (d, 1H), 6.48-6.44 (m, 2H), 4.64 (t, 1H), 3.97-3.89 (m, 4H), 3.80 (s, 3H), 3.18-3.15 (m, 2H), 3.08-3.04 (m, 2H), 1.77-1.72 (m, 2H), 1.14 (t, 3H), 0.99 (t, 3H).

MS 464 [M+H]$^+$.

Example 6: 1-(4-methoxyphenyl)-6-(4-((2-(methylamino)ethyl)amino)phenyl)-7-oxo-4,5,6,7-tetrahydro-1H-pyrazolo[3,4-c]pyridine-3-carboxamide Step 1: ethyl 6-(4-((2-((tert-butoxycarbonyl)(methyl)amino)ethyl)amino)phenyl)-1-(4-methoxyphenyl)-7-oxo-4,5,6,7-tetrahydro-1H-pyrazolo[3,4-c]pyridine-3-carboxylate

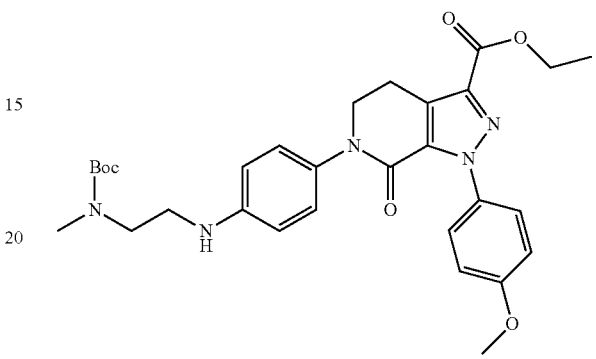

Tert-Butyl (2-((4-iodophenyl)amino)ethyl)(methyl)carbamate (1.14 g, 3.0 mmol), potassium carbonate (0.7 g, 5.0 mmol), ethyl 1-(4-methoxyphenyl)-7-oxo-4,5,6,7-tetrahydro-1H-pyrazolo[3,4-c]pyridine-3-carboxylate (0.8 g, 2.5 mmol), cupric iodide (0.1 g, 0.53 mmol) and 1,10-phenanthroline (0.18 g, 1.0 mmol) were successively added to DMSO (10 mL) at room temperature. The mixture was heated to 120° C. and stirred and reacted for 14 h under the nitrogen protection. The reaction mixture was cooled to room temperature, and then poured into ice-water (40 mL). The resulting mixture was extracted with EA. The organic phases were concentrated under vacuum to give a crude product. The crude product was purified by silica gel column chromatography (DCM:MeOH=50:1) to give 0.5 g of the title compound as a yellow solid in a yield of 35.5%.

Step 2: tert-butyl (2-((4-(3-carbamoyl-1-(4-methoxyphenyl)-7-oxo-4,5-dihydro-1H-pyrazolo[3,4-c]pyridin-6(7H)-yl)phenyl)amino)ethyl)(methyl)carbamate

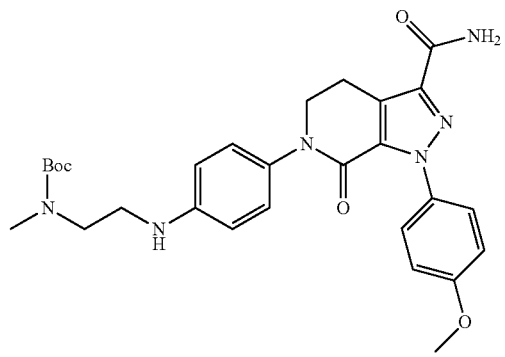 [SMILES: COc1ccc(-n2nc(C(N)=O)c3c2C(=O)N(c2ccc(NCCN(C)C(=O)OC(C)(C)C)cc2)CC3)cc1]

Ethyl 6-(4-((2-((tert-butoxycarbonyl)(methyl)amino)ethyl)amino)phenyl)-1-(4-methoxyphenyl)-7-oxo-4,5,6,7-tetrahydro-1H-pyrazolo[3,4-c]pyridine-3-carboxylate (0.5 g, 0.89 mmol) was dissolved in an ammonia gas/EG solution (10 mL) at room temperature. The mixture was placed in a seal tube and kept in a sealing condition, and stirred and reacted at 100° C. for 14 h. The reaction mixture was cooled to room temperature, and then poured into water (30 mL). The resulting mixture was extracted with EA. The organic phases were concentrated under vacuum to give a crude product. The crude product was purified by prep-HPLC to yield 406 mg of the title compound as a yellow solid in a yield of 85.3%.

Step 3: 1-(4-methoxyphenyl)-6-(4-((2-(methyl-amino)ethyl)amino)phenyl)-7-oxo-4,5,6,7-tetra-hydro-1H-pyrazolo[3,4-c]pyridine-3-carboxamide

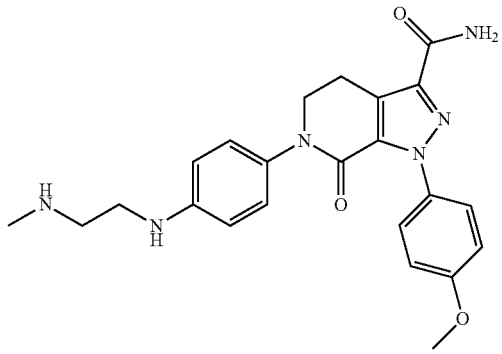 [SMILES: CNCCNc1ccc(N2CCc3c(C(N)=O)nn(-c4ccc(OC)cc4)c3C2=O)cc1]

Tert-Butyl (2-((4-(3-carbamoyl-1-(4-methoxyphenyl)-7-oxo-4,5-dihydro-1H-pyrazolo[3,4-c]pyridin-6(7H)-yl)phenyl)amino)ethyl)(methyl)carbamate (406 mg, 0.76 mmol) was dissolved in an HCl/EA solution (10 mL). The mixture was stirred and reacted at room temperature for 2 h, and adjusted to a neutral pH with an aqueous sodium hydroxide solution. The resulting mixture was concentrated under vacuum. The residue was purified by silica gel column chromatography (DCM:MeOH=20:1) to give 220 mg of the title compound as a lilac solid in a yield of 66.7%.

$^1$H-NMR (400 MHz, DMSO-d6&D$_2$O) δ: 7.48 (d, 2H), 7.12 (d, 2H), 7.01 (d, 2H), 6.69 (d, 2H), 3.96-3.93 (m, 2H), 3.81 (s, 3H), 3.38-3.35 (m, 2H), 3.19-3.16 (m, 2H), 3.10-3.07 (m, 2H), 2.59 (s, 3H).

MS 435 [M+H]$^+$

Example 7: 6-(3-chloro-4-((4-oxopentyl)oxy)phenyl)-1-(4-methoxyphenyl)-7-oxo-4,5,6,7-tetrahydro-1H-pyrazolo[3,4-c]pyridine-3-carboxamide Step 1: ethyl 6-(3-chloro-4-((4-oxopentyl)oxy)phenyl)-1-(4-methoxyphenyl)-7-oxo-4,5,6,7-tetrahydro-1H-pyrazolo[3,4-c]pyridine-3-carboxylate

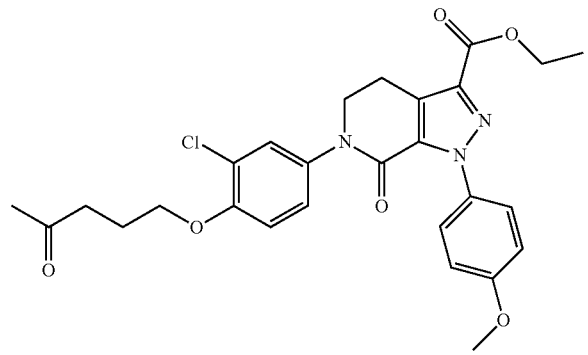 [SMILES: CCOC(=O)c1nn(-c2ccc(OC)cc2)c2c1CCN(c1ccc(OCCCC(C)=O)c(Cl)c1)C2=O]

5-(4-Bromo-2-chlorophenoxy)pentan-2-one (1.75 g, 6.0 mmol), potassium carbonate (2.54 g, 18.4 mmol), ethyl 1-(4-methoxyphenyl)-7-oxo-4,5,6,7-tetrahydro-1H-pyrazolo[3,4-c]pyridine-3-carboxylate (1.45 g, 4.6 mmol), cupric iodide (0.35 g, 1.84 mmol), N,N'-dimethyl-1,2-ethanediamine (200 mg, 2.3 mmol) and potassium iodide (1.68 g, 10.1 mmol) were successively added to DMSO (10 mL) at room temperature. The mixture was heated to 120° C. and stirred and reacted for 14 h under the nitrogen protection. The reaction mixture was poured into ice-water (100 mL). The resulting mixture was extracted with EA. The organic phases were concentrated under vacuum to give a crude product. The crude product was purified by prep-HPLC to yield 280 mg of the title compound as a white solid in a yield of 8.9%.

Step 2: 6-(3-chloro-4-((4-oxopentyl)oxy)phenyl)-1-(4-methoxyphenyl)-7-oxo-4,5,6,7-tetrahydro-1H-pyrazolo[3,4-c]pyridine-3-carboxamide

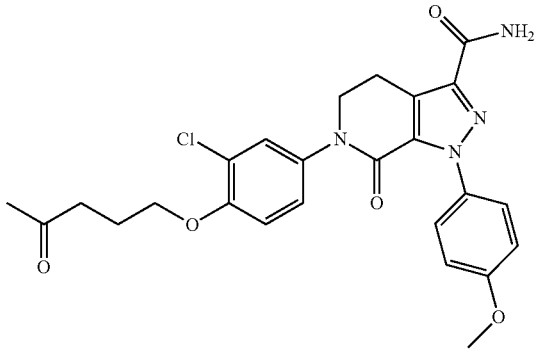 [SMILES: COc1ccc(-n2nc(C(N)=O)c3c2C(=O)N(c2ccc(OCCCC(C)=O)c(Cl)c2)CC3)cc1]

Ethyl 6-(3-chloro-4-((4-oxopentyl)oxy)phenyl)-1-(4-methoxyphenyl)-7-oxo-4,5,6,7-tetrahydro-1H-pyrazolo[3,4-c]pyridine-3-carboxylate (270 mg, 0.51 mmol) was dissolved in an ammonia gas/EG solution. The mixture was placed in a seal tube and kept in a sealing condition, and stirred and reacted at 100° C. for 14 h. The reaction mixture was poured into water (30 mL). The resulting mixture was extracted with EA. The organic phases were concentrated under vacuum to produce 150 mg of the title compound as a light yellow solid in a yield of 59.2%.

$^1$H-NMR (400 MHz, DMSO-d6) δ: 7.71 (s, 1H), 7.55-7.35 (m, 4H), 7.27 (dd, 1H), 7.14 (d, 1H), 7.00 (d, 2H), 4.05-3.97 (m, 4H), 3.80 (s, 3H), 3.21-3.17 (m, 2H), 2.62 (t, 2H), 2.12 (s, 3H), 1.95-1.91 (m, 2H)

MS: 497.8 [M+H]$^+$

Example 8: 1-(4-methoxyphenyl)-6-(4-(4-methyl-piperazin-1-yl)phenyl)-7-oxo-4,5,6,7-tetrahydro-1H-pyrazolo[3,4-c]pyridine-3-carboxamide Step 1: ethyl 1-(4-methoxyphenyl)-6-(4-(4-methyl-piperazin-1-yl)phenyl)-7-oxo-4,5,6,7-tetrahydro-1H-pyrazolo[3,4-c]pyridine-3-carboxylate

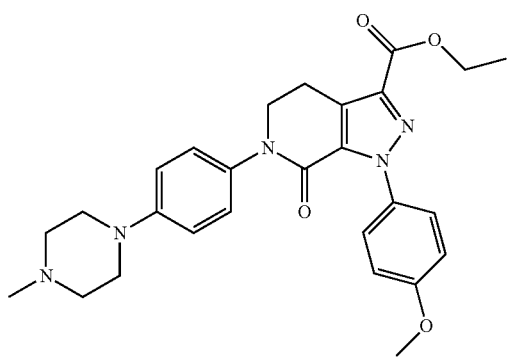 [SMILES: CCOC(=O)c1nn(-c2ccc(OC)cc2)c2c1CCN(c1ccc(N3CCN(C)CC3)cc1)C2=O]

1-(4-iodophenyl)-4-methylpiperazine (500 mg, 1.7 mmol), potassium carbonate (381 mg, 2.8 mmol), ethyl 1-(4-methoxyphenyl)-7-oxo-4,5,6,7-tetrahydro-1H-pyrazolo[3,4-c]pyridine-3-carboxylate (435 mg, 1.4 mmol), cupric iodide (26 mg, 0.14 mmol) and 1,10-phenanthroline (50 mg, 0.28 mmol) were successively added to DMSO (5 mL) at room temperature. The mixture was stirred and reacted at 120° C. for 14 h under the nitrogen protection. The reaction mixture was poured into ice-water (20 mL). The resulting mixture was extracted with EA. The organic phases were concentrated under vacuum to give a crude product. The crude product was purified by silica gel column chromatography to give 400 mg of the title compound as a light yellow solid in a yield of 48.0%.

Step 2: 1-(4-methoxyphenyl)-6-(4-(4-methylpiper-azin-1-yl)phenyl)-7-oxo-4,5,6,7-tetrahydro-1H-pyra-zolo[3,4-c]pyridine-3-carboxamide

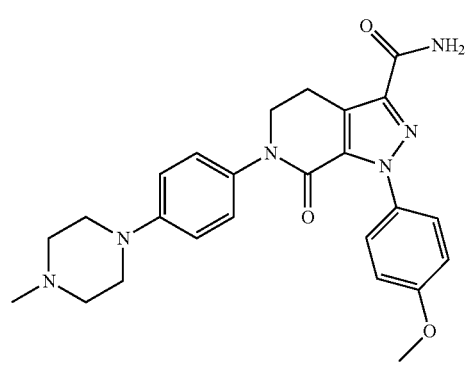 [SMILES: COc1ccc(-n2nc(C(N)=O)c3c2C(=O)N(c2ccc(N4CCN(C)CC4)cc2)CC3)cc1]

Ethyl 1-(4-methoxyphenyl)-6-(4-(4-methylpiperazin-1-yl)phenyl)-7-oxo-4,5,6,7-tetrahydro-1H-pyrazolo[3,4-c] pyridine-3-carboxylate (350 mg, 0.7 mmol) was dissolved in an ammonia gas/EG solution. Under a sealing condition, the mixture was stirred and reacted at 100° C. for 14 h. The reaction mixture was poured into water (30 mL). The resulting mixture was extracted with EA. The organic phases were concentrated under vacuum to produce 140 mg of the title compound as a yellow solid powder in a yield of 43.4%.

$^1$H-NMR (400 MHz, DMSO-d6) δ: 7.69 (s, 1H), 7.49 (d, 2H), 7.42 (s, 1H), 7.17 (d, 2H), 7.00 (d, 2H), 6.92 (d, 2H), 3.96 (t, 2H), 3.80 (s, 3H), 3.20-3.07 (m, 6H), 2.47-2.41 (m, 4H), 2.21 (s, 3H).

MS: 461.1 [M+H]$^+$

Example 9

1-(4-methoxyphenyl)-7-oxo-6-(3-(2-(piperazin-1-yl) ethyl)phenyl)-4,5,6,7-tetrahydro-1H-pyrazolo[3,4-c] pyridine-3-carboxamide Step 1: ethyl 6-(3-(2-(4-(tert-butoxycarbonyl)piper-azin-1-yl)ethyl)phenyl)-1-(4-methoxyphenyl)-7-oxo-4,5,6,7-tetrahydro-1H-pyrazolo[3,4-c]pyridine-3-carboxylate

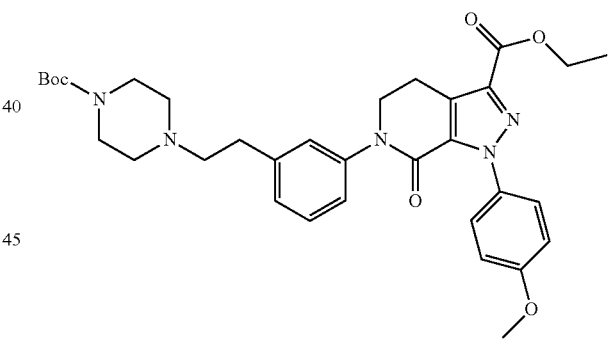

tert-Butyl 4-(3-bromophenethyl)piperazine-1-carboxylate (1.0 g, 2.7 mmol), potassium carbonate (750 mg, 5.4 mmol), ethyl 1-(4-methoxyphenyl)-7-oxo-4,5,6,7-tetrahydro-1H-pyrazolo[3,4-c]pyridine-3-carboxylate (700 mg, 2.2 mmol), cupric iodide (210 mg, 1.1 mmol), N,N'-dimethyl-1,2-eth-anediamine (120 mg, 1.4 mmol) and potassium iodide (900 mg, 5.4 mmol) were successively added to DMSO (10 mL) at room temperature. The mixture was stirred and reacted at 120° C. for 14 h under the nitrogen protection. The reaction mixture was poured into ice-water (30 mL). The resulting mixture was extracted with EA. The organic phases were concentrated to give a crude product. The crude product was purified by prep-HPLC to give 800 mg of the title compound as a yellow liquid in a yield of 49.1%.

Step 2: tert-butyl 4-(3-(3-carbamoyl-1-(4-methoxyphenyl)-7-oxo-4,5-dihydro-1H-pyrazolo[3,4-c]pyridin-6(7H)-yl)phenethyl)piperazine-1-carboxylate

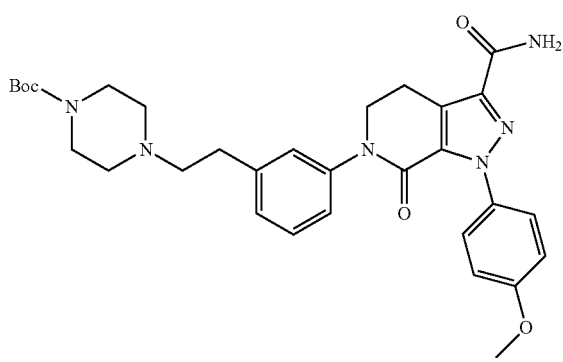 [SMILES: COc1ccc(-n2nc(C(N)=O)c3c2C(=O)N(c2cccc(CCN4CCN(C(=O)OC(C)(C)C)CC4)c2)CC3)cc1]

Ethyl 6-(3-(2-(4-(tert-butoxycarbonyl)piperazin-1-yl)ethyl)phenyl)-1-(4-methoxyphenyl)-7-oxo-4,5,6,7-tetrahydro-1H-pyrazolo[3,4-c]pyridine-3-carboxylate (800 mg, 1.3 mmol) was dissolved in an ammonia gas/EG solution. Under a sealing condition, the mixture was stirred and reacted at 100° C. for 14 h. The reaction mixture was poured into water (30 mL). The resulting mixture was extracted with EA. The organic phases were concentrated to produce 400 mg of the title compound as a yellow solid powder in a yield of 53.6%.

Step 3: 1-(4-methoxyphenyl)-7-oxo-6-(3-(2-(piperazin-1-yl)ethyl)phenyl)-4,5,6,7-tetrahydro-1H-pyrazolo[3,4-c]pyridine-3-carboxamide

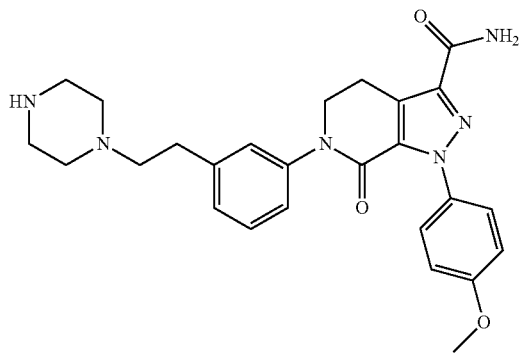 [SMILES: COc1ccc(-n2nc(C(N)=O)c3c2C(=O)N(c2cccc(CCN4CCNCC4)c2)CC3)cc1]

tert-Butyl 4-(3-(3-carbamoyl-1-(4-methoxyphenyl)-7-oxo-4,5-dihydro-1H-pyrazolo[3,4-c]pyridin-6(7H)-yl)phenethyl)piperazine-1-carboxylate (400 mg, 0.7 mmol) was dissolved in EA (4 mL). An HCl/MTBE solution (5 mL) was added dropwise into the mixture. After the completion of the dropwise addition, the mixture was stirred at room temperature for 2 h, adjusted to a neutral pH, concentrated under vacuum to give a crude product as an oil. The crude product was purified by silica gel column chromatography (DCM:MeOH=20:1) to give 150 mg of the title compound as a light brown solid in a yield of 45.2%.

$^1$H-NMR (400 MHz, DMSO-d6&D$_2$O) δ: 7.49 (d, 2H), 7.38 (t, 1H), 7.30 (s, 1H), 7.26 (d, 1H), 7.20 (d, 1H), 7.02 (d, 2H), 4.06 (t, 2H), 3.81 (s, 3H), 3.50-3.16 (m, 12H), 3.06-2.96 (m, 2H).

MS 475 [M+H]$^+$.

Example 10: 6-(3-methoxy-4-(piperazin-1-ylmethyl)phenyl)-1-(4-methoxyphenyl)-7-oxo-4,5,6,7-tetrahydro-1H-pyrazolo[3,4-c]pyridine-3-carboxamide Step 1: ethyl 6-(4-((4-(tert-butoxycarbonyl)piperazin-1-yl)methyl)-3-methoxyphenyl)-1-(4-methoxyphenyl)-7-oxo-4,5,6,7-tetrahydro-1H-pyrazolo[3,4-c]pyridine-3-carboxylate

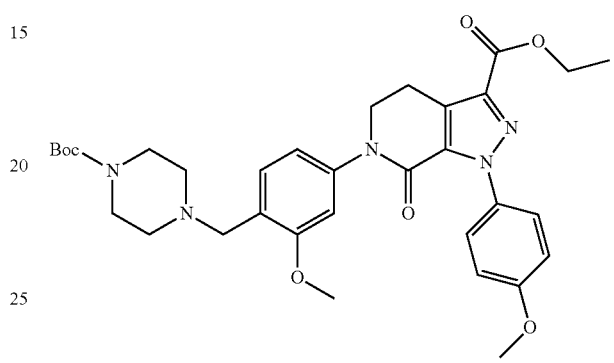

tert-Butyl 4-(4-bromo-2-methoxybenzyl)piperazine-1-carboxylate (2.0 g, 5.1 mmol), Ethyl 1-(4-methoxyphenyl)-7-oxo-4,5,6,7-tetrahydro-1H-pyrazolo[3,4-c]pyridine-3-carboxylate (1.6 g, 5.1 mmol), potassium carbonate (1.4 g, 10 mmol), cupric iodide (0.2 g, 1.1 mmol) and N,N'-dimethyl-1,2-ethanediamine (0.1 g, 1.1 mmol) were successively added to DMSO (25 mL) at room temperature. After the nitrogen purge, the mixture was heated to 100° C. and reacted for 14 h. The reaction mixture was poured into water (100 mL). The resulting mixture was extracted with EA. The organic phases were concentrated under vacuum to give a crude product. The crude product was purified by prep-HPLC to give 600 mg of the title compound as a white solid in a yield of 19.0%.

Step 2: tert-butyl 4-(4-(3-carbamoyl-1-(4-methoxyphenyl)-7-oxo-4,5-dihydro-1H-pyrazolo[3,4-c]pyridin-6(7H)-yl)-2-methoxybenzyl)piperazine-1-carboxylate

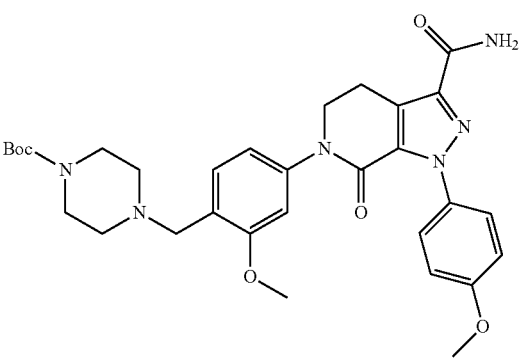 [SMILES: COc1ccc(-n2nc(C(N)=O)c3c2C(=O)N(c2ccc(CN4CCN(C(=O)OC(C)(C)C)CC4)c(OC)c2)CC3)cc1]

Ethyl 6-(4-((4-(tert-butoxycarbonyl)piperazin-1-yl)methyl)-3-methoxyphenyl)-1-(4-methoxyphenyl)-7-oxo-4,5,6,7-tetrahydro-1H-pyrazolo[3,4-c]pyridine-3-carboxylate (0.6 g, 0.99 mmol) was added into a seal tube, and then NH3/EG (3 mL) was added. After being dissolved, the content in the seal tube was heated to 100° C. and reacted for 14 h. After the completion of the reaction, the reaction mixture was poured into cold water (50 mL). A white solid separated out. The mixture was filtered by suction. The filter cake was dried to produce 400 mg of the title compound as a white solid in a yield of 68.5%.

Step 3: 6-(3-methoxy-4-(piperazin-1-ylmethyl)phenyl)-1-(4-methoxyphenyl)-7-oxo-4,5,6,7-tetrahydro-1H-pyrazolo[3,4-c]pyridine-3-carboxamide

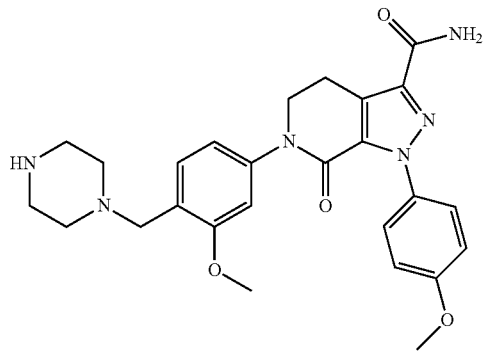 [SMILES: COc1ccc(-n2nc(C(N)=O)c3c2C(=O)N(c2ccc(CN4CCNCC4)c(OC)c2)CC3)cc1]

tert-Butyl 4-(4-(3-carbamoyl-1-(4-methoxyphenyl)-7-oxo-4,5-dihydro-1H-pyrazolo[3,4-c]pyridin-6(7H)-yl)-2-methoxybenzyl)piperazine-1-carboxylate (400 mg, 0.7 mmol) was dissolved in MeOH (10 mL). To the reaction system was introduce an HCl gas until the reaction was completed. The reaction mixture was adjusted to a neutral pH. The resulting mixture was concentrated under vacuum and purified by silica gel column chromatography (DCM:MeOH=30:1) to give 160 mg of the title compound as a light yellow solid powder in a yield of 46.6%.

$^1$H-NMR (400 MHz, DMSO-d6&D$_2$O) δ: 7.54-7.48 (m, 3H), 7.14 (d, 1H), 7.07-6.99 (m, 3H), 4.33 (s, 2H), 4.10 (t, 2H), 3.84 (s, 3H), 3.81 (s, 3H), 3.49-3.33 (m, 8H), 3.23 (t, 2H).
MS: 491.2 [M+H]$^+$

Example 11: 1-(4-methoxyphenyl)-6-(3-methyl-4-(piperazine-1-carbonyl)phenyl)-7-oxo-4,5,6,7-tetrahydro-1H-pyrazolo[3,4-c]pyridine-3-carboxamide Step 1: ethyl 6-(4-(4-(tert-butoxycarbonyl)piperazine-1-carbonyl)-3-methylphenyl)-1-(4-methoxyphenyl)-7-oxo-4,5,6,7-tetrahydro-1H-pyrazolo[3,4-c]pyridine-3-carboxylate

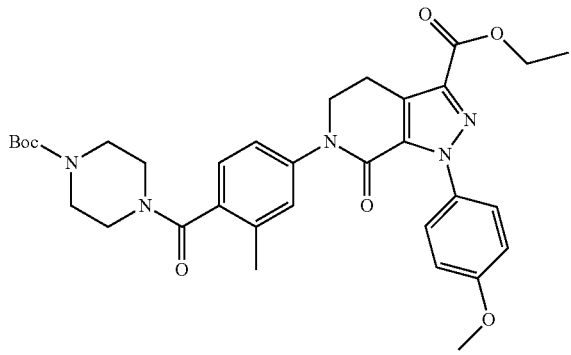 [SMILES: CCOC(=O)c1nn(-c2ccc(OC)cc2)c2c1CCN(c1ccc(C(=O)N3CCN(C(=O)OC(C)(C)C)CC3)c(C)c1)C2=O]

Tert-Butyl 4-(4-bromo-2-methylbenzoyl)piperazine-1-carboxylate (1.9 g, 5.0 mmol), Ethyl 1-(4-methoxyphenyl)-7-oxo-4,5,6,7-tetrahydro-1H-pyrazolo[3,4-c]pyridine-3-carboxylate (1.57 g, 5.0 mmol), potassium carbonate (1.4 g, 10.0 mmol), cupric iodide (0.2 g, 1.0 mmol) and N,N'-dimethyl-1,2-ethanediamine (0.1 g, 1.1 mmol) were added to DMSO (15 mL) at room temperature successively. The mixture was stirred and reacted at 120° C. for 14 h under the nitrogen protection. The reaction mixture was poured into water (20 mL). The resulting mixture was extracted with EA. The organic phases were concentrated under vacuum to give a crude product. The crude product was purified by prep-HPLC to give 500 mg of the title compound as a white solid in a yield of 16.2%.

Step 2: tert-butyl 4-(4-(3-carbamoyl-1-(4-methoxyphenyl)-7-oxo-4,5-dihydro-1H-pyrazolo[3,4-c]pyridin-6(7H)-yl)-2-methylbenzoyl)piperazine-1-carboxylate

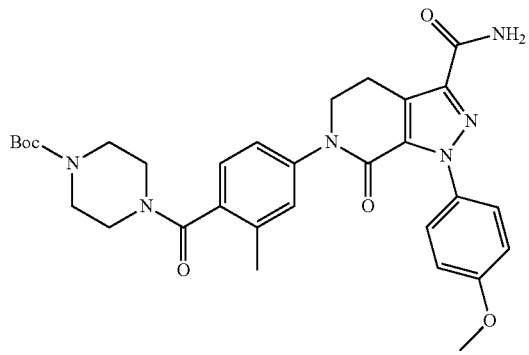 [SMILES: COc1ccc(-n2nc(C(N)=O)c3c2C(=O)N(c2ccc(C(=O)N4CCN(C(=O)OC(C)(C)C)CC4)c(C)c2)CC3)cc1]

Ethyl 6-(4-(4-(tert-butoxycarbonyl)piperazine-1-carbonyl)-3-methylphenyl)-1-(4-methoxyphenyl)-7-oxo-4,5,6,7-tetrahydro-1H-pyrazolo[3,4-c]pyridine-3-carboxylate (0.5 g, 0.81 mmol) was added into a seal tube, and then NH3/EG (3 mL) was added. After being dissolved, the content in the seal tube was heated to 100° C. and reacted for 14 h. After the completion of the reaction, the reaction mixture was poured into cold water (50 mL). A solid separated out. The mixture was filtered by suction. The filter cake was dried to produce 300 mg of the title compound as a light yellow solid in a yield of 63.0%.

Step 3: 1-(4-methoxyphenyl)-6-(3-methyl-4-(piperazine-1-carbonyl)phenyl)-7-oxo-4,5,6,7-tetrahydro-1H-pyrazolo[3,4-c]pyridine-3-carboxamide

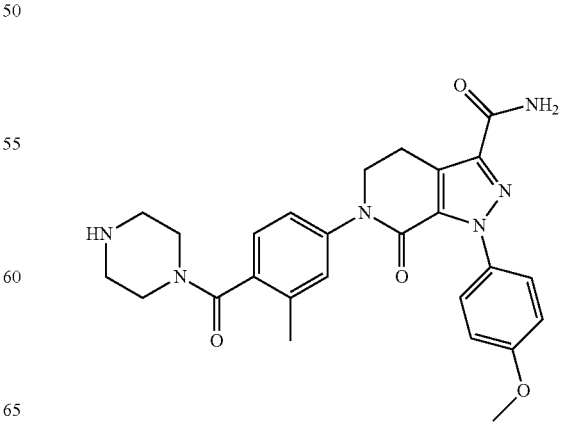

Tert-Butyl 4-(4-(3-carbamoyl-1-(4-methoxyphenyl)-7-oxo-4,5-dihydro-1H-pyrazolo[3,4-c]pyridin-6(7H)-yl)-2-methylbenzoyl)piperazine-1-carboxylate (300 mg, 0.51 mmol) was dissolved in MeOH (10 mL). To the reaction system was introduce an HCl gas until the reaction was completed. The mixture was concentrated under vacuum. The residue was dissolved in water and purified by prep-HPLC to give 110 mg of the title compound as a white solid in a yield of 44.2%.

$^1$H-NMR (400 MHz, DMSO d6) δ: 7.72 (s, 1H), 7.49 (d, 2H), 7.44 (s, 1H), 7.27-7.16 (m, 3H), 7.00 (d, 2H), 4.05 (t, 2H), 3.80 (s, 3H), 3.60-3.52 (m, 2H), 3.20 (t, 2H), 3.07-3.00 (m, 2H), 2.78-2.68 (m, 2H), 2.63-2.53 (m, 2H), 2.20 (s, 3H).

MS: 489.3 [M+H]$^+$

Example 12: 1-(4-methoxyphenyl)-7-oxo-6-(3-((2-phenoxyethyl)amino)phenyl)-4,5,6,7-tetrahydro-1H-pyrazolo[3,4-c]pyridine-3-carboxamide Step 1: 1-(4-methoxyphenyl)-7-oxo-6-(3-((2-phenoxyethyl)amino)phenyl)-4,5,6,7-tetrahydro-1H-pyrazolo[3,4-c]pyridine-3-carboxylic acid

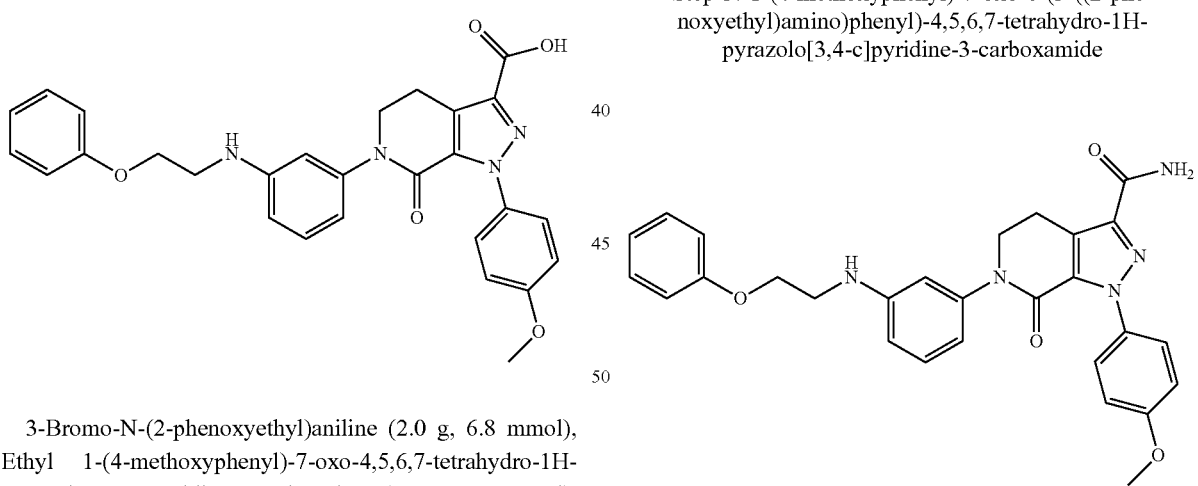

3-Bromo-N-(2-phenoxyethyl)aniline (2.0 g, 6.8 mmol), Ethyl 1-(4-methoxyphenyl)-7-oxo-4,5,6,7-tetrahydro-1H-pyrazolo[3,4-c]pyridine-3-carboxylate (2.1 g, 6.8 mmol), potassium phosphate (5.0 g, 23.5 mmol), cupric iodide (260 mg, 1.36 mmol) and N,N'-dimethyl-1,2-ethanediamine (250 mg, 2.8 mmol) were dissolved in DMSO (30 mL) at room temperature. After the nitrogen purge, the mixture was heated to 120° C., and stirred and reacted for 14 h. The reaction mixture was cooled to room temperature, and water (250 mL) was added. The resulting mixture was extracted with EA. The organic phases were concentrated under vacuum to produce 3.1 g of the title compound as a brown oil, which was directly used in the next step.

Step 2: ethyl 1-(4-methoxyphenyl)-7-oxo-6-(3-((2-phenoxyethyl)amino)phenyl)-4,5,6,7-tetrahydro-1H-pyrazolo[3,4-c]pyridine-3-carboxylate

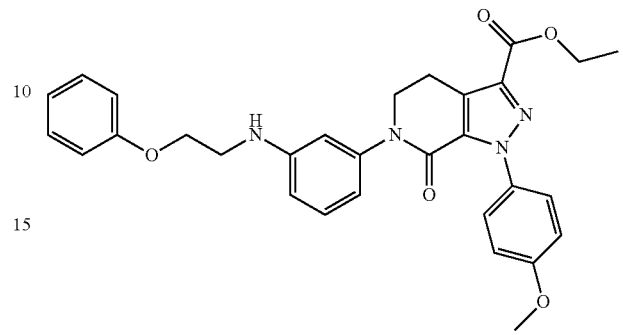

1-(4-methoxyphenyl)-7-oxo-6-(3-((2-phenoxyethyl)amino)phenyl)-4,5,6,7-tetrahydro-1H-pyrazolo[3,4-c]pyridine-3-carboxylic acid (2.0 g, 4.0 mmol) was dissolved in EtOH (20 mL) at room temperature. To the resulting mixture was added dropwise SOCl2 (1.4 g, 11.8 mmol) in an ice-water bath. After the completion of the dropwise addition, the mixture was heated to 40° C., and stirred and reacted for 14 h. The reaction mixture was cooled to room temperature, and concentrated. The residue was purified by silica gel column chromatography (DCM:MeOH=50:1) to give 300 mg of the title compound as a brown solid in a yield of 14.2%.

Step 3: 1-(4-methoxyphenyl)-7-oxo-6-(3-((2-phenoxyethyl)amino)phenyl)-4,5,6,7-tetrahydro-1H-pyrazolo[3,4-c]pyridine-3-carboxamide Ethyl 1-(4-methoxyphenyl)-7-oxo-6-(3-((2-phenoxyethyl)amino)phenyl)-4,5,6,7-tetrahydro-1H-pyrazolo[3,4-c]pyridine-3-carboxylate (0.1 g, 0.19 mmol) was added into a seal tube, and then NH3/EG (4.5 mL) was added. After being dissolved, the content in the seal tube was heated to 100° C. and reacted for 14 h. After the completion of the reaction, the reaction mixture was poured into cold water (10 mL). A solid separated out. The mixture was filtered by suction. The filter cake was dried to produce 40 mg of the title compound as a flesh-color solid in a yield of 42.4%.

1H-NMR (400 MHz, DMSO-d6) δ: 7.70 (s, 1H), 7.50 (d, 1H), 7.42 (s, 1H), 7.31-7.23 (m, 2H), 7.08 (t, 1H), 7.02-6.89 (m, 5H), 6.61 (s, 1H), 6.56-6.47 (m, 2H), 5.88 (t, 1H), 4.09 (t, 2H), 3.98 (t, 2H), 3.79 (s, 3H), 3.40 (q, 2H), 3.17 (t, 2H) MS: 498.2 [M+H]$^+$

Example 13: 1-(4-methoxyphenyl)-6-(3-(((1-methyl-1H-pyrazol-5-yl)methyl)amino)phenyl)-7-oxo-4,5,6,7-tetrahydro-1H-pyrazolo[3,4-c]pyridine-3-carboxamide Step 1: 1-(4-methoxyphenyl)-6-(3-(((1-methyl-1H-pyrazol-5-yl)methyl)amino)phenyl)-7-oxo-4,5,6,7-tetrahydro-1H-pyrazolo[3,4-c]pyridine-3-carboxylic acid

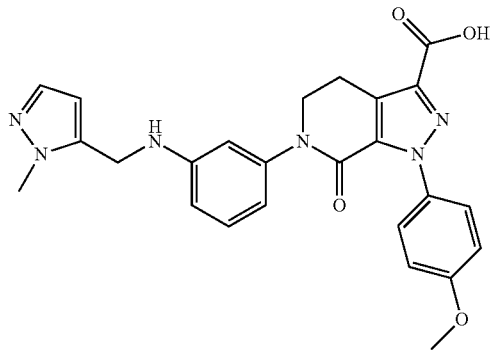 [SMILES: COc1ccc(-n2nc(C(=O)O)c3c2C(=O)N(c2cccc(NCc4ccnn4C)c2)CC3)cc1]

3-Bromo-N-((1-methyl-1H-pyrazol-5-yl)methyl)aniline (2.0 g, 7.5 mmol), Ethyl 1-(4-methoxyphenyl)-7-oxo-4,5,6,7-tetrahydro-1H-pyrazolo[3,4-c]pyridine-3-carboxylate (2.4 g, 7.5 mmol), potassium phosphate (4.0 g, 18.8 mmol), cupric iodide (285 mg, 1.5 mmol) and N,N'-dimethyl-1,2-ethanediamine (265 mg, 3 mmol) were successively added to DMSO (30 mL) at room temperature. After the nitrogen purge, the mixture was heated to 120° C. and stirred for 14 h. The reaction mixture was cooled to room temperature, and water (250 mL) was added. The resulting mixture was extracted with EA. The organic phases were concentrated under vacuum to produce 2.9 g of the title compound as a brown oil, which was directly used in the next step.

Step 2: ethyl 1-(4-methoxyphenyl)-6-(3-(((1-methyl-1H-pyrazol-5-yl)methyl)amino)phenyl)-7-oxo-4,5,6,7-tetrahydro-1H-pyrazolo[3,4-c]pyridine-3-carboxylate

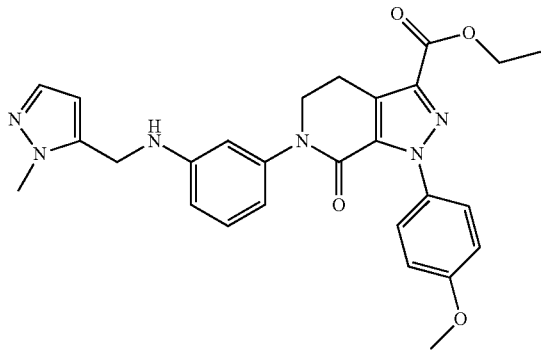 [SMILES: CCOC(=O)c1nn(-c2ccc(OC)cc2)c2c1CCN(c1cccc(NCc3ccnn3C)c1)C2=O]

1-(4-Methoxyphenyl)-6-(3-(((1-methyl-1H-pyrazol-5-yl)methyl)amino)phenyl)-7-oxo-4,5,6,7-tetrahydro-1H-pyrazolo[3,4-c]pyridine-3-carboxylic acid (2.9 g, 6.1 mmol) was dissolved in MeOH (40 mL) at room temperature. To the resulting mixture was added dropwise SOCl2 (2.2 g, 18.5 mmol) in an ice-water bath. After the completion of the dropwise addition, the mixture was heated to 40° C. and stirred for 14 h. The reaction mixture was cooled to room temperature, and evaporated to remove the solvent to give a crude product. The crude product was purified by silica gel column chromatography (DCM:MeOH=100:1) to give 500 mg of the title compound as a white solid in a yield of 16.4%.

Step 3: 1-(4-methoxyphenyl)-6-(3-(((1-methyl-1H-pyrazol-5-yl)methyl)amino)phenyl)-7-oxo-4,5,6,7-tetrahydro-1H-pyrazolo[3,4-c]pyridine-3-carboxamide

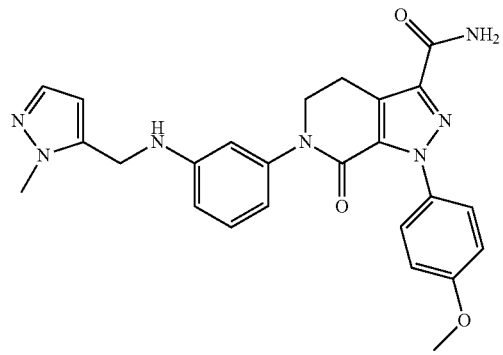 [SMILES: COc1ccc(-n2nc(C(N)=O)c3c2C(=O)N(c2cccc(NCc4ccnn4C)c2)CC3)cc1]

In a seal tube, ethyl 1-(4-methoxyphenyl)-6-(3-(((1-methyl-1H-pyrazol-5-yl)methyl)amino)phenyl)-7-oxo-4,5,6,7-tetrahydro-1H-pyrazolo[3,4-c]pyridine-3-carboxylate (500 mg, 1.0 mmol) was dissolved in NH3/EG (20 mL) at room temperature. The content in the seal tube was heated to 100° C., and stirred and reacted for 14 h. Then to the mixture was added water (100 mL). The resulting mixture was extracted with EA. The organic phases were concentrated to give a crude product. The crude product was purified by prep-HPLC to give 120 mg of the title compound as a light brown solid in a yield of 25.4%.

$^1$H-NMR (400 MHz, DMSO-d6) δ: 7.70 (s, 1H), 7.48 (dd, 2H,), 7.42 (s, 1H), 7.28 (d, 1H), 7.07 (t, 1H), 6.99 (dd, 2H), 6.64 (t, 1H), 6.54-6.51 (m, 2H), 6.19 (d, 1H), 6.14 (t, 11H), 4.27 (d, 2H), 3.97 (t, 2H), 3.79 (d, 6H), 3.17 (t, 2H).

MS 472 [M+H]$^+$.

Example 14: 6-(3-(((3-(1H-imidazol-1-yl)propyl)amino)methyl)phenyl)-1-(4-methoxyphenyl)-7-oxo-4,5,6,7-tetrahydro-1H-pyrazolo[3,4-c]pyridine-3-carboxamide

Step 1: ethyl 6-(3-(((3-(1H-imidazol-1-yl)propyl)amino)methyl)phenyl)-1-(4-methoxyphenyl)-7-oxo-4,5,6,7-tetrahydro-1H-pyrazolo[3,4-c]pyridine-3-carboxylate

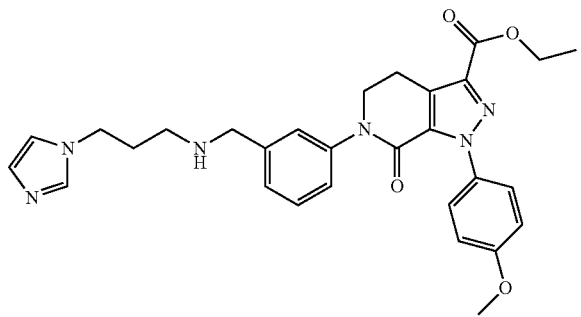 [SMILES: CCOC(=O)c1nn(-c2ccc(OC)cc2)c2c1CCN(c1cccc(CNCCCn3ccnc3)c1)C2=O]

N-(3-bromobenzyl)-3-(1H-imidazol-1-yl)propan-1-amine (706 mg, 2.4 mmol) and Ethyl 1-(4-methoxyphenyl)-7-oxo-4,5,6,7-tetrahydro-1H-pyrazolo[3,4-c]pyridine-3-carboxylate (500 mg, 1.6 mmol) were added to DMSO (5 mL) at room temperature. Then to the resulting mixture were successively added potassium iodide (797 mg, 4.8 mmol), potassium carbonate (883 mg, 6.4 mmol), cupric iodide (122 mg, 0.64 mmol) and N,N'-dimethyl-1,2-ethanediamine (70.4 mg, 0.8 mmol) at room temperature. The mixture was heated to 120° C. and reacted for 14 h under the nitrogen protection. The reaction mixture was cooled to room temperature, and then poured into water (50 mL). The resulting mixture was extracted with EA. The organic phases were concentrated under vacuum to give a crude product. The crude product was purified by silica gel column chromatography (DCM:MeOH=10:1) to give 480 mg of the title compound as a yellow solid in a yield of 56.9%.

Step 2: 6-(3-(((3-(1H-imidazol-1-yl)propyl)amino)methyl)phenyl)-1-(4-methoxyphenyl)-7-oxo-4,5,6,7-tetrahydro-1H-pyrazolo[3,4-c]pyridine-3-carboxamide

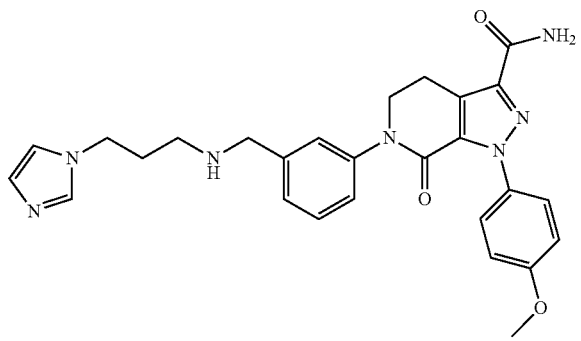 [SMILES: COc1ccc(-n2nc(C(N)=O)c3c2C(=O)N(c2cccc(CNCCCn4ccnc4)c2)CC3)cc1]

Ethyl 6-(3-(((3-(1H-imidazol-1-yl)propyl)amino)methyl)phenyl)-1-(4-methoxyphenyl)-7-oxo-4,5,6,7-tetrahydro-1H-pyrazolo[3,4-c]pyridine-3-carboxylate (480 mg, 0.9 mmol) was added into a seal tube, and then NH3/EG (4 mL) was added. After the seal tube was sealed, the resulting mixture was heated to 100° C., and reacted for 14 h. The resulting mixture was poured into water (100 mL). The resulting mixture was extracted with DCM. The organic phases were concentrated to give a crude product. The crude product was purified by prep-HPLC to give 110 mg of the title compound as a yellow viscous waxy solid in a yield of 24.2%.

$^1$H-NMR (400 MHz, DMSO d6) δ: 7.71 (s, 1H), 7.56 (s, 1H), 7.52-7.46 (m, 2H), 7.43 (s, 1H), 7.35-7.29 (m, 2H), 7.24-7.17 (m, 2H), 7.11 (s, 1H), 7.01-6.96 (m, 2H), 6.85 (s, 1H), 4.07-3.96 (m, 4H), 3.79 (s, 3H), 3.74-3.67 (m, 2H), 3.20 (t, 2H), 2.48-2.41 (m, 2H), 1.90-1.80 (m, 2H).

MS 500 [M+H]$^+$

Example 15: 1-(4-methoxyphenyl)-7-oxo-6-(4-(piperidin-1-yl)butyl)-4,5,6,7-tetrahydro-1H-pyrazolo[3,4-c]pyridine-3-carboxamide

Step 1: ethyl 6-(4-acetoxybutyl)-1-(4-methoxyphenyl)-7-oxo-4,5,6,7-tetrahydro-1H-pyrazolo[3,4-c]pyridine-3-carboxylate

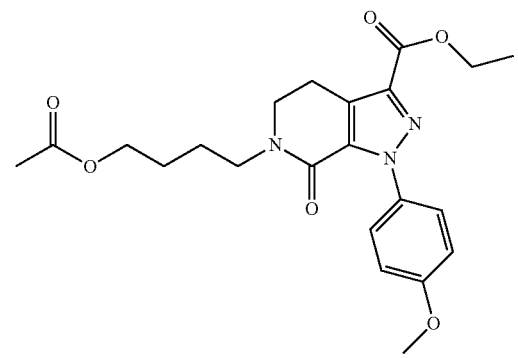 [SMILES: CCOC(=O)c1nn(-c2ccc(OC)cc2)c2c1CCN(CCCCOC(C)=O)C2=O]

Ethyl 1-(4-methoxyphenyl)-7-oxo-4,5,6,7-tetrahydro-1H-pyrazolo[3,4-c]pyridine-3-carboxylate (1.0 g, 3.2 mmol) was dissolved in DMF (40 mL) at room temperature. To the resulting mixture were successively added KTB (potassium tert-butoxide) (0.7 g, 6.2 mmol) and 4-bromobutyl acetate (0.7 g, 3.6 mmol). The mixture was reacted at room temperature for 16 h. To the resulting mixture was added water (100 mL) to quench the reaction. The resulting mixture was extracted with EA. The organic phases were concentrated under vacuum to give a crude product. The crude product was purified by silica gel column chromatography (DCM:MeOH=200:1) to give 470 mg of the title compound as a brown yellow oil in a yield of 34.2%.

Step 2: 4-(3-carbamoyl-1-(4-methoxyphenyl)-7-oxo-4,5-dihydro-1H-pyrazolo[3,4-c]pyridin-6(7H)-yl) butyl acetate

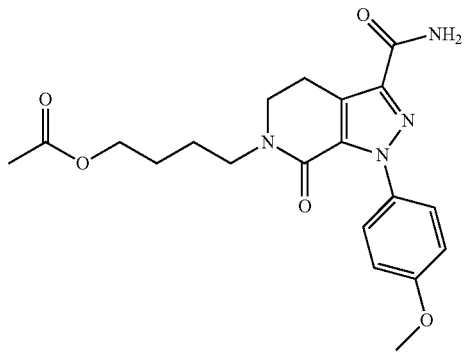 [SMILES: COc1ccc(-n2nc(C(N)=O)c3c2C(=O)N(CCCCOC(C)=O)CC3)cc1]

Ethyl 6-(4-acetoxybutyl)-1-(4-methoxyphenyl)-7-oxo-4,5,6,7-tetrahydro-1H-pyrazolo[3,4-c]pyridine-3-carboxylate (470 mg, 1.1 mmol) was added into a seal tube, and then NH3/EG (4 mL) was added. After the seal tube was sealed, the mixture was heated to 100° C. and reacted for 17 h. The reaction mixture was poured into water (100 mL). The resulting mixture was extracted with DCM. The organic phases were concentrated under vacuum to produce 370 mg of the title compound as a yellow oil, which was directly used in the next step.

Step 3: 4-(3-carbamoyl-1-(4-methoxyphenyl)-7-oxo-4,5-dihydro-1H-pyrazolo[3,4-c]pyridin-6(7H)-yl) butyl methanesulfonate

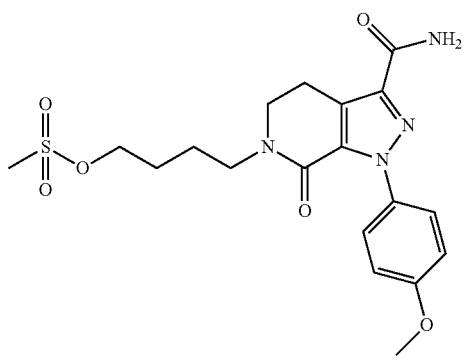 [SMILES: COc1ccc(-n2nc(C(N)=O)c3c2C(=O)N(CCCCOS(C)(=O)=O)CC3)cc1]

4-(3-Carbamoyl-1-(4-methoxyphenyl)-7-oxo-4,5-dihydro-1H-pyrazolo[3,4-c]pyridin-6(7H)-yl)butyl acetate (370 mg, 0.93 mmol) was dissolved in DCM (5 mL). To the resulting mixture was added TEA (208 mg, 2.06 mmol), and then added dropwise MsCl (142 mg, 1.23 mmol) in an ice bath. The mixture was reacted for 14 h at room temperature. The reaction mixture was poured into water (100 mL). The resulting mixture was extracted with DCM. The organic phases were concentrated under vacuum to produce 400 mg of the title compound as a yellow oil, which was directly used in the next step.

Step 4: 1-(4-methoxyphenyl)-7-oxo-6-(4-(piperidin-1-yl)butyl)-4,5,6,7-tetrahydro-1H-pyrazolo[3,4-c]pyridine-3-carboxamide

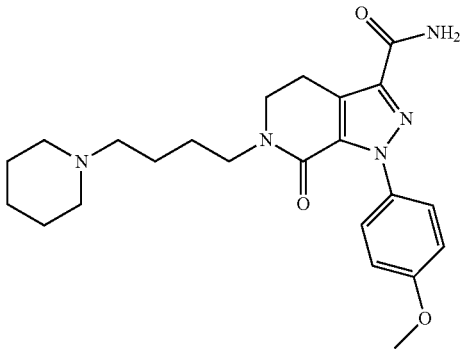 [SMILES: COc1ccc(-n2nc(C(N)=O)c3c2C(=O)N(CCCCN2CCCCC2)CC3)cc1]

4-(3-Carbamoyl-1-(4-methoxyphenyl)-7-oxo-4,5-dihydro-1H-pyrazolo[3,4-c]pyridin-6(7H)-yl)butyl methanesulfonate (400 mg, 0.92 mmol) and piperidine (140 mg, 1.65 mmol) were dissolved in 1,4-dioxane (5 mL). Potassium carbonate (303 mg, 2.2 mmol) was added into the mixture. The mixture was heated to 80° C. and reacted for 14 h. The reaction mixture was poured into water (100 mL). The resulting mixture was extracted with EA. The organic phases were concentrated under vacuum to give a crude product. The crude product was purified by prep-HPLC to yield 170 mg of the title compound as a brown viscous waxy solid in a yield of 43.6%.

$^1$H-NMR (400 MHz, DMSO d6) δ: 7.64 (s, 1H), 7.49-7.41 (m, 2H), 7.38 (s, 1H), 7.04-6.97 (m, 2H), 3.81 (s, 3H), 3.61 (t, 2H), 3.42-3.34 (m, 2H), 3.02 (t, 2H), 2.35-2.12 (m, 6H), 1.56-1.40 (m, 6H), 1.40-1.27 (m, 4H).

MS: 425.9 [M+H]$^+$

Example 16: 6-(4-isobutyramidophenyl)-1-(4-methoxyphenyl)-7-oxo-4,5,6,7-tetrahydro-1H-pyrazolo[3,4-c]pyridine-3-carboxamide

Step 1: ethyl 6-(4-isobutyramidophenyl)-1-(4-methoxyphenyl)-7-oxo-4,5,6,7-tetrahydro-1H-pyrazolo[3,4-c]pyridine-3-carboxylate

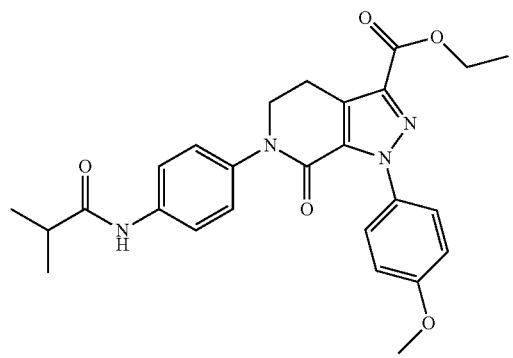 [SMILES: CCOC(=O)c1nn(-c2ccc(OC)cc2)c2c1CCN(c1ccc(NC(=O)C(C)C)cc1)C2=O]

Ethyl 1-(4-methoxyphenyl)-7-oxo-4,5,6,7-tetrahydro-1H-pyrazolo[3,4-c]pyridine-3-carboxylate (4.0 g, 12.7 mmol) and N-(4-iodophenyl)isobutyramide (3.8 g, 13.1 mmol) were added to DMSO (60 mL) at room temperature. Potassium carbonate (3.7 g, 26.7 mmol), cupric iodide (1.1 g, 5.77 mmol) and 1,10-phenanthroline (1.1 g, 6.10 mmol) were successively added to the mixture under the nitrogen protection. The mixture was heated to 120° C. and reacted for 12 h. After the completion of the reaction, water was added to the reaction mixture. The resulting mixture was extracted with EA. The organic phases were concentrated under vacuum to give a crude product. The crude product was purified by silica gel column chromatography (PE:EA=1:3) to give 4.0 g of the title compound as a white solid in a yield of 66.2%.

Step 2: 6-(4-isobutyramidophenyl)-1-(4-methoxyphenyl)-7-oxo-4,5,6,7-tetrahydro-1H-pyrazolo[3,4-c]pyridine-3-carboxamide

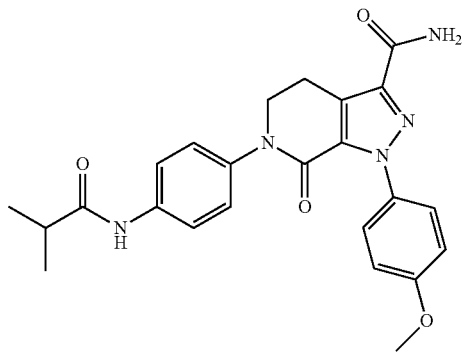 [SMILES: COc1ccc(-n2nc(C(N)=O)c3c2C(=O)N(c2ccc(NC(=O)C(C)C)cc2)CC3)cc1]

Ethyl 6-(4-isobutyramidophenyl)-1-(4-methoxyphenyl)-7-oxo-4,5,6,7-tetrahydro-1H-pyrazolo[3,4-c]pyridine-3-carboxylate (2.0 g, 4.2 mmol) was added into a seal tube. To the seal tube was added ethylene glycol (16 mL). Ammonia gas was introduced to the seal tube for 0.5 h, and then the seal tube was sealed. The mixture was heated to 130° C. and reacted for 5 h. After the completion of the reaction, the reaction mixture was cooled to room temperature. The cooled mixture was poured into cold water. A solid separated out. The mixture was filtered. The filter cake was dried to produce 1.2 g of the title compound as a white solid in a yield of 63.9%.

$^1$H-NMR (600 MHz, DMSO) δ 1.095 (d, 6H), 2.555-2.601 (m, 1H), 3.178-3.200 (m, 2H), 3.802 (s, 3H), 3.991-4.013 (m, 2H), 6.996 (d, 2H), 7.260 (d, 2H), 7.428 (s, 1H), 7.491 (d, 2H), 7.596 (d, 2H), 7.703 (s, 1H), 9.860 (s, 1H)

MS 448.0 [M+H]$^+$

Example 17: 1-(4-methoxyphenyl)-7-oxo-6-(4-(2-oxopyrrolidin-1-yl)phenyl)-4,5,6,7-tetrahydro-1H-pyrazolo[3,4-c]pyridine-3-carboxamide Step 1: ethyl 1-(4-methoxyphenyl)-7-oxo-6-(4-(2-oxopyrrolidin-1-yl)phenyl)-4,5,6,7-tetrahydro-1H-pyrazolo[3,4-c]pyridine-3-carboxylate

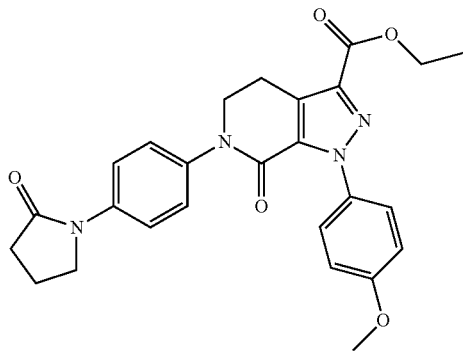 [SMILES: CCOC(=O)c1nn(-c2ccc(OC)cc2)c2c1CCN(c1ccc(N3CCCC3=O)cc1)C2=O]

Ethyl 1-(4-methoxyphenyl)-7-oxo-4,5,6,7-tetrahydro-1H-pyrazolo[3,4-c]pyridine-3-carboxylate (4.0 g, 12.7 mmol) and 1-(4-iodophenyl)pyrrolidin-2-one (3.8 g, 13.3 mmol) were added to DMSO (60 mL) at room temperature. Potassium carbonate (3.7 g, 26.7 mmol), cupric iodide (1.1 g, 5.77 mmol) and 1,10-phenanthroline (1.1 g, 6.10 mmol) were successively added to the mixture under the nitrogen protection. The mixture was heated to 120° C. and reacted for 12 h. After the completion of the reaction, water was added to the mixture. The resulting mixture was extracted with EA. The organic phases were concentrated under vacuum to give a crude product. The crude product was purified by silica gel column chromatography (PE:EA=1:1 to 1:5) to give 4.0 g of the title compound as a white solid in a yield of 66.6%.

Step 2: 1-(4-methoxyphenyl)-7-oxo-6-(4-(2-oxopyrrolidin-1-yl)phenyl)-4,5,6,7-tetrahydro-1H-pyrazolo[3,4-c]pyridine-3-carboxamide

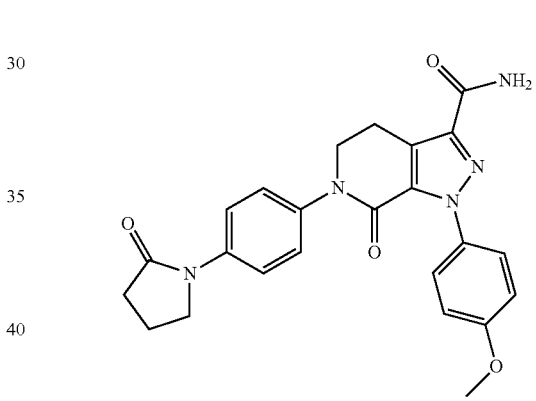

Ethyl 1-(4-methoxyphenyl)-7-oxo-6-(4-(2-oxopyrrolidin-1-yl)phenyl)-4,5,6,7-tetrahydro-1H-pyrazolo[3,4-c]pyridine-3-carboxylate (1.5 g, 3.2 mmol) was added into a seal tube. To the seal tube was added ethylene glycol (16 mL). Ammonia gas was introduced to the seal tube for 0.5 h, and then the seal tube was sealed. The mixture was heated to 130° C. and reacted for 5 h. After the completion of the reaction, the reaction mixture was cooled to room temperature and then poured into cold water. A solid separated out. The mixture was filtered. The filter cake was dried to produce 1.0 g of the title compound as a white solid in a yield of 71.4%.

$^1$H NMR (600 MHz, DMSO) δ 2.029-2.080 (m, 2H), 2.477-2.504 (m, 2H), 3.187-3.209 (m, 2H), 3.798 (s, 3H), 3.809-3.833 (m, 2H), 4.011-4.033 (m, 2H), 6.995 (d, 2H), 7.346 (d, 2H), 7.438 (s, 1H), 7.499 (d, 2H), 7.650 (d, 2H), 7.712 (s, 1H)

MS 446.2 [M+H]$^+$

Example 18: 1-(3-chloro-4-methoxyphenyl)-7-oxo-6-(4-(2-oxopiperidin-1-yl)phenyl)-4,5,6,7-tetrahydro-1H-pyrazolo[3,4-c]pyridine-3-carboxamide

Step 1: ethyl 2-chloro-2-(2-(3-chloro-4-methoxyphenyl)hydrazono)acetate

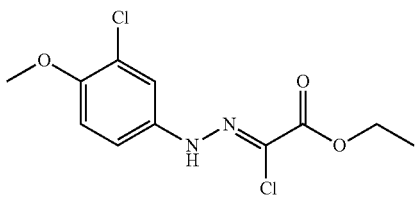 [SMILES: CCOC(=O)/C(Cl)=N/Nc1ccc(OC)c(Cl)c1]

3-Chloro-4-methoxyaniline (10 g, 63.5 mmol) was dispersed in water (500 mL) at room temperature. The mixture was cooled to −5 to 0° C. Concentrated hydrochloric acid (20 mL), an aqueous sodium nitrite solution (30 mL), a solution of ethyl 2-chloro-3-oxobutanoate (10.8 g, 65.6 mmol) in ethanol (100 mL), and a solution of sodium acetate (15.6 g, 0.19 mmol) in water (150 mL) were successively added to the mixture. After the completion of the addition, the mixture was warmed up to room temperature, and stirred and reacted for 6 h. After the completion of the reaction, the mixture was filtered. The filter cake was dried under vacuum to give 15.0 g of the title compound in a yield of 81.1%.

Step 2: ethyl 1-(3-chloro-4-methoxyphenyl)-7-oxo-4,5,6,7-tetrahydro-1H-pyrazolo[3,4-c]pyridine-3-carboxylate

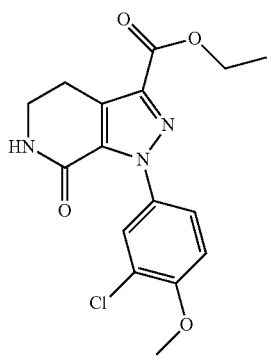 [SMILES: CCOC(=O)c1nn(-c2ccc(OC)c(Cl)c2)c2c1CCNC2=O]

ethyl 2-chloro-2-(2-(3-chloro-4-methoxyphenyl)hydrazono)acetate (10.0 g, 34.3 mmol), 3-chloro-5,6-dihydropyridin-2(1H)-one (6.0 g, crude product) and triethylamine (20 mL) were successively added to toluene (100 mL) at room temperature. The mixture was heated to 110° C. and reacted under reflux for 3 h. The mixture was cooled to room temperature, and concentrated under vacuum. To the resulting residue were added EA and water. The resulting mixture was left to stand and separated into two phases. The aqueous layer was extracted with EA. The organic phases were concentrated under vacuum to give a crude product. The crude product was purified by silica gel column chromatography (PE:EA=1:1) to give 1.5 g of the title compound in a yield of 12.5%.

Step 3: ethyl 1-(3-chloro-4-methoxyphenyl)-7-oxo-6-(4-(2-oxopiperidin-1-yl)phenyl)-4,5,6,7-tetrahydro-1H-pyrazolo[3,4-c]pyridine-3-carboxylate

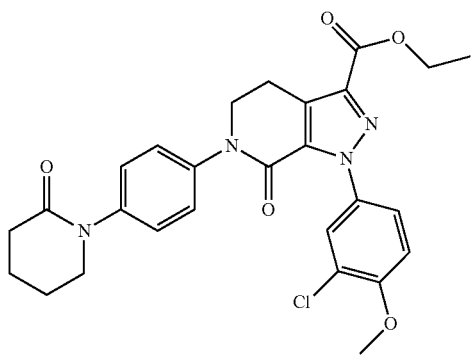 [SMILES: CCOC(=O)c1nn(-c2ccc(OC)c(Cl)c2)c2c1CCN(c1ccc(N3CCCCC3=O)cc1)C2=O]

1-(4-Iodophenyl)piperidin-2-one (1.22 g, 4.0 mmol), ethyl 1-(3-chloro-4-methoxyphenyl)-7-oxo-4,5,6,7-tetrahydro-1H-pyrazolo[3,4-c]pyridine-3-carboxylate (1.3 g, 3.72 mmol) and potassium carbonate (1.08 g, 7.81 mmol) were successively added to DMSO (26 mL) at room temperature. To the mixture were added cupric iodide (330 mg, 1.74 mmol) and 1,10-phenanthroline (310 mg, 1.74 mmol) under the nitrogen protection. The mixture was heated to 120° C. and reacted for 12 h. After the completion of the reaction, water was added into the mixture. The resulting mixture was extracted with EA. The organic phases were concentrated to give a crude product. The crude product was purified by silica gel column chromatography (PE:EA=1:1) to give 1.5 g of the title compound as a light yellow solid in a yield of 77.2%.

Step 4: 1-(3-chloro-4-methoxyphenyl)-7-oxo-6-(4-(2-oxopiperidin-1-yl)phenyl)-4,5,6,7-tetrahydro-1H-pyrazolo[3,4-c]pyridine-3-carboxamide

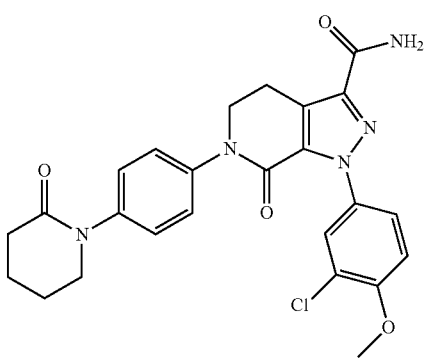 [SMILES: COc1ccc(-n2nc(C(N)=O)c3c2C(=O)N(c2ccc(N4CCCCC4=O)cc2)CC3)cc1Cl]

Ethyl 1-(3-chloro-4-methoxyphenyl)-7-oxo-6-(4-(2-oxopiperidin-1-yl)phenyl)-4,5,6,7-tetrahydro-1H-pyrazolo[3,4-c]pyridine-3-carboxylate (1.5 g, 2.87 mmol) was added into a seal tube. To the seal tube was added ethylene glycol (16 mL). Ammonia gas was introduced to the seal tube for 0.5 h, and then the seal tube was sealed. The mixture was heated to 130° C. and reacted for 5 h. After the completion of the reaction, the reaction mixture was cooled to room temperature and then poured into cold water. A solid separated out. The mixture was filtered. The filter cake was dried to produce 0.74 g of the title compound as an off-white solid in a yield of 52.2%.

$^1$H-NMR (600 MHz, DMSO) δ 1.826-1.866 (m, 4H), 2.376-2.397 (m, 2H), 3.198-3.220 (m, 2H), 3.586-3.604 (m, 2H), 4.053-4.074 (m, 2H), 7.171 (s, 1H,), 7.266-7.294 (m, 4H), 7.357-7.372 (d, 1H), 7.505-7.529 (m, 4H) 7.788 (s, 1H) MS 496.0 [M+H]$^+$

Example 19: 1-(6-methoxypyridin-3-yl)-7-oxo-6-(4-(2-oxopiperidin-1-yl)phenyl)-4,5,6,7-tetrahydro-1H-pyrazolo[3,4-c]pyridine-3-carboxamide Step 1: ethyl 2-chloro-2-(2-(2-methoxypyridin-5-yl)hydrazono)acetate

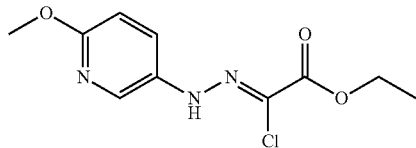 [SMILES: CCOC(=O)/C(Cl)=N/Nc1ccc(OC)nc1]

2-methoxy-5-amine-pyridine (3.0 g, 24.2 mmol) was dispersed in water (15 mL). The resulting mixture was stirred and cooled to −5 to 0° C. To the cooled mixture were successively added concentrated hydrochloric acid (6 mL), an aqueous sodium nitrite solution (9 mL), a solution of ethyl 2-chloro-3-oxobutanoate (4.08 g, 24.9 mmol) in ethanol (30 mL), a solution of sodium acetate (5.94 g, 72.3 mmol) in water (90 mL). After the completion of the addition, the mixture was warmed up to room temperature, and stirred and reacted for 6 h. After the completion of the reaction, the resulting mixture was filtered by suction. The resulting filter cake was dried in vacuum, and purified by silica gel column chromatography (PE:EA=10:1) to give 4.3 g of the title compound in a yield of 69.0%.

Step 2: ethyl 1-(6-methoxypyridin-3-yl)-7-oxo-4,5,6,7-tetrahydro-1H-pyrazolo[3,4-c]pyridine-3-carboxylate

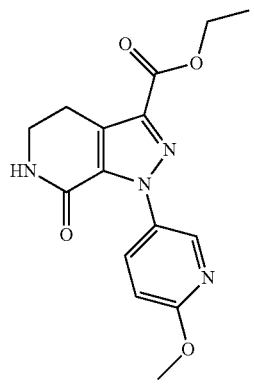 [SMILES: CCOC(=O)c1nn(-c2ccc(OC)nc2)c2c1CCNC2=O]

Ethyl 2-chloro-2-(2-(2-methoxypyridin-5-yl)hydrazono)acetate (2.58 g, 10 mmol), 3-morpholino-5,6-dihydropyridin-2(1H)-one (1.82 g, 10 mmol), and triethylamine (3.8 mL) were successively added to toluene (26 mL) at room temperature. The mixture was heated to 110° C., and reacted under reflux for 3 h. The mixture was then cooled to room temperature and concentrated in vacuum to dryness. To the residue was added with DCM (30 mL). To the mixture was added dropwise trifluoroacetic acid (2.5 mL) at room temperature. The resulting mixture was stirred and reacted for 2 h. After the completion of the reaction, to the resulting solution was added water. The resulting mixture was extracted with DCM. The organic phases were concentrated under vacuum. The residue was purified by silica gel column chromatography (PE:EA=1:1) to give 1.8 g of the title compound in a yield of 56.9%.

Step 3: ethyl 1-(6-methoxypyridin-3-yl)-7-oxo-6-(4-(2-oxopiperidin-1-yl)phenyl)-4,5,6,7-tetrahydro-1H-pyrazolo[3,4-c]pyridine-3-carboxylate

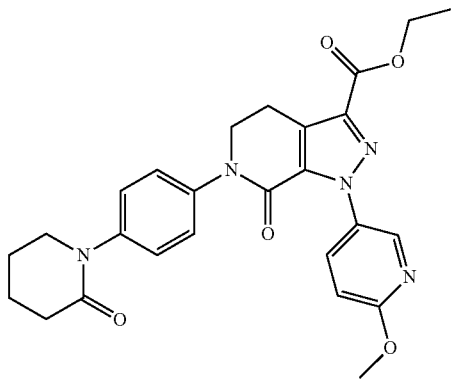 [SMILES: CCOC(=O)c1nn(-c2ccc(OC)nc2)c2c1CCN(c1ccc(N3CCCCC3=O)cc1)C2=O]

At room temperature, 1-(4-Iodophenyl)piperidin-2-one (1.9 g, 6.3 mmol), ethyl 1-(6-methoxypyridin-3-yl)-7-oxo-4,5,6,7-tetra hydro-1H-pyrazolo[3,4-c]pyridine-3-carboxylate (1.8 g, 5.7 mmol), and potassium carbonate (1.7 g, 11.97 mmol) were successively added to DMSO (25 mL). Cupric iodide (520 mg, 2.7 mmol) and 1,10-phenanthroline (490 mg, 2.7 mmol) were added to the mixture under the nitrogen protection. The mixture was heated to 120° C. and reacted for 12 h. After the completion of the reaction, the mixture was cooled to room temperature. To the cooled mixture was added water. The resulting mixture was extracted with EA. The organic phases were concentrated under vacuum to produce a crude product. The crude product was purified by silica gel column chromatography (PE:EA=1:1) to give 0.65 g of the title compound as an oil in a yield of 23.3%.

Step 4: 1-(6-methoxypyridin-3-yl)-7-oxo-6-(4-(2-oxopiperidin-1-yl)phenyl)-4,5,6,7-tetrahydro-1H-pyrazolo[3,4-c]pyridine-3-carboxamide

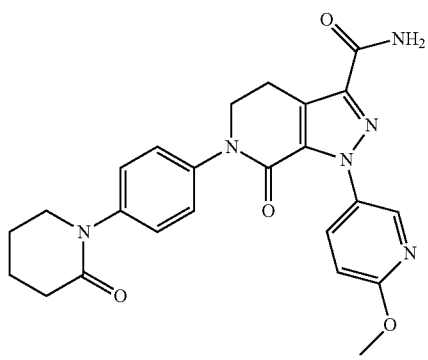 [SMILES: COc1ccc(-n2nc(C(N)=O)c3c2C(=O)N(c2ccc(N4CCCCC4=O)cc2)CC3)cn1]

Ethyl 1-(6-methoxypyridin-3-yl)-7-oxo-6-(4-(2-oxopiperidin-1-yl)phenyl)-4,5,6,7-tetrahydro-1H-pyrazolo[3,4-c]pyridine-3-carboxylate (0.65 g, 1.3 mmol) was added to a seal tube. To the seal tube was added ethylene glycol (16 mL). Ammonia gas was introduced to the seal tube for 0.5 h, and then the seal tube was sealed. The mixture was heated to 120° C. and reacted for 5 h. After the completion of the reaction, the reaction mixture was cooled to room temperature and then poured into cold water. A solid separated out. The mixture was filtered. The filter cake is dried to produce 150 mg of the title compound as an off-white powder in a yield of 24.5%.

$^1$H-NMR (600 MHz, DMSO) δ 1.829-1.850 (m, 4H), 2.378-2.386 (m, 2H), 3.209-3.219 (m, 2H), 3.585-3.593 (m, 2H), 3.895-3.904 (m, 2H), 4.05-4.059 (m, 2H), 6.917-6.930 (m, 2H), 7.279-7.351 (m, 4H), 7.483 (s, 1H), 7.766 (s, 1H), 7.4949-7.958 (s, 1H), 8.405 (s, 1H);

MS 461.2 [M+H]$^+$

Example 20: 1-(3-(difluoromethoxy)phenyl)-7-oxo-6-(4-(2-oxopiperidin-1-yl)phenyl)-4,5,6,7-tetrahydro-1H-pyrazolo[3,4-c]pyridine-3-carboxamide Step 1: ethyl 2-chloro-2-(2-(3-(difluoromethoxy)phenyl)hydrazono)acetate

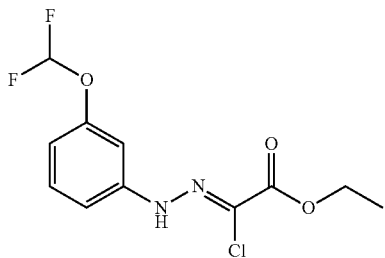 [SMILES: CCOC(=O)/C(Cl)=N/Nc1cccc(OC(F)F)c1]

3-(difluoromethoxy)aniline (10.0 g, 62.8 mmol) was added water (50 mL). The resulting mixture was stirred and cooled to −5 to 0° C. To the cooled mixture were added concentrated hydrochloric acid (16.7 mL), an aqueous sodium nitrite solution (28 mL), a solution of ethyl 2-chloro-3-oxobutanoate (10.6 g, 64.7 mmol) in ethanol (100 mL) and a solution of sodium acetate (15.5 g, 188.4 mmol) in water (120 mL). The resulting mixture was warmed up to room temperature, and stirred and reacted for 6 h. After the completion of the reaction, the reaction mixture was filtered. The filter cake was dried under vacuum to produce 16.0 g of the title compound in a yield of 87.3%.

Step 2: ethyl 1-(3-(difluoromethoxy)phenyl)-7-oxo-4,5,6,7-tetrahydro-1H-pyrazolo[3,4-c]pyridine-3-carboxylate

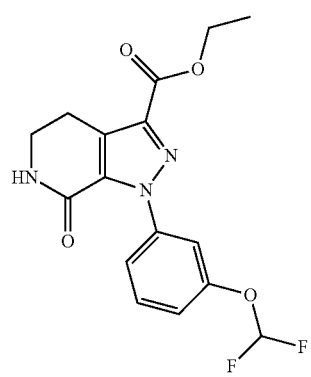 [SMILES: CCOC(=O)c1nn(-c2cccc(OC(F)F)c2)c2c1CCNC2=O]

Ethyl 2-chloro-2-(2-(3-(difluoromethoxy)phenyl)hydrazono)acetate (2.9 g, 10.0 mmol), 3-morpholino-5,6-dihydropyridin-2(1H)-one (1.8 g, 10.0 mmol), and triethylamine (2 mL) were successively added to toluene (30 mL) at room temperature. The mixture was heated to 110° C., and reacted under reflux for 3 h. The mixture was cooled to room temperature and concentrated under vacuum. To the residue was added to DCM (25 mL). The resulting mixture was cooled to 0° C. To the cooled mixture was added trifluoroacetic acid (3 mL). The resulting mixture was warmed up to room temperature, and stirred for 1 h. The resulting mixture was concentrated under vacuum to produce a crude product. The crude product was purified by silica gel column chromatography (DCM:MeOH=1:1) to give 0.9 g of the title compound as a khaki solid in a yield of 25.7%.

Step 3: ethyl 1-(3-(difluoromethoxy)phenyl)-7-oxo-6-(4-(2-oxopiperidin-1-yl)phenyl)-4,5,6,7-tetrahydro-1H-pyrazolo[3,4-c]pyridine-3-carboxylate

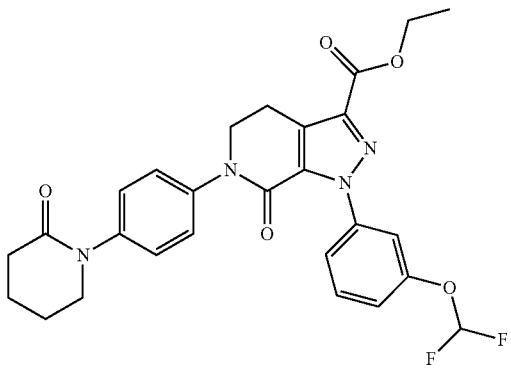 [SMILES: CCOC(=O)c1nn(-c2cccc(OC(F)F)c2)c2c1CCN(c1ccc(N3CCCCC3=O)cc1)C2=O]

1-(4-Iodophenyl)piperidin-2-one (0.85 g, 2.82 mmol), ethyl 1-(3-(difluoromethoxy)phenyl)-7-oxo-4,5,6,7-tetrahydro-1H-pyrazolo[3,4-c]pyridine-3-carboxylate (0.9 g, 2.56 mmol) and potassium carbonate (0.74 g, 5.38 mmol) were successively added to DMSO (20 mL) at room temperature. To the resulting mixture were added cupric iodide (230 mg, 1.2 mmol) and 1,10-phenanthroline (220 mg, 1.2 mmol) under the nitrogen protection. The mixture was heated to 120° C. and reacted for 12 h. After the completion of the reaction, water was added to the mixture. The resulting mixture was extracted with EA. The organic phases were concentrated to produce a crude product. The crude product was purified by silica gel column chromatography (PE:EA=1:1) to give 0.74 g of the title compound as a white solid in a yield of 55.1%.

Step 4: 1-(3-(difluoromethoxy)phenyl)-7-oxo-6-(4-(2-oxopiperidin-1-yl)phenyl)-4,5,6,7-tetrahydro-1H-pyrazolo[3,4-c]pyridine-3-carboxamide

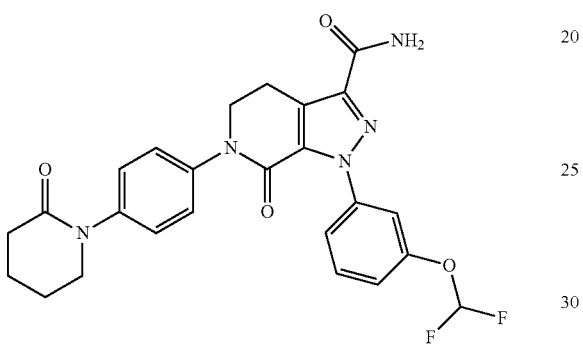

Ethyl 1-(3-(difluoromethoxy)phenyl)-7-oxo-6-(4-(2-oxopiperidin-1-yl)phenyl)-4,5,6,7-tetrahydro-1H-pyrazolo[3,4-c]pyridine-3-carboxylate (0.74 g, 1.41 mmol) was added to a seal tube. To the seal tube was added ethylene glycol (16 mL). Ammonia gas was introduced to the seal tube for 0.5 h, and then the seal tube was sealed. The mixture was heated to 120° C. and reacted for 5 h. After the completion of the reaction, the reaction mixture was cooled to room temperature and then poured into cold water. A solid separated out. The mixture was filtered. The filter cake was dried to produce 450 mg of the title compound as an off-white solid in a yield of 64.5%.

$^1$H-NMR (600 MHz, DMSO) δ 1.826-1.866 (m, 4H), 2.376-2.397 (m, 2H), 3.198-3.220 (m, 2H), 3.586-3.604 (m, 2H), 4.053-4.074 (m, 2H), 7.171 (s, 1H,), 7.266-7.294 (m, 4H), 7.357-7.372 (d, 1H), 7.505-7.529 (m, 4H) 7.788 (s, 1H) MS 496.0 [M+H]$^+$

Example 21: 1-(2-chloro-4-methoxyphenyl)-7-oxo-6-(4-(2-oxopiperidin-1-yl)phenyl)-4,5,6,7-tetrahydro-1H-pyrazolo[3,4-c]pyridine-3-carboxamide Step 1: ethyl 2-chloro-2-(2-(2-chloro-4-methoxyphenyl)hydrazono)acetate

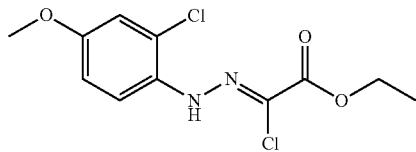 [SMILES: CCOC(=O)/C(Cl)=N/Nc1ccc(OC)cc1Cl]

At room temperature, 2-chloro-4-methoxyaniline (5.0 g, 31.7 mmol) was added to water (15 mL). The resulting mixture was cooled to −5 to 0° C. To the mixture were successively added concentrated hydrochloric acid (6 mL), an aqueous sodium nitrite solution (9 mL), a solution of ethyl 2-chloro-3-oxobutanoate (5.22 g, 31.7 mmol) in ethanol (30 mL) and a solution of sodium acetate (7.80 g, 95.1 mmol) in water (90 mL). After the completion of the addition, the mixture was stirred at a lower temperature for 0.5 h. Then the mixture was warmed to room temperature, and stirred and reacted for 6 h. During the reaction, a solid separated out. After the completion of the reaction, the reaction mixture was filtered. The filter cake was dried under vacuum. The residue was purified by silica gel column chromatography (PE:EA=10:1) to give 7.9 g of the title compound in a yield of 85.5%.

Step 2: ethyl 1-(2-chloro-4-methoxyphenyl)-7-oxo-4,5,6,7-tetrahydro-1H-pyrazolo[3,4-c]pyridine-3-carboxylate

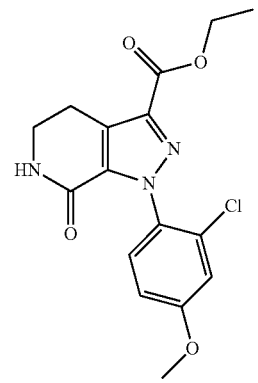 [SMILES: CCOC(=O)c1nn(-c2ccc(OC)cc2Cl)c2c1CCNC2=O]

Ethyl 2-chloro-2-(2-(2-chloro-4-methoxyphenyl)hydrazono)acetate (5.82 g, 20 mmol), 3-morpholino-5,6-dihydropyridin-2(1H)-one (3.64 g, 20.0 mmol) and triethylamine (6.07 g, 60 mmol) were successively added to toluene (26 mL) at room temperature. The mixture was heated to 110° C., and reacted under reflux for 12 h. The mixture was cooled to room temperature, and concentrated under vacuum to dryness. To the residue was added DCM (30 mL) and trifluoroacetic acid (2.5 mL). The resulting mixture was stirred and reacted for 2 h. After the completion of the reaction, the reaction mixture was washed with water. The aqueous phase was exacted with DCM. Then the organic phases were concentrated under vacuum. The residue was purified by silica gel column chromatography (PE:EA=1:1) to give 0.8 g of the title compound in a yield of 11.4%.

Step 3: ethyl 1-(2-chloro-4-methoxyphenyl)-7-oxo-6-(4-(2-oxopiperidin-1-yl)phenyl)-4,5,6,7-tetrahydro-1H-pyrazolo[3,4-c]pyridine-3-carboxylate

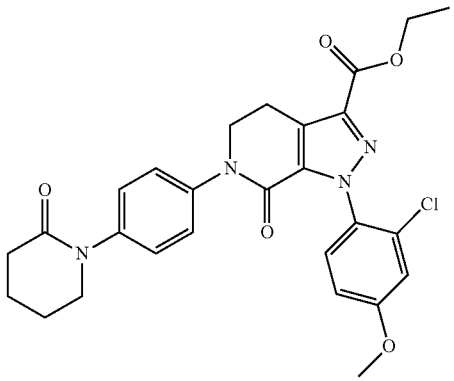 [SMILES: CCOC(=O)c1nn(-c2ccc(OC)cc2Cl)c2c1CCN(c1ccc(N3CCCCC3=O)cc1)C2=O]

At room temperature, to DMSO (25 mL) were successively added 1-(4-iodophenyl)piperidin-2-one (0.94 g, 3.1 mmol), ethyl 1-(2-chloro-4-methoxyphenyl)-7-oxo-4,5,6,7-tetrahydro-1H-pyrazolo[3,4-c]pyridine-3-carboxylate (0.70 g, 2.0 mmol) and potassium carbonate (0.58 g, 4.2 mmol). To the resulting mixture were added cupric iodide (180 mg, 0.94 mmol) and 1,10-phenanthroline (170 mg, 0.94 mmol) under a nitrogen atmosphere. The mixture was heated to 120° C. and reacted for 12 h. After the completion of the reaction, the resulting mixture was cooled to room temperature. To the cooled mixture was added water. The resulting mixture was extracted with EA. The organic phases were concentrated under vacuum to produce a crude product. The crude product was purified by silica gel column chromatography (PE:EA=1:1) to give 0.5 g of the title compound as an oil in a yield of 47.8%.

Step 4: 1-(2-chloro-4-methoxyphenyl)-7-oxo-6-(4-(2-oxopiperidin-1-yl)phenyl)-4,5,6,7-tetrahydro-1H-pyrazolo[3,4-c]pyridine-3-carboxamide

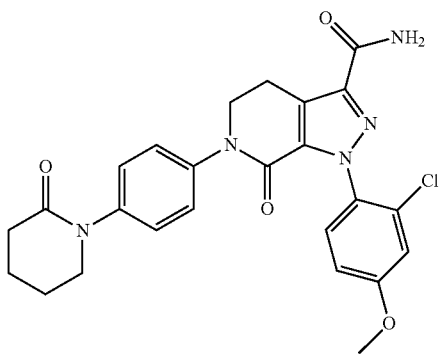 [SMILES: COc1ccc(-n2nc(C(N)=O)c3c2C(=O)N(c2ccc(N4CCCCC4=O)cc2)CC3)c(Cl)c1]

Ethyl 1-(2-chloro-4-methoxyphenyl)-7-oxo-6-(4-(2-oxopiperidin-1-yl)phenyl)-4,5,6,7-tetrahydro-1H-pyrazolo[3,4-c]pyridine-3-carboxylate (0.5 g, 0.95 mmol) was added to a seal tube. To the seal tube was added ethylene glycol (16 mL). Ammonia gas was introduced to the seal tube for 0.5 h, and then the seal tube was sealed. The mixture was heated to 120° C. and reacted for 5 h. After the completion of the reaction, the reaction mixture was cooled to room temperature and then poured into cold water. A solid separated out. The mixture was filtered. The filter cake was dried to produce 420 mg of the title compound as an off-white solid in a yield of 89.5%.

$^1$H NMR (600 MHz, DMSO) δ 1.830-1.853 (m, 4H), 2.378 (m, 2H), 3.23 (m, 2H), 3.579 (m, 2H), 3.834 (s, 3H), 4.053 (m, 2H), 7.014-7.018 (m, 1H), 7.195 (m, 1H), 7.262-7.320 (m, 4H), 7.453 (m, 1H), 7.508-7.521 (m, 1H), 7.773 (s, 1H)

MS 494.2 [M+H]$^+$

Example 22: 1-(4-methoxy-2-methylphenyl)-7-oxo-6-(4-(2-oxopiperidin-1-yl)phenyl)-4,5,6,7-tetrahydro-1H-pyrazolo[3,4-c]pyridine-3-carboxamide Step 1: ethyl 2-chloro-2-(2-(4-methoxy-2-methylphenyl)hydrazono)acetate

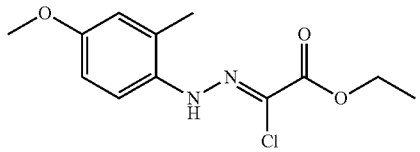

At room temperature, 4-methoxy-2-methylaniline (5.0 g, 36.4 mmol) was added to water (15 mL). The resulting mixture was stirred and cooled to −5 to 0° C. To the mixture were successively added concentrated hydrochloric acid (6 mL), an aqueous sodium nitrite solution (9 mL), a solution of ethyl 2-chloro-3-oxobutanoate (6.0 g, 36.4 mmol) in ethanol (30 mL) and a solution of sodium acetate (8.96 g, 109.2 mmol) in water (90 mL). After the completion of the addition, the mixture was stirred at a lower temperature for 0.5 h. Then the mixture was warmed to room temperature, and stirred and reacted for 6 h. During the reaction, a solid separated out. After the completion of the reaction, the reaction mixture was filtered. The filter cake was dried under vacuum. The residue was purified by silica gel column chromatography (PE:EA=10:1) to give 5.5 g of the title compound.

Step 2: ethyl 1-(4-methoxy-2-methylphenyl)-7-oxo-4,5,6,7-tetrahydro-1H-pyrazolo[3,4-c]pyridine-3-carboxylate

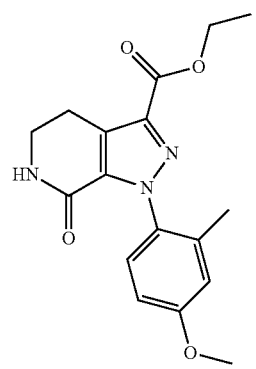 [SMILES: CCOC(=O)c1nn(-c2ccc(OC)cc2C)c2c1CCNC2=O]

Ethyl 2-chloro-2-(2-(4-methoxy-2-methylphenyl)hydrazono)acetate (5.41 g, 20 mmol), 3-morpholino-5,6-dihydropyridin-2(1H)-one (3.64 g, 20.0 mmol) and triethylamine (6.07 g, 60 mmol) were successively added to toluene (26 mL) at room temperature. The mixture was heated to 110° C., and reacted under reflux for 12 h. The mixture was cooled to room temperature and concentrated in vacuum to dryness. To the residue were added DCM (30 mL) and trifluoroacetic acid (2.5 mL). The resulting mixture was stirred and reacted for 2 h. After the completion of the reaction, the reaction mixture was washed with water and the resulting aqueous phase was exacted with DCM. Then the organic phases were concentrated under vacuum. The residue was purified by silica gel column chromatography (PE:EA=1:1) to give 1.3 g of the title compound in a yield of 19.7%.

Step 3: ethyl 1-(4-methoxy-2-methylphenyl)-7-oxo-6-(4-(2-oxopiperidin-1-yl)phenyl)-4,5,6,7-tetrahydro-1H-pyrazolo[3,4-c]pyridine-3-carboxylate

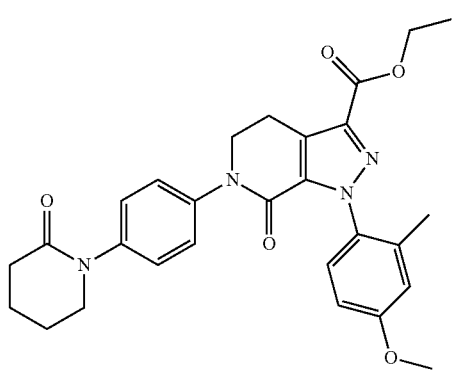 [SMILES: CCOC(=O)c1nn(-c2ccc(OC)cc2C)c2c1CCN(c1ccc(N3CCCCC3=O)cc1)C2=O]

1-(4-Iodophenyl)piperidin-2-one (0.99 g, 3.3 mmol), ethyl 1-(4-methoxy-2-methylphenyl)-7-oxo-4,5,6,7-tetrahydro-1H-pyrazolo[3,4-c]pyridine-3-carboxylate (0.99 g, 3.0 mmol) and potassium carbonate (0.87 g, 6.3 mmol) were successively added to DMSO (25 mL) at room temperature. Cupric iodide (271 mg, 1.41 mmol) and 1,10-phenanthroline (254 mg, 1.41 mmol) were added under a nitrogen atmosphere. The mixture was heated to 120° C. and reacted for 12 h. After the completion of the reaction, the reaction mixture was cooled to room temperature, and water was added. The resulting mixture was extracted with EA. The organic phases were concentrated under vacuum to produce a crude product. The crude product was purified by silica gel column chromatography (PE:EA=1:1) to give 1.1 g of the title compound as an oil in a yield of 73.3%.

Step 4: 1-(4-methoxy-2-methylphenyl)-7-oxo-6-(4-(2-oxopiperidin-1-yl)phenyl)-4,5,6,7-tetrahydro-1H-pyrazolo[3,4-c]pyridine-3-carboxamide

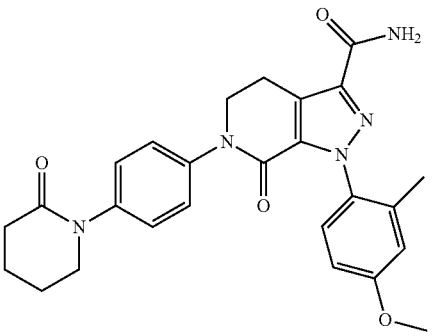 [SMILES: COc1ccc(-n2nc(C(N)=O)c3c2C(=O)N(c2ccc(N4CCCCC4=O)cc2)CC3)c(C)c1]

Ethyl 1-(4-methoxy-2-methylphenyl)-7-oxo-6-(4-(2-oxopiperidin-1-yl)phenyl)-4,5,6,7-tetrahydro-1H-pyrazolo[3,4-c]pyridine-3-carboxylate (1.0 g, 1.99 mmol) was added to a seal tube. To the seal tube was added ethylene glycol (20 mL). Ammonia gas was introduced to the seal tube for 0.5 h, and then the seal tube was sealed. The mixture was heated to 120° C. and reacted for 5 h. After the completion of the reaction, the reaction mixture was cooled to room temperature and then poured into cold water. A solid separated out. The mixture was filtered. The filter cake was dried to produce 750 mg of the title compound as an off-white solid in a yield of 79.4%.

$^1$H NMR (600 MHz, DMSO) δ 1.817-1.855 (m, 4H), 1.988 (s, 3H) 2.365-2.385 (m, 2H), 3.214-3.236 (m, 2H), 3.564-3.581 (m, 2H), 3.782 (s, 3H), 4.037-4.059 (m, 2H), 6.814-6.828 (m, 1H), 6.893 (s, 1H), 7.235-7.264 (m, 3H), 7.307-7.321 (m, 2H), 7.408 (s, 1H), 7.729 (s, 1H)

MS 474.2 [M+H]$^+$

Example 23: 1-(2-methoxypyridin-3-yl)-7-oxo-6-(4-(2-oxopiperidin-1-yl)phenyl)-4,5,6,7-tetrahydro-1H-pyrazolo[3,4-c]pyridine-3-carboxamide Step 1: ethyl 2-chloro-2-(2-(2-methoxypyridin-3-yl)hydrazono)acetate

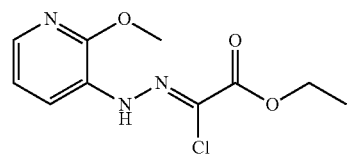 [SMILES: CCOC(=O)/C(Cl)=N/Nc1cccnc1OC]

2-methoxypyridin-3-amine (5.0 g, 40.3 mmol) was added water (15 mL). The resulting mixture was stirred and cooled to −5 to 0° C. To the mixture were successively added concentrated hydrochloric acid (6 mL), an aqueous sodium nitrite solution (9 mL), a solution of ethyl 2-chloro-3-oxobutanoate (6.63 g, 40.3 mmol) in ethanol (30 mL) and a solution of sodium acetate (9.91 g, 120.9 mmol) in water (90 mL). After the completion of the addition, the mixture was stirred at a lower temperature for 0.5 h. Then the mixture was warmed to room temperature, and stirred and reacted for 6 h. During the reaction, a solid separated out. After the completion of the reaction, the reaction mixture was filtered.

The filter cake was dried under vacuum. The residue was purified by silica gel column chromatography (PE:EA=10:1) to give 6.3 g of the title compound in a yield of 60.5%.

Step 2: ethyl 1-(2-methoxypyridin-3-yl)-7-oxo-4,5,6,7-tetrahydro-1H-pyrazolo[3,4-c]pyridine-3-carboxylate

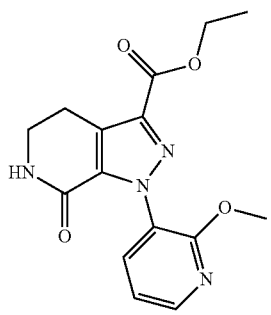 [SMILES: CCOC(=O)c1nn(-c2cccnc2OC)c2c1CCNC2=O]

Ethyl 2-chloro-2-(2-(2-methoxypyridin-3-yl)hydrazono) acetate (5.15 g, 20 mmol), 3-morpholino-5,6-dihydropyridin-2(1H)-one (3.64 g, 20 mmol) and triethylamine (6.07 g, 60 mmol) were successively added to toluene (26 mL) at room temperature. The mixture was heated to 110° C., and reacted under reflux for 12 h. The mixture was cooled to room temperature and concentrated in vacuum to dryness. To the residue was added DCM (30 mL) and trifluoroacetic acid (2.5 mL). The resulting mixture was stirred and reacted for 2 h. After the completion of the reaction, the reaction mixture was washed with water and the aqueous phase was extracted with DCM. Then the organic phases were concentrated under vacuum. The residue was purified by silica gel column chromatography (PE:EA=1:1) to give 0.6 g of the title compound in yield of 9.5%.

Step 3: ethyl 1-(2-methoxypyridin-3-yl)-7-oxo-6-(4-(2-oxopiperidin-1-yl)phenyl)-4,5,6,7-tetrahydro-1H-pyrazolo[3,4-c]pyridine-3-carboxylate

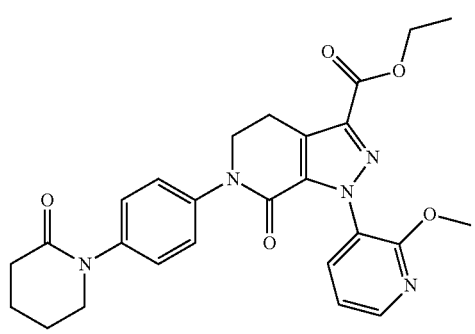 [SMILES: CCOC(=O)c1nn(-c2cccnc2OC)c2c1CCN(c1ccc(N3CCCCC3=O)cc1)C2=O]

To DMSO (25 mL) were successively added 1-(4-Iodophenyl)piperidin-2-one (0.60 g, 2.0 mmol), ethyl 1-(2-methoxypyridin-3-yl)-7-oxo-4,5,6,7-tetrahydro-1H-pyrazolo[3,4-c]pyridine-3-carboxylate (0.60 g, 1.9 mmol) and potassium carbonate (0.55 g, 4.0 mmol) at room temperature. To the resulting mixture were added cupric iodide (171 mg, 0.89 mmol) and 1,10-phenanthroline (160 mg, 0.89 mmol) under a nitrogen atmosphere. The mixture was heated to 120° C. and reacted for 12 h. After the completion of the reaction, the reaction mixture was cooled to room temperature, and water was added. The resulting mixture was extracted with EA. The organic phases were concentrated to produce a crude product. The crude product was purified by silica gel column chromatography (PE:EA=1:1) to give 0.6 g of the title compound as an oil in a yield of 64.2%.

Step 4: 1-(2-methoxypyridin-3-yl)-7-oxo-6-(4-(2-oxopiperidin-1-yl)phenyl)-4,5,6,7-tetrahydro-1H-pyrazolo[3,4-c]pyridine-3-carboxamide

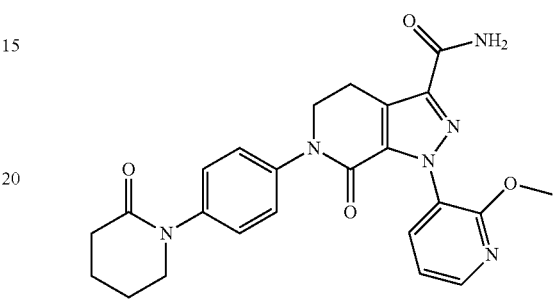

Ethyl 1-(2-methoxypyridin-3-yl)-7-oxo-6-(4-(2-oxopiperidin-1-yl)phenyl)-4,5,6,7-tetrahydro-1H-pyrazolo[3,4-c]pyridine-3-carboxylate (0.6 g, 1.22 mmol) was added to a seal tube. To the seal tube was added ethylene glycol (10 mL). Ammonia gas was introduced to the seal tube for 0.5 h, and then the seal tube was sealed. The mixture was heated to 120° C. and reacted for 3 h. After the completion of the reaction, the reaction mixture was cooled to room temperature and then poured into cold water. A solid separated out. The mixture was filtered. The filter cake was dried to produce 340 mg of the title compound as an off-white solid in a yield of 60.5%.

$^1$H-NMR (600 MHz, DMSO) δ: 1.818-1.856 (m, 4H), 2.375-2.380 (m, 2H), 3.219-3.222 (m, 2H), 3.575-3.581 (m, 2H), 3.828 (s, 3H), 4.052 (s, 2H), 7.128-7.148 (m, 1H), 7.261-7.276 (d, 2H), 7.314-7.328 (d, 2H), 7.454 (s, 1H), 7.756 (s, 1H), 7.874-7.886 (m, 1H), 8.279-8.285 (d, 11H)
MS 461.2 [M+H]$^+$

Example 24: 1-(2-(difluoromethoxy)phenyl)-7-oxo-6-(4-(2-oxopiperidin-1-yl)phenyl)-4,5,6,7-tetrahydro-1H-pyrazolo[3,4-c]pyridine-3-carboxamide Step 1: ethyl 2-chloro-2-(2-(2-(difluoromethoxy)phenyl)hydrazono)acetate

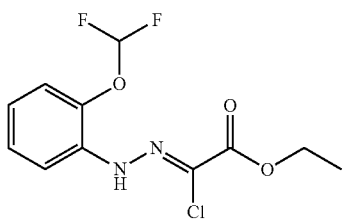 [SMILES: CCOC(=O)/C(Cl)=N/Nc1ccccc1OC(F)F]

2-(difluoromethoxy)aniline (24.0 g, 150 mmol) was added water (120 mL). The resulting mixture was stirred and cooled to −5 to 0° C. To the mixture were successively added concentrated hydrochloric acid (40 mL), an aqueous sodium nitrite solution (66 mL), a solution of ethyl 2-chloro-3-oxobutanoate (25.2 g, 150 mmol) in ethanol (120 mL) and a solution of sodium acetate (36.9 g, 450 mmol) in water (360 mL). After the completion of the addition, the mixture was stirred for 0.5 h at a lower temperature. Then the resulting mixture was warmed up to room temperature, and stirred and reacted for 6 h. During the reaction, a solid separated out. After the completion of the reaction, the reaction mixture was filtered. The filter cake was dried under vacuum. The resulting residue was purified by silica gel column chromatography (PE:EA=10:1) to give 35.0 g of the title compound in a yield of 79.7%.

Step 2: ethyl 1-(2-(difluoromethoxy)phenyl)-7-oxo-4,5,6,7-tetrahydro-1H-pyrazolo[3,4-c]pyridine-3-carboxylate

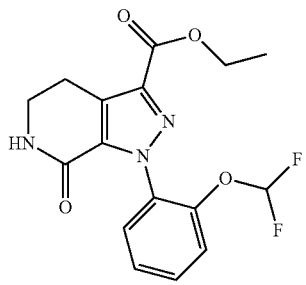 [SMILES: CCOC(=O)c1nn(-c2ccccc2OC(F)F)c2c1CCNC2=O]

Ethyl 2-chloro-2-(2-(2-(difluoromethoxy)phenyl)hydrazono)acetate (5.0 g, 17.1 mmol), 3-morpholino-5,6-dihydropyridin-2(1H)-one (3.12 g, 17.1 mmol) and triethylamine (5.19 g, 51.3 mmol) were successively added to toluene (60 mL) at room temperature. The mixture was heated to 110° C., and reacted under reflux for 12 h. The mixture was cooled to room temperature and concentrated in vacuum to dryness. To the residue were slowly added DCM (50 mL) and trifluoroacetic acid (5.0 mL). The resulting mixture was stirred and reacted for 2 h. After the completion of the reaction, the resulting mixture was washed with water. The aqueous phase was extracted with DCM. The organic phases were concentrated under vacuum to dryness. The residue was purified by silica gel column chromatography (PE:EA=1:1) to give 0.9 g of the title compound in a yield of 15.0%.

Step 3: ethyl 1-(2-(difluoromethoxy)phenyl)-7-oxo-6-(4-(2-oxopiperidin-1-yl)phenyl)-4,5,6,7-tetrahydro-1H-pyrazolo[3,4-c]pyridine-3-carboxylate

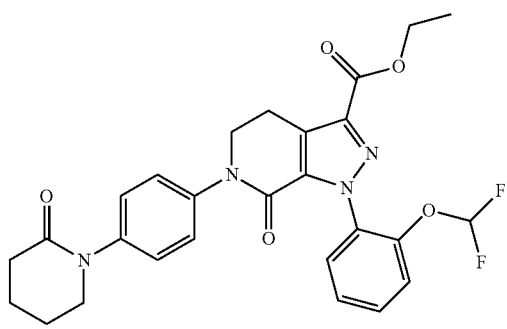 [SMILES: CCOC(=O)c1nn(-c2ccccc2OC(F)F)c2c1CCN(c1ccc(N3CCCCC3=O)cc1)C2=O]

At room temperature, to DMSO (20 mL) were successively added 1-(4-iodophenyl)piperidin-2-one (0.85 g, 2.82 mmol), ethyl 1-(2-(difluoromethoxy)phenyl)-7-oxo-4,5,6,7-tetrahydro-1H-pyrazolo[3,4-c]pyridine-3-carboxylate (0.90 g, 2.6 mmol) and potassium carbonate (0.75 g, 5.5 mmol). Under the nitrogen protection, to the mixture were added cupric iodide (235 mg, 1.2 mmol) and 1,10-phenanthroline (216 mg, 1.2 mmol). The mixture was heated to 120° C. and reacted for 12 h. After the completion of the reaction, the reaction mixture was cooled to room temperature, and water was added. The resulting mixture was extracted with EA. The organic phases were concentrated to produce a crude product. The crude product was purified by silica gel column chromatography (PE:EA=1:1) to give 0.9 g of the title compound as an oil in a yield of 66.2%.

Step 4: 1-(2-(difluoromethoxy)phenyl)-7-oxo-6-(4-(2-oxopiperidin-1-yl)phenyl)-4,5,6,7-tetrahydro-1H-pyrazolo[3,4-c]pyridine-3-carboxamide

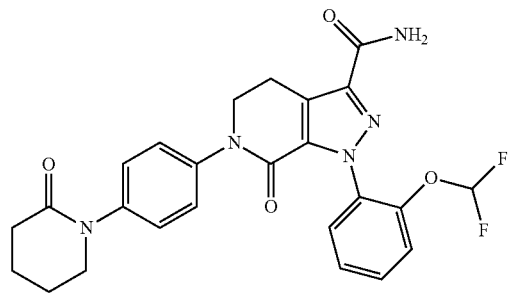 [SMILES: NC(=O)c1nn(-c2ccccc2OC(F)F)c2c1CCN(c1ccc(N3CCCCC3=O)cc1)C2=O]

Ethyl 1-(2-(difluoromethoxy)phenyl)-7-oxo-6-(4-(2-oxopiperidin-1-yl)phenyl)-4,5,6,7-tetrahydro-1H-pyrazolo[3,4-c]pyridine-3-carboxylate (0.9 g, 1.72 mmol) was added to a seal tube. To the seal tube was added ethylene glycol (10 mL). Ammonia gas was introduced to the seal tube for 0.5 h, and then the seal tube was sealed. The mixture was heated to 120° C. and reacted for 3 h. After the completion of the reaction, the reaction mixture was cooled to room temperature and then poured into cold water. A solid separated out. The mixture was filtered. The filter cake was dried to produce 420 mg as a khaki solid in a yield of 49.3%.

$^1$H-NMR (600 MHz, DMSO) δ: 1.819-1.857 (m, 4H), 2.376-2.383 (m, 2H), 3.225-3.231 (m, 2H), 3.576-3.562 (m, 2H), 4.038-4.044 (m, 2H), 7.088 (s, 1H), 7.210-7.317 (m, 5H), 7.371-7.422 (m, 1H), 7.481 (s, 1H), 7.567-7.620 (m, 2H), 7.758 (s, 1H)

MS 496.1 [M+H]$^-$

Example 25: 1-(4-(2-amino-2-oxoethoxy)phenyl)-7-oxo-6-(4-(2-oxopiperidin-1-yl)phenyl)-4,5,6,7-tetrahydro-1H-pyrazolo[3,4-c]pyridine-3-carboxamide Step 1: ethyl 2-chloro-2-(2-(4-(2-ethoxy-2-oxoethoxy)phenyl)hydrazono)acetate

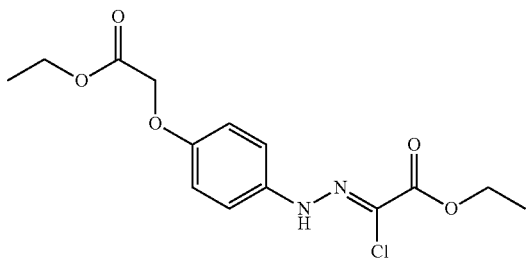 [SMILES: CCOC(=O)COc1ccc(N/N=C(\Cl)C(=O)OCC)cc1]

At room temperature, ethyl 2-(4-aminophenoxy)acetate (5.0 g, 25.6 mmol) was added to water (28 mL). The resulting mixture was stirred and cooled to −5 to 0° C. To the mixture were successively added concentrated hydrochloric acid (11 mL), an aqueous sodium nitrite solution (18 mL), a solution of ethyl 2-chloro-3-oxobutanoate (4.5 g, 27.3 mmol) in ethanol (47 mL) and a solution of sodium acetate (6.3 g, 76.8 mmol) in water (28 mL). After the completion of the addition, the mixture was stirred at a lower temperature for 0.5 h. The resulting mixture was warmed up to room temperature, and stirred and reacted for 6 h. During the reaction, a solid separated out. After the completion of the reaction, the mixture was filtered. The filter cake was washed with water, dried under vacuum, and purified by silica gel column chromatography (PE:EA=10:1) to give 4.2 g of the title compound in a yield of 50.0%.

Step 2: ethyl 1-(4-(2-ethoxy-2-oxoethoxy)phenyl)-7-oxo-4,5,6,7-tetra hydro-1H-pyrazolo[3,4-c]pyridine-3-carboxylate

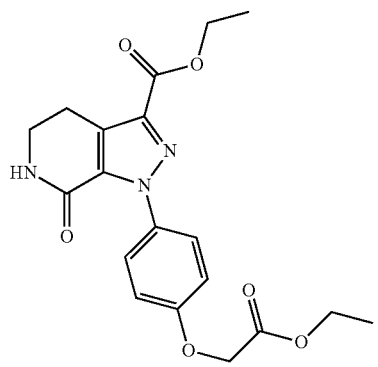 [SMILES: CCOC(=O)COc1ccc(-n2nc(C(=O)OCC)c3c2C(=O)NCC3)cc1]

Ethyl 2-chloro-2-(2-(4-(2-ethoxy-2-oxoethoxy)phenyl)hydrazono)acetate (4.23 g, 12.9 mmol), 3-morpholino-5,6-dihydropyridin-2(1H)-one (2.57 g, 14.1 mmol) and triethylamine (3.91 g, 38.7 mmol) were successively added to toluene (25 mL) at room temperature. The mixture was heated to 110° C., and reacted under reflux for 12 h. The mixture was cooled to room temperature and concentrated in vacuum to dryness. To the residue were added DCM (50 mL) and trifluoroacetic acid (5.0 mL). The resulting mixture was stirred and reacted for 2 h. After the completion of the reaction, the resulting mixture was washed with water. The aqueous phase was extracted with DCM. The organic phases were concentrated under vacuum. The residue was purified by silica gel column chromatography (PE:EA=1:1) to give 1.32 g of the title compound in a yield of 26.4%.

Step 3: ethyl 1-(4-(2-ethoxy-2-oxoethoxy)phenyl)-7-oxo-6-(4-(2-oxopiperidin-1-yl)phenyl)-4,5,6,7-tetra hydro-1H-pyrazolo[3,4-c]pyridine-3-carboxylate

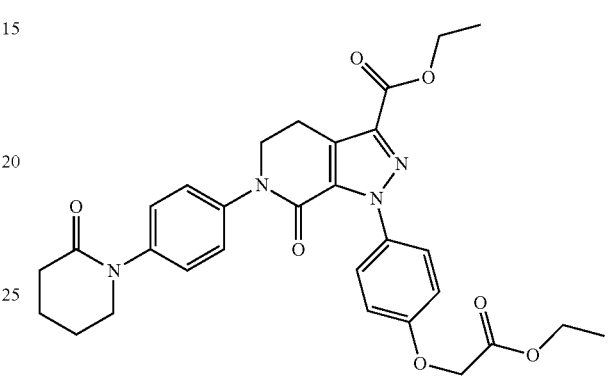

At room temperature, to DMSO (25 mL) were successively added 1-(4-iodophenyl)piperidin-2-one (1.11 g, 3.7 mmol), ethyl 1-(4-(2-ethoxy-2-oxoethoxy)phenyl)-7-oxo-4,5,6,7-tetrahydro-1H-pyrazolo[3,4-c]pyridine-3-carboxylate (1.32 g, 3.4 mmol) and potassium carbonate (0.98 g, 7.1 mmol). Cupric iodide (310 mg, 1.6 mmol) and 1,10-phenanthroline (290 mg, 1.6 mmol) were added to the resulting mixture under the nitrogen protection. The mixture was heated to 120° C. and reacted for 12 h. After the completion of the reaction, the reaction mixture was cooled to room temperature, and water was added. The resulting mixture was extracted with EA. The organic phases were concentrated under vacuum to produce a crude product. The crude product was purified by silica gel column chromatography (PE:EA=1:1) to give 0.44 g of the title compound in a yield of 23.1%.

Step 4: 1-(4-(2-amino-2-oxoethoxy)phenyl)-7-oxo-6-(4-(2-oxopiperidin-1-yl)phenyl)-4,5,6,7-tetrahydro-1H-pyrazolo[3,4-c]pyridine-3-carboxamide

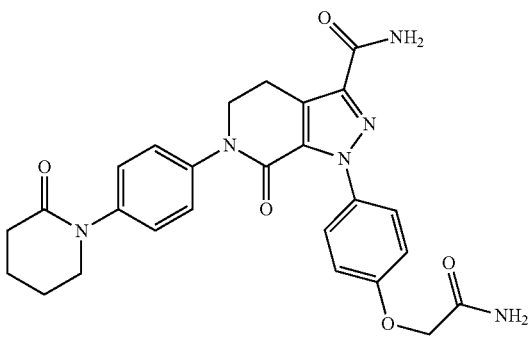 [SMILES: NC(=O)COc1ccc(-n2nc(C(N)=O)c3c2C(=O)N(c2ccc(N4CCCCC4=O)cc2)CC3)cc1]

Ethyl 1-(4-(2-ethoxy-2-oxoethoxy)phenyl)-7-oxo-6-(4-(2-oxopiperidin-1-yl)phenyl)-4,5,6,7-tetrahydro-1H-pyrazolo[3,4-c]pyridine-3-carboxylate (0.44 g, 0.78 mmol) was added to a seal tube. To the seal tube was added ethylene glycol (10 mL). Ammonia gas was introduced to the seal tube for 0.5 h, and then the seal tube was sealed. The mixture was heated to 120° C. and reacted for 3 h. After the completion of the reaction, the reaction mixture was cooled to room temperature and then poured into cold water. A solid separated out. The mixture was filtered. The filter cake was dried to produce 210 mg of the title product as a light yellow solid in a yield of 53.6%.

$^1$H-NMR (600 MHz, DMSO) δ: 1.825-1.864 (m, 4H), 2.386-2.389 (m, 2H), 3. 201 (m, 2H), 3.582-3.600 (m, 2H), 4.145 (m, 2H), 4.952 (s, 2H), 6.860 (s, 1H), 7.276-7.288 (d, 2H), 7.358-7.367 (d, 2H), 7.388 (s, 1H), 7.440 (s, 1H), 7.484-7.498 (d, 2H), 7.572-7.583 (d, 2H), 7.750 (s, 1H)

MS 503.1 [M+H]$^+$

Example 26: 1-(3-fluoro-4-methoxyphenyl)-7-oxo-6-(4-(3-oxomorpholino)phenyl)-4,5,6,7-tetrahydro-1H-pyrazolo[3,4-c]pyridine-3-carboxamide Step 1: ethyl 2-chloro-2-(2-(3-fluoro-4-methoxyphenyl)hydrazono)acetate

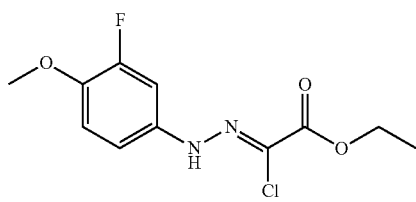

At room temperature, 3-fluoro-4-methoxyaniline (21.0 g, 0.15 mol) was added to water (100 mL). The resulting mixture was stirred and cooled to −5 to 0° C. To the resulting mixture were successively added concentrated hydrochloric acid (45 mL), an aqueous sodium nitrite solution (70 mL), a solution of ethyl 2-chloro-3-oxobutanoate (24.7 g, 0.15 mol) in ethanol (150 mL) and a solution of sodium acetate (36.9 g, 0.45 mol) in water (150 mL). After the completion of the addition, the mixture was stirred at a lower temperature for 0.5 h. Then the resulting mixture was warmed up to room temperature, and stirred and reacted for 6 h. During the reaction, a solid separated out. After the completion of the reaction, the resulting mixture was filtered. The filter cake was dried under vacuum, and purified by silica gel column chromatography (PE:EA=10:1) to give 36.5 g of the title compound in a yield of 88.6%.

Step 2: ethyl 1-(3-fluoro-4-methoxyphenyl)-7-oxo-4,5,6,7-tetrahydro-1H-pyrazolo[3,4-c]pyridine-3-carboxylate

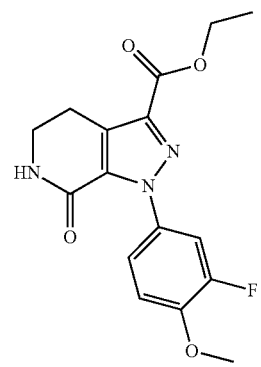 [SMILES: CCOC(=O)c1nn(-c2ccc(OC)c(F)c2)c2c1CCNC2=O]

Ethyl 2-chloro-2-(2-(3-fluoro-4-methoxyphenyl)hydrazono)acetate (8.0 g, 29.1 mmol), 3-morpholino-5,6-dihydropyridin-2(1H)-one (6.0 g, 31.9 mmol), and triethylamine (8.6 g, 85.2 mmol) were successively added to toluene (60 mL) at room temperature. The mixture was heated to 110° C., and reacted under reflux for 12 h. The mixture was cooled to room temperature and concentrated in vacuum to dryness. To the residue were added DCM (100 mL) and trifluoroacetic acid (6.0 mL). The resulting mixture was stirred and reacted for 2 h. After the completion of the reaction, the resulting mixture was washed with water. The aqueous phase was extracted with DCM. The organic phases were combined, dried over Na2SO4, and filtered. The filtrate was concentrated under vacuum. The residue was purified by silica gel column chromatography (PE:EA=1:1) to give 2.8 g of the title compound in a yield of 29.6%.

Step 3: ethyl 1-(3-fluoro-4-methoxyphenyl)-7-oxo-6-(4-(3-oxomorpholino)phenyl)-4,5,6,7-tetrahydro-1H-pyrazolo[3,4-c]pyridine-3-carboxylate

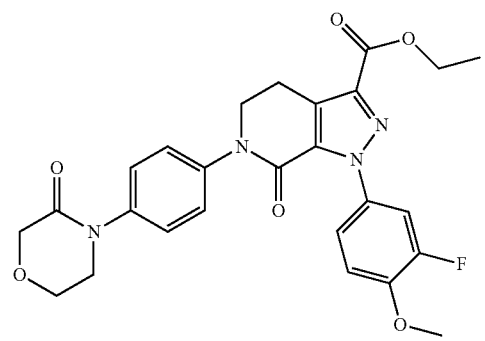 [SMILES: CCOC(=O)c1nn(-c2ccc(OC)c(F)c2)c2c1CCN(c1ccc(N3CCOCC3=O)cc1)C2=O]

At room temperature, to DMSO (20 mL) were successively added 1-(4-iodophenyl)piperidin-2-one (0.9 g, 3.0 mmol), ethyl 1-(3-fluoro-4-methoxyphenyl)-7-oxo-4,5,6,7-tetrahydro-1H-pyrazolo[3,4-c]pyridine-3-carboxylate (1.0 g, 3.0 mmol) and potassium carbonate (0.87 g, 6.3 mmol). Under the nitrogen protection, to the resulting mixture were added cupric iodide (270 mg, 1.4 mmol) and 1,10-phenanthroline (255 mg, 1.4 mmol). The mixture was heated to 120° C. and reacted for 12 h. After the completion of the reaction, the reaction mixture was cooled to room temperature, and water was added. The resulting mixture was extracted with EA. The resulting organic phases were concentrated under vacuum to produce a crude product. The crude product was purified by silica gel column chromatography (PE:EA=1:1) to give 1.0 g of the title compound in a yield of 65.5%.

Step 4: 1-(3-fluoro-4-methoxyphenyl)-7-oxo-6-(4-(3-oxomorpholino)phenyl)-4,5,6,7-tetrahydro-1H-pyrazolo[3,4-c]pyridine-3-carboxamide

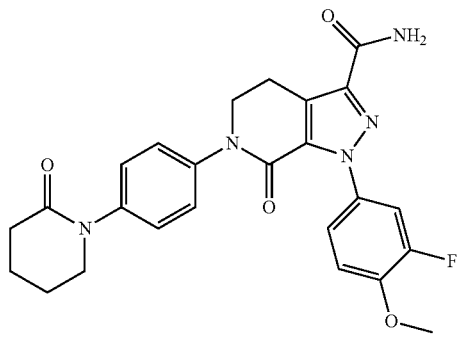 [SMILES: COc1ccc(-n2nc(C(N)=O)c3c2C(=O)N(c2ccc(N4CCCCC4=O)cc2)CC3)cc1F]

Ethyl 1-(3-fluoro-4-methoxyphenyl)-7-oxo-6-(4-(3-oxomorpholino)phenyl)-4,5,6,7-tetrahydro-1H-pyrazolo[3,4-c]pyridine-3-carboxylate (1.0 g, 2.0 mmol) was added to a seal tube. To the seal tube was added ethylene glycol (10 mL). Ammonia gas was introduced to the seal tube for 0.5 h, and then the seal tube was sealed. The mixture was heated to 120° C. and reacted for 3 h. After the completion of the reaction, the reaction mixture was cooled to room temperature and then poured into cold water. A solid separated out. The mixture was filtered, and dried to produce 360 mg of the title compound as a light yellow solid in a yield of 37.5%.

$^1$H NMR (600 MHz, DMSO) δ: 3.156-3.162 (m, 2H), 3.220-3.230 (m, 3H), 3.434-3.594 (m, 2H), 3.576-3.594 (m, 2H), 3.829 (s, 2H), 3.892-3.923 (m, 2H), 6.595-6.609 (d, 2H), 7.043-7.057 (d, 2H), 7.219-7.241 (m, 1H), 7.289-7.304 (m, 1H), 7.417 (s, 1H), 7.571-7.599 (dd, 1H), 7.763 (1H, s) MS 480.1 [M+H]$^+$

Example 27: 1-(3-fluoro-4-methoxyphenyl)-7-oxo-6-(4-(2-oxopyrrolidin-1-yl)phenyl)-4,5,6,7-tetrahydro-1H-pyrazolo[3,4-c]pyridine-3-carboxamide Step 1: ethyl 1-(3-fluoro-4-methoxyphenyl)-7-oxo-6-(4-(2-oxopyrrolidin-1-yl)phenyl)-4,5,6,7-tetrahydro-1H-pyrazolo[3,4-c]pyridine-3-carboxylate

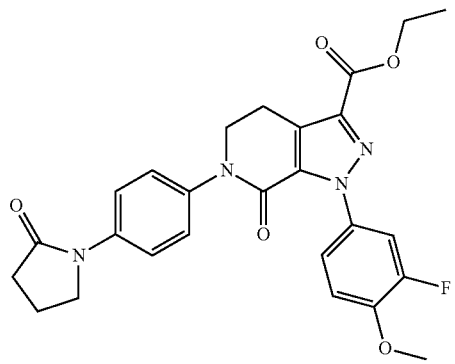 [SMILES: CCOC(=O)c1nn(-c2ccc(OC)c(F)c2)c2c1CCN(c1ccc(N3CCCC3=O)cc1)C2=O]

At room temperature, to DMSO (20 mL) were successively added 1-(4-Iodophenyl)pyrrolidin-2-one (0.95 g, 3.3 mmol), ethyl 1-(3-fluoro-4-methoxyphenyl)-7-oxo-4,5,6,7-tetrahydro-1H-pyrazolo[3,4-c]pyridine-3-carboxylate (1.05 g, 3.1 mmol) and potassium carbonate (0.87 g, 6.3 mmol). Under the nitrogen protection, to the resulting mixture were added cupric iodide (270 mg, 1.4 mmol) and 1,10-phenanthroline (250 mg, 1.4 mmol). The mixture was heated to 120° C. and reacted for 12 h. After the completion of the reaction, the reaction mixture was cooled to room temperature, and water was added. The resulting mixture was extracted with EA. The organic phases were concentrated under vacuum to produce a crude product. The crude product was purified by silica gel column chromatography (PE:EA=1:1) to give 0.8 g of the title compound in a yield of 52.4%.

Step 2: 1-(3-fluoro-4-methoxyphenyl)-7-oxo-6-(4-(2-oxopyrrolidin-1-yl)phenyl)-4,5,6,7-tetrahydro-1H-pyrazolo[3,4-c]pyridine-3-carboxamide

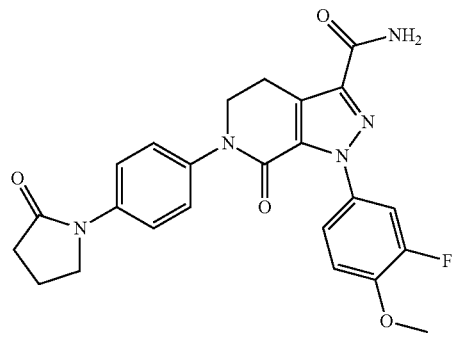 [SMILES: COc1ccc(-n2nc(C(N)=O)c3c2C(=O)N(c2ccc(N4CCCC4=O)cc2)CC3)cc1F]

Ethyl 1-(3-fluoro-4-methoxyphenyl)-7-oxo-6-(4-(2-oxopyrrolidin-1-yl)phenyl)-4,5,6,7-tetrahydro-1H-pyrazolo[3,4-c]pyridine-3-carboxylate (0.8 g, 1.6 mmol) was added to a seal tube. To the seal tube was added ethylene glycol (10 mL). Ammonia gas was introduced to the seal tube for 0.5 h, and then the seal tube was sealed. The mixture was heated to 120° C. and reacted for 3 h. After the completion of the reaction, the reaction mixture was cooled to room temperature and then poured into cold water. A solid separated out. The mixture was filtered. The filter cake was dried to produce 500 mg of the title compound as a khaki solid in a yield of 67.4%.

$^1$H NMR (600 MHz, DMSO) δ: 2.053-2.064 (m, 2H), 3.189-3.198 (m, 2H), 3.301-3.395 (m, 1H), 3.821-3.832 (m, 5H), 4.017-4.027 (m, 2H), 4.441 (s, 1H), 7.234-7.247 (m, 1H), 7.352-7.467 (m, 4H), 7.581-7.749 (m, 4H)

MS 464.0 [M+H]$^+$

Example 28: 1-(4-methoxyphenyl)-6-(4-(N-methylisobutyramido)phenyl)-7-oxo-4,5,6,7-tetrahydro-1H-pyrazolo[3,4-c]pyridine-3-carboxamide Step 1: ethyl 1-(4-methoxyphenyl)-6-(4-(N-methylisobutyramido)phenyl)-7-oxo-4,5,6,7-tetrahydro-1H-pyrazolo[3,4-c]pyridine-3-carboxylate

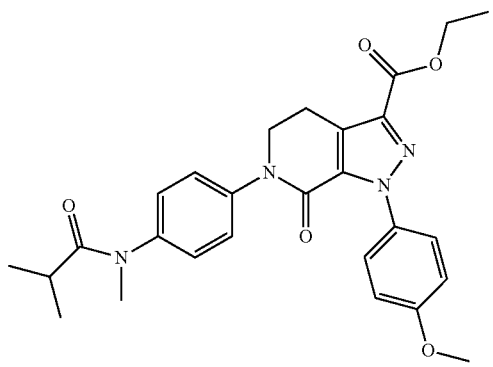 [SMILES: CCOC(=O)c1nn(-c2ccc(OC)cc2)c2c1CCN(c1ccc(N(C)C(=O)C(C)C)cc1)C2=O]

At room temperature, to DMSO (5 mL) were successively added N-(4-iodophenyl)-N-methylisobutyramide (1.00 g, 3.3 mmol), ethyl 1-(4-methoxyphenyl)-7-oxo-4,5,6,7-tetrahydro-1H-pyrazolo[3,4-c]pyridine-3-carboxylate (0.95 g, 3.0 mmol), 1,10-phenanthroline (0.25 g, 1.41 mmol) and potassium carbonate (0.87 g, 6.3 mmol). Under the nitrogen protection, the mixture was stirred and reacted at 120° C. for 12 h. The reaction mixture was poured into ice-water (50 mL). The resulting mixture was extracted with EA. The organic phases were concentrated under vacuum to produce a crude product. The crude product was purified by prep-HPLC to give 0.15 g of the title compound as a khaki solid in a yield of 10.2%.

Step 2: 1-(4-methoxyphenyl)-6-(4-(N-methylisobutyramido)phenyl)-7-oxo-4,5,6,7-tetrahydro-1H-pyrazolo[3,4-c]pyridine-3-carboxamide

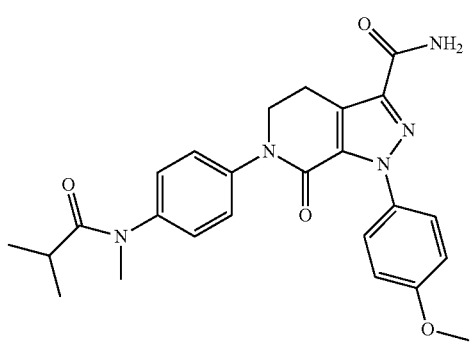 [SMILES: COc1ccc(-n2nc(C(N)=O)c3c2C(=O)N(c2ccc(N(C)C(=O)C(C)C)cc2)CC3)cc1]

Ethyl 1-(4-methoxyphenyl)-6-(4-(N-methylisobutyramido)phenyl)-7-oxo-4,5,6,7-tetrahydro-1H-pyrazolo[3,4-c]pyridine-3-carboxylate (0.15 g, 0.3 mmol) was added to a seal tube. To the seal tube was added ethylene glycol (20 mL). Ammonia gas was introduced to the seal tube for 0.5 h, and then the seal tube was sealed. The mixture was heated to 120° C. and reacted for 3 h. After the completion of the reaction, the reaction mixture was cooled to room temperature and then poured into cold water. A solid separated out. The mixture was filtered. The filter cake was dried to produce 75 mg of the title compound as an off-white solid in a yield of 54.2%.

$^1$H NMR (600 MHz, DMSO) δ: 0.915-0.924 (m, 6H), 3.124 (s, 3H), 3.200-3.221 (m, 2H), 3.550-3.558 (m, 1H), 3.804 (s, 3H), 4.070-4.092 (m, 2H), 6.995-7.009 (m, 2H), 7.333-7.346 (m, 2H), 7.426-7.447 (m, 3H), 7.496-7.511 (m, 2H), 8.405 (1H, s)

MS 462.2 [M+H]

Example 29: 1-(4-ethoxy-3-fluorophenyl)-7-oxo-6-(4-(2-oxopiperidin-1-yl)phenyl)-4,5,6,7-tetrahydro-1H-pyrazolo[3,4-c]pyridine-3-carboxamide Step 1: ethyl 2-chloro-2-(2-(4-ethoxy-3-fluorophenyl)hydrazono)acetate

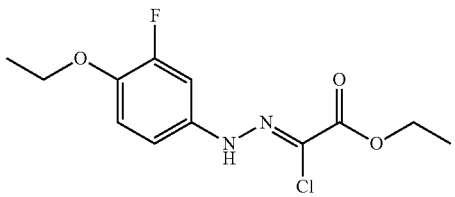 [SMILES: CCOC(=O)/C(Cl)=N/Nc1ccc(OCC)c(F)c1]

At room temperature, 4-ethoxy-3-fluoroaniline (3.8 g, 24.5 mmol) was added to water (25 mL). The resulting mixture was stirred and cooled to −5 to 0° C. To the resulting mixture were successively added concentrated hydrochloric acid (10 mL), an aqueous sodium nitrite solution (12 mL), a solution of ethyl 2-chloro-3-oxobutanoate (4.2 g, 25.5 mmol) in ethanol (40 mL) and a solution of sodium acetate (6.1 g, 74.4 mmol) in water (25 mL). After the completion of the addition, the mixture was stirred at a lower temperature for 0.5 h. Then the resulting mixture was warmed up to room temperature, and stirred and reacted for 6 h. During the reaction, a solid separated out. After the completion of the reaction, the resulting mixture was filtered. The filter cake was dried under vacuum, and purified by silica gel column chromatography (PE:EA=10:1) to produce 5.3 g of the title compound in a yield of 74.6%.

Step 2: ethyl 1-(4-ethoxy-3-fluorophenyl)-7-oxo-4,5,6,7-tetrahydro-1H-pyrazolo[3,4-c]pyridine-3-carboxylate

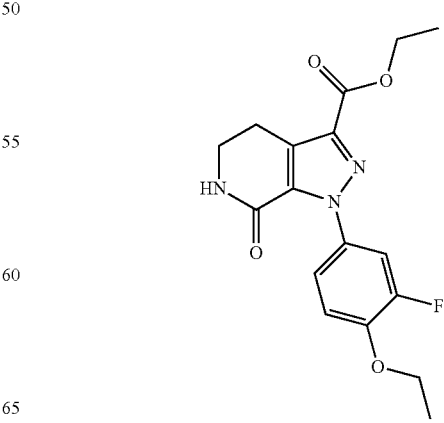

Ethyl 2-chloro-2-(2-(4-ethoxy-3-fluorophenyl)hydrazono)acetate (5.3 g, 18.4 mmol), 3-morpholino-5,6-dihydropyridin-2(1H)-one (3.4 g, 18.6 mmol) and triethylamine (5.6 g, 55.2 mmol) were successively added to toluene (60 mL) at room temperature. The mixture was heated to 110° C., and reacted under reflux for 12 h. The mixture was cooled to room temperature and concentrated in vacuum to dryness. To the residue were added DCM (40 mL) and trifluoroacetic acid (5.0 mL). The resulting mixture was stirred and reacted for 2 h. After the completion of the reaction, the resulting mixture was washed with water. The aqueous phase was extracted with DCM. The resulting organic phases were concentrated under vacuum and purified by silica gel column chromatography (PE:EA=1:1) to give 4.9 g of the title compound in a yield of 76.5%.

Step 3: ethyl 1-(4-ethoxy-3-fluorophenyl)-7-oxo-6-(4-(2-oxopiperidin-1-yl)phenyl)-4,5,6,7-tetrahydro-1H-pyrazolo[3,4-c]pyridine-3-carboxylate

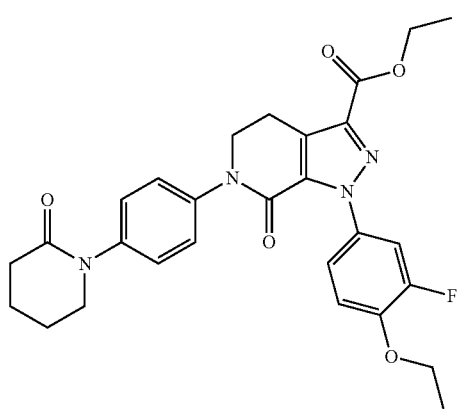 [SMILES: CCOC(=O)c1nn(-c2ccc(OCC)c(F)c2)c2c1CCN(c1ccc(N3CCCCC3=O)cc1)C2=O]

At room temperature, 1-(4-Iodophenyl)piperidin-2-one (2.5 g, 8.3 mmol), ethyl 1-(4-ethoxy-3-fluorophenyl)-7-oxo-4,5,6,7-tetrahydro-1H-pyrazolo[3,4-c]pyridine-3-carboxylate (2.4 g, 6.9 mmol) and potassium carbonate (2.1 g, 15.1 mmol) were successively added to DMSO (35 mL). Under the nitrogen protection, to the resulting mixture were added cupric iodide (650 mg, 3.4 mmol) and 1,10-phenanthroline (613 mg, 3.4 mmol). The mixture was heated to 120° C. and reacted for 12 h. After the completion of the reaction, the reaction mixture was cooled to room temperature, and water was added. The resulting mixture was extracted with EA. The organic phases were concentrated under vacuum to produce a crude product. The crude product was purified by silica gel column chromatography (PE:EA=1:1) to give 1.0 g of the title compound in a yield of 26.7%.

Step 4: 1-(4-ethoxy-3-fluorophenyl)-7-oxo-6-(4-(2-oxopiperidin-1-yl)phenyl)-4,5,6,7-tetrahydro-1H-pyrazolo[3,4-c]pyridine-3-carboxamide

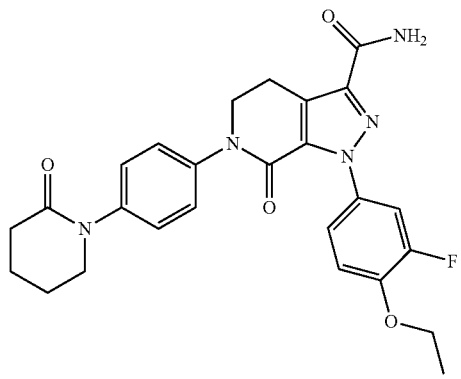 [SMILES: CCOc1ccc(-n2nc(C(N)=O)c3c2C(=O)N(c2ccc(N4CCCCC4=O)cc2)CC3)cc1F]

Ethyl 1-(4-ethoxy-3-fluorophenyl)-7-oxo-6-(4-(2-oxopiperidin-1-yl)phenyl)-4,5,6,7-tetrahydro-1H-pyrazolo[3,4-c]pyridine-3-carboxylate (1.0 g, 1.9 mmol) was added to a seal tube. To the seal tube was added ethylene glycol (10 mL). Ammonia gas was introduced to the seal tube for 0.5 h, and then the seal tube was sealed. The mixture was heated to 120° C. and reacted for 3 h. After the completion of the reaction, the reaction mixture was cooled to room temperature and then poured into cold water. A solid separated out. The mixture was filtered. The filter cake was dried to produce 550 mg of the title compound as a khaki solid in a yield of 58.3%.

$^1$H NMR (600 MHz, DMSO) δ: 1.362-1.368 (In, 3H), 1.825-1.864 (m, 4H), 2.386-2.389 (m, 2H), 3.195-3.201 (m, 2H), 3.582-3.600 (m, 2H), 4.031-4.052 (m, 2H), 4.141-4.175 (m, 2H), 7.224-7.239 (m, 1H), 7.275-7.289 (d, 2H), 7.348-7.362 (d, 2H), 7.388-7.402 (d, 1H), 7.470 (s, 1H), 7.564-7.588 (dd, 1H), 7.757 (s, 1H)

MS 492.4 [M+H]$^+$

Example 30: 1-(4-methoxyphenyl)-7-oxo-6-(4-(2-oxoazepan-1-yl)phenyl)-4,5,6,7-tetrahydro-1H-pyrazolo[3,4-c]pyridine-3-carboxamide Step 1: ethyl 6-(4-(6-bromohexanamido)phenyl)-1-(4-methoxyphenyl)-7-oxo-4,5,6,7-tetrahydro-1H-pyrazolo[3,4-c]pyridine-3-carboxylate

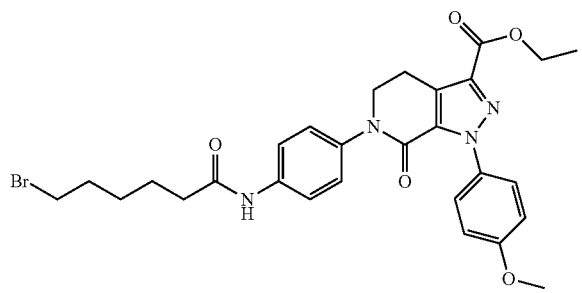 [SMILES: CCOC(=O)c1nn(-c2ccc(OC)cc2)c2c1CCN(c1ccc(NC(=O)CCCCCBr)cc1)C2=O]

6-Bromohexanoic acid (2.02 g, 10.4 mmol), 4-dimethylaminopyridine (0.20 g, 1.64 mmol) and ethyl 6-(4-aminophenyl)-1-(4-methoxyphenyl)-7-oxo-4,5,6,7-tetrahydro- 1H-pyrazolo[3,4-c]pyridine-3-carboxylate (4.00 g, 9.8 mmol) were added to DCM (40 mL) at room temperature. The mixture was stirred and reacted for 4 h at room temperature. After the completion of the reaction, the resulting mixture was concentrated under vacuum to afford 2.70 g of the title compound as a light yellow solid in a yield of 47.2%.

Step 2: ethyl 1-(4-methoxyphenyl)-7-oxo-6-(4-(2-oxoazepan-1-yl)phenyl)-4,5,6,7-tetrahydro-1H-pyrazolo[3,4-c]pyridine-3-carboxylate

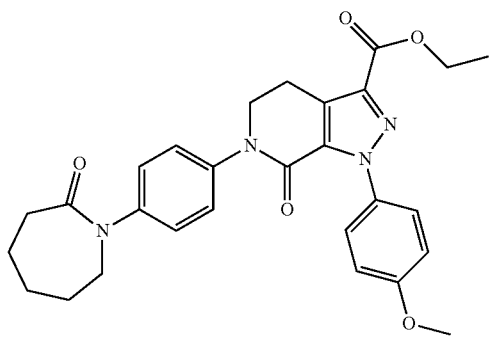 [SMILES: CCOC(=O)c1nn(-c2ccc(OC)cc2)c2c1CCN(c1ccc(N3CCCCCC3=O)cc1)C2=O]

Potassium tert-butoxide (0.62 g, 5.5 mmol) and ethyl 6-(4-(6-bromohexanamido)phenyl)-1-(4-methoxyphenyl)-7-oxo-4,5,6,7-tetra hydro-1H-pyrazolo[3,4-c]pyridine-3-carboxylate (2.60 g, 4.4 mmol) were successively added to THF (30 mL) at 0 to 5° C. The mixture was warmed up to room temperature, and reacted for 3 h. After the completion of the reaction, the reaction mixture was added into an icy diluted hydrochloric acid solution (0.5 mol/L). The resulting mixture was extracted with EA. The organic phases were concentrated under vacuum. The residue was purified by silica gel column chromatography (PE:EA=1:1) to give 270 mg of the title compound as a light yellow solid in a yield of 11.9%.

Step 3: 1-(4-methoxyphenyl)-7-oxo-6-(4-(2-oxoazepan-1-yl)phenyl)-4,5,6,7-tetrahydro-1H-pyrazolo[3,4-c]pyridine-3-carboxamide

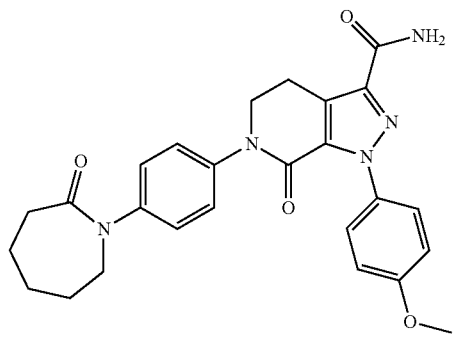 [SMILES: COc1ccc(-n2nc(C(N)=O)c3c2C(=O)N(c2ccc(N4CCCCCC4=O)cc2)CC3)cc1]

Ethyl 1-(4-methoxyphenyl)-7-oxo-6-(4-(2-oxoazepan-1-yl)phenyl)-4,5,6,7-tetrahydro-1H-pyrazolo[3,4-c]pyridine-3-carboxylate (0.25 g, 0.5 mmol) was added to a seal tube. To the seal tube was added ethylene glycol (20 mL). Ammonia gas was introduced to the seal tube for 0.5 h, and then the seal tube was sealed. The mixture was heated to 120° C. and reacted for 3 h. After the completion of the reaction, the reaction mixture was cooled to room temperature and then poured into cold water. A solid separated out. The mixture was filtered. The filter cake was dried to produce 150 mg of the title compound as an off-white solid in a yield of 63.4%.

$^1$H NMR (600 MHz, DMSO) δ 1.727 (m, 6H), 2.586-2.602 (m, 2H), 3.189-3.211 (m, 2H), 3.714-3.723 (m, 2H), 3.805 (s, 3H), 4.029-4.051 (m, 2H), 6.988-7.002 (d, 2H), 7.198-7.212 (d, 2H), 7.322-7.336 (d, 2H), 7.433 (s, 1H), 7.492-7.507 (d, 2H), 7.711 (s, 1H)

MS 474.2 [M+H]$^+$

Example 31: 1-(3-(ethoxymethyl)phenyl)-7-oxo-6-(4-(2-oxopiperidin-1-yl)phenyl)-4,5,6,7-tetrahydro-1H-pyrazolo[3,4-c]pyridine-3-carboxamide Step 1: ethyl 2-chloro-2-(2-(3-(ethoxymethyl)phenyl)hydrazono)acetate

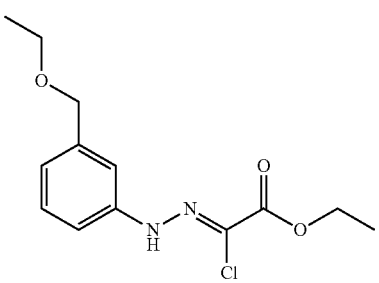 [SMILES: CCOCc1cccc(N/N=C(\Cl)C(=O)OCC)c1]

At room temperature, 3-(ethoxymethyl)aniline (3.3 g, 22 mmol) was added to water (20 mL). The mixture was stirred and cooled to −5 to 0° C. To the resulting mixture were successively added concentrated hydrochloric acid (10 mL), an aqueous sodium nitrite solution (15 mL), a solution of ethyl 2-chloro-3-oxobutanoate (3.7 g, 23 mmol) in ethanol (20 mL) and a solution of sodium acetate (5.4 g, 66 mmol) in water (20 mL). After the completion of the addition, the mixture was stirred at a lower temperature for 0.5 h. Then the resulting mixture was warmed up to room temperature, and stirred and reacted for 4 h. After the completion of the reaction, the reaction mixture was extracted with DCM and the organic phase was concentrated under vacuum to give 4.5 g of the title compound as an oil in a yield of 71.8%.

Step 2: ethyl 1-(3-(ethoxymethyl)phenyl)-7-oxo-4,5,6,7-tetrahydro-1H-pyrazolo[3,4-c]pyridine-3-carboxylate

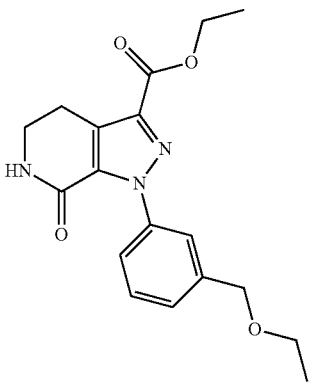 [SMILES: CCOCc1cccc(-n2nc(C(=O)OCC)c3c2C(=O)NCC3)c1]

Ethyl 2-chloro-2-(2-(3-(ethoxymethyl)phenyl)hydrazono)acetate (4.0 g, 14.1 mmol), 3-morpholino-5,6-dihydropyridin-2(1H)-one (3.1 g, 16.9 mmol) and triethylamine (4.3 g, 42.3 mmol) were successively added to toluene (40 mL) at room temperature. The mixture was heated to 110° C., and reacted under reflux for 12 h. The mixture was cooled to room temperature and concentrated in vacuum to dryness. To the residue were added DCM (40 mL) and trifluoroacetic acid (5 mL). The resulting mixture was stirred and reacted for 2 h. After the completion of the reaction, the resulting mixture was washed with water. The aqueous phase was extracted with DCM. The organic phases were concentrated under vacuum. The residue was purified by silica gel column chromatography (PE:EA=1:1) to give 1.2 g of the title compound in a yield of 24.8%.

Step 3: ethyl 1-(3-(ethoxymethyl)phenyl)-7-oxo-6-(4-(2-oxopiperidin-1-yl)phenyl)-4,5,6,7-tetrahydro-1H-pyrazolo[3,4-c]pyridine-3-carboxylate

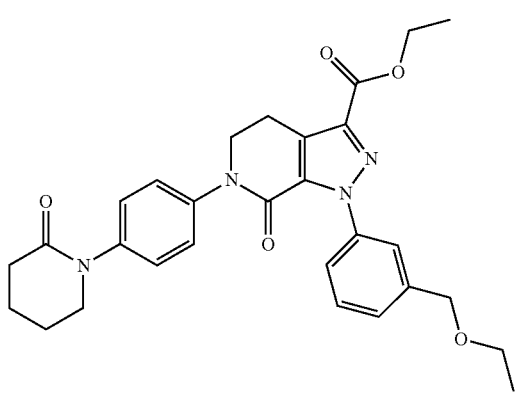 [SMILES: CCOCc1cccc(-n2nc(C(=O)OCC)c3c2C(=O)N(c2ccc(N4CCCCC4=O)cc2)CC3)c1]

At room temperature, 1-(4-iodophenyl)piperidin-2-one (0.80 g, 2.6 mmol), ethyl 1-(3-(ethoxymethyl)phenyl)-7-oxo-4,5,6,7-tetrahydro-1H-pyrazolo[3,4-c]pyridine-3-carboxylate (0.77 g, 2.2 mmol) and potassium carbonate (0.68 g, 4.9 mmol) were successively added to DMSO (10 mL). Under the nitrogen protection, to the resulting mixture were added cupric iodide (210 mg, 1.1 mmol) and 1,10-phenanthroline (197 mg, 1.1 mmol). The mixture was heated to 120° C. and reacted for 12 h. After the completion of the reaction, the reaction mixture was cooled to room temperature, and water was added. The resulting mixture was extracted with EA. The resulting organic phases were concentrated under vacuum to give a crude product. The crude product was purified by silica gel column chromatography (PE:EA=1:1) to give 0.2 g of the title compound as an oil in a yield of 16.8%.

Step 4: 1-(3-(ethoxymethyl)phenyl)-7-oxo-6-(4-(2-oxopiperidin-1-yl)phenyl)-4,5,6,7-tetrahydro-1H-pyrazolo[3,4-c]pyridine-3-carboxamide

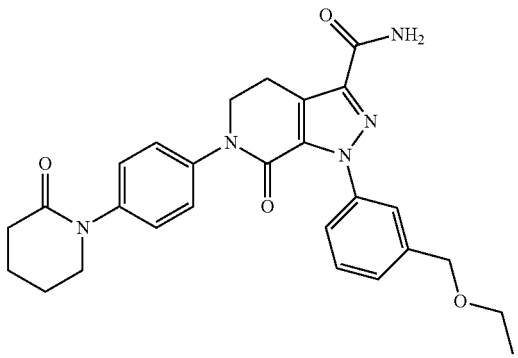 [SMILES: CCOCc1cccc(-n2nc(C(N)=O)c3c2C(=O)N(c2ccc(N4CCCCC4=O)cc2)CC3)c1]

Ethyl 1-(3-(ethoxymethyl)phenyl)-7-oxo-6-(4-(2-oxopiperidin-1-yl)phenyl)-4,5,6,7-tetrahydro-1H-pyrazolo[3,4-c]pyridine-3-carboxylate (0.2 g, 0.39 mmol) was added to a seal tube. To the seal tube was added ethylene glycol (10 mL). Ammonia gas was introduced to the seal tube for 0.5 h, and then the seal tube was sealed. The mixture was heated to 120° C. and reacted for 3 h. After the completion of the reaction, the reaction mixture was cooled to room temperature and then poured into cold water. A solid separated out. The mixture was filtered. The filter cake was dried to produce 110 mg of the title compound as an off-white solid in a yield of 56.4%.

$^1$H NMR (600 MHz, DMSO) δ 1.134-1.166 (m, 3H), 1.830-1.859 (m, 4H), 2.378-2.387 (d, 2H), 3.205-3.214 (d, 2H), 3.492-3.512 (m, 2H), 3.586-3.594 (d, 2H), 4.063-4.072 (d, 2H), 4.498-4.506 (d, 2H), 7.265-7.287 (m, 2H), 7.341-7.397 (m, 3H), 7.418-7.452 (m, 2H), 7.463-7.532 (m, 2H), 7.753 (s, 1H)

MS 488.5 [M+H]$^+$

Example 32: 1-(4-methoxyphenyl)-6-(4-(3-methyl-2-oxopyridin-1(2H)-yl)phenyl)-7-oxo-4,5,6,7-tetrahydro-1H-pyrazolo[3,4-c]pyridine-3-carboxamide Step 1: ethyl 1-(4-methoxyphenyl)-6-(4-(3-methyl-2-oxopyridin-1(2H)-yl)phenyl)-7-oxo-4,5,6,7-tetrahydro-1H-pyrazolo[3,4-c]pyridine-3-carboxylate

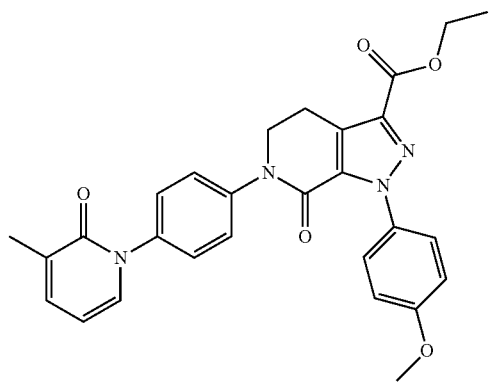 [SMILES: CCOC(=O)c1nn(-c2ccc(OC)cc2)c2c1CCN(c1ccc(-n3cccc(C)c3=O)cc1)C2=O]

At room temperature, ethyl 6-(4-iodophenyl)-1-(4-methoxyphenyl)-7-oxo-4,5,6,7-tetrahydro-1H-pyrazolo[3,4-c]pyridine-3-carboxylate (0.52 g, 1.0 mmol), 3-methylpyridin-2(1H)-one (0.16 g, 1.5 mmol) and potassium carbonate (0.29 g, 2.1 mmol) were successively added to DMSO (25 mL). Under the nitrogen protection, to the resulting mixture were added cupric iodide (91 mg, 0.47 mmol) and 1,10-phenanthroline (88 mg, 0.49 mmol). The mixture was heated to 120° C. and reacted for 12 h. After the completion of the reaction, the reaction mixture was cooled to room temperature, and water was added. The resulting mixture was extracted with EA. The organic phases were concentrated to produce a crude product. The crude product was purified by silica gel column chromatography (PE:EA=1:1) to give 0.25 g of the title compound as a khaki solid in a yield of 50.2%.

Step 2: 1-(4-methoxyphenyl)-6-(4-(3-methyl-2-oxopyridin-1(2H)-yl)phenyl)-7-oxo-4,5,6,7-tetrahydro-1H-pyrazolo[3,4-c]pyridine-3-carboxamide

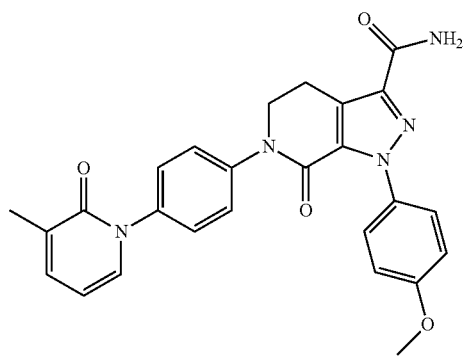 [SMILES: COc1ccc(-n2nc(C(N)=O)c3c2C(=O)N(c2ccc(-n4cccc(C)c4=O)cc2)CC3)cc1]

Ethyl 1-(4-methoxyphenyl)-6-(4-(3-methyl-2-oxopyridin-1(2H)-yl)phenyl)-7-oxo-4,5,6,7-tetrahydro-1H-pyrazolo[3,4-c]pyridine-3-carboxylate (0.25 g, 0.5 mmol) was added to a seal tube. To the seal tube was added ethylene glycol (20 mL). Ammonia gas was introduced to the seal tube for 0.5 h, and then the seal tube was sealed. The mixture was heated to 120° C. and reacted for 3 h. After the completion of the reaction, the reaction mixture was cooled to room temperature and then poured into cold water. A solid separated out. The mixture was filtered. The filter cake was dried to produce 145 mg of the title compound as an off-white solid in a yield of 61.8%.

$^1$H NMR (600 MHz, DMSO) δ 2.035-2.049 (m, 3H), 3.228-3.239 (m, 2H), 3.799-3.814 (m, 3H), 4.100-4.111 (m, 2H), 6.234-6.248 (m, 1H), 6.993-7.022 (m, 2H), 7.398-7.536 (m, 9H), 7.754 (s, 1H)

MS 470.2 [M+H]$^+$

Example 33: 1-(4-methoxyphenyl)-6-(4-(4-methyl-2-oxopyridin-1(2H)-yl)phenyl)-7-oxo-4,5,6,7-tetrahydro-1H-pyrazolo[3,4-c]pyridine-3-carboxamide Step 1: ethyl 1-(4-methoxyphenyl)-6-(4-(4-methyl-2-oxopyridin-1(2H)-yl)phenyl)-7-oxo-4,5,6,7-tetrahydro-1H-pyrazolo[3,4-c]pyridine-3-carboxylate

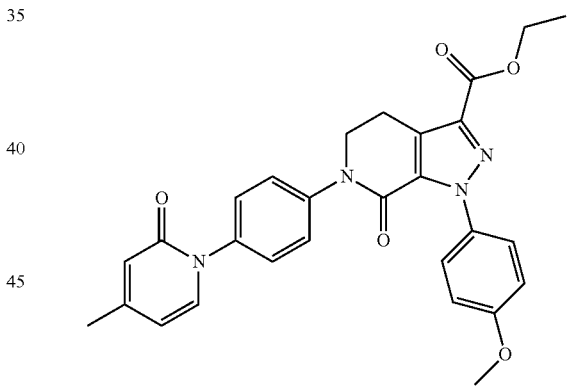

At room temperature, ethyl 6-(4-iodophenyl)-1-(4-methoxyphenyl)-7-oxo-4,5,6,7-tetrahydro-1H-pyrazolo[3,4-c]pyridine-3-carboxylate (0.52 g, 1.0 mmol), 4-methylpyridin-2(1H)-one (0.16 g, 1.5 mmol) and potassium carbonate (0.29 g, 2.1 mmol) were added to DMSO (25 mL). Under the nitrogen protection, to the resulting mixture were added cupric iodide (91 mg, 0.47 mmol) and 1,10-phenanthroline (88 mg, 0.49 mmol). The mixture was heated to 120° C. and reacted for 12 h. After the completion of the reaction, the reaction mixture was cooled to room temperature, and water was added. The resulting mixture was extracted with EA. The organic phases were concentrated to produce a crude product. The crude product was purified by silica gel column chromatography (PE:EA=1:1) to give 0.34 g of the title compound as a khaki solid in a yield of 68.3%.

Step 2: 1-(4-methoxyphenyl)-6-(4-(4-methyl-2-oxopyridin-1(2H)-yl)phenyl)-7-oxo-4,5,6,7-tetrahydro-1H-pyrazolo[3,4-c]pyridine-3-carboxamide

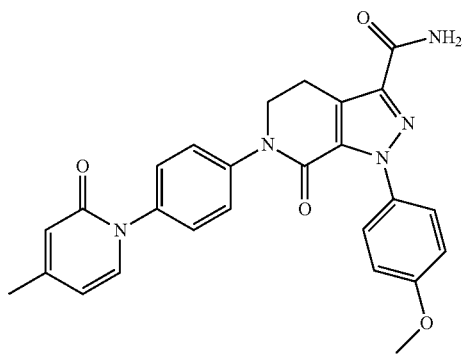 [SMILES: COc1ccc(-n2nc(C(N)=O)c3c2C(=O)N(c2ccc(-n4ccc(C)cc4=O)cc2)CC3)cc1]

Ethyl 1-(4-methoxyphenyl)-6-(4-(4-methyl-2-oxopyridin-1(2H)-yl)phenyl)-7-oxo-4,5,6,7-tetrahydro-1H-pyrazolo[3,4-c]pyridine-3-carboxylate (0.34 g, 0.68 mmol) was added to a seal tube. To the seal tube was added ethylene glycol (20 mL). Ammonia gas was introduced to the seal tube for 0.5 h, and then the seal tube was sealed. The mixture was heated to 120° C. and reacted for 3 h. After the completion of the reaction, the reaction mixture was cooled to room temperature and then poured into cold water. A solid separated out. The mixture was filtered. The filter cake was dried to produce 210 mg of the title compound as an off-white solid in a yield of 65.8%.

$^1$H NMR (600 MHz, DMSO) δ 2.181 (s, 3H), 3.218-3.239 (m, 2H), 3.804 (s, 3H), 4.083-4.105 (m, 2H), 6.177-6.189 (m, 1H), 6.290 (s, 1H), 6.997-7.012 (m, 2H), 7.387-7.401 (m, 2H), 7.449-7.483 (m, 3H), 7.512-7.527 (m, 3H), 7.729 (s, 1H)

MS 470.2 [M+H]$^+$

Example 34: N1-(4-(3-carbamoyl-1-(4-methoxyphenyl)-7-oxo-4,5-dihydro-1H-pyrazolo[3,4-c]pyridin-6(7H)-yl)phenyl)succinamide Step 1: 4-((4-(3-(ethoxycarbonyl)-1-(4-methoxyphenyl)-7-oxo-4,5-dihydro-1H-pyrazolo[3,4-c]pyridin-6(7H)-yl)phenyl)amino)-4-oxobutanoic acid

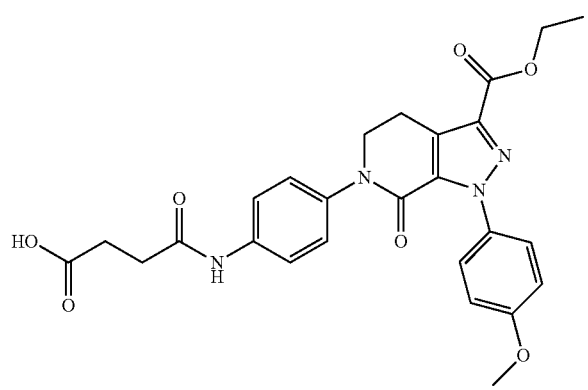 [SMILES: CCOC(=O)c1nn(-c2ccc(OC)cc2)c2c1CCN(c1ccc(NC(=O)CCC(=O)O)cc1)C2=O]

Succinic acid (2.4 g, 20 mmol), EDCl (11.4 g, 60 mmol), DMAP (0.4 g, 3.3 mmol) and ethyl 6-(4-aminophenyl)-1-(4-methoxyphenyl)-7-oxo-4,5,6,7-tetra hydro-1H-pyrazolo[3,4-c]pyridine-3-carboxylate (8.2 g, 20 mmol) were successively added to DCM (60 mL) at room temperature. The mixture was stirred and reacted for 3 h at room temperature. After the completion of the reaction, the reaction mixture was washed with diluted hydrochloric acid (0.5 mol/L) and water, dried over anhydrous Na2SO4 and filtered by suction. The filtrate was concentrated under vacuum to produce 2.0 g of the title compound as a light yellow solid in a yield of 19.7%.

Step 2: ethyl 6-(4-(2,5-dioxopyrrolidin-1-yl)phenyl)-1-(4-methoxyphenyl)-7-oxo-4,5,6,7-tetrahydro-1H-pyrazolo[3,4-c]pyridine-3-carboxylate

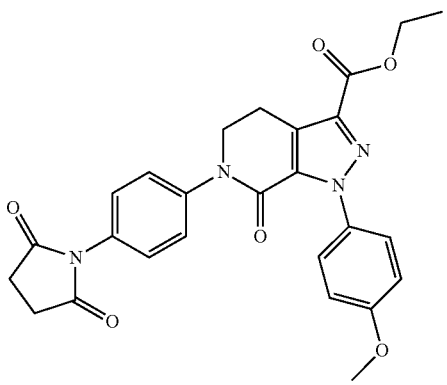 [SMILES: CCOC(=O)c1nn(-c2ccc(OC)cc2)c2c1CCN(c1ccc(N3C(=O)CCC3=O)cc1)C2=O]

To a flask were successively added 4-((4-(3-(ethoxycarbonyl)-1-(4-methoxyphenyl)-7-oxo-4,5-dihydro-1H-pyrazolo[3,4-c]pyridin-6(7H)-yl)phenyl)amino)-4-oxobutanoic acid (2.0 g, 4.0 mmol), acetic anhydride (20 mL) and sodium acetate (0.4 g) at room temperature. The mixture was reacted for 1 h at room temperature. After the completion of the reaction, EA and water were added to the reaction mixture. The resulting mixture was left to stand and separated into two phases. The aqueous phase was extracted with EA. The organic phases were concentrated under vacuum to afford 1.8 g of the title compound as a solid in a yield of 92.1%.

Step 3: N1-(4-(3-carbamoyl-1-(4-methoxyphenyl)-7-oxo-4,5-dihydro-1H-pyrazolo[3,4-c]pyridin-6(7H)-yl)phenyl)succinamide

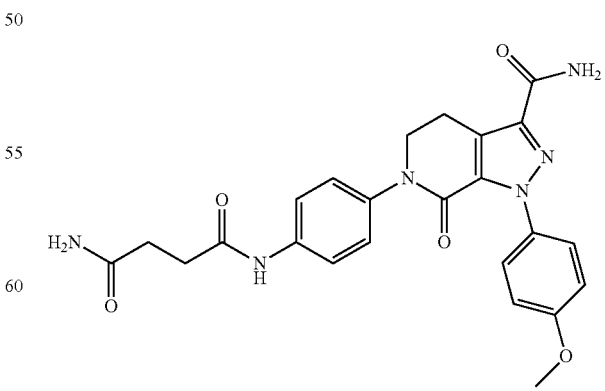

ethyl 6-(4-(2,5-dioxopyrrolidin-1-yl)phenyl)-1-(4-methoxyphenyl)-7-oxo-4,5,6,7-tetrahydro-1H-pyrazolo[3, 4-c]pyridine-3-carboxylate (0.9 g, 1.8 mmol) was added to a seal tube. To the seal tube was added ethylene glycol (15 mL). Ammonia gas was introduced to the seal tube for 0.5 h, and then the seal tube was sealed. The mixture was heated to 120° C. and reacted for 3 h. After the completion of the reaction, the reaction mixture was cooled to room temperature and then poured into cold water. A solid separated out. The mixture was filtered. The filter cake was dried to produce 200 mg of the title compound as a khaki solid in a yield of 23.3%.

$^1$H NMR (600 MHz, DMSO) δ 2.370-2.394 (m, 2H), 3.176-3.197 (m, 2H), 3.801 (s, 3H), 3.992-4.014 (m, 2H), 6.760 (s, 1H), 6.989-7.003 (d, 2H), 7.251-7.265 (d, 2H), 7.324 (s, 1H), 7.430 (s, 1H), 7.483-7.498 (d, 2H), 7.568-7.582 (d, 2H), 7.707 (s, 1H), 9.980 (s, 1H)

MS 477.5 [M+H]$^+$

Example 35: 6-(4-(2,5-dioxopyrrolidin-1-yl)phenyl)-1-(4-methoxyphenyl)-7-oxo-4,5,6,7-tetrahydro-1H-pyrazolo[3,4-c]pyridine-3-carboxamide

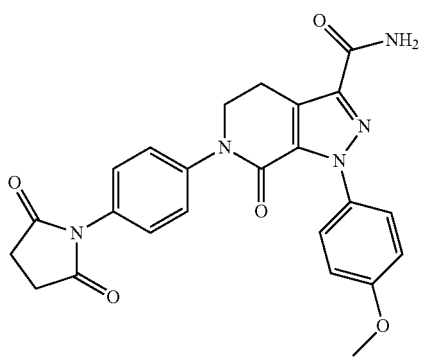 [SMILES: COc1ccc(-n2nc(C(N)=O)c3c2C(=O)N(c2ccc(N4C(=O)CCC4=O)cc2)CC3)cc1]

Ethyl 6-(4-(2,5-dioxopyrrolidin-1-yl)phenyl)-1-(4-methoxyphenyl)-7-oxo-4,5,6,7-tetrahydro-1H-pyrazolo[3,4-c]pyridine-3-carboxylate (0.9 g, 1.8 mmol) was added to a seal tube. To the seal tube was added ethylene glycol (15 mL). Ammonia gas was introduced to the seal tube for 0.5 h, and then the seal tube was sealed. The mixture was heated to 120° C. and reacted for 3 h. After the completion of the reaction, the reaction mixture was cooled to room temperature and then poured into cold water. A solid separated out. The mixture was filtered. The filter cake was dried to produce 100 mg of the title compound as a khaki solid in a yield of 12.1%.

$^1$H NMR (600 MHz, DMSO) δ 3.141-3.163 (m, 2H), 3.799 (s, 3H), 3.909-3.920 (m, 2H), 5.097 (m, 2H), 6.527-6.541 (d, 2H), 6.949-6.997 (m, 4H), 7.409 (s, 1H), 7.469-7.484 (d, 2H), 7.680 (s, 1H);

MS 460.2 [M+H]$^+$

What is claimed is:

1. A compound of formula (I), a tautomer thereof, or an optical isomer thereof, or a pharmaceutically acceptable salt thereof:

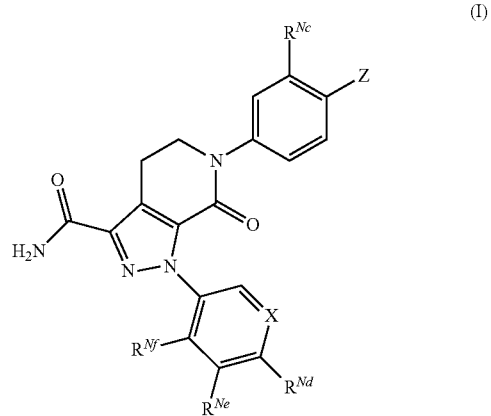

wherein

X is selected from CH;

Z is selected from

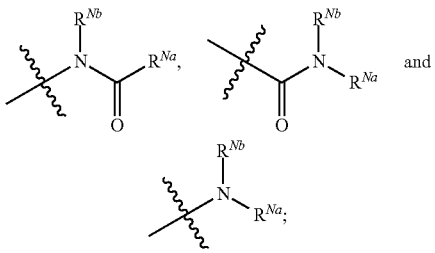

$R^{Na}$ and $R^{Nb}$ are each independently selected from hydrogen, $C_{1-6}$alkyl, $C_{2-6}$alkenyl, $C_{2-6}$alkynyl, $C_{1-6}$alkoxy-$C_{0-6}$alkyl, $(C_{0-6}$alkyl$)(C_{0-6}$alkyl$)$N—$C_{1-6}$alkyl, $(C_{2-6}$alkylene$)$N—$C_{1-6}$alkyl or carbamoyl-$C_{1-6}$alkyl; or $R^{Na}$ and $R^{Nb}$, together with the atoms attached thereto, form a 5, 6 or 7-membered cyclic moiety, wherein the 5, 6 or 7-membered cyclic moiety is substituted by one $R^{Ng}$, wherein the $R^{Ng}$ is selected from hydrogen, $C_{1-4}$alkyl, hydroxyl, $C_{1-4}$alkoxy, halogen, oxo and amino, the 5, 6 or 7-membered cyclic moiety, besides the N atom attaching to $R^{Nb}$, comprises 0, 1, 2, 3 or 4 heteroatoms selected from N, O and S, the 5, 6 or 7-membered cyclic moiety comprises 0, 1, 2 or 3 double bonds;

$R^{Nc}$ is selected from hydrogen, $C_{1-6}$alkyl and $C_{1-6}$alkoxy;

$R^{Nd}$ is ethoxy;

$R^{Ne}$ is selected from hydrogen, halogen, $C_{1-6}$alkoxy, halogen-substituted $C_{1-6}$alkoxy, carbamoyl-$C_{1-6}$alkyl and $C_{1-6}$alkoxy-$C_{1-6}$alkyl;

$R^{Nf}$ is selected from hydrogen, halogen, $C_{1-6}$alkoxy, halogen-substituted $C_{1-6}$alkoxy, carbamoyl-$C_{1-6}$alkyl and $C_{1-6}$alkoxy-$C_{1-6}$alkyl.

2. The compound of formula (I) according to claim 1, a tautomer thereof, or an optical isomer thereof, or a pharmaceutically acceptable salt thereof, wherein Z is selected from

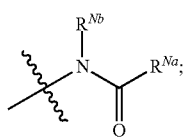

$R^{Na}$ and $R^{Nb}$, together with the atoms attached thereto, form a 5, 6 or 7-membered cyclic moiety,
wherein
the 5, 6 or 7-membered cyclic moiety is substituted by one $R^{Ng}$, wherein the $R^{Ng}$ is selected from hydrogen, $C_{1-4}$alkyl, hydroxyl, $C_{1-4}$alkoxy, halogen, oxo and amino,
the 5, 6 or 7-membered cyclic moiety, besides the N atom attaching to $R^{Nb}$, comprises 0, 1, 2, 3 or 4 heteroatoms selected from N, O and S,
the 5, 6 or 7-membered cyclic moiety comprises 0, 1, 2 or 3 double bonds.

3. The compound of formula (I) according to claim 1, a tautomer thereof, or an optical isomer thereof, or a pharmaceutically acceptable salt thereof, wherein
Z is selected from:

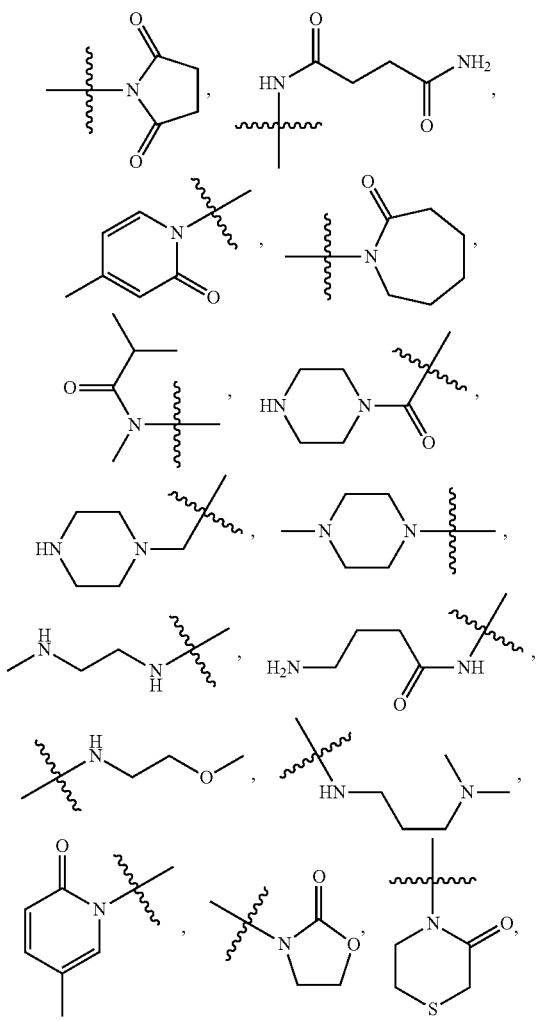

-continued

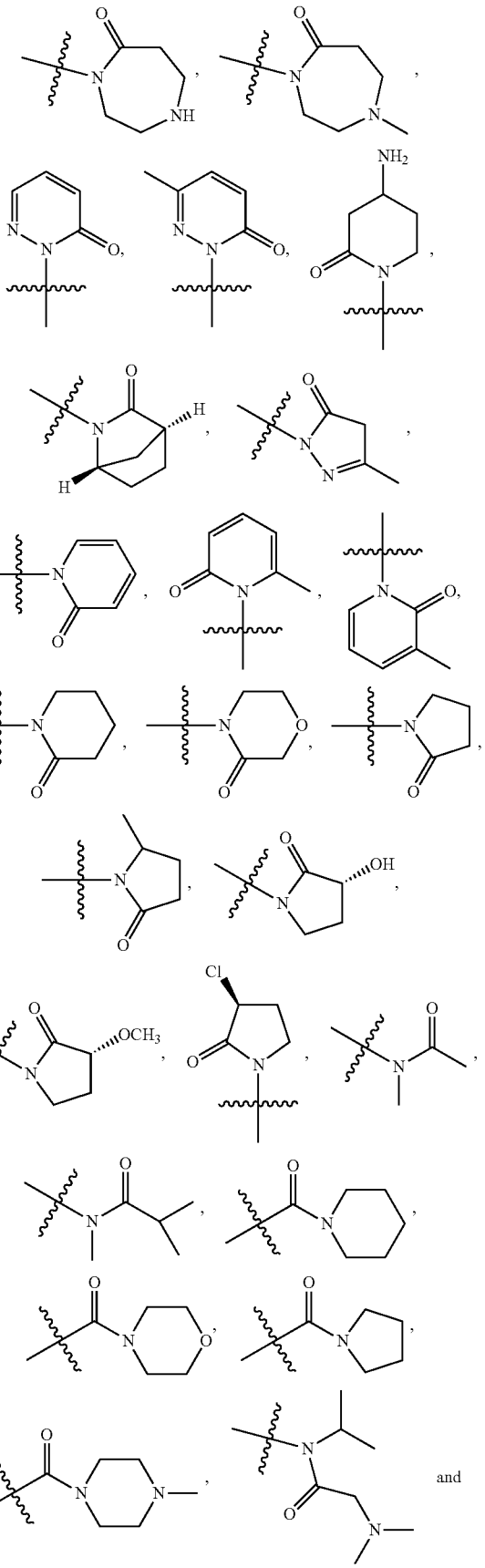

and

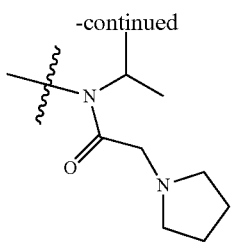

4. The compound of formula (I) according to claim 1, a tautomer thereof, or an optical isomer thereof, or a pharmaceutically acceptable salt thereof, wherein
$R^{Nc}$ is selected from hydrogen and methyl.

5. The compound of formula (I) according to claim 1, a tautomer thereof, or an optical isomer thereof, or a pharmaceutically acceptable salt thereof, wherein
$R^{Ne}$ is selected from hydrogen, chlorine and fluorine.

6. The compound of formula (I) according to claim 1, a tautomer thereof, or an optical isomer thereof, or a pharmaceutically acceptable salt thereof, wherein
$R^{Nf}$ is selected from hydrogen, chlorine and fluorine.

7. The compound of formula (I) according to claim 1, a tautomer thereof, or an optical isomer thereof, or a pharmaceutically acceptable salt thereof, wherein
Z is selected from

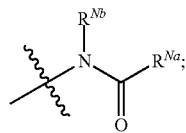

$R^{Na}$ and $R^{Nb}$, together with the atoms attached thereto, form a 5, 6 or 7-membered cyclic moiety,
wherein
the 5, 6 or 7-membered cyclic moiety is substituted by one $R^{Ng}$, wherein the $R^{Ng}$ is selected from hydrogen, $C_{1-4}$alkyl, hydroxyl, $C_{1-4}$alkoxy, halogen, oxo and amino,
the 5, 6 or 7-membered cyclic moiety, besides the N atom attaching to $R^{Nb}$, comprises 0, 1, 2, 3 or 4 heteroatoms selected from N, O and S,
the 5, 6 or 7-membered cyclic moiety comprises 0, 1, 2 or 3 double bonds,
at least one of $R^{Nc}$, $R^{Ng}$, $R^{Ne}$ and $R^{Nf}$ is not hydrogen.

8. The compound of formula (I) according to claim 1, a tautomer thereof, or an optical isomer thereof, or a pharmaceutically acceptable salt thereof, wherein
X is CH;
Z is selected from

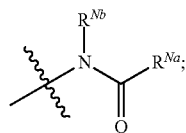

$R^{Na}$ and $R^{Nb}$, together with the atoms attached thereto, form a 5, 6 or 7-membered cyclic moiety,
wherein
the 5, 6 or 7-membered cyclic moiety is substituted by one $R^{Ng}$, wherein the $R^{Ng}$ is selected from hydrogen and methyl,
the 5, 6 or 7-membered cyclic moiety, besides the N atom attaching to $R^{Nb}$, comprises 0, 1, 2, 3 or 4 heteroatoms selected from N, O and S,
the 5, 6 or 7-membered cyclic moiety comprises 0, 1, 2 or 3 double bonds,
$R^{Nd}$ is ethoxy;
$R^{Nc}$ is methyl.

9. The compound of formula (I) according to claim 8, a tautomer thereof, or an optical isomer thereof, or a pharmaceutically acceptable salt thereof,
wherein
Z is selected from:

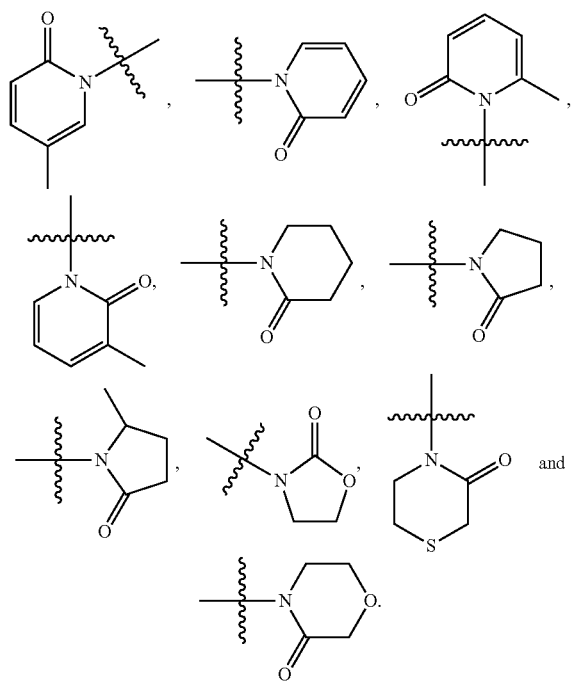

10. A compound, a tautomer thereof, or an optical isomer thereof, or a pharmaceutically acceptable salt thereof, wherein said compound is selected from:

| | |
|---|---|
| 29' | 1-(4-ethoxy-3-fluorophenyl)-7-oxo-6-(4-(2-oxopiperidin-1-yl)phenyl)-4,5,6,7-tetrahydro-1H-pyrazolo[3,4-c]pyridine-3-carboxamide |
| 27 | 1-(3-fluoro-4-ethoxyphenyl)-6-(4-(3-methyl-2-oxopyridin-1(2H)-yl)phenyl)-7-oxo-4,5,6,7-tetrahydro-1H-pyrazolo[3,4-c]pyridine-3-carboxamide |
| 28 | 1-(4-ethoxyphenyl)-6-(4-(3-methyl-2-oxopyridin-1(2H)-yl)phenyl)-7-oxo-4,5,6,7-tetrahydro-1H-pyrazolo[3,4-c]pyridine-3-carboxamide |
| 29 | 1-(3-chloro-4-ethoxyphenyl)-6-(4-(2-oxopiperidin-1-yl)phenyl)-7-oxo-4,5,6,7-tetrahydro-1H-pyrazolo[3,4-c]pyridine-3-carboxamide |
| 30 | 1-(3-chloro-4-ethoxyphenyl)-6-(4-(3-methyl-2-oxopyridin-1(2H)-yl)phenyl)-7-oxo-4,5,6,7-tetra hydro-1H-pyrazolo[3,4-c]pyridine-3-carboxamide |
| 31 | 1-(4-ethoxyphenyl)-6-(3-methyl-4-(2-oxopiperidin-1-yl)phenyl)-7-oxo-4,5,6,7-tetrahydro-1H-pyrazolo[3,4-c]pyridine-3-carboxamide |
| 32 | 1-(3-fluoro-4-ethoxyphenyl)-6-(3-methyl-4-(2-oxopiperidin-1-yl)phenyl)-7-oxo-4,5,6,7-tetra hydro-1H-pyrazolo[3,4-c]pyridine-3-carboxamide |
| 33 | 1-(4-ethoxyphenyl)-6-(3-methyl-4-(3-oxomorpholino)phenyl)-7-oxo-4,5,6,7-tetrahydro-1H-pyrazolo[3,4-c]pyridine-3-carboxamide |

| | -continued |
|---|---|
| 34 | 1-(3-fluoro-4-ethoxyphenyl)-6-(3-methyl-4-(3-oxomorpholino)phenyl)-7-oxo-4,5,6,7-tetrahydro-1H-pyrazolo[3,4-c]pyridine-3-carboxamide |
| 35 | 1-(4-ethoxyphenyl)-6-(3-methyl-4-(2-oxopyrrolidin-1-yl)phenyl)-7-oxo-4,5,6,7-tetrahydro-1H-pyrazolo[3,4-c]pyridine-3-carboxamide |
| 36 | 1-(3-fluoro-4-ethoxyphenyl)-6-(3-methyl-4-(2-oxopyrrolidin-1-yl)phenyl)-7-oxo-4,5,6,7-tetrahydro-1H-pyrazolo[3,4-c]pyridine-3-carboxamide |
| 37 | 1-(4-ethoxyphenyl)-6-(3-methyl-4-(2-oxopyridin-1(2H)-yl)phenyl)-7-oxo-4,5,6,7-tetrahydro-1H-pyrazolo[3,4-c]pyridine-3-carboxamide |
| 38 | 1-(3-fluoro-4-ethoxyphenyl)-6-(3-methyl-4-(2-oxopyridin-1(2H)-yl)phenyl)-7-oxo-4,5,6,7-tetrahydro-1H-pyrazolo[3,4-c]pyridine-3-carboxamide |
| 39 | 1-(4-ethoxyphenyl)-6-(3-methyl-4-(3-methyl-2-oxopyridin-1(2H)-yl)phenyl)-7-oxo-4,5,6,7-tetrahydro-1H-pyrazolo[3,4-c]pyridine-3-carboxamide |
| 40 | 1-(3-fluoro-4-ethoxyphenyl)-6-(3-methyl-4-(3-methyl-2-oxopyridin-1(2H)-yl)phenyl)-7-oxo-4,5,6,7-tetrahydro-1H-pyrazolo[3,4-c]pyridine-3-carboxamide. |

11. A pharmaceutical composition, containing the compound according to claim 1, a tautomer thereof, or an optical isomer thereof, or a pharmaceutically acceptable salt thereof.

12. A method for treating a disease that inhibits Factor Xa positive effect comprising administering the compound of claim 1, a tautomer thereof, or an optical isomer thereof, or a pharmaceutically acceptable salt thereof to a patient optionally with a low bleeding risk, wherein the disease is selected from thromboembolism, disseminated intravascular coagulation, myocardial infarction, stenocardia, reocclusion and restenosis after angioplasty or aortocoronary bypass, stroke, transient partial seizures, peripheral arterial occlusive disease, pulmonary embolism and deep venous thrombosis.

13. A method for treating a disease that inhibits Factor Xa positive effect comprising administering the pharmaceutical composition of claim 11 to a patient optionally with a low bleeding risk, wherein the disease is selected from thromboembolism, disseminated intravascular coagulation, myocardial infarction, stenocardia, reocclusion and restenosis after angioplasty or aortocoronary bypass, stroke, transient partial seizures, peripheral arterial occlusive disease, pulmonary embolism and deep venous thrombosis.

14. A method for preparing the compound of formula (I) according to claim 1, a tautomer thereof, or an optical isomer thereof, or a pharmaceutically acceptable salt thereof, comprising ammonifying the compound of formula (II) to achieve the compound of formula (I):

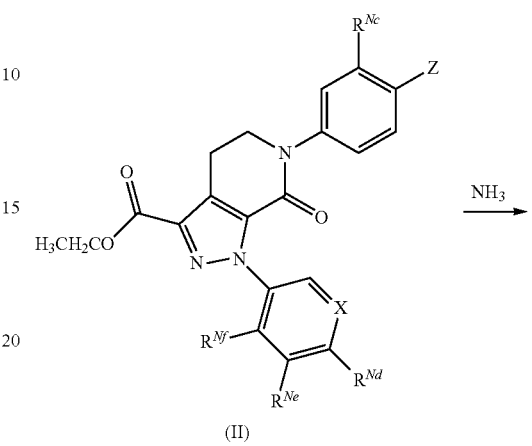

(II)

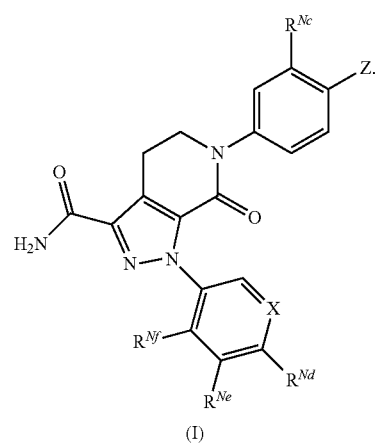

(I)

* * * * *